United States Patent
Li et al.

(10) Patent No.: US 10,190,133 B2
(45) Date of Patent: Jan. 29, 2019

(54) COMPOSITIONS AND METHODS FOR IMPROVING ABIOTIC STRESS TOLERANCE

(71) Applicant: China Agricultural University, Beijing (CN)

(72) Inventors: Zichao Li, Beijing (CN); Haiyan Xiong, Beijing (CN); Pengli Liu, Beijing (CN); Jingie Li, Beijing (CN); Hongliang Zhang, Beijing (CN)

(73) Assignee: China Agricultural University, Beijing (CN)

( * ) Notice: Subject to any disclaimer, the term of this patent is extended or adjusted under 35 U.S.C. 154(b) by 0 days.

(21) Appl. No.: 14/908,219

(22) PCT Filed: Jul. 29, 2014

(86) PCT No.: PCT/CN2014/083234
§ 371 (c)(1),
(2) Date: Jan. 28, 2016

(87) PCT Pub. No.: WO2015/014273
PCT Pub. Date: Feb. 5, 2015

(65) Prior Publication Data
US 2016/0340688 A1 Nov. 24, 2016

(30) Foreign Application Priority Data

Jul. 29, 2013 (CN) .......................... 2013 1 0322316
Jul. 29, 2013 (CN) .......................... 2013 1 0322634

(51) Int. Cl.
| | |
|---|---|
| C12N 15/00 | (2006.01) |
| A01H 1/00 | (2006.01) |
| A01H 5/00 | (2018.01) |
| C12N 15/82 | (2006.01) |
| C07K 14/415 | (2006.01) |
| A01H 1/02 | (2006.01) |
| C12Q 1/6895 | (2018.01) |

(52) U.S. Cl.
CPC ........... *C12N 15/8273* (2013.01); *A01H 1/02* (2013.01); *C07K 14/415* (2013.01); *C12N 15/825* (2013.01); *C12N 15/8261* (2013.01); *C12N 15/8269* (2013.01); *C12N 15/8271* (2013.01); *C12Q 1/6895* (2013.01); *C12Q 2600/13* (2013.01); *C12Q 2600/158* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 2004/0123343 A1* | 6/2004 | La Rosa | C07K 14/415 800/278 |
| 2006/0123505 A1 | 6/2006 | Kikuchi et al. | |

FOREIGN PATENT DOCUMENTS

| | | |
|---|---|---|
| WO | WO 02/088310 A2 | 11/2002 |
| WO | WO 2007/089244 A1 | 8/2007 |
| WO | WO 2009/127441 A2 | 10/2009 |
| WO | WO 2011/011412 A2 | 1/2011 |

OTHER PUBLICATIONS

Ohyanagi, H. et al., "The Rice Annotation Project Database (RAP-DB):hub for *Oryza sativa* ssp. japonica genome information", Nucleic Acids Research, (2006), vol. 34; 4 pages.
International Preliminary Report on Patentability corresponding to International Application No. PCT/CN2014/083234; dated Feb. 2, 2016, 6 pages.
International Search Report and Written Opinion corresponding to International Application No. PCT/CN2014/083234; dated Nov. 2, 2014, 11 pages.
Ching et al. "Brittle stalk2 encodes a putative glycosylphosphatidylinositol-anchored protein that affects mechanical strength of maize tissues by altering the composition and structure of secondary cell walls", *Planta: An International Journal of Plant Biology*, 224:1174-1184, Jun. 3, 2006.
Database Geneseq, "Plant-derived crop improvement protein, SEQ:611", Mar. 31, 2011, Retrieved from EBI accession No. GSP:AZF27254.
Database Geneseq, "Rice BC1L4 protein, SEQ ID 1 #2", Jan. 7, 2010, Retrieved from EBI accession No. GSP: AXS64839.
European Partial Supplementary Search Report Corresponding to European Patent Application No. 14 83 2117; dated Jan. 3, 2017; 8 Pages.
Sindhu et al. "Maize Brittle stalk2 Encodes a COBRA-Like Protein Expressed in Early Organ Development But Required for Tissue Flexibility at Maturity", *Plant Physiology*, Dec. 2007, vol. 145, pp. 1444-1459.

* cited by examiner

*Primary Examiner* — Phuong T Bui
(74) *Attorney, Agent, or Firm* — Myers Bigel, P.A.

(57) ABSTRACT

The present invention relates to compositions and methods for improving the abiotic stress tolerance of plants. Plants and plant parts identified, selected and/or produced using compositions and methods of the present invention are also provided.

22 Claims, 37 Drawing Sheets
Specification includes a Sequence Listing.

COMPOSITIONS AND METHODS FOR IMPROVING ABIOTIC STRESS TOLERANCE

STATEMENT REGARDING ELECTRONIC FILING OF A SEQUENCE LISTING

A Sequence Listing in ASCII text format, submitted under 37 C.F.R. § 1.821, entitled 9207-130_ST25.txt, 136,288 bytes in size, generated on Aug. 2, 2016 and filed via EFS-Web, is provided in lieu of a paper copy. This Sequence Listing is incorporated by reference into the specification for its disclosures.

RELATED APPLICATIONS

This application is a 35 U.S.C. § 371 national phase application of United States Application Serial No. PCT/CN2014/083234, filed Jul. 29, 2014, which claims priority to Chinese Patent Application Nos. 201310322634.4, filed Jul. 29, 2013, and 201310322316.8, filed Jul. 29, 2013, the disclosure of each of which is hereby incorporated by reference in its entirety.

FIELD OF THE INVENTION

The present invention relates to compositions and methods for improving the abiotic stress tolerances of plants.

BACKGROUND OF THE INVENTION

Abiotic stress is a major factor affecting the normal growth and development of plants and limiting crop yields. At present, the impact of drought stress on crop yields around the world ranks first among abiotic stress factors; the damage caused by drought is equivalent to the damage caused by all natural disasters combined and has become the predominant obstruction to agricultural development in many areas.

Identifying genes that enhance the drought tolerance of plants could lead to more efficient crop production by allowing for the identification, selection and production of plants with enhanced drought tolerance.

SUMMARY OF THE INVENTION

The present invention provides abiotic stress tolerant plants and plant parts, as well as methods and compositions for identifying, selecting and/or producing abiotic stress tolerant plants and plant parts.

In some embodiments, the present invention provides a nonnaturally occurring plant or plant part that expresses one or more exogenous COBL4 proteins and/or one or more exogenous ERF62 proteins. For example, in some embodiments, the present invention provides a plant or plant part having within its genome one or more exogenous nucleic acids comprising, consisting essentially of or consisting of the nucleotide sequence set forth in any one of SEQ ID NOs: 1-27, a nucleotide sequence that encodes a polypeptide comprising the amino acid sequence of any one of SEQ ID NOs: 28-44, a nucleotide sequence that is at least 95% identical to the nucleotide sequence set forth in any one of SEQ ID NOs: 1-27, a nucleotide sequence that encodes a polypeptide comprising an amino acid sequence that is at least 95% identical to the amino acid sequence of any one of SEQ ID NOs: 28-44, a nucleotide sequence that is complementary to any one of the aforementioned nucleotide sequences and/or a nucleotide sequence that specifically hybridizes to any one of the aforementioned nucleotide sequences under stringent hybridization conditions.

In some embodiments, the present invention provides a nonnaturally occurring nucleic acid that comprises, consists essentially of or consists of a nucleotide sequence encoding one or more COBL4 proteins and/or one or more ERF62 proteins. For example, in some embodiments, the present invention provides a nucleic acid comprising, consisting essentially of or consisting of the nucleotide sequence set forth in any one of SEQ ID NOs: 1-27, a nucleotide sequence that encodes a polypeptide comprising the amino acid sequence of any one of SEQ ID NOs: 28-44, a nucleotide sequence that is at least 95% identical to the nucleotide sequence set forth in any one of SEQ ID NOs: 1-27, a nucleotide sequence that encodes a polypeptide comprising an amino acid sequence that is at least 95% identical to the amino acid sequence of any one of SEQ ID NOs: 28-44, a nucleotide sequence that is complementary to any one of the aforementioned nucleotide sequences and/or a nucleotide sequence that specifically hybridizes to any one of the aforementioned nucleotide sequences under stringent hybridization conditions.

In some embodiments, the present invention provides a nonnaturally occurring virus or bacterium that expresses one or more exogenous COBL4 proteins and/or one or more exogenous ERF62 proteins. For example, in some embodiments, the present invention provides a recombinant virus or bacterium that expresses a nonnaturally occurring nucleic acid of the present invention.

In some embodiments, the present invention provides a nonnaturally occurring COBL4 protein. For example, in some embodiments, the present invention provides a protein comprising, consisting essentially of or consisting of the amino acid sequence of any one of SEQ ID NOs: 28-35. In some embodiments, the protein has an amino acid sequence that is at least 95% identical to one or more of SEQ ID NOs: 28-35.

In some embodiments, the present invention provides a nonnaturally occurring ERF62 protein. For example, in some embodiments, the present invention provides a protein comprising, consisting essentially of or consisting of the amino acid sequence of any one of SEQ ID NOs: 36-44. In some embodiments, the protein has an amino acid sequence that is at least 95% identical to one or more of SEQ ID NOs: 36-44.

In some embodiments, the present invention provides uses for nucleic acids, expression cassettes, vectors, recombinant virus, recombinant bacteria and proteins of the present invention for enhancing abiotic stress tolerance in a plant or plant part.

In some embodiments, the present invention provides uses for nucleic acids, expression cassettes, vectors, recombinant virus, recombinant bacteria and proteins of the present invention for producing an abiotic stress tolerant in a plant or plant part.

In some embodiments, the present invention provides a method of increasing the abiotic stress tolerance of a plant or plant part, the method comprising increasing the expression and/or activity of one or more COBL4 proteins and/or of one or more ERF62 proteins in the plant or plant part.

In some embodiments, the present invention provides a method of increasing the expression and/or activity of one or more COBL4 proteins in a plant or plant part, the method comprising increasing the expression of one or more nucleic acids encoding the COBL4 protein(s) in the plant or plant part. In some such embodiments, increasing the expression of one or more nucleic acids encoding the COBL4 protein(s) in the plant or plant part comprises expressing one or more exogenous nucleic acids encoding the COBL4 protein(s) in the plant or plant part. In some such embodiments, increasing the expression of one or more nucleic acids encoding the COBL4 protein(s) in the plant or plant part further comprises introducing one or more exogenous nucleic acids encoding the COBL4 protein(s) into the plant or plant part. Such methods may be useful for producing plants and plant parts having enhanced abiotic stress tolerance.

In some embodiments, the present invention provides a method of increasing the expression and/or activity of one or more ERF62 proteins in a plant or plant part, the method comprising: (a) increasing the expression of one or more nucleic acids encoding the ERF62 protein(s) in the plant or plant part. In some such embodiments, increasing the expression of one or more nucleic acids encoding the ERF62 protein(s) in the plant or plant part comprises expressing one or more exogenous nucleic acids encoding the ERF62 protein(s) in the plant or plant part. In some such embodiments, increasing the expression of one or more nucleic acids encoding the ERF62 protein(s) in the plant or plant part further comprises introducing one or more exogenous nucleic acids encoding the ERF62 protein(s) into the plant or plant part. Such methods may be useful for producing plants and plant parts having enhanced abiotic stress tolerance.

In some embodiments, the present invention provides a method of identifying a plant or plant part having enhanced abiotic stress tolerance, the method comprising detecting, in a plant or plant part, one or more nucleic acids that comprises, consists essentially of or consists of the nucleotide sequence set forth in any one of SEQ ID NOs: 1-27, a nucleotide sequence that encodes a polypeptide comprising the amino acid sequence of any one of SEQ ID NOs: 28-44, a nucleotide sequence that is at least 95% identical to the nucleotide sequence set forth in any one of SEQ ID NOs: 1-27, a nucleotide sequence that encodes a polypeptide comprising an amino acid sequence that is at least 95% identical to the amino acid sequence of any one of SEQ ID NOs: 28-44, a nucleotide sequence that is complementary to any one of the aforementioned nucleotide sequences and/or a nucleotide sequence that specifically hybridizes to any one of the aforementioned nucleotide sequences under stringent hybridization conditions.

In some embodiments, the present invention provides a method of producing a plant having enhanced abiotic stress tolerance, the method comprising detecting, in a plant part, one or more nucleic acids comprising, consisting essentially of or consisting of the nucleotide sequence set forth in any one of SEQ ID NOs: 1-27, a nucleotide sequence that encodes a polypeptide comprising the amino acid sequence of any one of SEQ ID NOs: 28-44, a nucleotide sequence that is at least 95% identical to the nucleotide sequence set forth in any one of SEQ ID NOs: 1-27, a nucleotide sequence that encodes a polypeptide comprising an amino acid sequence that is at least 95% identical to the amino acid sequence of any one of SEQ ID NOs: 28-44, a nucleotide sequence that is complementary to any one of the aforementioned nucleotide sequences and/or a nucleotide sequence that specifically hybridizes to any one of the aforementioned nucleotide sequences under stringent hybridization conditions; and producing a plant from the plant part.

In some embodiments, the present invention provides a method of producing a plant having enhanced abiotic stress tolerance, the method comprising introducing, into a plant part, one or more nucleic acids comprising, consisting essentially of or consisting of the nucleotide sequence set forth in any one of SEQ ID NOs: 1-27, a nucleotide sequence that encodes a polypeptide comprising the amino acid sequence of any one of SEQ ID NOs: 28-44, a nucleotide sequence that is at least 95% identical to the nucleotide sequence set forth in any one of SEQ ID NOs: 1-27, a nucleotide sequence that encodes a polypeptide comprising an amino acid sequence that is at least 95% identical to the amino acid sequence of any one of SEQ ID NOs: 28-44, a nucleotide sequence that is complementary to any one of the aforementioned nucleotide sequences and/or a nucleotide sequence that specifically hybridizes to any one of the aforementioned nucleotide sequences under stringent hybridization conditions; and producing a plant from the plant part.

In some embodiments, the present invention provides a method of producing a plant enhanced abiotic stress tolerance, the method comprising crossing a first parent plant or plant part with a second parent plant or plant part, wherein the first parent plant or plant part comprises within its genome one or more exogenous nucleic acids comprising, consisting essentially of or consisting of the nucleotide sequence set forth in any one of SEQ ID NOs: 1-27, a nucleotide sequence that encodes a polypeptide comprising the amino acid sequence of any one of SEQ ID NOs: 28-44, a nucleotide sequence that is at least 95% identical to the nucleotide sequence set forth in any one of SEQ ID NOs: 1-27, a nucleotide sequence that encodes a polypeptide comprising an amino acid sequence that is at least 95% identical to the amino acid sequence of any one of SEQ ID NOs: 28-44, a nucleotide sequence that is complementary to any one of the aforementioned nucleotide sequences and/or a nucleotide sequence that specifically hybridizes to any one of the aforementioned nucleotide sequences under stringent hybridization conditions.

The foregoing and other objects and aspects of the present invention are explained in detail in the drawings and specification set forth below.

BRIEF DESCRIPTION OF THE DRAWINGS

FIG. 7 is a multiple sequence alignment showing the amino acid sequences of OsCOBL4$_{IRAT109}$ and several of its homologues. The underlined section of sequences represents an N-terminal signal peptide. The section of sequences encompassed by the box represents a conserved CCVS domain. Point mutations between OsCOBL4$_{IRAT109}$ and OsCOBL4Nipponbare are circled (from top to bottom: SEQ ID NO:28, SEQ ID NO:29, SEQ ID NO:30, SEQ ID NO:31, SEQ ID NO:32, SEQ ID NO:33, SEQ ID NO:34, SEQ ID NO:35).

FIG. 20 is a multiple sequence alignment showing the amino acid sequences of OsERF62$_{IRAT109}$ and several of its homologues. The underlined sections of sequences represent an N-terminal MCGGAI(L/I) motif and a nuclear localization signal (NIL), respectively. The section of sequences encompassed by the box represents a conserved AP2 domain.

DETAILED DESCRIPTION

Figure 1A:
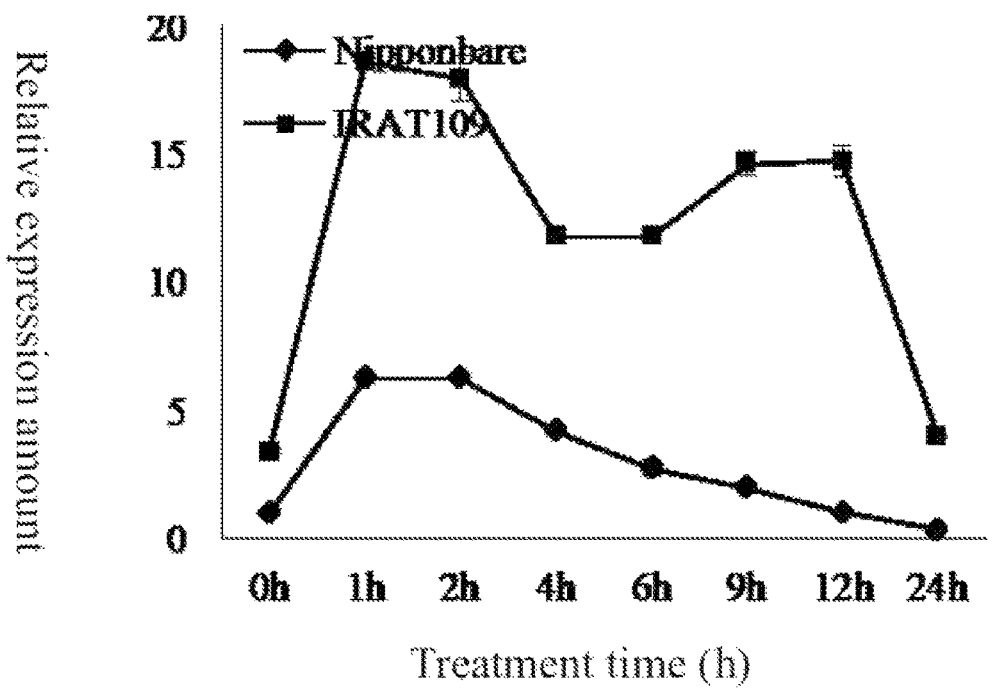
FIGS. 1A-1H are graphs showing the relative expression levels of endogenous *Oryza sativa* ssp *japonica* COBRA-like protein 4 (OsCOBL4) (1A-1D) and endogenous *Oryza sativa* ssp *japonica* ERF62 (OsERF62) (1E-1H) in upland rice variety *Oryza sativa* ssp *japonica* cv. IRAT109 (IRAT109; Zhihong, High quality *Japonica* upland rice variety IRAT109 and its cultivation techniques. ANHUI AGR. No. 06 (1994); publically available from China Agricultural University) and lowland rice variety *Oryza sativa* ssp *japonica* cv. Nipponbare (Nipponbare; Lowland rice variety "Nipponbare". BULL. AGR. SCI. TECH. No. 02 (1973); publicly available from China Agricultural University) under various growth conditions: 1A,1E=abscisic acid (ABA) treatment; 1B,1F=dehydration treatment; 1C,1G=$H_2O_2$ treatment; 1D,1H=PEG treatment.
Figure 1B:
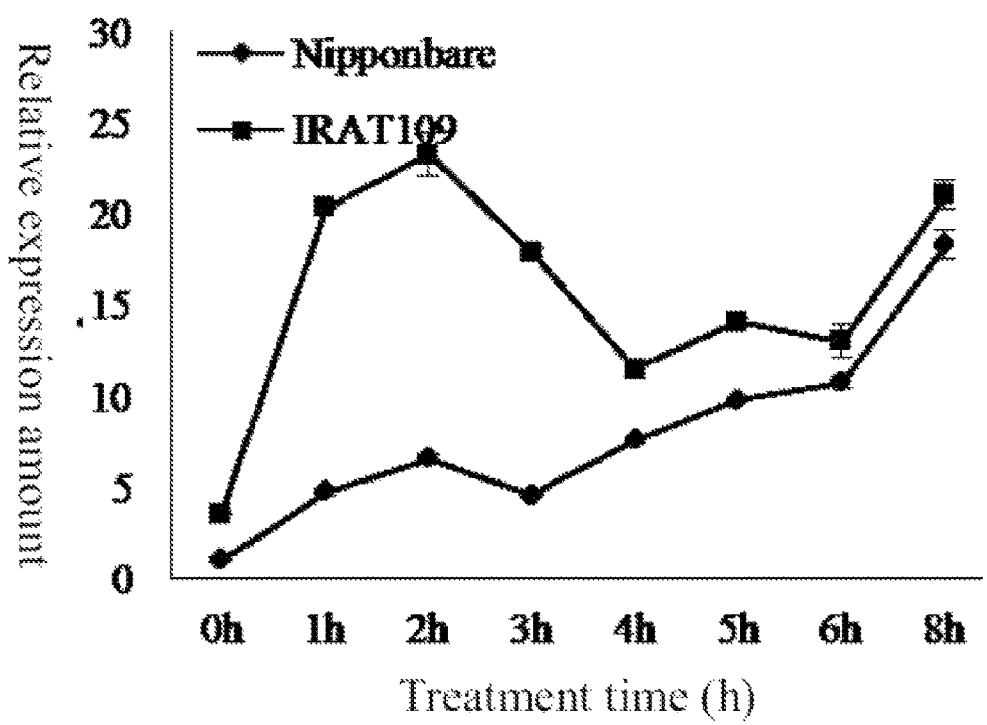
Figure 1C:
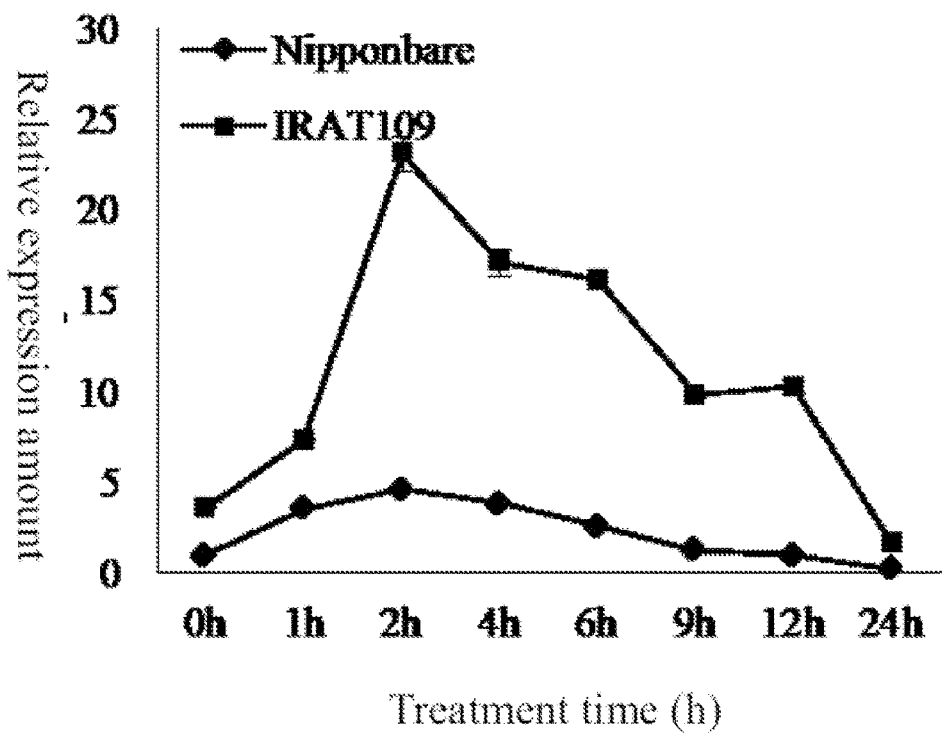
Figure 1D:
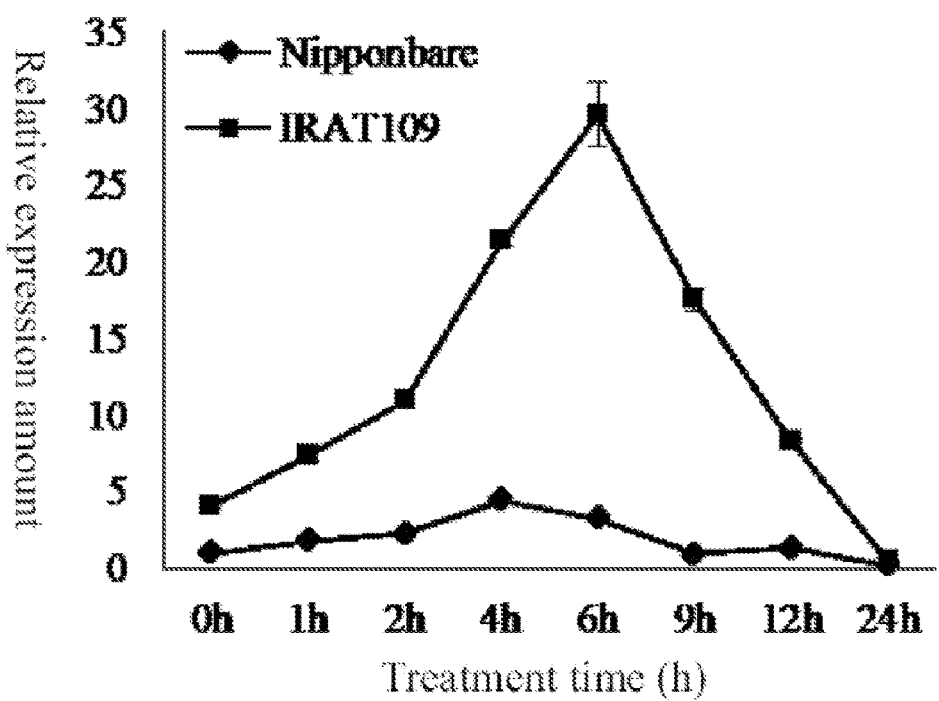
Figure 1E:
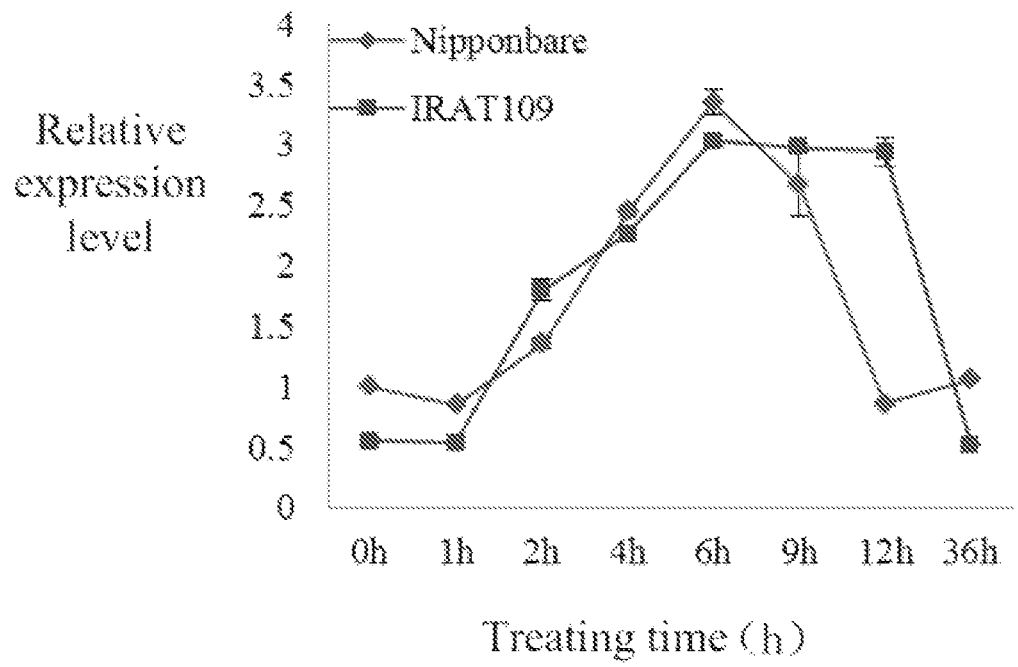
Figure 1F:
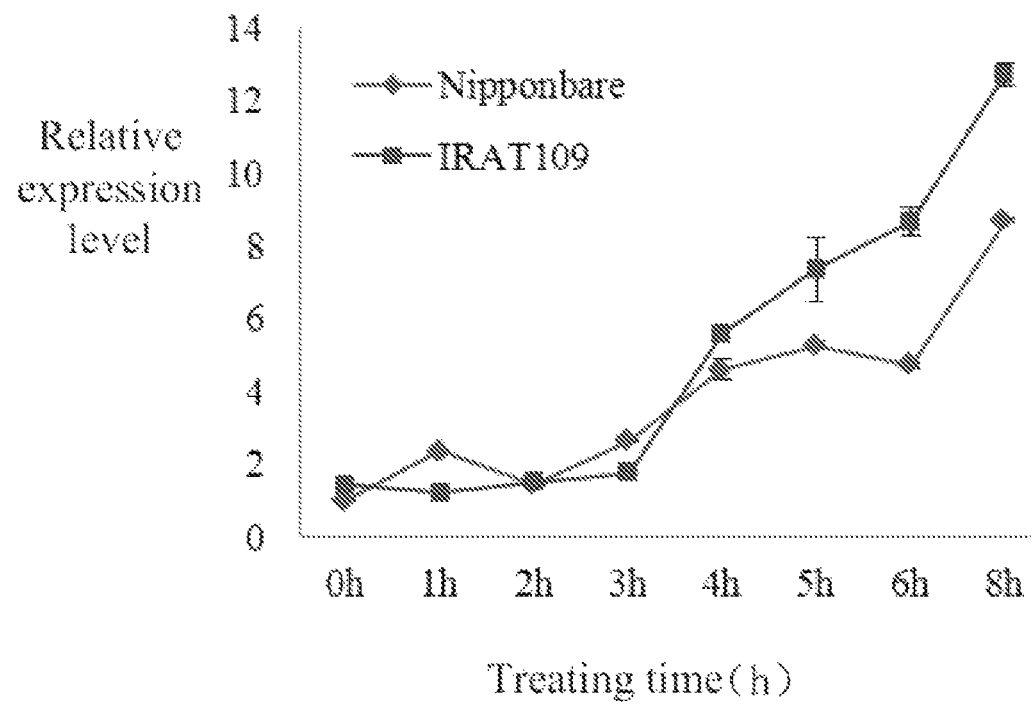
Figure 1G:
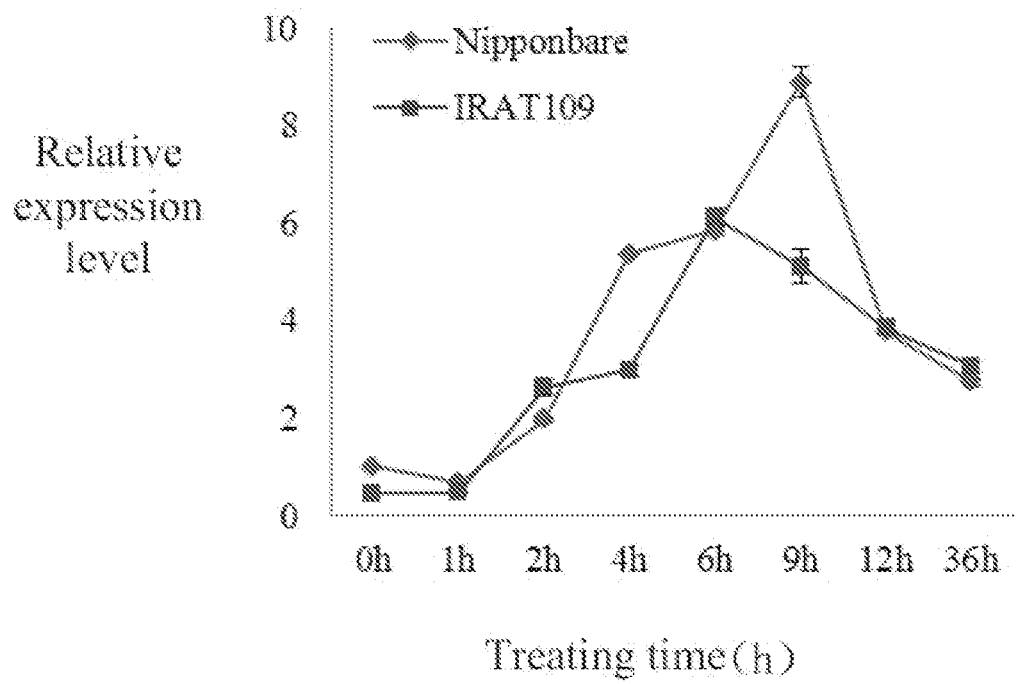
Figure 1H:
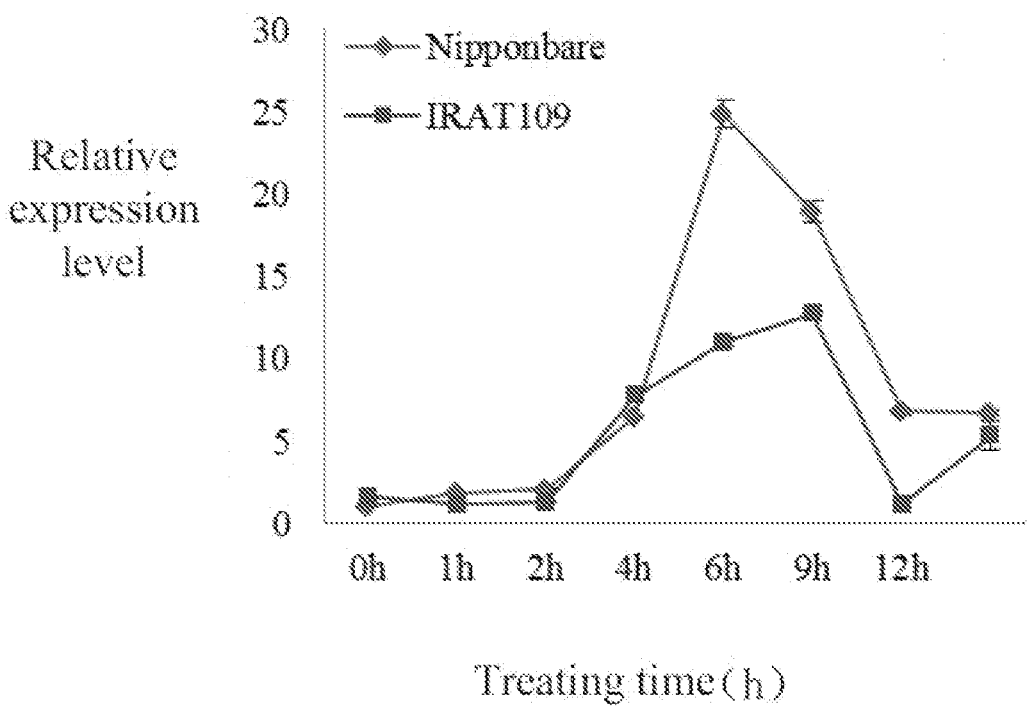

The present invention provides compositions and methods for identifying, selecting and/or producing plants and plant parts having enhanced abiotic stress tolerances (e.g., enhanced drought tolerances, enhanced osmotic stress tolerances, enhanced salt stress tolerances and/or enhanced temperature stress tolerances), as well as plants and plant parts identified, selected and/or produced using compositions and methods of the present invention.

Although the following terms are believed to be well understood by one of ordinary skill in the art, the following definitions are set forth to facilitate understanding of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

All patents, patent publications, non-patent publications referenced herein are incorporated by reference in their entireties for all purposes and to the same extent as if each was specifically and individually indicated to be incorporated by reference.

As used herein, the terms "a" or "an" or "the" may refer to one or more than one, unless the context clearly and unequivocally indicates otherwise. For example, "an" endogenous nucleic acid can mean one endogenous nucleic acid or a plurality of endogenous nucleic acids.

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, refers to a variation of 0.1%, 0.25%, 0.5%, 0.75%, 1%, 2%, 3%, 4%, 5%, 6,%, 7%, 8%, 9%, 10%, 15% or even 20% of the specified amount. Thus, if a given composition is described as comprising "about 50% X," it is to be understood that, in some embodiments, the composition comprises 50% X whilst in other embodiments it may comprise anywhere from 40 to 60% X (i.e., 50±10%).

As used herein, the terms "abiotic stress" and "abiotic stress conditions" refer to non-living factors that negatively affect a plant's ability to grow, reproduce and/or survive (e.g., drought, flooding, extreme temperatures, extreme light conditions, extreme osmotic pressures, extreme salt concentrations, high winds, natural disasters and poor edaphic conditions (e.g., extreme soil pH, nutrient-deficient soil, compacted soil, etc.).

As used herein, the terms "abiotic stress tolerance" and "abiotic stress tolerant" refer to a plant's ability to endure and/or thrive under abiotic stress conditions. When used in reference to a plant part, the terms refer to the ability of a plant that arises from that plant part to endure and/or thrive under abiotic stress conditions.

A characteristic is "associated with" a trait when it is linked to it and when the presence of the characteristic is an indicator of whether and/or to what extent the desired trait or trait form will occur in a plant/plant part comprising the characteristic. Similarly, a characteristic is "associated with" an allele when it is linked to it and when the presence of the characteristic is an indicator of whether the allele is present in a plant/plant part comprising the characteristic. For example, "a characteristic associated with enhanced drought tolerance" refers to a characteristic whose presence or absence can be used to predict whether and/or to what extent a plant will display a drought tolerant phenotype.

As used herein, the terms "backcross" and "backcrossing" refer to the process whereby a progeny plant is repeatedly crossed back to one of its parents. In a backcrossing scheme, the "donor" parent refers to the parental plant with the desired allele or locus to be introgressed. The "recipient" parent (used one or more times) or "recurrent" parent (used two or more times) refers to the parental plant into which the gene or locus is being introgressed. The initial cross gives rise to the F1 generation. The term "BC1" refers to the second use of the recurrent parent, "BC2" refers to the third use of the recurrent parent, and so on.

As used herein, the transitional phrase "consisting essentially of" is to be interpreted as encompassing the recited materials or steps and those that do not materially affect the basic and novel characteristic(s) of the claimed invention.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other cultivars/varieties within the same species.

As used herein, the terms "decrease," "decreases," "decreasing" and similar terms refer to a reduction of at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5% or more. In some embodiments, the reduction results in no or essentially no activity (i.e., an insignificant or undetectable amount of activity).

As used herein, the terms "drought tolerance" and "drought tolerant" refer to a plant's ability to endure and/or thrive under drought stress conditions. When used in reference to a plant part, the terms refer to the ability of a plant that arises from that plant part to endure and/or thrive under drought conditions. In general, a plant or plant part is designated as "drought tolerant" if it displays "enhanced drought tolerance."

As used herein, the term "COBL4 protein" refers to a protein belonging to the COBRA family, such as *Oryza sativa* ssp *japonica* cv. IRAT109 COBRA-like 4 protein (OsCOBL4$_{IRAT109}$), *Oryza sativa* ssp *japonica* cv. Nipponbare COBRA-like 4 protein (OsCOBL4$_{Nipponbare}$) and homologues thereof. Examples of COBL4 proteins include, but are not limited to, proteins having the amino acid sequence of any one of SEQ ID NOs: 28-35 and proteins having an amino acid sequence that is at least about 70%, 75%, 80%, 85%, 90%, 91%, 92%, 93%, 94%, 95%, 96%, 97%, 98%, 99%, 99.5% or more identical to the amino acid sequence of any one of SEQ ID NOs: 28-35. In some embodiments, the COBL4 protein comprises an N-terminal signal peptide that is at least about 90%, 91%, 92%, 93%, 94%, 95%, 96%, 97%, 98%, 99%, 99.5% or more identical to amino acids 1 to 27 of SEQ ID NO: 28-35 and/or a CVS domain that is at least about 90%, 91%, 92%, 93%, 94%, 95%, 96%, 97%, 98%, 99%, 99.5% or more identical to amino acids 226 to 229 of SEQ ID NO: 28-35. In some embodiments, the COBL4 protein is encoded by a nucleic acid comprising a nucleotide sequence that is at least 90%, 91%, 92%, 93%, 94%, 95%, 96%, 97%, 98%, 99%, 99.5% or more identical to any one of SEQ ID NOs: 1-13.

As used herein, the term "ERF62 protein" refers to an AP2 domain-containing protein, such as *Oryza sativa* ssp *japonica* cv. IRAT109 ERF62 (OsERF62-IRAT109), *Oryza sativa* ssp *japonica* cv. IRAT109 Japonica Group ERF71 (OsERF71-IRAT109; Rice Genome Annotation Project Accession No. LOC_Os06g09390.1) and homologues thereof. Examples of ERF62 proteins include, but are not limited to, proteins having the amino acid sequence of any one of SEQ ID NOs: 36-44 and proteins having an amino acid sequence that is at least about 70%, 75%, 80%, 85%, 90%, 91%, 92%, 93%, 94%, 95%, 96%, 97%, 98%, 99%, 99.5% or more identical to the amino acid sequence of any one of SEQ ID NOs: 36-44. In some embodiments, the ERF62 protein comprises an AP2 domain that is at least about 90%, 91%, 92%, 93%, 94%, 95%, 96%, 97%, 98%, 99%, 99.5% or more identical to amino acids 95 to 167 of SEQ ID NO: 36-44 and/or an N-terminal MCGGAI(L/I) motif that is at least about 90%, 91%, 92%, 93%, 94%, 95%, 96%, 97%, 98%, 99%, 99.5% or more identical to amino acids 1 to 7 of SEQ ID NO: 36-44. In some embodiments, the ERF62 protein is encoded by a nucleic acid comprising a nucleotide sequence that is at least 90%, 91%, 92%, 93%, 94%, 95%, 96%, 97%, 98%, 99%, 99.5% or more identical to any one of SEQ ID NOs: 14-27.

As used herein, the term "enhanced abiotic stress tolerance" refers to an improvement in the ability of a plant or plant part to grow, reproduce and/or survive under abiotic stress conditions, as compared to one or more controls (e.g., a native plant/plant part of the same species). "Enhanced abiotic stress tolerance" may refer to any improvement in a plant's or plant part's ability to thrive and/or endure when grown under abiotic stress conditions, including, but not limited to, decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield (e.g., increased biomass, increased seed yield, increased grain moisture at harvest (GMSTP), increased grain weight per plot (GWTPN), increased percent yield recovery (PYREC), decreased yield reduction (YRED), and/or decreased percent barren (PB)) when grown under abiotic stress conditions. A plant or plant part that exhibits enhanced abiotic stress tolerance may be designated as "abiotic stress tolerant."

As used herein, the term "enhanced drought tolerance" refers to an improvement in one or more water optimization traits as compared to one or more controls (e.g., a native plant/plant part of the same species). A plant or plant part that exhibits decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield (e.g., increased biomass, increased seed yield, increased YGSMN, increased GMSTP, increased GWTPN, increased PYREC, decreased YRED, and/or decreased PB) as compared to a control plant (e.g., one or both of its parents) when each is grown under the same drought stress conditions displays enhanced drought tolerance and may be designated as "drought tolerant." In some embodiments, the plant or plant part exhibits an increased survival rate after being subjected to PED-simulated drought stress conditions (e.g., incubation in a 200 g/L PEG6000 solution).

As used herein, the term "enhanced osmotic stress tolerance" refers to an improvement in one or more osmotic pressure optimization traits as compared to one or more controls (e.g., a native plant/plant part of the same species). A plant or plant part that exhibits decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield (e.g., increased biomass, increased seed yield, increased YGSMN, increased GMSTP, increased GWTPN, increased PYREC, decreased YRED, and/or decreased PB) as compared to a control plant (e.g., one or both of its parents) when each is grown under the same osmotic stress conditions displays enhanced osmotic stress tolerance and may be designated as "osmotic stress tolerant." In some embodiments, the plant or plant part exhibits an increased survival rate after being subjected to mannitol-induced osmotic stress conditions. (e.g., incubation in a 200 mM mannitol solution).

As used herein, the term "enhanced salt stress tolerance" refers to an improvement in one or more salt optimization traits as compared to one or more controls (e.g., a native plant/plant part of the same species). A plant or plant part that exhibits decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield (e.g., increased biomass, increased seed yield, increased YGSMN, increased GMSTP, increased GWTPN, increased PYREC, decreased YRED, and/or decreased PB) as compared to a control plant (e.g., one or both of its parents) when each is grown under the same salt stress conditions displays enhanced salt stress tolerance and may be designated as "salt stress tolerant."

As used herein, the term "enhanced temperature stress tolerance" refers to an improvement in one or more temperature tolerance traits as compared to one or more controls (e.g., a native plant/plant part of the same species). A plant or plant part that exhibits decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased biomass, increased chlorophyll content, increased grain yield at standard moisture percentage (YGSMN), increased GMSTP, increased GWTPN, increased PYREC, decreased YRED, and/or decreased PB as compared to a control plant (e.g., one or both of its parents) when each is grown under the same temperature stress conditions displays enhanced temperature stress tolerance and may be designated as "temperature stress tolerant."

It is to be understood that "drought tolerant," "osmotic stress tolerant," "salt stress tolerant," and "temperature stress tolerant" plants and plant parts may also be referred to as a "abiotic stress tolerant" because drought stress, osmotic stress, salt stress and temperature stress are all abiotic stresses.

As used herein, with respect to nucleic acids, the term "exogenous" refers to a nucleic acid that is not in the natural genetic background of the cell/organism in which it resides. In some embodiments, the exogenous nucleic acid comprises one or more nucleic acid sequences that are not found in the natural genetic background of the cell/organism. In some embodiments, the exogenous nucleic acid comprises one or more additional copies of a nucleic acid that is endogenous to the cell/organism.

As used herein with respect to nucleotide sequences, the terms "express" and "expression" refer to transcription and/or translation of the sequences.

As used herein with respect to nucleic acids, the term "fragment" refers to a nucleic acid that is reduced in length relative to a reference nucleic acid and that comprises, consists essentially of and/or consists of a nucleotide sequence of contiguous nucleotides identical or almost identical (e.g., 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. In some embodiments, the nucleic acid fragment comprises, consists essentially of or consists of at least about 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, or more consecutive nucleotides. In some embodiments, the nucleic acid fragment comprises, consists essentially of or consists of less than about 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450 or 500 consecutive nucleotides.

As used herein with respect to polypeptides, the term "fragment" refers to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, or more consecutive amino acids. In some embodiments, the polypeptide fragment comprises, consists essentially of or consists of less than about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450 or 500 consecutive amino acids.

As used herein with respect to nucleic acids, the term "functional fragment" refers to nucleic acid that encodes a functional fragment of a polypeptide.

As used herein with respect to polypeptides, the term "functional fragment" refers to polypeptide fragment that retains at least about 20%, 25%, 30%, 35%, 40%, 45%, 50%, 55%, 60%, 65%, 70%, 75%, 80%, 85%, 90%, 95%, 96%, 97%, 98%, 99%, 99.5% or more of at least one biological activity of the full-length polypeptide (e.g., the ability to up- or down-regulate gene expression). In some embodiments, the functional fragment actually has a higher level of at least one biological activity of the full-length polypeptide.

As used herein, the term "germplasm" refers to genetic material of or from an individual plant, a group of plants (e.g., a plant line, variety or family), or a clone derived from a plant line, variety, species, or culture. The genetic material can be part of a cell, tissue or organism, or can be isolated from a cell, tissue or organism.

As used herein, the term "heterologous" refers to a nucleotide/polypeptide that originates from a foreign species, or, if from the same species, is substantially modified from its native form in composition and/or genomic locus by deliberate human intervention.

As used herein, the terms "increase," "increases," "increasing" and similar terms refer to an elevation of at least about 20%, 25%, 30%, 35%, 40%, 45%, 50%, 75%, 100%, 125%, 150%, 175%, 200%, 350%, 300%, 350%, 400%, 450%, 500% or more.

As used herein, the term "informative fragment" refers to a nucleotide sequence comprising a fragment of a larger nucleotide sequence, wherein the fragment allows for the identification of one or more alleles within the larger nucleotide sequence. For example, an informative fragment of the nucleotide sequence of SEQ ID NO: 1 comprises a fragment of the nucleotide sequence of SEQ ID NO: 1 and allows for the identification of one or more alleles located within the portion of the nucleotide sequence corresponding to that fragment of SEQ ID NO: 1.

As used herein with respect to nucleotides and polypeptides, the term "isolated" refers to a nucleotide or polypeptide that is substantially free of cellular material, viral material, culture medium (when produced by recombinant DNA techniques), or chemical precursors or other chemicals (when chemically synthesized). An "isolated fragment" is a fragment of a nucleotide or polypeptide that is not naturally occurring as a fragment and would not be found in the natural state. "Isolated" does not mean that the preparation is technically pure (homogeneous), but rather that it is sufficiently pure to provide the nucleotide or polypeptide in a form in which it can be used for the intended purpose. In certain embodiments, the composition comprising the nucleotide or polypeptide is at least about 50%, 55%, 60%, 65%, 70%, 75%, 80%, 85%, 90%, 95%, 96%, 97%, 98%, or 99% or more pure.

As used herein with respect to cells, the term "isolated" refers to a cell that is separated from other components with which it is normally associated in its natural state. For example, an isolated plant cell may be a plant cell in culture medium and/or a plant cell in a suitable carrier. "Isolated" does not mean that the preparation is technically pure (homogeneous), but rather that it is sufficiently pure to provide the cell in a form in which it can be used for the intended purpose. In certain embodiments, the composition comprising the cell is at least about 50%, 55%, 60%, 65%, 70%, 75%, 80%, 85%, 90%, 95%, 96%, 97%, 98%, or 99% or more pure.

As used herein with respect to nucleic acids, the term "nonfunctional fragment" refers to nucleic acid that encodes a nonfunctional fragment of a polypeptide.

As used herein with respect to polypeptides, the term "nonfunctional fragment" refers to polypeptide fragment that exhibits none or essentially none (i.e., less than about 10%, 9%, 8%, 7%, 6%, 5%, 4%, 3%, 2%, 1% or less) of the biological activities of the full-length polypeptide.

As used herein with respect to nucleic acids, proteins, plant cells, plant parts, plants, viruses and bacteria, the term "nonnaturally occurring" refers to a nucleic acids, proteins, plant parts, plants, viruses or bacteria that does not naturally exist in nature. In some embodiments, the nonnaturally occurring plant part, plant, virus or bacteria comprises one of more exogenous nucleotide sequences. For example, in some embodiments, the nonnaturally occurring plant part, plant, virus or bacteria comprises one or more nonnaturally occurring copies of a naturally occurring nucleotide sequence (i.e., extraneous copies of a gene that naturally occurs in that species). Nonnaturally occurring plants and plant parts may be produced by any suitable method, including, but not limited to, transforming a plant or plant part with an exogenous nucleic acid, transfecting a plant or plant part with an exogenous nucleic acid, and crossing a naturally occurring plant or plant part with a nonnaturally occurring plant or plant part. It is to be understood that all nucleic acids, proteins, plant parts, plants, viruses and bacteria provided by the present invention are nonnaturally occurring.

As used herein, the term "nucleic acid" refers to deoxyribonucleotide, ribonucleotide and deooxyribonucleotide-ribonucleotide polymers in either single- or double-stranded form and, unless otherwise limited, encompasses analogues having the essential nature of natural nucleotides in that they hybridize to single-stranded nucleic acids in a manner similar to naturally occurring nucleotides (e.g., peptide nucleic acids).

As used herein, the term "nucleotide" refers to a monomeric unit from which DNA or RNA polymers are constructed and which consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the terms "nucleotide sequence," "polynucleotide," "nucleic acid sequence," "nucleic acid molecule" and "nucleic acid fragment" refer to a polymer of RNA, DNA, or RNA and DNA that is single- or double-stranded, optionally containing synthetic, non-natural and/or altered nucleotide bases.

As used herein, the term "nucleotide sequence identity" refers to the presence of identical nucleotides at corresponding positions of two polynucleotides. Polynucleotides have "identical" sequences if the sequence of nucleotides in the two polynucleotides is the same when aligned for maximum correspondence (e.g., in a comparison window). Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence identity" for polynucleotides, such as about 50, 55, 60, 65, 70, 75, 80, 85, 90, 95, 98, 99 or 100 percent sequence identity, can be determined by comparing two optimally aligned sequences over a comparison window, wherein the portion of the polynucleotide sequence in the comparison window can include additions or deletions (i.e., gaps) as compared to the reference sequence for optimal alignment of the two sequences. The percentage is calculated by: (a) determining the number of positions at which the identical nucleic acid base occurs in both sequences; (b) dividing the number of matched positions by the total number of positions in the window of comparison; and (c) multiplying the result by 100. Optimal alignment of sequences for comparison can also be conducted by computerized implementations of known algorithms, or by visual inspection. Readily available sequence comparison and multiple sequence alignment algorithms are, respectively, the Basic Local Alignment Search Tool (BLAST) and ClustalW programs, both available on the internet. Other suitable programs include, but are not limited to, GAP, BestFit, Plot Similarity, and FASTA, which are part of the Accelrys GCG Package available from Accelrys, Inc. of San Diego, Calif., United States of America. In some embodiments, a percentage of sequence identity refers to sequence identity over the full length of one of the sequences being compared. In some embodiments, a calculation to determine a percentage of sequence identity does not include in the calculation any nucleotide positions in which either of the compared nucleic acids includes an "N" (i.e., where any nucleotide could be present at that position).

As used herein with respect to nucleic acids, the term "operably linked" refers to a functional linkage between two or more nucleic acids. For example, a promoter sequence may be described as being "operably linked" to a heterologous nucleic acid sequence because the promoter sequences initiates and/or mediates transcription of the heterologous nucleic acid sequence. In some embodiments, the operably linked nucleic acid sequences are contiguous and/or are in the same reading frame.

As used herein, the term "osmotic pressure optimization trait" refers to any trait that can be shown to influence the growth, yield and/or survival of a plant under different sets of growth conditions related to osmotic pressure.

As used herein, the terms "osmotic stress tolerance" and "osmotic stress tolerant" refer to a plant's ability to endure and/or thrive under osmotic stress conditions. When used in reference to a plant part, the terms refer to the ability of a plant that arises from that plant part to endure and/or thrive under osmotic stress conditions. In general, a plant or plant part is designated as "osmotic stress tolerant" if it displays "enhanced osmotic stress tolerance."

As used herein, the term "percent barren" (PB) refers to the percentage of plants in a given area (e.g., plot) with no grain. It is typically expressed in terms of the percentage of plants per plot and can be calculated as:

$$\frac{\text{number of plants in the plot with no grain}}{\text{total number of plants in the plot}} \times 100$$

As used herein, the term "percent yield recovery" (PYREC) refers to the effect an allele and/or combination of alleles has on the yield of a plant grown under stress conditions (e.g., drought stress conditions) as compared to that of a plant that is genetically identical except insofar as it lacks the allele and/or combination of alleles. PYREC is calculated as:

$$1 - \frac{\text{yield under non-stress (w/ allele(s) of interest)} - \text{yield under stress conditions (w/ allele(s) of interest)}}{\text{yield under non-stress (w/out allele(s) of interest)} - \text{yield under stress conditions (w/out allele(s) of interest)}} \times 100$$

By way of example and not limitation, if a control plant yields 200 bushels under full irrigation conditions, but yields only 100 bushels under drought stress conditions, then its percentage yield loss would be calculated at 50%. If an otherwise genetically identical hybrid that contains the allele(s) of interest yields 125 bushels under drought stress conditions and 200 bushels under full irrigation conditions, then the percentage yield loss would be calculated as 37.5% and the PYREC would be calculated as 25% [1.00−(200−125)/(200−100)×100)].

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait." In other cases, a phenotype is the result of several genes. It is noted that, as used herein, the term "water optimization phenotype" takes into account environmental conditions that might affect water optimization such that the water optimization effect is real and reproducible.

As used herein, the term "plant" may refer to any suitable plant, including, but not limited to, spermatophytes (e.g., angiosperms and gymnosperms) and embryophytes (e.g., bryophytes, ferns and fern allies). In some embodiments, the plant is a monocotyledonous (monocot) plant such as a rice, maize, wheat, barley, sorghum, millet, oat, triticale, rye, buckwheat, fonio, quinoa, sugar cane, bamboo, banana, ginger, onion, lily, daffodil, iris, amaryllis, orchid, canna, bluebell, tulip, garlic, secale, einkorn, spelt, emmer, durum, kamut, grass (e.g., gramma grass), teff, milo, flax, *Tripsacum* sp., or teosinte plant. In some embodiments, the plant is a dicotyledonous (dicot) plant such as a blackberry, raspberry, strawberry, barberry, bearberry, blueberry, coffee berry, cranberry, crowberry, currant, elderberry, gooseberry, goji berry, honeyberry, lemon, lime, lingonberry, mangosteen, orange, pepper, persimmon, pomegranate, prune, cotton, clover, acai, plum, peach, nectarin, cherry, guava, almond, pecan, walnut, amaranth, apple, sweet pea, pear, potato, soybean, sugar beet, sunflower, sweet potato, tamarind, tea, tobacco or tomato plant.

As used herein, the term "plant cell" refers to a cell existing in, taken from and/or derived from a plant (e.g., a cell derived from a plant cell/tissue culture). Thus, the term "plant cell" may refer to an isolated plant cell, a plant cell in a culture, a plant cell in an isolated tissue/organ and/or a plant cell in a whole plant.

As used herein, the term "plant part" refers to at least a fragment of a whole plant or to a cell culture or tissue culture derived from a plant. Thus, the term "plant part" may refer to plant cells, plant tissues and plant organs, as well as cell/tissue cultures derived from plant cells, plant tissues and plant cultures. Embodiments of the present invention may comprise and/or make use of any suitable plant part, including, but not limited to, anthers, branches, buds, calli, clumps, cobs, cotyledons, ears, embryos, filaments, flowers, fruits, husks, kernels, leaves, lodicules, ovaries, palea, panicles, pedicels, pods, pollen, protoplasts, roots, root tips, seeds, silks, stalks, stems, stigma, styles, and tassels. In some embodiments, the plant part is a plant germplasm.

As used herein, the term "polynucleotide" refers to a deoxyribopolynucleotide, ribopolynucleotide or analogs thereof that have the essential nature of a natural deoxyribopolynucleotide/ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

As used herein, the terms "polypeptide," "peptide" and "protein" refer to a polymer of amino acid residues. The terms encompass amino acid polymers in which one or more amino acid residue is an artificial chemical analogue of a corresponding naturally occurring amino acid, as well as to naturally occurring amino acid polymers.

As used herein, the terms "progeny" and "progeny plant" refer to a plant generated from a vegetative or sexual reproduction from one or more parent plants. A progeny plant may be obtained by cloning or selfing a single parent plant, or by crossing two parental plants.

As used herein, the terms "promoter" and "promoter sequence" refer to nucleic acid sequences involved in the regulation of transcription initiation. A "plant promoter" is a promoter capable of initiating transcription in plant cells. Exemplary plant promoters include, but are not limited to, those that are obtained from plants, plant viruses and bacteria that comprise genes expressed in plant cells such *Agrobacterium* or *Rhizobium*. A "tissue-specific promoter" is a promoter that preferentially initiates transcription in a certain tissues. A "stress-inducible promoter" is a promoter that preferentially initiates transcription under certain environmental conditions. A "developmental stage-specific promoter" is a promoter that preferentially initiates transcription during certain developmental stages.

As used herein, the term "salt optimization trait" refers to any trait that can be shown to influence the growth, yield and/or survival of a plant under different sets of growth conditions related to salt availability.

As used herein, the terms "salt stress tolerance" and "salt stress tolerant" refer to a plant's ability to endure and/or thrive under salt stress conditions (i.e., low salt concentrations and/or high salt concentrations). When used in reference to a plant part, the terms refer to the ability of a plant that arises from that plant part to endure and/or thrive under salt stress conditions. In general, a plant or plant part is designated as "salt stress tolerant" if it displays "enhanced salt stress tolerance."

As used herein, the terms "selectively hybridize" and "specifically hybridize" refer to the hybridization of a nucleic acid sequence to a specified nucleic acid target sequence, wherein the nucleic acid sequence preferentially hybridizes to the specified nucleic acid target sequence (e.g., at least about a two-fold difference as compared to its hybridization with non-target nucleic acid sequences) to the substantial exclusion of non-target nucleic acids.

As used herein, the term "stringent hybridization conditions" refers to conditions under which a nucleic acid will selectively hybridize to a target nucleic acid sequence. In some embodiments, stringent hybridization conditions comprise 7% sodium dodecyl sulfate (SDS), 0.5 M $Na_3PO_4$, 1 mM EDTA at 50° C. with washing in 2×SSC, 0.1% SDS at 50° C. In some embodiments, stringent hybridization conditions comprise 7% SDS, 0.5 M $Na_3PO_4$, 1 mM EDTA at 50° C. with washing in 1×SSC, 0.1% SDS at 50° C. In some embodiments, stringent hybridization conditions comprise 7% SDS, 0.5 M $Na_3PO_4$, 1 mM EDTA at 50° C. with washing in 0.5×SSC, 0.1% SDS at 50° C. In some embodiments, stringent hybridization conditions comprise 7% SDS, 0.5 M $Na_3PO_4$, 1 mM EDTA at 50° C. with washing in 0.1×SSC, 0.1% SDS at 50° C. In some embodiments, stringent hybridization conditions comprise 7% SDS, 0.5 M $Na_3PO_4$, 1 mM EDTA at 50° C. with washing in 0.1×SSC, 0.1% SDS at 65° C. In some embodiments, stringent hybridization conditions comprise 6×SSC, 0.5% SDS at 65° C. with washing in 2×SSC, 0.1% SDS and 1×SSC, 0.1% SDS at 65° C. In some embodiments, stringent hybridization conditions comprise a wash stringency of 50% formamide with 5×Denhardt's solution, 0.5% SDS and 1×SSPE at 42° C.

As used herein, the terms "temperature stress tolerance" and "temperature stress tolerant" refer to a plant's ability to endure and/or thrive under temperature stress conditions (i.e., low temperature conditions and/or high temperature conditions). When used in reference to a plant part, the terms refer to the ability of a plant that arises from that plant part to endure and/or thrive under temperature stress conditions. In general, a plant or plant part is designated as "temperature stress tolerant" if it displays "enhanced temperature stress tolerance."

As used herein, the term "temperature tolerance trait" refers to any trait that can be shown to influence the growth, yield and/or survival of a plant under different sets of growth conditions related to temperature.

As used herein, the terms "transfection" and "transduction" refer to the uptake of an exogenous nucleic acid (RNA and/or DNA) by a plant cell. A cell has been "transfected" or "transduced" with an exogenous nucleic acid when such nucleic acid has been introduced or delivered into the cell. A cell has been "transformed" by an exogenous nucleic acid when the transfected or transduced nucleic acid imparts a phenotypic change to the cell and/or a change in an activity or function of the cell. The transforming nucleic acid can be integrated (covalently linked) into chromosomal DNA making up the genome of the cell or it can be present as a stable plasmid.

As used herein with respect to plants and plant parts, the term "transgenic" refers to a plant or plant part that comprises one or more exogenous nucleic acids. Generally, the exogenous nucleic acid is stably integrated within the genome such that the polynucleotide is passed on to successive generations. The exogenous nucleic acid may be integrated into the genome alone or as part of a recombinant expression cassette. "Transgenic" may be used to designate any plant or plant part the genotype of which has been altered by the presence of an exogenous nucleic acid, including those transgenics initially so altered and those created by sexual crosses or asexual propagation from the initial transgenic. As used herein, the term "transgenic" does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, the term "vector" refers to a nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo (i.e., is capable of replication under its own control). The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes). Vectors may be introduced into cells by any suitable method known in the art, including, but not limited to, transfection, electroporation, microinjection, transduction, cell fusion, DEAE dextran, calcium phosphate precipitation, lipofection (lysosome fusion), and use of a gene gun or nucleic acid vector transporter.

As used herein, the term "water optimization trait" refers to any trait that can be shown to influence the yield of a plant under different sets of growth conditions related to water availability.

As used herein, the term "yield reduction" (YD) refers to the degree to which yield is reduced in plants grown under stress conditions. YD is calculated as:

$$\frac{\text{yield under non-stress conditions} - \text{yield under stress conditions}}{\text{yield under non-stress conditions}} \times 100$$

The present invention provides nonnaturally occurring nucleic acids useful for enhancing abiotic stress tolerance (e.g., drought stress tolerance, osmotic stress tolerance, salt stress tolerance and/or temperature stress tolerance) in a plant or plant part.

Nucleic acids of the present invention may comprise any nucleotide sequence(s) the expression of which increases the expression and/or activity of one or more COBL4 proteins and/or ERF62 proteins in a plant or plant part, thereby enhancing the abiotic stress tolerance of the plant or plant part.

Nucleic acids of the present invention may comprise, consist essentially of or consist of a nucleotide sequence that encodes one or more COBL4 proteins and/or one or more ERF62 proteins. For example, in some embodiments, the nucleic acid comprises, consists essentially of or consists of a nucleotide sequence that encodes one or more of SEQ ID NOs: 28-44 (e.g., the nucleotide sequence of any one of SEQ ID NOs: 1-27. In some embodiments, each COBL4 protein encoded by the nucleotide sequence has an amino acid sequence that is at least about 70%, 75%, 80%, 85%, 90%, 91%, 92%, 93%, 94%, 95%, 96%, 97%, 98%, 99% 99.5% or more identical to the amino acid sequence of one or more of SEQ ID NOs: 1-13. In some embodiments, each ERF62 protein encoded by the nucleotide sequence has an amino acid sequence that is at least about 70%, 75%, 80%, 85%, 90%, 91%, 92%, 93%, 94%, 95%, 96%, 97%, 98%, 99% 99.5% or more identical to the amino acid sequence of one or more of SEQ ID NOs: 14-27.

Nucleic acids of the present invention may comprise, consist essentially of or consist of:
  (a) one or more of the nucleotide sequences set forth in SEQ ID NOs: 1-27;
  (b) one or more nucleotide sequences that is at least about 70%, 75%, 80%, 85%, 90%, 91%, 92%, 93%, 94%, 95%, 96%, 97%, 98%, 99%, 99.5% or more identical to one or more of the nucleotide sequences set forth in SEQ ID NOs: 1-27;

(c) one or more nucleotide sequences that encodes a polypeptide comprising, consisting essentially of or consisting of the amino acid sequence set forth in any one of SEQ ID NOs: 28-44;

(d) one or more nucleotide sequences that encodes a polypeptide comprising, consisting essentially of or consisting of an amino acid sequence that is at least about 70%, 75%, 80%, 85%, 90%, 91%, 92%, 93%, 94%, 95%, 96%, 97%, 98%, 99%, 99.5% or more identical to one or more of the amino acid sequences set forth in SEQ ID NOs: 28-44;

(e) a nucleotide sequence that is complementary to any one of the nucleotide sequences described in (a) to (d) above;

(f) a nucleotide sequence that hybridizes to any one of the nucleotide sequences described in (a) to (e) above under stringent hybridization conditions;

(g) a functional fragment of any one of the nucleotide sequences described in (a) to (f) above, wherein the functional fragment encodes a polypeptide that comprises an N-terminal signal peptide sequence that is at least about 70%, 75%, 80%, 85%, 90%, 91%, 92%, 93%, 94%, 95%, 96%, 97%, 98%, 99%, 99.5% or more identical to amino acids 1 to 27 of SEQ ID NO: 28 and a CCVS domain that is at least about 70%, 75%, 80%, 85%, 90%, 91%, 92%, 93%, 94%, 95%, 96%, 97%, 98%, 99%, 99.5% or more identical to amino acids 226 to 229 of SEQ ID NO: 28; and/or (h) a functional fragment of any one of the nucleotide sequences described in (a) to (f) above, wherein the functional fragment encodes a polypeptide that comprises an AP2 domain that is at least about 70%, 75%, 80%, 85%, 90%, 91%, 92%, 93%, 94%, 95%, 96%, 97%, 98%, 99%, 99.5% or more identical to amino acids 110 to 167 of SEQ ID NO: 36.

Nucleic acids of the present invention may comprise any suitable promoter sequence(s), including, but not limited to, constitutive promoters, tissue-specific promoters, stress-inducible promoters and developmental stage-specific promoters.

In some embodiments, the nucleic acid comprises one or more constitutive promoter sequences. For example, the nucleic acid may comprise one or more CaMV 19S, CaMV 35S, *Arabidopsis* At6669, maize H3 histone, rice actin, actin 2, rice cyclophilin, pEMU, GOS2, constitutive root tip CT2, and/or ubiquitin (e.g., maize Ubi) promoter sequences. Thus, in some embodiments, the nucleic acid comprises a nucleotide sequence encoding one or more COBL4 proteins and/or one or more ERF62 proteins operably linked to one or more constitutive promoter sequences.

In some embodiments, the nucleic acid comprises one or more tissue-specific promoter sequences. For example, the nucleic acid may comprise one or more leaf-, ligule-, node-, panicle-, root-, sheath-, stem-, and/or vascular bundle-specific promoter sequences. Thus, in some embodiments, the nucleic acid comprises a nucleotide sequence encoding one or more COBL4 proteins and/or one or more ERF62 proteins operably linked to one or more tissue-specific promoter sequences.

In some embodiments, the nucleic acid comprises one or more stress-inducible promoter sequences. For example, the nucleic acid may comprise one or more drought stress-inducible, salt stress-inducible, heat stress-inducible, light stress-inducible and/or osmotic stress-inducible promoter sequences. Thus, in some embodiments, the nucleic acid comprises a nucleotide sequence encoding one or more COBL4 proteins and/or one or more ERF62 proteins operably linked to one or more stress-inducible promoter sequences.

In some embodiments, the nucleic acid comprises one or more developmental stage-specific promoter sequences. For example, the nucleic acid may comprise a promoter sequence that drives expression prior to and/or during the seedling and/or reproductive stage(s) of development. Thus, in some embodiments, the nucleic acid comprises a nucleotide sequence encoding one or more COBL4 proteins and/or one or more ERF62 proteins operably linked to one or more developmental stage-specific promoter sequences.

In some embodiments, the nucleic acid comprises one or more termination sequences. For example, the nucleic acid may comprise a termination sequence comprising a stop signal for RNA polymerase and a polyadenylation signal for polyadenylase. Thus, in some embodiments, the nucleic acid comprises a nucleotide sequence encoding one or more COBL4 proteins and/or one or more ERF62 proteins operably linked to one or more termination sequences.

In some embodiments, the nucleic acid comprises codons specific for expression in plants.

In some embodiments, the nucleic acid is an isolated nucleotide.

Nucleic acids of the present invention may comprise any suitable transgene(s), including, but not limited to, transgenes that encode gene products that provide herbicide-resistance, pest-resistance and/or disease-resistance.

In some embodiments, the nucleic acid comprises one or more transgenes encoding a gene product that provides resistance to one or more herbicides. For example, the nucleic acid may comprise a transgene that encodes a gene product that provides glyphosate-, Sulfonylurea-, imidazolinione-, dicamba-, glufisinate-, phenoxy proprionic acid-, cycloshexome-, traizine-, benzonitrile-, and/or broxynil-resistance.

In some embodiments, the nucleic acid comprises one or more transgenes encoding a gene product that provides resistance to one or more pests. For example, the nucleic acid may comprise a transgene that encodes a gene product that provides bacterial-, fungal-, gastropod-, insect-, nematode-, oomycete-, phytoplasma-, protozoa-, and/or viral-resistance.

In some embodiments, the nucleic acid comprises one or more transgenes encoding a gene product that provides resistance to one or more diseases.

Nucleic acids of the present invention may encode any suitable epitope tag, including, but not limited to, poly-Arg tags (e.g., RRRRR (SEQ ID NO:45) and RRRRRR SEQ ID NO:46) and poly-His tags (e.g., HHHHHH (SEQ ID NO:47)). In some embodiments, the nucleic acid comprises a nucleotide sequence encoding a poly-Arg tag, a poly-His tag, a FLAG tag (i.e., DYKDDDDK (SEQ ID NO:48)), a Strep-tag II™ (GE Healthcare, Pittsburgh, Pa., USA) (i.e., WSHPQFEK (SEQ ID NO:49)), and/or a c-myc tag (i.e., EQKLISEEDL (SEQ ID NO:50)).

Nucleic acids of the present invention may comprise any suitable number of nucleotides. In some embodiments, the nucleic acid is 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000 or more nucleotides in length. In some embodiments, the nucleic acid is less than about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 nucleotides in length. In some embodiments, the nucleic acid is about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 nucleotides in length.

In some embodiments, the expression and/or activity of one or more COBL4 proteins and/or one or more ERF62 proteins in a plant or plant part expressing a nucleic acid of the present invention is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant (e.g., a native plant of the same species) grown under the same (or substantially the same) environmental conditions. For example, the expression and/or activity of OsCOBL4 may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more in a rice plant expressing a nucleic acid comprising any one of SEQ ID NOs: 1-13. Similarly, the expression and/or activity of OsERF62 may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more in a rice plant expressing a nucleic acid comprising any one of SEQ ID NOs: 14-27.

In some embodiments, the abiotic stress tolerance (e.g., drought stress tolerance, osmotic stress tolerance, salt stress tolerance and/or temperature stress tolerance) of a plant or plant part expressing a nucleic acid of the present invention is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part (e.g., a native plant of the same species) grown under the same (or substantially the same) environmental conditions. For example, the drought stress tolerance of a plant or plant part expressing any one of SEQ ID NOs: 1-27 may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part grown under the same (or substantially the same) drought stress conditions.

Plants and plant parts expressing nucleic acids of the present invention may exhibit a variety of abiotic stress tolerant phenotypes, including, but not limited to, decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield (e.g., increased biomass, increased seed yield, increased grain yield at standard moisture percentage (YGSMN), increased grain moisture at harvest (GMSTP), increased grain weight per plot (GWTPN), increased percent yield recovery (PYREC), decreased yield reduction (YRED), and/or decreased percent barren (PB)) when grown under abiotic stress conditions (e.g., drought stress conditions, osmotic stress conditions, salt stress conditions and/or temperature stress conditions). In some embodiments, one or more abiotic stress tolerant phenotypes is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300%, or more as compared to a control plant or plant part (e.g., a native plant of the same species) when each is grown under the same (or substantially the same) environmental conditions.

In some embodiments, the yield (e.g., seed yield, biomass, GWTPN, PYREC and/or YGSMN) of a plant or plant part expressing a nucleic acid of the present invention is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part (e.g., a native plant of the same species) grown under the same (or substantially the same) environmental conditions. For example, the seed yield and/or biomass of a plant or plant part expressing any one of SEQ ID NOs: 1-27 may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part grown under the same (or substantially the same) drought stress conditions.

In some embodiments, the accumulation of dehydrins and/or late embryogenesis abundant proteins, survival rate, growth potential, height, chlorophyll content and/or GMSTP of a plant or plant part expressing a nucleic acid of the present invention is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part (e.g., a native plant of the same species) grown under the same (or substantially the same) environmental conditions. For example, the survival rate and/or chlorophyll content of a plant or plant part expressing any one of SEQ ID NOs: 1-27 may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part grown under the same (or substantially the same) drought stress conditions.

In some embodiments, the water loss, accumulation of reactive oxygen species, accumulation of salts, YRED, and/or PB of a plant or plant part expressing a nucleic acid of the present invention is decreased by at least about 5%, 10%, 15%, 20%, 25%, 30%, 35%, 40%, 45%, 50%, 55%, 60%, 65%, 75%, 80%, 85%, 90%, 95%, 96%, 97%, 98%, 99%, 99.5% or more as compared to a control plant or plant part (e.g., a native plant of the same species) grown under the same (or substantially the same) environmental conditions. For example, the YRED and/or PB of a plant expressing any one of SEQ ID NOs: 1-27 may be decreased by at least about 5%, 10%, 15%, 20%, 25%, 30%, 35%, 40%, 45%, 50%, 55%, 60%, 65%, 75%, 80%, 85%, 90%, 95%, 96%, 97%, 98%, 99%, 99.5% or more as compared to a control plant grown under the same (or substantially the same) drought stress conditions.

In some embodiments, the root architecture and/or osmotic pressure regulation of a plant or plant part expressing a nucleic acid of the present invention is improved as compared to a control plant or plant part (e.g., a native plant of the same species) grown under the same (or substantially the same) environmental conditions. For example, the root architecture and/or osmotic pressure regulation of a plant or plant part expressing any one of SEQ ID NOs: 1-27 may be improved as compared to a control plant or plant part grown under the same (or substantially the same) drought stress conditions.

The present invention also provides expression cassettes comprising one or more nucleic acids of the present invention. In some embodiments, the expression cassette comprises a nucleic acid encoding a nucleic acid that confers at least one property (e.g., resistance to a selection agent) that can be used to detect, identify or select transformed plant cells and tissues.

The present invention also provides vectors comprising one or more nucleic acids and/or expression cassettes of the present invention. In some embodiments, the vector is a pROKI, pBin438, pCAMBIA (e.g., pCAMBIA1302, pCAMBIA2301, pCAMBIA1301, pCAMBIA1391-Xa, pCAMBIA1391-Xb) (CAMBIA Co., Brisbane, Australia) or pBI121 vector.

The present invention also provides recombinant viruses and recombinant bacteria comprising one or more nucleic acids, expression cassettes and/or vectors of the present invention.

The present invention also provides nonnaturally occurring proteins useful for enhancing abiotic stress tolerance (e.g., drought stress tolerance, osmotic stress tolerance, salt stress tolerance and/or temperature stress tolerance) in a plant or plant part.

Proteins of the present invention may comprise any amino acid sequence the expression of which enhances the abiotic stress tolerance of a plant or plant part. In some embodiments, the protein comprises, consists essentially of or consists of an amino acid sequence that is at least about 70%, 75%, 80%, 85%, 90%, 91%, 92%, 93%, 94%, 95%, 96%, 97%, 98%, 99% 99.5% or more identical to the amino acid sequence of one or more of SEQ ID NOs: 28-44. In some embodiments, the protein comprises a functional fragment of a COBL4 protein (e.g., a functional fragment of any one of SEQ ID NOs: 28-35) and, optionally, comprises an N-terminal signal peptide sequence that is at least about 70%, 75%, 80%, 85%, 90%, 91%, 92%, 93%, 94%, 95%, 96%, 97%, 98%, 99%, 99.5% or more identical to amino acids XXX to YYY of SEQ ID NO: 28-35 and/or a CCVS domain that is at least about 70%, 75%, 80%, 85%, 90%, 91%, 92%, 93%, 94%, 95%, 96%, 97%, 98%, 99%, 99.5% or more identical to amino acids XXX to YYY of SEQ ID NO: 28-35. In some embodiments, the protein comprises a functional fragment of a ERF62 protein (e.g., a functional fragment of any one of SEQ ID NOs: 36-44) and, optionally, comprises an AP2 domain that is at least about 70%, 75%, 80%, 85%, 90%, 91%, 92%, 93%, 94%, 95%, 96%, 97%, 98%, 99%, 99.5% or more identical to amino acids 110 to 167 of SEQ ID NO: 36-44

In some embodiments, the protein is an isolated protein.

Proteins of the present invention may comprise any suitable epitope tag, including, but not limited to, poly-Arg tags (e.g., RRRRR (SEQ ID NO:45) and RRRRRR SEQ ID NO:46) and poly-His tags (e.g., HHHHHH (SEQ ID NO:47)). In some embodiments, the nucleic acid comprises a nucleotide sequence encoding a poly-Arg tag, a poly-His tag, a FLAG tag (i.e., DYKDDDDK (SEQ ID NO:48)), a Strep-tag II™ (GE Healthcare, Pittsburgh, Pa., USA) (i.e., WSHPQFEK (SEQ ID NO:49)), and/or a c-myc tag (i.e., EQKLISEEDL (SEQ ID NO:50)).

Proteins of the present invention may comprise any suitable number of amino acids. In some embodiments, the proteins is 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 450, 500 or more amino acids in length. In some embodiments, the protein is less than about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 450 or 500 amino acids in length. In some embodiments, the protein is about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 450 or 500 amino acids in length.

In some embodiments, the expression and/or activity of one or more COBL4 proteins and/or one or more ERF62 proteins in a plant or plant part expressing a protein of the present invention is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant (e.g., a native plant of the same species) grown under the same (or substantially the same) environmental conditions. For example, the expression and/or activity of OsCOBL4 may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more in a rice plant expressing a nucleic acid encoding any one of SEQ ID NOs: 28-35. Similarly, the expression and/or activity of OsEF62 may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more in a rice plant expressing a nucleic acid encoding any one of SEQ ID NOs: 36-44.

In some embodiments, the abiotic stress tolerance (e.g., drought stress tolerance, osmotic stress tolerance, salt stress tolerance and/or temperature stress tolerance) of a plant expressing a protein of the present invention is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant (e.g., a native plant of the same species) grown under the same (or substantially the same) environmental conditions. For example, the drought stress tolerance of a plant or plant part expressing any one of SEQ ID NOs: 28-44 may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant grown under the same (or substantially the same) drought stress conditions.

Plants and plant parts expressing proteins of the present invention may exhibit a variety of abiotic stress tolerant phenotypes, including, but not limited to, decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield (e.g., increased biomass, increased seed yield, increased grain yield at standard moisture percentage (YGSMN), increased grain moisture at harvest (GMSTP), increased grain weight per plot (GWTPN), increased percent yield recovery (PYREC), decreased yield reduction (YRED), and/or decreased percent barren (PB)) when grown under abiotic stress conditions (e.g., drought stress conditions, osmotic stress conditions, salt stress conditions and/or temperature stress conditions). In some embodiments, one or more abiotic stress tolerant phenotypes is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300%, or more as compared to a control plant or plant part (e.g., a native plant of the same species) when each is grown under the same (or substantially the same) environmental conditions.

In some embodiments, the yield (e.g., seed yield, biomass, GWTPN, PYREC and/or YGSMN) of a plant or plant part expressing a protein of the present invention is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part (e.g., a native plant of the same species) grown under the same (or substantially the same) environmental conditions. For example, the seed yield and/or biomass of a plant or plant part expressing any one of SEQ ID NOs: 28-44 may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part grown under the same (or substantially the same) drought stress conditions.

In some embodiments, the accumulation of dehydrins and/or late embryogenesis abundant proteins, survival rate, growth potential, height, chlorophyll content and/or GMSTP of a plant or plant part expressing a protein of the present invention is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part (e.g., a native plant of the same species) grown under the same (or substantially the same) environmental conditions. For example, the survival rate and/or chlorophyll content of a plant or plant part expressing any one of SEQ ID NOs: 28-44 may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part grown under the same (or substantially the same) drought stress conditions.

In some embodiments, the water loss, accumulation of reactive oxygen species, YRED, and/or PB of a plant or plant part expressing a protein of the present invention is decreased by at least about 5%, 10%, 15%, 20%, 25%, 30%, 35%, 40%, 45%, 50%, 55%, 60%, 65%, 75%, 80%, 85%, 90%, 95%, 96%, 97%, 98%, 99%, 99.5% or more as compared to a control plant or plant part (e.g., a native plant of the same species) grown under the same (or substantially the same) environmental conditions. For example, the YRED and/or PB of a plant expressing any one of SEQ ID NOs: 28-44 may be decreased by at least about 5%, 10%, 15%, 20%, 25%, 30%, 35%, 40%, 45%, 50%, 55%, 60%, 65%, 75%, 80%, 85%, 90%, 95%, 96%, 97%, 98%, 99%, 99.5% or more as compared to a control plant grown under the same (or substantially the same) drought stress conditions.

In some embodiments, the root architecture and/or osmotic pressure regulation of a plant or plant part expressing a protein of the present invention is improved as compared to a control plant (e.g., a native plant of the same species) grown under the same (or substantially the same) environmental conditions. For example, the root architecture and/or osmotic pressure regulation of a plant or plant part expressing any one of SEQ ID NOs: 28-44 may be improved as compared to a control plant or plant part grown under the same (or substantially the same) drought stress conditions.

The present invention extends to uses of nucleic acids, expression cassettes, vectors, recombinant viruses, recombinant bacteria and proteins of the present invention, including, but not limited to, uses for enhancing abiotic stress tolerance (e.g., drought stress tolerance, osmotic stress tolerance, salt stress tolerance and/or temperature stress tolerance) in a plant or plant part and uses for identifying, selecting and/or producing abiotic stress tolerant plants (e.g., drought stress tolerant, osmotic stress tolerant, salt stress tolerant and/or temperature stress tolerant plants and plant parts).

The present invention also provides nonnaturally occurring plants and plant parts having enhanced abiotic stress tolerance.

Plants and plant parts of the present invention may comprise any suitable exogenous nucleic acid(s). In some embodiments, the plant or plant part comprises at least one exogenous nucleic acid that encodes one or more proteins of the present invention and/or comprises, consists essentially of or consists of one or more nucleic acids of the present invention.

In some embodiments, the plant or plant part comprises within its genome an exogenous nucleic acid that comprises, consists essentially of or consists of:
- (a) one or more of the nucleotide sequences set forth in SEQ ID NOs: 1-27;
- (b) one or more nucleotide sequences that is at least about 70%, 75%, 80%, 85%, 90%, 91%, 92%, 93%, 94%, 95%, 96%, 97%, 98%, 99%, 99.5% or more identical to one or more of the nucleotide sequences set forth in SEQ ID NOs: 1-27;
- (c) one or more nucleotide sequences that encodes a polypeptide comprising, consisting essentially of or consisting of the amino acid sequence set forth in any one of SEQ ID NOs: 28-44;
- (d) one or more nucleotide sequences that encodes a polypeptide comprising, consisting essentially of or consisting of an amino acid sequence that is at least about 70%, 75%, 80%, 85%, 90%, 91%, 92%, 93%, 94%, 95%, 96%, 97%, 98%, 99%, 99.5% or more identical to one or more of the amino acid sequences set forth in SEQ ID NOs: 28-44;
- (e) a nucleotide sequence that is complementary to any one of the nucleotide sequences described in (a) to (d) above;
- (f) a nucleotide sequence that hybridizes to any one of the nucleotide sequences described in (a) to (e) above under stringent hybridization conditions;
- (g) a functional fragment of any one of the nucleotide sequences described in (a) to (f) above, wherein the functional fragment encodes a polypeptide that comprises an N-terminal signal peptide sequence that is at least about 70%, 75%, 80%, 85%, 90%, 91%, 92%, 93%, 94%, 95%, 96%, 97%, 98%, 99%, 99.5% or more identical to amino acids 1 to 27 of SEQ ID NO: 28 and a CCVS domain that is at least about 70%, 75%, 80%, 85%, 90%, 91%, 92%, 93%, 94%, 95%, 96%, 97%, 98%, 99%, 99.5% or more identical to amino acids 226 to 229 of SEQ ID NO: 28; and/or
- (h) a functional fragment of any one of the nucleotide sequences described in (a) to (f) above, wherein the functional fragment encodes a polypeptide that comprises an AP2 domain that is at least about 70%, 75%, 80%, 85%, 90%, 91%, 92%, 93%, 94%, 95%, 96%, 97%, 98%, 99%, 99.5% or more identical to amino acids 110 to 167 of SEQ ID NO: 36.

In some embodiments, the plant or plant part comprises an exogenous nucleic acid comprising one or more constitutive promoter sequences. For example, the plant or plant part may comprise an exogenous nucleic acid that comprises one or more CaMV 19S, CaMV 35S, *Arabidopsis* At6669, maize H3 histone, rice actin, actin 2, rice cyclophilin, pEMU, GOS2, constitutive root tip CT2, and/or ubiquitin (e.g., maize Ubi) promoter sequences. Thus, in some embodiments, the plant or plant part comprises an exogenous nucleic acid that comprises one or more of the nucleotide sequences described in (a) to (tt) above operably linked to one or more constitutive promoter sequences.

In some embodiments, the plant or plant part comprises an exogenous nucleic acid comprising one or more tissue-specific promoter sequences. For example, the plant or plant part may comprise an exogenous nucleic acid that comprises one or more leaf-, ligule-, node-, panicle-, root-, sheath-, stem-, and/or vascular bundle-specific promoter sequences. Thus, in some embodiments, the plant or plant part comprises an exogenous nucleic acid that comprises one or more of the nucleotide sequences described in (a) to (tt) above operably linked to one or more tissue-specific promoter sequences.

In some embodiments, the plant or plant part comprises an exogenous nucleic acid comprising one or more stress-inducible promoter sequences. For example, the plant or plant part may comprise an exogenous nucleic acid that comprises one or more drought stress-inducible, osmotic stress-inducible, salt-inducible, temperature stress-inducible, and/or light stress-inducible promoter sequences. Thus, in some embodiments, the plant or plant part comprises an exogenous nucleic acid that comprises one or more of the nucleotide sequences described in (a) to (tt) above operably linked to one or more stress-inducible promoter sequences.

In some embodiments, the plant or plant part comprises an exogenous nucleic acid comprising one or more developmental stage-specific promoter sequences. For example, the plant or plant part may comprise an exogenous nucleic acid that comprises a promoter sequence that drives expression prior to and/or during the seedling and/or reproductive stage(s) of development. Thus, in some embodiments, the nucleic acid comprises one or more of the nucleotide sequences described in (a) to (tt) above operably linked to one or more developmental stage-specific promoter sequences. In some embodiments, the plant or plant part comprises an exogenous nucleic acid comprising one or more termination sequences. For example, the plant or plant part may comprise an exogenous nucleic acid that comprises a termination sequence comprising a stop signal for RNA polymerase and a polyadenylation signal for polyadenylase. Thus, in some embodiments, the plant or plant part comprises an exogenous nucleic acid that comprises one or more of the nucleotide sequences describes in (a) to (tt) above operably linked to one or more termination sequences.

In some embodiments, plants and plant parts of the present invention exhibit increased expression and/or activity of one or more COBL4 proteins (e.g., increased microfirbil orientating activity), increased expression and/or activity of one or more ERF62 proteins (e.g., increased DNA binding activity).

In some embodiments, the plant or plant part expresses one or more COBL4 proteins (e.g., a COBL4 protein having an amino acid sequence that is at least about 70%, 75%, 80%, 85%, 90%, 91%, 92%, 93%, 94%, 95%, 96%, 97%, 98%, 99%, 99.5% or more identical to the amino acid sequence of one or more of SEQ ID NOs: 1-13) at an increased level as compared to a control plant or plant part (e.g., a native plant of the same species) when each is grown under the same (or substantially the same) environmental conditions. In some such embodiments, expression of the COBL4 protein(s) is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300%, or more as compared to the control plant.

In some embodiments, the plant or plant part expresses one or more ERF62 proteins (e.g., an ERF62 protein having an amino acid sequence that is at least about 70%, 75%, 80%, 85%, 90%, 91%, 92%, 93%, 94%, 95%, 96%, 97%, 98%, 99%, 99.5% or more identical to the amino acid sequence of one or more of SEQ ID NOs: 14-27) at an increased level as compared to a control plant or plant part (e.g., a native plant of the same species) when each is grown under the same (or substantially the same) environmental conditions. In some such embodiments, expression of the ERF62 protein(s) is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300%, or more as compared to the control plant.

Plants and plant parts of the present invention may exhibit a variety of abiotic stress tolerant phenotypes, including, but not limited to, decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield (e.g., increased biomass, increased seed yield, increased grain yield at standard moisture percentage (YGSMN), increased grain moisture at harvest (GMSTP), increased grain weight per plot (GWTPN), increased percent yield recovery (PYREC), decreased yield reduction (YRED), and/or decreased percent barren (PB)) when grown under abiotic stress conditions (e.g., drought stress conditions, osmotic stress conditions, salt stress conditions and/or temperature stress conditions). In some embodiments, one or more abiotic stress tolerant phenotypes is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300%, or more as compared to a control plant or plant part (e.g., a native plant of the same species) when each is grown under the same (or substantially the same) environmental conditions.

In some embodiments, the yield (e.g., seed yield, biomass, GWTPN, PYREC and/or YGSMN) of the plant or plant part is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part (e.g., a native plant of the same species) grown under the same (or substantially the same) environmental conditions. For example, the seed yield and/or biomass of the plant or plant part may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part grown under the same (or substantially the same) drought stress conditions.

In some embodiments, the accumulation of dehydrins and/or late embryogenesis abundant proteins, survival rate, growth potential, height, chlorophyll content and/or GMSTP of the plant or plant part is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part (e.g., a native plant of the same species) grown under the same (or substantially the same) environmental conditions. For example, the survival rate and/or chlorophyll content of the plant or plant part may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part grown under the same (or substantially the same) drought stress conditions.

In some embodiments, the water loss, accumulation of reactive oxygen species, YRED, and/or PB of the plant or plant part is decreased by at least about 5%, 10%, 15%, 20%, 25%, 30%, 35%, 40%, 45%, 50%, 55%, 60%, 65%, 75%, 80%, 85%, 90%, 95%, 96%, 97%, 98%, 99%, 99.5% or more as compared to a control plant or plant part (e.g., a native plant of the same species) grown under the same (or substantially the same) environmental conditions. For example, the YRED and/or PB of the plant may be decreased by at least about 5%, 10%, 15%, 20%, 25%, 30%, 35%, 40%, 45%, 50%, 55%, 60%, 65%, 75%, 80%, 85%, 90%, 95%, 96%, 97%, 98%, 99%, 99.5% or more as compared to a control plant grown under the same (or substantially the same) drought stress conditions.

In some embodiments, the root architecture and/or osmotic pressure regulation of the plant or plant part is improved as compared to a control plant (e.g., a native plant of the same species) grown under the same (or substantially the same) environmental conditions. For example, the root architecture and/or osmotic pressure regulation of the plant or plant part may be improved as compared to a control plant or plant part grown under the same (or substantially the same) drought stress conditions.

Plants and plant parts of the present invention may be of any suitable plant type, including, but not limited to, plants belonging to the superfamily Viridiplantae. In some embodiments the plant or plant part is a fodder crop, a food crop, an ornamental plant, a tree or a shrub. For example, in some embodiments, the plant or plant part is a variety of *Acer* spp., *Actinidia* spp., *Abelmoschus* spp., *Agropyron* spp., *Allium* spp., *Amaranthus* spp., *Ananas comosus*, *Annona* spp., *Apium graveolens*, *Arachis* spp, *Artocarpus* spp., *Asparagus officinalis*, *Avena* spp. (e.g. *Avena sativa*, *Avena fatua*, *Avena byzantina*, *Avena fatua* var. *sativa*, *Avena hybrida*), *Averrhoa carambola*, *Benincasa hispida*, *Bertholletia excelsea*, *Beta vulgaris*, *Brassica* spp. (e.g. *Brassica napus*, *Brassica rapa* ssp. [canola, oilseed rape, turnip rape]), *Cadaba farinosa*, *Camellia sinensis*, *Canna indica*, *Capsicum* spp., *Carex data*, *Carica papaya*, *Carissa macrocarpa*, *Carya* spp., *Carthamus tinctorius*, *Castanea* spp., *Cichorium endivia*, *Cinnamomum* spp., *Citrullus lanatus*, *Citrus* spp., *Cocos* spp., *Coffea* spp., *Colocasia esculenta*, *Cola* spp., *Coriandrum sativum*, *Corylus* spp., *Crataegus* spp., *Crocus sativus*, *Cucurbita* spp., *Cucumis* spp., *Cynara* spp., *Daucus carota*, *Desmodium* spp., *Dimocarpus longan*, *Dioscorea* spp., *Diospyros* spp., *Echinochloa* spp., *Elaeis* (e.g. *Elaeis guineensis*, *Elaeis oleifera*), *Eleusine coracana*, *Eriobotrya japonica*, *Eugenia uniflora*, *Fagopyrum* spp., *Fagus* spp., *Ficus carica*, *Fortunella* spp., *Fragaria* spp., *Ginkgo biloba*, *Glycine* spp. (e.g. *Glycine max*, *Soja hispida* or *Soja max*), *Gossypium hirsutum*, *Helianthus* spp. (e.g. *Helianthus annuus*), *Hemerocallis fulva*, *Hibiscus* spp., *Hordeum* spp. (e.g. *Hordeum vulgare*), *Ipomoea batatas*, *Juglans* spp., *Lactuca sativa*, *Lathyrus* spp., *Lens culinaris*, *Linum usitatissimum*, *Litchi chinensis*, *Lotus* spp., *Luffa acutangula*, *Lupinus* spp., *Luzula sylvatica*, *Lycopersicon* spp. (e.g. *Lycopersicon esculentum*, *Lycopersicon lycopersicum*, *Lycopersicon pyriforme*), *Macrotyloma* spp., *Malus* spp., *Malpighia emarginata*, *Mammea americana*, *Mangifera indica*, *Manihot* spp., *Manilkara zapota*, *Medicago sativa*, *Melilotus* spp., *Mentha* spp., *Miscanthus* spp., *Momordica* spp., *Morus nigra*, *Musa* spp., *Nicotiana* spp., *Olea* spp., *Opuntia* spp., *Ornithopus* spp., *Oryza* spp. (e.g. *Oryza sativa*, *Oryza latifolia*), *Panicum miliaceum*, *Passiflora edulis*, *Pastinaca sativa*, *Persea* spp., *Petroselinum crispum*, *Phaseolus* spp., *Phoenix* spp., *Physalis* spp., *Pinus* spp., *Pistacia vera*, *Pisum* spp., *Poa* spp., *Populus* spp., *Prosopis* spp., *Prunus* spp., *Psidium* spp., *Punica granatum*, *Pyrus communis*, *Quercus* spp., *Raphanus sativus*, *Rheum rhabarbarum*, *Ribes* spp., *Ricinus communis*, *Rubus* spp., *Saccharum* spp., *Sambucus* spp., *Secale cereale*, *Sesamum* spp., *Sinapis* sp., *Solanum* spp. (e.g. *Solanum tuberosum*, *Solanum integrifolium* or *Solanum lycopersicum*), *Sorghum bicolor*, *Spinacia* spp., *Syzygium* spp., *Tagetes* spp., *Tamarindus indica*, *Theobroma cacao*, *Trifolium* spp., *Triticosecale rimpaui*, *Triticum* spp. (e.g. *Triticum aestivum*, *Triticum durum*, *Triticum turgidum*, *Triticum hybernum*, *Triticum macha*, *Triticum sativum* or *Triticum vulgare*), *Tropaeolum minus*, *Tropaeolum majus*, *Vaccinium* spp., *Vicia* spp., *Vigna* spp., *Viola odorata*, *Vitis* spp., *Zea mays*, *Zizania palustris* or *Ziziphus* spp., amongst others. In some embodiments, the plant or plant part is a rice, maize, wheat, barley, sorghum, millet, oat, triticale, rye, buckwheat, fonio, quinoa, sugar cane, bamboo, banana, ginger, onion, lily, daffodil, iris, amaryllis, orchid, canna, bluebell, tulip, garlic, secale, einkorn, spelt, emmer, durum, kamut, grass (e.g., gramma grass), teff, milo, flax, *Tripsacum* sp., or teosinte plant or plant part. In some embodiments, the plant or plant part is a blackberry, raspberry, strawberry, barberry, bearberry, blueberry, coffee berry, cranberry, crowberry, currant, elderberry, gooseberry, goji berry, honeyberry, lemon, lime, lingonberry, mangosteen, orange, pepper, persimmon, pomegranate, prune, cotton, clover, acai, plum, peach, nectarin, cherry, guava, almond, pecan, walnut, apple, amaranth, sweet pea, pear, potato, soybean, sugar beet, sunflower, sweet potato, tamarind, tea, tobacco or tomato plant or plant part.

Plants and plant parts of the present invention may be produced using any suitable method, including, but not limited to, methods of the present invention.

The present invention extends to products harvested from plants and plant parts of the present invention, including, but not limited to, plant cells and harvestable plant parts such as seeds, leaves, fruits, flowers, stems, rhizomes, tubers and bulbs. In some embodiments, the harvested product is a plant cell (e.g., a embryo or ovule) or plant part capable of producing a plant or plant part having increased expression and/or activity of one or more COBL4 proteins, increased expression and/or activity of one or more ERF62 proteins, and/or enhanced abiotic stress tolerance (e.g., enhanced drought tolerance, enhanced osmotic stress tolerance, enhanced salt stress tolerance and/or enhanced temperature stress tolerance). In some embodiments, the harvested product is a plant cell (e.g., a embryo or ovule) or plant part capable of producing a plant or plant that exhibits decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield (e.g., increased biomass, increased seed yield, increased grain yield at standard moisture percentage (YGSMN), increased grain moisture at harvest (GMSTP), increased grain weight per plot (GWTPN), increased percent yield recovery (PYREC), decreased yield reduction (YRED), and/or decreased percent barren (PB)) when grown under abiotic stress conditions (e.g., drought stress conditions, osmotic stress conditions, salt stress conditions and/or temperature stress conditions).

The present invention also extends to products derived from harvestable plant parts, including, but not limited to, dry pellets and powders, oils, fats, fatty acids, starches and proteins.

The present invention also provides methods of enhancing abiotic stress tolerance (e.g., drought stress tolerance, osmotic stress tolerance, salt stress tolerance and/or temperature stress tolerance) in a plant or plant part.

Abiotic stress tolerance (e.g., drought stress tolerance, osmotic stress tolerance, salt stress tolerance and/or temperature stress tolerance) may be enhanced by increasing the expression and/or activity of one or more COBL4 proteins and/or by increasing the expression and/or activity of one or more ERF62 proteins. Thus, methods of enhancing abiotic stress tolerance in a plant or plant part may comprise, consist essentially of or consist of increasing the expression and/or activity of one or more COBL4 proteins and/or one or more ERF62 proteins in the plant or plant part.

The expression and/or activity of COBL4 proteins may be increased via any suitable method, including, but not limited to, overexpression of native COBL4 proteins, expression of exogenous COBL4 proteins, overexpression of one or more COBL4 precursors, down-regulation and/or inhibition of one or more COBL4 inhibitors, overexpression of one or more native enzymes involved in COBL4 synthesis and expression of one or more exogenous enzymes involved in COBL4 synthesis. In some embodiments, the expression and/or activity of one or more COBL4 proteins is increased by:
  (a) increasing the expression and/or activity of one or more native COBL4 proteins in the plant or plant part; and/or
  (b) increasing the expression and/or activity of one or more exogenous COBL4 proteins in the plant or plant part;
  (c) increasing the expression and/or activity of one or more COBL4 protein precursors in the plant or plant part;
  (d) decreasing the expression and/or activity of one or more COBL4 protein inhibitors in the plant or plant part;
  (e) increasing the expression and/or activity of one or more native enzymes involved in COBL4 protein synthesis in the plant or plant part; and/or
  (f) increasing the expression and/or activity of one or more exogenous enzymes involved in COBL4 protein synthesis in the plant or plant part.

In some embodiments of the present invention, the expression of one or more COBL4 proteins is increased by introducing an exogenous nucleic acid encoding the COBL4 protein(s) into the plant or plant part. For example, in some embodiments, an exogenous nucleic acid encoding one or more of SEQ ID NOs: 27-35 (e.g., an exogenous nucleic acid comprising one or more of SEQ ID NOs: 1-13) is introduced into the plant or plant part, thereby increasing expression of the COBL4 protein(s).

The expression and/or activity of ERF62 proteins may be increased via any suitable method, including, but not limited to, overexpression of native ERF62 proteins, expression of exogenous ERF62 proteins, overexpression of one or more ERF62 precursors, down-regulation and/or inhibition of one or more ERF62 inhibitors, overexpression of one or more native enzymes involved in ERF62 synthesis and expression of one or more exogenous enzymes involved in ERF62 synthesis. In some embodiments, the expression and/or activity of one or more ERF62 proteins is/are increased by:
  (a) increasing the expression and/or activity of one or more native ERF62 proteins in the plant or plant part; and/or
  (b) increasing the expression and/or activity of one or more exogenous ERF62 proteins in the plant or plant part;
  (c) increasing the expression and/or activity of one or more ERF62 protein precursors in the plant or plant part;
  (d) decreasing the expression and/or activity of one or more ERF62 protein inhibitors in the plant or plant part;
  (e) increasing the expression and/or activity of one or more native enzymes involved in ERF62 protein synthesis in the plant or plant part; and/or
  (f) increasing the expression and/or activity of one or more exogenous enzymes involved in ERF62 protein synthesis in the plant or plant part.

In some embodiments of the present invention, the expression of one or more ERF62 proteins is increased by introducing an exogenous nucleic acid encoding the ERF62 protein(s) into the plant or plant part. For example, in some embodiments, an exogenous nucleic acid encoding one or more of SEQ ID NOs: 36-44 (e.g., an exogenous nucleic acid comprising one or more of SEQ ID NOs: 14-27) is introduced into the plant or plant part, thereby increasing expression of the ERF62 protein(s).

Thus, in some embodiments, abiotic stress tolerance (e.g., drought stress tolerance, osmotic stress tolerance, salt stress tolerance and/or temperature stress tolerance) may be enhanced by introducing/expressing an exogenous nucleic acid comprising:
  (a) one or more of the nucleotide sequences set forth in SEQ ID NOs: 1-27;
  (b) one or more nucleotide sequences that is at least about 70%, 75%, 80%, 85%, 90%, 91%, 92%, 93%, 94%, 95%, 96%, 97%, 98%, 99%, 99.5% or more identical to one or more of the nucleotide sequences set forth in SEQ ID NOs: 1-27;
  (c) one or more nucleotide sequences that encodes a polypeptide comprising, consisting essentially of or consisting of the amino acid sequence set forth in any one of SEQ ID NOs: 28-44;
  (d) one or more nucleotide sequences that encodes a polypeptide comprising, consisting essentially of or consisting of an amino acid sequence that is at least about 70%, 75%, 80%, 85%, 90%, 91%, 92%, 93%, 94%, 95%, 96%, 97%, 98%, 99%, 99.5% or more identical to one or more of the amino acid sequences set forth in SEQ ID NOs: 28-44;
  (e) a nucleotide sequence that is complementary to any one of the nucleotide sequences described in (a) to (d) above;

(f) a nucleotide sequence that hybridizes to any one of the nucleotide sequences described in (a) to (e) above under stringent hybridization conditions;

(g) a functional fragment of any one of the nucleotide sequences described in (a) to (f) above, wherein the functional fragment encodes a polypeptide that comprises an N-terminal signal peptide sequence that is at least about 70%, 75%, 80%, 85%, 90%, 91%, 92%, 93%, 94%, 95%, 96%, 97%, 98%, 99%, 99.5% or more identical to amino acids 1 to 27 of SEQ ID NO: 28 and a CCVS domain that is at least about 70%, 75%, 80%, 85%, 90%, 91%, 92%, 93%, 94%, 95%, 96%, 97%, 98%, 99%, 99.5% or more identical to amino acids 226 to 229 of SEQ ID NO: 28; and/or (h) a functional fragment of any one of the nucleotide sequences described in (a) to (f) above, wherein the functional fragment encodes a polypeptide that comprises an AP2 domain that is at least about 70%, 75%, 80%, 85%, 90%, 91%, 92%, 93%, 94%, 95%, 96%, 97%, 98%, 99%, 99.5% or more identical to amino acids 110 to 167 of SEQ ID NO: 36.

The present invention also provides methods of identifying, selecting and/or producing a plant or plant part having enhanced abiotic stress tolerance (e.g., enhanced drought tolerance, enhanced osmotic stress tolerance, enhanced salt stress tolerance and/or enhanced temperature stress tolerance).

Methods of identifying plants and plant parts having enhanced abiotic stress tolerance may comprise, consist essentially of or consist of detecting, in the plant or plant part, a nucleic acid (e.g., an exogenous nucleic acid) comprising:

(a) one or more of the nucleotide sequences set forth in SEQ ID NOs: 1-27;

(b) one or more nucleotide sequences that is at least about 70%, 75%, 80%, 85%, 90%, 91%, 92%, 93%, 94%, 95%, 96%, 97%, 98%, 99%, 99.5% or more identical to one or more of the nucleotide sequences set forth in SEQ ID NOs: 1-27;

(c) one or more nucleotide sequences that encodes a polypeptide comprising, consisting essentially of or consisting of the amino acid sequence set forth in any one of SEQ ID NOs: 28-44;

(d) one or more nucleotide sequences that encodes a polypeptide comprising, consisting essentially of or consisting of an amino acid sequence that is at least about 70%, 75%, 80%, 85%, 90%, 91%, 92%, 93%, 94%, 95%, 96%, 97%, 98%, 99%, 99.5% or more identical to one or more of the amino acid sequences set forth in SEQ ID NOs: 28-44;

(e) a nucleotide sequence that is complementary to any one of the nucleotide sequences described in (a) to (d) above;

(f) a nucleotide sequence that hybridizes to any one of the nucleotide sequences described in (a) to (e) above under stringent hybridization conditions;

(g) a functional fragment of any one of the nucleotide sequences described in (a) to (f) above, wherein the functional fragment encodes a polypeptide that comprises an N-terminal signal peptide sequence that is at least about 70%, 75%, 80%, 85%, 90%, 91%, 92%, 93%, 94%, 95%, 96%, 97%, 98%, 99%, 99.5% or more identical to amino acids 1 to 27 of SEQ ID NO: 28 and a CCVS domain that is at least about 70%, 75%, 80%, 85%, 90%, 91%, 92%, 93%, 94%, 95%, 96%, 97%, 98%, 99%, 99.5% or more identical to amino acids 226 to 229 of SEQ ID NO: 28; and/or (h) a functional fragment of any one of the nucleotide sequences described in (a) to (f) above, wherein the functional fragment encodes a polypeptide that comprises an AP2 domain that is at least about 70%, 75%, 80%, 85%, 90%, 91%, 92%, 93%, 94%, 95%, 96%, 97%, 98%, 99%, 99.5% or more identical to amino acids 110 to 167 of SEQ ID NO: 36.

Methods of producing plants and plant parts having enhanced abiotic stress tolerance may comprise, consist essentially of or consist of:

(a) detecting, in a plant part, the presence of a nucleic acid (e.g., an exogenous nucleic acid) encoding one or more COBL4 proteins and/or one or more ERF62 proteins (e.g., a nucleic acid comprising a nucleotide sequence that is at least 70%, 75%, 80%, 85%, 90%, 91%, 92%, 93%, 94%, 95%, 96%, 97%, 98%, 99%, 99.5% or more identical to the nucleotide sequence set forth in any one of SEQ ID NOs: 1-27), and producing a plant from the plant part;

(b) introducing, into a plant part, an exogenous nucleic acid encoding one or more COBL4 proteins and/or one or more ERF62 proteins (e.g., an exogenous nucleic acid comprising a nucleotide sequence that is at least 70%, 75%, 80%, 85%, 90%, 91%, 92%, 93%, 94%, 95%, 96%, 97%, 98%, 99%, 99.5% or more identical to the nucleotide sequence set forth in any one of SEQ ID NOs: 1-27), and growing the plant part into a plant; such methods may further comprise detecting the exogenous nucleic acid in the plant part and/or in the plant produced from the plant part;

(c) introducing, into a plant part, an exogenous nucleic acid encoding one or more COBL4 proteins and/or one or more ERF62 proteins (e.g., an exogenous nucleic acid comprising a nucleotide sequence that is at least 70%, 75%, 80%, 85%, 90%, 91%, 92%, 93%, 94%, 95%, 96%, 97%, 98%, 99%, 99.5% or more identical to the nucleotide sequence set forth in any one of SEQ ID NOs: 1-27), detecting the presence of the exogenous nucleic acid in the plant part, and growing the plant part into a plant;

(d) crossing a first parent plant or plant part with a second parent plant or plant part, wherein the first parent plant or plant part comprises within its genome a nucleic acid (e.g., an exogenous nucleic acid) encoding one or more COBL4 proteins and/or one or more ERF62 proteins (e.g., an exogenous nucleic acid comprising a nucleotide sequence that is at least 70%, 75%, 80%, 85%, 90%, 91%, 92%, 93%, 94%, 95%, 96%, 97%, 98%, 99%, 99.5% or more identical to the nucleotide sequence set forth in any one of SEQ ID NOs: 1-27); and/or (e) introgressing an exogenous nucleic acid encoding one or more COBL4 proteins and/or one or more ERF62 proteins (e.g., an exogenous nucleic acid comprising a nucleotide sequence that is at least 70%, 75%, 80%, 85%, 90%, 91%, 92%, 93%, 94%, 95%, 96%, 97%, 98%, 99%, 99.5% or more identical to the nucleotide sequence set forth in any one of SEQ ID NOs: 1-27) into a plant or plant part lacking the exogenous nucleic acid.

In some embodiments, methods of producing plants having enhanced abiotic stress tolerance comprise, consist essentially of or consist of detecting, in a plant part, the presence of a nucleic acid (e.g., an exogenous nucleic acid) comprising, consisting essentially of or consisting of:

(a) one or more of the nucleotide sequences set forth in SEQ ID NOs: 1-27;
(b) one or more nucleotide sequences that is at least about 70%, 75%, 80%, 85%, 90%, 91%, 92%, 93%, 94%, 95%, 96%, 97%, 98%, 99%, 99.5% or more identical to one or more of the nucleotide sequences set forth in SEQ ID NOs: 1-27;
(c) one or more nucleotide sequences that encodes a polypeptide comprising, consisting essentially of or consisting of the amino acid sequence set forth in any one of SEQ ID NOs: 28-44;
(d) one or more nucleotide sequences that encodes a polypeptide comprising, consisting essentially of or consisting of an amino acid sequence that is at least about 70%, 75%, 80%, 85%, 90%, 91%, 92%, 93%, 94%, 95%, 96%, 97%, 98%, 99%, 99.5% or more identical to one or more of the amino acid sequences set forth in SEQ ID NOs: 28-44;
(e) a nucleotide sequence that is complementary to any one of the nucleotide sequences described in (a) to (d) above;
(f) a nucleotide sequence that hybridizes to any one of the nucleotide sequences described in (a) to (e) above under stringent hybridization conditions;
(g) a functional fragment of any one of the nucleotide sequences described in (a) to (f) above, wherein the functional fragment encodes a polypeptide that comprises an N-terminal signal peptide sequence that is at least about 70%, 75%, 80%, 85%, 90%, 91%, 92%, 93%, 94%, 95%, 96%, 97%, 98%, 99%, 99.5% or more identical to amino acids 1 to 27 of SEQ ID NO: 28 and a CCVS domain that is at least about 70%, 75%, 80%, 85%, 90%, 91%, 92%, 93%, 94%, 95%, 96%, 97%, 98%, 99%, 99.5% or more identical to amino acids 226 to 229 of SEQ ID NO: 28; and/or
(h) a functional fragment of any one of the nucleotide sequences described in (a) to (f) above, wherein the functional fragment encodes a polypeptide that comprises an AP2 domain that is at least about 70%, 75%, 80%, 85%, 90%, 91%, 92%, 93%, 94%, 95%, 96%, 97%, 98%, 99%, 99.5% or more identical to amino acids 110 to 167 of SEQ ID NO: 36; and
producing a plant from the plant part.

In some embodiments, methods of producing plants having enhanced abiotic stress tolerance comprise, consist essentially of or consist of introducing, into a plant part, an exogenous nucleic acid comprising, consisting essentially of or consisting of:
(a) one or more of the nucleotide sequences set forth in SEQ ID NOs: 1-27;
(b) one or more nucleotide sequences that is at least about 70%, 75%, 80%, 85%, 90%, 91%, 92%, 93%, 94%, 95%, 96%, 97%, 98%, 99%, 99.5% or more identical to one or more of the nucleotide sequences set forth in SEQ ID NOs: 1-27;
(c) one or more nucleotide sequences that encodes a polypeptide comprising, consisting essentially of or consisting of the amino acid sequence set forth in any one of SEQ ID NOs: 28-44;
(d) one or more nucleotide sequences that encodes a polypeptide comprising, consisting essentially of or consisting of an amino acid sequence that is at least about 70%, 75%, 80%, 85%, 90%, 91%, 92%, 93%, 94%, 95%, 96%, 97%, 98%, 99%, 99.5% or more identical to one or more of the amino acid sequences set forth in SEQ ID NOs: 28-44;
(e) a nucleotide sequence that is complementary to any one of the nucleotide sequences described in (a) to (d) above;
(f) a nucleotide sequence that hybridizes to any one of the nucleotide sequences described in (a) to (e) above under stringent hybridization conditions;
(g) a functional fragment of any one of the nucleotide sequences described in (a) to (f) above, wherein the functional fragment encodes a polypeptide that comprises an N-terminal signal peptide sequence that is at least about 70%, 75%, 80%, 85%, 90%, 91%, 92%, 93%, 94%, 95%, 96%, 97%, 98%, 99%, 99.5% or more identical to amino acids 1 to 27 of SEQ ID NO: 28 and a CCVS domain that is at least about 70%, 75%, 80%, 85%, 90%, 91%, 92%, 93%, 94%, 95%, 96%, 97%, 98%, 99%, 99.5% or more identical to amino acids 226 to 229 of SEQ ID NO: 28; and/or
(h) a functional fragment of any one of the nucleotide sequences described in (a) to (f) above, wherein the functional fragment encodes a polypeptide that comprises an AP2 domain that is at least about 70%, 75%, 80%, 85%, 90%, 91%, 92%, 93%, 94%, 95%, 96%, 97%, 98%, 99%, 99.5% or more identical to amino acids 110 to 167 of SEQ ID NO: 36; and
growing the plant part into a plant.

In some embodiments, methods of producing plants having enhanced abiotic stress tolerance comprise, consist essentially of or consist of crossing a first parent plant or plant part with a second parent plant or plant part, wherein the first parent plant or plant part comprises within its genome a nucleic acid (e.g., an exogenous nucleic acid) comprising, consisting essentially of or consisting of:
(a) one or more of the nucleotide sequences set forth in SEQ ID NOs: 1-27;
(b) one or more nucleotide sequences that is at least about 70%, 75%, 80%, 85%, 90%, 91%, 92%, 93%, 94%, 95%, 96%, 97%, 98%, 99%, 99.5% or more identical to one or more of the nucleotide sequences set forth in SEQ ID NOs: 1-27;
(c) one or more nucleotide sequences that encodes a polypeptide comprising, consisting essentially of or consisting of the amino acid sequence set forth in any one of SEQ ID NOs: 28-44;
(d) one or more nucleotide sequences that encodes a polypeptide comprising, consisting essentially of or consisting of an amino acid sequence that is at least about 70%, 75%, 80%, 85%, 90%, 91%, 92%, 93%, 94%, 95%, 96%, 97%, 98%, 99%, 99.5% or more identical to one or more of the amino acid sequences set forth in SEQ ID NOs: 28-44;
(e) a nucleotide sequence that is complementary to any one of the nucleotide sequences described in (a) to (d) above;
(f) a nucleotide sequence that hybridizes to any one of the nucleotide sequences described in (a) to (e) above under stringent hybridization conditions;
(g) a functional fragment of any one of the nucleotide sequences described in (a) to (f) above, wherein the functional fragment encodes a polypeptide that comprises an N-terminal signal peptide sequence that is at least about 70%, 75%, 80%, 85%, 90%, 91%, 92%, 93%, 94%, 95%, 96%, 97%, 98%, 99%, 99.5% or more identical to amino acids 1 to 27 of SEQ ID NO: 28 and a CCVS domain that is at least about 70%, 75%, 80%, 85%, 90%, 91%, 92%, 93%, 94%, 95%, 96%, 97%, 98%, 99%, 99.5% or more identical to amino acids 226 to 229 of SEQ ID NO: 28; and/or (h) a functional fragment of any one of the nucleotide sequences described in (a) to (f) above, wherein the functional fragment encodes a polypeptide that comprises an AP2 domain that is at least about 70%, 75%, 80%, 85%, 90%, 91%, 92%, 93%, 94%, 95%, 96%, 97%, 98%, 99%, 99.5% or more identical to amino acids 110 to 167 of SEQ ID NO: 36.

In some embodiments, methods of producing plants having enhanced abiotic stress tolerance comprise, consist essentially of or consist of crossing a first plant or plant part that comprises an exogenous nucleic acid encoding one or more COBL4 proteins and/or one or more ERF62 proteins with a second plant or plant part that lacks the exogenous nucleic acid and repeatedly backcrossing progeny plants comprising the exogenous nucleic acid (or a functional fragment thereof) with the second plant or plant part to produce an introgressed plant or plant part comprising the exogenous nucleic acid (or a functional fragment thereof). Such methods may further comprise selecting the introgressed plant or plant part (for inclusion in a breeding program, for example).

In some embodiments, methods of producing plants and plant parts having enhanced abiotic stress tolerance comprise, consist essentially of or consist of crossing a first plant or plant part that comprises an exogenous nucleic acid with a second plant or plant part that lacks the exogenous nucleic acid and repeatedly backcrossing progeny plants comprising the exogenous nucleic acid (or a functional fragment thereof) with the second plant or plant part to produce an introgressed plant or plant part comprising the exogenous nucleic acid (or a functional fragment thereof), wherein the exogenous nucleic acid comprises, consists essentially of or consists of:

(a) one or more of the nucleotide sequences set forth in SEQ ID NOs: 1-27;

(b) one or more nucleotide sequences that is at least about 70%, 75%, 80%, 85%, 90%, 91%, 92%, 93%, 94%, 95%, 96%, 97%, 98%, 99%, 99.5% or more identical to one or more of the nucleotide sequences set forth in SEQ ID NOs: 1-27;

(c) one or more nucleotide sequences that encodes a polypeptide comprising, consisting essentially of or consisting of the amino acid sequence set forth in any one of SEQ ID NOs: 28-44;

(d) one or more nucleotide sequences that encodes a polypeptide comprising, consisting essentially of or consisting of an amino acid sequence that is at least about 70%, 75%, 80%, 85%, 90%, 91%, 92%, 93%, 94%, 95%, 96%, 97%, 98%, 99%, 99.5% or more identical to one or more of the amino acid sequences set forth in SEQ ID NOs: 28-44;

(e) a nucleotide sequence that is complementary to any one of the nucleotide sequences described in (a) to (d) above;

(f) a nucleotide sequence that hybridizes to any one of the nucleotide sequences described in (a) to (e) above under stringent hybridization conditions;

(g) a functional fragment of any one of the nucleotide sequences described in (a) to (f) above, wherein the functional fragment encodes a polypeptide that comprises an N-terminal signal peptide sequence that is at least about 70%, 75%, 80%, 85%, 90%, 91%, 92%, 93%, 94%, 95%, 96%, 97%, 98%, 99%, 99.5% or more identical to amino acids 1 to 27 of SEQ ID NO: 28 and a CCVS domain that is at least about 70%, 75%, 80%, 85%, 90%, 91%, 92%, 93%, 94%, 95%, 96%, 97%, 98%, 99%, 99.5% or more identical to amino acids 226 to 229 of SEQ ID NO: 28; and/or (h) a functional fragment of any one of the nucleotide sequences described in (a) to (f) above, wherein the functional fragment encodes a polypeptide that comprises an AP2 domain that is at least about 70%, 75%, 80%, 85%, 90%, 91%, 92%, 93%, 94%, 95%, 96%, 97%, 98%, 99%, 99.5% or more identical to amino acids 110 to 167 of SEQ ID NO: 36.

Such methods may further comprise selecting the introgressed plant or plant part (for inclusion in a breeding program, for example).

Any suitable nucleic acid may be detected in/introduced into the plant or plant part, including, but not limited to, nucleic acids of the present invention. In some embodiments, the nucleic acid detected in/introduced into the plant or plant part is a nucleic acid encoding one or more of SEQ ID NOs: 28-44 (e.g., an exogenous nucleic acid comprising one or more of SEQ ID NOs: 1-27).

Exogenous nucleic acids may be introduced into the plant or plant part via any suitable method, including, but not limited to, microparticle bombardment, liposome-mediated transfection, receptor-mediated delivery, *Agrobacterium*-mediated transformation and/or whiskers-mediated transformation. In some embodiments, the exogenous nucleic acid is introduced into a plant part by crossing a first plant or plant part comprising the exogenous nucleic acid with a second plant or plant part that lacks the exogenous nucleic acid.

Nucleic acids encoding COBL4 proteins and/or ERF62 proteins may be detected using any suitable method, including, but not limited to, DNA sequencing, mass spectrometry and capillary electrophoresis. In some embodiments, the nucleic acid (or an informative fragment thereof) is detected in one or more amplification products from a nucleic acid sample from the plant or plant part. In some such embodiments, the amplification product(s) comprise(s) the nucleotide sequence of any one of SEQ ID NOs: 1-27, the reverse complement thereof, an informative fragment thereof, or an informative fragment of the reverse complement thereof.

Nucleic acids encoding COBL4 proteins and/or ERF62 proteins may be detected using any suitable probe. In some embodiments, the nucleic acid (or an informative fragment thereof) is detected using a probe comprising the nucleotide sequence of any one of SEQ ID NOs: 1-27, the reverse complement thereof, an informative fragment thereof, or an informative fragment of the reverse complement thereof. In some embodiments, the probe comprises one or more detectable moieties, such as digoxigenin, fluorescein, acridine-ester, biotin, alkaline phosphatase, horseradish peroxidase, β-glucuronidase, β-galactosidase, luciferase, ferritin or a radioactive isotope.

Methods of the present invention may be used to identify, select and/or produce plants and plant parts that exhibit a variety of abiotic stress tolerant phenotypes, including, but not limited to, decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield (e.g., increased biomass, increased seed yield, increased grain yield at standard moisture percentage (YGSMN), increased grain moisture at harvest (GMSTP), increased grain weight per plot (GWTPN), increased percent yield recovery (PYREC), decreased yield reduction (YRED), and/or decreased percent barren (PB)) when grown under abiotic stress conditions (e.g., drought stress conditions, osmotic stress conditions, salt stress conditions and/or temperature stress conditions). In some embodiments, one or more abiotic stress tolerant phenotypes is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300%, or more as compared to a control plant or plant part (e.g., a native plant of the same species) when each is grown under the same (or substantially the same) environmental conditions.

In some embodiments, the plant or plant part expresses one or more COBL4 proteins (e.g., one or more proteins having the amino sequence that is at least about 70%, 75%, 80%, 85%, 90%, 91%, 92%, 93%, 94%, 95%, 96%, 97%, 98%, 99%, 99.5% or more identical to the amino sequence one or more of SEQ ID NOs: 28-35) at an increased level as compared to a control plant or plant part (e.g., a native plant of the same species) when each is grown under the same (or substantially the same) environmental conditions. In some such embodiments, expression of the COBL4 protein(s) is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300%, or more as compared to the control plant or plant part.

In some embodiments, the plant or plant part expresses one or more ERF62 proteins (e.g., one or more proteins having the amino sequence that is at least about 70%, 75%, 80%, 85%, 90%, 91%, 92%, 93%, 94%, 95%, 96%, 97%, 98%, 99%, 99.5% or more identical to the amino sequence one or more of SEQ ID NOs: 36-44) at an increased level as compared to a control plant or plant part (e.g., a native plant of the same species) when each is grown under the same (or substantially the same) environmental conditions. In some such embodiments, expression of the ERF62 protein(s) is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300%, or more as compared to the control plant or plant part.

In some embodiments, the yield (e.g., seed yield, biomass, GWTPN, PYREC and/or YGSMN) of the plant or plant part is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part (e.g., a native plant of the same species) grown under the same (or substantially the same) environmental conditions. For example, the seed yield and/or biomass of the plant or plant part may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part grown under the same (or substantially the same) drought stress conditions.

In some embodiments, the accumulation of dehydrins and/or late embryogenesis abundant proteins, survival rate, growth potential, height, chlorophyll content and/or GMSTP of the plant or plant part is increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part (e.g., a native plant of the same species) grown under the same (or substantially the same) environmental conditions. For example, the survival rate and/or chlorophyll content of the plant or plant part may be increased by at least about 5%, 10%, 15%, 20%, 25%, 30%, 35%, 40%, 45%, 50%, 55%, 60%, 65%, 75%, 80%, 85%, 90%, 95%, 100%, 125%, 150%, 175%, 200%, 250%, 300% or more as compared to a control plant or plant part grown under the same (or substantially the same) drought stress conditions.

In some embodiments, the water loss, accumulation of reactive oxygen species, YRED, and/or PB of the plant or plant part is decreased by at least about 5%, 10%, 15%, 20%, 25%, 30%, 35%, 40%, 45%, 50%, 55%, 60%, 65%, 75%, 80%, 85%, 90%, 95%, 96%, 97%, 98%, 99%, 99.5% or more as compared to a control plant or plant part (e.g., a native plant of the same species) grown under the same (or substantially the same) environmental conditions. For example, the YRED and/or PB of the plant may be decreased by at least about 5%, 10%, 15%, 20%, 25%, 30%, 35%, 40%, 45%, 50%, 55%, 60%, 65%, 75%, 80%, 85%, 90%, 95%, 96%, 97%, 98%, 99%, 99.5% or more as compared to a control plant grown under the same (or substantially the same) drought stress conditions.

In some embodiments, the root architecture and/or osmotic pressure regulation of the plant or plant part is improved as compared to a control plant (e.g., a native plant of the same species) grown under the same (or substantially the same) environmental conditions. For example, the root architecture and/or osmotic pressure regulation of the plant or plant part may be improved as compared to a control plant or plant part grown under the same (or substantially the same) drought stress conditions.

Methods of the present invention may be used to identify, select and/or produce plants and plant parts of any suitable plant type, including, but not limited to, plants belonging to the superfamily Viridiplantae. In some embodiments the plant or plant part is a fodder crop, a food crop, an ornamental plant, a tree or a shrub. For example, in some embodiments, the plant or plant part is a variety of *Acer* spp., *Actinidia* spp., *Abelmoschus* spp., *Agropyron* spp., *Allium* spp., *Amaranthus* spp., *Ananas comosus*, *Annona* spp., *Apium graveolens*, *Arachis* spp, *Artocarpus* spp., *Asparagus officinalis*, *Avena* spp. (e.g. *Avena sativa*, *Avena fatua*, *Avena byzantina*, *Avena fatua* var. *sativa*, *Avena hybrida*), *Averrhoa carambola*, *Benincasa hispida*, *Bertholletia excelsea*, *Beta vulgaris*, *Brassica* spp. (e.g. *Brassica napus*, *Brassica rapa* ssp. [canola, oilseed rape, turnip rape]), *Cadaba farinosa*, *Camellia sinensis*, *Canna indica*, *Capsicum* spp., *Carex elata*, *Carica papaya*, *Carissa macrocarpa*, *Carya* spp., *Carthamus tinctorius*, *Castanea* spp., *Cichorium endivia*, *Cinnamomum* spp., *Citrullus lanatus*, *Citrus* spp., *Cocos* spp., *Coffea* spp., *Colocasia esculenta*, *Cola* spp., *Coriandrum sativum*, *Corylus* spp., *Crataegus* spp., *Crocus sativus*, *Cucurbita* spp., *Cucumis* spp., *Cynara* spp., *Daucus carota*, *Desmodium* spp., *Dimocarpus longan*, *Dioscorea* spp., *Diospyros* spp., *Echinochloa* spp., *Elaeis* (e.g. *Elaeis guineensis*, *Elaeis oleifera*), *Eleusine coracana*, *Eriobotrya japonica*, *Eugenia uniflora*, *Fagopyrum* spp., *Fagus* spp., *Ficus carica*, *Fortunella* spp., *Fragaria* spp., *Ginkgo biloba*, *Glycine* spp. (e.g. *Glycine max*, *Soja hispida* or *Soja* max), *Gossypium hirsutum*, *Helianthus* spp. (e.g. *Helianthus annuus*), *Hemerocallis fulva*, *Hibiscus* spp., *Hordeum* spp. (e.g. *Hordeum vulgare*), *Ipomoea batatas*, *Juglans* spp., *Lactuca sativa*, *Lathyrus* spp., *Lens culinaris*, *Linum usitatissimum*, *Litchi chinensis*, *Lotus* spp., *Luffa acutangula*, *Lupinus* spp., *Luzula sylvatica*, *Lycopersicon* spp. (e.g. *Lycopersicon esculentum*, *Lycopersicon lycopersicum*, *Lycopersicon pyriforme*), *Macrotyloma* spp., *Malus* spp., *Malpighia emarginata*, *Mammea americana*, *Mangifera indica*, *Manihot* spp., *Manilkara zapota*, *Medicago sativa*, *Melilotus* spp., *Mentha* spp., *Miscanthus* spp., *Momordica* spp., *Morus nigra*, *Musa* spp., *Nicotiana* spp., *Olea* spp., *Opuntia* spp., *Ornithopus* spp., *Oryza* spp. (e.g. *Oryza sativa*, *Oryza latifolia*), *Panicum miliaceum*, *Passiflora edulis*, *Pastinaca sativa*, *Persea* spp., *Petroselinum crispum*, *Phaseolus* spp., *Phoenix* spp., *Physalis* spp., *Pinus* spp., *Pistacia vera*, *Pisum* spp., *Poa* spp., *Populus* spp., *Prosopis* spp., *Prunus* spp., *Psidium* spp., *Punica granatum*, *Pyrus communis*, *Quercus* spp., *Raphanus sativus*, *Rheum rhabarbarum*, *Ribes* spp., *Ricinus communis*, *Rubus* spp., *Saccharum* spp., *Sambucus* spp., *Secale cereale*, *Sesamum* spp., *Sinapis* sp., *Solanum* spp. (e.g. *Solanum tuberosum*, *Solanum integrifolium* or *Solanum lycopersicum*), *Sorghum bicolor*, *Spinacia* spp., *Syzygium* spp., *Tagetes* spp., *Tamarindus indica*, *Theobroma cacao*, *Trifolium* spp., *Triticosecale rimpaui*, *Triticum* spp. (e.g. *Triticum aestivum*, *Triticum durum*, *Triticum turgidum*, *Triticum hybernum*, *Triticum macha*, *Triticum sativum* or *Triticum vulgare*), *Tropaeolum minus*, *Tropaeolum majus*, *Vaccinium* spp., *Vicia* spp., *Vigna* spp., *Viola odorata*, *Vitis* spp., *Zea mays*, *Zizania palustris* or *Ziziphus* spp., amongst others.

In some embodiments, the plant or plant part is a rice, maize, wheat, barley, sorghum, millet, oat, triticale, rye, buckwheat, fonio, quinoa, sugar cane, bamboo, banana, ginger, onion, lily, daffodil, iris, amaryllis, orchid, canna, bluebell, tulip, garlic, secale, einkorn, spelt, emmer, durum, kamut, grass (e.g., gramma grass), teff, milo, flax, *Tripsacum* sp., or teosinte plant or plant part. In some embodiments, the plant or plant part is a blackberry, raspberry, strawberry, barberry, bearberry, blueberry, coffee berry, cranberry, crowberry, currant, elderberry, gooseberry, goji berry, honeyberry, lemon, lime, lingonberry, mangosteen, orange, pepper, persimmon, pomegranate, prune, cotton, clover, acai, plum, peach, nectarin, cherry, guava, almond, pecan, walnut, apple, amaranth, sweet pea, pear, potato, soybean, sugar beet, sunflower, sweet potato, tamarind, tea, tobacco or tomato plant or plant part.

The present invention extends to products harvested from plants and plant parts produced according to methods of the present invention, including, but not limited to, plant cells and harvestable plant parts such as seeds, leaves, fruits, flowers, stems, rhizomes, tubers and bulbs. In some embodiments, the harvested product is a plant cell (e.g., a embryo or ovule) or plant part capable of producing a plant or plant part having increased expression and/or activity of one or more COBL4 proteins, increased expression and/or activity of one or more ERF62 proteins, and/or enhanced abiotic stress tolerance (e.g., enhanced drought tolerance, enhanced osmotic stress tolerance, enhanced salt stress tolerance and/or enhanced temperature stress tolerance). In some embodiments, the harvested product is a plant cell (e.g., a embryo or ovule) or plant part capable of producing a plant or plant that exhibits decreased water loss, decreased accumulation of one or more reactive oxygen species, decreased accumulation of one or more salts, increased salt excretion, increased accumulation of one or more dehydrins, improved root architecture, improved osmotic pressure regulation, increased accumulation of one or more late embryogenesis abundant proteins, increased survival rate, increased growth rate, increased height, increased chlorophyll content and/or increased yield (e.g., increased biomass, increased seed yield, increased grain yield at standard moisture percentage (YGSMN), increased grain moisture at harvest (GMSTP), increased grain weight per plot (GWTPN), increased percent yield recovery (PYREC), decreased yield reduction (YRED), and/or decreased percent barren (PB)) when grown under abiotic stress conditions (e.g., drought stress conditions, osmotic stress conditions, salt stress conditions and/or temperature stress conditions).

The present invention also extends to products derived from plants produced according to methods of the present invention, including, but not limited to, dry pellets and powders, oils, fats, fatty acids, starches and proteins.

EXAMPLES

The following examples are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

Example 1

Over-expression of OsCOBL4 or OsERF62 Enhances Abiotic Stress Tolerance

Exposure to abiotic stress conditions resulted in the upregulation of both OsCOBL4 expression and OsERF62 expression (FIGS. 1A-1H), indicating that OsCOBL4 and OsERF62 are associated with one or more abiotic stress responses. As shown in FIGS. 4A-6B, overexpression of OsCOBL4 and OsERF62 gave rise to enhanced abiotic stress tolerance in transgenic rice plants.

Part I. OsCOBL4 and OsERF62 Expression were Upregulated in Rice Exposed to Abiotic Stress Conditions Water-cultured four-week-old seedlings of upland rice variety IRAT109 and lowland rice variety Nipponbare were subjected to the following abiotic stress treatments: ABA treatment (roots were soaked in 100 µM ABA solution and cultured under illumination for 1, 2, 4, 6, 9, 12, 24 or 36 hours); dehydration treatment (roots were left in the air for 1, 2, 3, 4, 5, 6 or 8 hours); $H_2O_2$ treatment (roots were soaked in 1 mM $H_2O_2$ solution and left in the air 1, 2, 4, 6, 9, 12 or 24 hours); PEG treatment (roots were soaked in 200 g/L polyethylene glycol (PEG6000) aqueous solution for 1, 2, 4, 6, 9, 12 or 24 hours); or control treatment (roots remained in water culture). Following treatment, leaves were collected and quickly frozen using liquid nitrogen and stored at −80° C. for further use.

Total RNA was extracted from the harvested leaves and purified. Reverse transcription was performed using M-MLV reverse transcriptase to synthesize cDNA, then the cDNA was used as a template to amplify 244 bp fragments of OsCOBL4 (forward primer: 5'-TGT-GTTTCTCTCTCGTCGTTCG-3' ((SEQ ID NO:51) corresponding to nucleotides 756 to 777 of SEQ ID NO 3); reverse primer: 5'-TCTTTGAGCATCAAGTGCCAGT-3' ((SEQ ID NO:52) corresponding to nucleotides 958 to 979 of SEQ ID NO: 3)); a 142 bp fragment of OsERF62 gene (forward primer: 5'-ATGGCTTGCTTGATTACCGAA-3' ((SEQ ID NO:53) corresponding to nucleotides 1203 to 1223 of SEQ ID NO 16); reverse primer: 5'-AGACCCCG-TAAAAGTAGCCCA-3' ((SEQ ID NO:54) corresponding to nucleotides 1324 to 1344 of SEQ ID NO: 16); and a 255 bp fragment (255 bp) of the Nipponbare Actin gene (forward primer: 5'-ATTTGGCACCACACATTCTAC-3' (SEQ ID NO:55); reverse primer: 5'-ATAACCTTCGTAGAT-TGGGACT-3' (SEQ ID NO:56)), which was used as an internal reference for real-time quantitative analysis.

Real-time fluorescence quantitative PCR was carried out on a real-time fluorescence quantitative PCR apparatus (Applied Biosystems® 7500 Real Time PCR system, Life Technologies, Grand Island, N.Y., USA); one parallel experiment was performed with three repetitions. The relative expression levels of OsCOBL4, OsERF62, and Actin were calculated by the method reported by Livak K J and Schmittgen T D (*Analysis of relative gene expression data using real-time quantitative PCR and the 2(−Delta Delta C (T)) Method*, METHODS 25(4):402 (2001).

As shown in FIGS. 1A-1H, the expressions of OsCOBL4 and OsERF62 were upregulated in response to each of the abiotic stress treatments, indicating that OsCOBL4 and OsERF62 are associated with one or more abiotic stress responses (more particularly, to one or more drought stress responses). The expression of OsCOBL4 was greater in upland rice variety IRAT109 than in lowland rice variety Nipponbare.

Part II. Isolation of Genes Associated with Enhanced Abiotic Stress Tolerance

Seedlings of upland rice variety IRAT109 were cultivated under normal conditions. Total RNA was extracted using the Trizol method and purified. Reverse transcription was performed using M-MLV reverse transcriptase to obtain cDNA. Using the cDNA as a template, two genes were amplified: OsCOBL4$_{IRAT109}$ (forward primer: 5'-TTGGCGCGCCA-CACACCGAGTCATCGCTCG-3' (SEQ ID NO:57) (the underlined nucleotides are the digestion recognition sequence of restriction endonuclease AscI); reverse primer: 5'-CCTTAATTAACCCCTGCCACGAATCTGCTAT-3' (SEQ ID NO:58) (the underlined bases are the digestion recognition sequence of restriction endonuclease PacI)) and OsERF62$_{IRAT109}$ (forward primer: 5'-CGGGGTAC-CAAAGGCATTCGCAACACACA-3' (SEQ ID NO:59) (the underlined base pairs are the digestion recognition sequence of restriction endonuclease KpnI); reverse primer: 5'-CCTTAATTAACCAAAATACATTACGACTGGAC-3' (SEQ ID NO:60) (the underlined nucleotides are the digestion recognition sequence of restriction endonuclease PacI)). The amplification products were subjected to agarose gel electrophoresis, and amplification products corresponding to OsCOBL4$_{IRAT109}$ and OsERF62$_{IRAT109}$ were recovered and purified for sequencing.

The sequence of the 1589 bp fragment corresponding to OsCOBL4$_{IRAT109}$ is shown herein as SEQ ID NO: 3. OsCOBL4$_{IRAT109}$ (SEQ ID NO: 28) is encoded by nucleotides 78 to 1355 of SEQ ID NO: 3 (shown herein as SEQ ID NO: 1). Nucleotides 11 to 1579 of SEQ ID NO: 3 (shown herein as SEQ ID NO: 2) represent the full-length cDNA sequence encoding OsCOBL4$_{IRAT109}$.

The sequence of the 1580 bp fragment corresponding to OsERF62$_{IRAT109}$ is shown as SEQ ID NO: 16. OsERF62$_{IRAT109}$ (SEQ ID NO: 36) is encoded by nucleotides 102 to 1106 of SEQ ID NO: 16 (shown herein as SEQ ID NO: 14). Nucleotides 10 to 1570 of SEQ ID NO: 16 (shown herein as SEQ ID NO: 15) represent the full-length cDNA sequence encoding OsERF62$_{IRAT109}$.

Part III. Construction of Recombinant Expression Vectors Comprising OsCOBL4 or OsERF62

The 1589 bp DNA fragment corresponding to OsCOBL4$_{IRAT109}$ was cleaved by double digestion with AscI and PacI, and the digestion product was ligated into a pMDC32 vector (Farre and Kay, *PRR7 protein levels are regulated by light and the circadian clock in Arabidopsis*, PLANT J. 52:548 (2007); publicly available from China Agricultural University) between the AscI and PacI digestion sites (i.e., downstream of the dual tobacco mosaic virus 35S promoter) to produce a recombinant 35S::OsCOBL4$_{IRAT109}$ vector.

The 1580 bp DNA fragment corresponding to OsERF62$_{IRAT109}$ was cleaved by double digestion with KpnI and PacI, and the digestion product was ligated into a pMDC32 vector between the KpnI and PacI digestion sites (i.e., downstream of the dual tobacco mosaic virus 35S promoter) to produce a recombinant 35S::OsEF62$_{IRAT109}$ vector.

Proper insertion of the OsCOBL4$_{IRAT109}$ and OsERF62$_{IRAT109}$ digestion products was verified by sequencing and enzyme digestion.

Part IV. Production of Recombinant *Agrobacterium tumefaciens* Comprising 35S::OsCOBL4$_{IRAT109}$ or 35S::OsERF62$_{IRAT109}$

*Agrobacterium tumefaciens* EHA105 (Shiwu et al., *Study on factors affecting conversion efficiency of Agrobacterium tumefaciens EHA105 competent cells*, J. TROPICAL BIOL. 3(1) (March 2012); publicly available from China Agricultural University) was transformed with recombinant 35S::OsCOBL4$_{IRAT109}$ vector or recombinant 35S::OsERF62$_{IRAT109}$ vector using the freeze-thaw method to produce recombinant *Agrobacterium* EHA105/35S::OsCOBL4$_{IRAT109}$ and recombinant *Agrobacterium* EHA105/35S::OsERF62$_{IRAT109}$.

Part V. Production of Transgenic Nipponbare Rice Plants Expressing OsCOBL4$_{IRAT109}$ or OsERF62$_{IRAT109}$ Embryogenic calli of lowland rice variety Nipponbare were infected with recombinant *Agrobacterium* EHA105/35S::OsCOBL4$_{IRAT109}$ or recombinant *Agrobacterium* EHA105/35S::OsERF62$_{IRAT109}$ to produce T$_0$-generation OsCOBL4$_{IRAT109}$ transgenic Nipponbare rice lines and T$_0$-generation OsERF62$_{IRAT109}$ transgenic Nipponbare rice lines:

(Step 1) Recombinant *Agrobacterium* EHA105/35S::OsCOBL4 and recombinant *Agrobacterium* EHA105/35S::OsERF62 were separately spread YEP culture media (10 g/L peptone+10 g/L yeast extract+5 g/L NaCl+15 g/L agar powder, 50 mg/L kanamycin, 20 mg/L rifampin, pH 7.0) and cultured at 28° C. for 2-3 days. A single bacterial plaque from each culture was picked and inoculated into separate YEP liquid media (10 g/L peptone+10 g/L yeast extract +5 g/L NaCl+15 g/L agar powder, 50 mg/L kanamycin, 20 mg/L rifampin, pH 7.0), cultured at 28° C. at 240 rpm until OD$_{600}$ reached 0.8-1.0, then inoculated in an inoculation amount of 1% into fresh YEP liquid medium and cultured at 28° C. at 240 rpm until OD$_{600}$ reached 0.5-0.6. Cells were collected by centrifugation, resuspended in AAM culture media (AA salts (AA large amount, AA microamount, iron salts)+MS vitamins+AA amino acids+500 mg/L casein hydrolysate+68.5 g/L sucrose+36 g/L glucose+20 mg/L acetosyringone, pH 5.2) and cultured at 28° C. at 240 rpm until OD$_{600}$ reached 0.3-0.4. The resulting cultures were used as infection solutions in Step 2.

(Step 2) Embryogenic calli of lowland rice variety Nipponbare were soaked in one of the infection solutions for 30 min and then removed. After removing excess infection solution with sterile filter paper, the calli were cultured in separate co-culture media (NB medium basic components (N6 macroelements, B5 microelements, B5 organic components, 150 mg/L inositol, 300 mg/L casein hydrolysate, 500 mg/L glutamine, 600 mg/L proline, 30 g/L sucrose, and 3 g/L plant gels)+2 mg/L 2,4-D+10 g/L glucose+20 mg/L acetosyringone, pH 5.4) for 2-3 days.

(Step 3) Calli co-cultured in Step 2 were rinsed 3-4 times with sterile water under oscillation, and then washed with 500 mg/L cephalosporin aqueous solution under oscillation for 40 min until the supernatant was completely clear. Washed calli were taken out and put into sterile culture dishes containing filter paper and air-dried at 0.4 m/s for 4 hours. Dried calli were transferred to delay-screening culture media (NB medium basic components+2 mg/L 2,4-D+ 500 mg/L cephalosporin, pH 5.8) and cultured in the dark for 3-7 days, then transferred to consecutive screening culture media (3-4 weeks for each screening medium; first screening medium: NB medium basic components+2 mg/L 2,4-D+500 mg/L cephalosporin+50 mg/L hygromycin, pH 58; second screening medium: NB medium basic components+2 mg/L 2,4-D+50 mg/L hygromycin, pH 5.8).

(Step 4) Calli screened in Step 3 were cultured in pre-differentiation culture media (NB medium basic components+1 mg/L 6-BA+2 mg/L NAA+5 mg/L ABA+50 mg/L hygromycin, pH 5.8) in the dark for 2-3 weeks and then transferred to differentiation culture media (NB medium basic components+2 mg/L 6-BA+1 mg/L NAA+1 mg/L KT+50 mg/L hygromycin, pH 5.8) where they were cultured under illumination for 2-3 weeks; when buds grew to a length of about 1 cM, the cultures were transferred to sound seedling culture media (½ MS medium basic components+ 0.5 mg/L NAA+0.25 mg/L paclobutrazol, pH 5.8) and cultured for 30 days. The sealing films were removed, and the hardening-seedling cultures were performed for one week, then the seedlings were transplanted into soil.

Figure 2A:
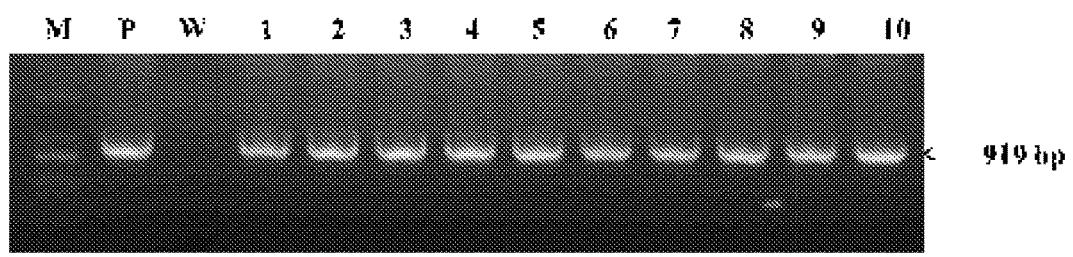
FIG. 2A shows an agarose gel containing DNA fragments from Nipponbare rice plants, wherein lane M is a molecular weight standard with fragments 2000, 1000, 750, 500, or 250 base pairs in size (from top to bottom), lane P is a positive control, plasmid pMDC32, lane W is a wild-type Nipponbare rice plant. Lanes 1-10 are $T_0$-generation OsCOBL4$_{IRAT109}$ transgenic Nipponbare rice plants.
Figure 2B:
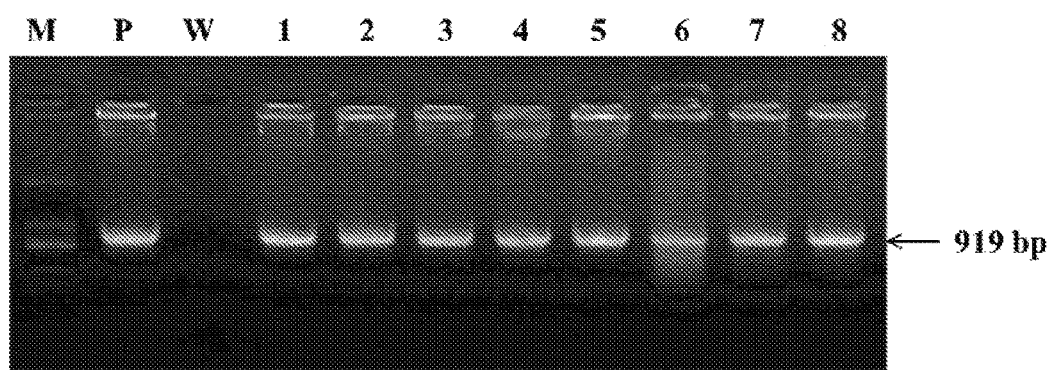
FIG. 2B shows an agarose gel containing DNA fragments from Nipponbare rice plants, wherein lane M is a molecular weight standard with fragments 2000, 1000, 750, 500, or 250 base pairs in size (from top to bottom), lane P is a positive control, plasmid pMDC32, lane W is a wild-type Nipponbare rice plant, and lanes 1-8 are $T_0$-generation OsERF62$_{IRAT109}$ transgenic Nipponbare rice plants.

(Step 5) $T_0$-generation OsCOBL4$_{IRAT109}$ transgenic Nipponbare rice plants and $T_0$-generation OsERF62$_{IRAT109}$ transgenic Nipponbare rice plants were identified by PCR at the DNA level using hygromycin phosphotransferase (HPT) as the target gene (forward primer: 5'-AAAAGTTCGACA-GCGTCTCCGACC-3' (SEQ ID NO:61); reverse primer: 5'-TCTACACAGCCATCGGTCCAGACG-3' (SEQ ID NO:62)). The target fragment was 919 nucleotides in length. Plants containing the target fragment were deemed positive and plants lacking the target fragment were deemed negative. FIGS. 2A-2B.

The transgenic plants produced in Step 4 and deemed positive in Step 5 are referred to as $T_0$-generation transgenic Nipponbare rice plants. The $T_1$ generation comprises seeds produced by selfing $T_0$ generation plants and plants growing therefrom. The $T_2$ generation comprises seeds produced by selfing the $T_1$ generation and plants growing therefrom. $T_3$ generation comprises seeds produced by selfing $T_2$ generation plants and plants growing therefrom.

Part VI. Overexpression of OsCOBL4 and OsERF62 in Transgenic Nipponbare Rice

Leaves were collected from wild-type Nipponbare rice lines, $T_2$-generation OsCOBL4$_{IRAT109}$ transgenic Nipponbare rice lines and $T_2$-generation OsERF62$_{IRAT109}$ transgenic Nipponbare rice lines, all of which were planted in an open field. Total RNA was extracted from the leaves using the TRIZOL method and purified. Reverse transcription was performed using M-MLV reverse transcriptase to synthesize cDNA, then the cDNA was used as a template to amplify 244 bp fragments of OsCOBL4 (forward primer: 5'-TGT-GTTTCTCTCTCGTCGTTCG-3' (SEQ ID NO:51) (corresponding to nucleotides 756 to 777 of SEQ ID NO 3); reverse primer: 5'-TCTTTGAGCATCAAGTGCCAGT-3' (SEQ ID NO:52) (corresponding to nucleotides 958 to 979 of SEQ ID NO: 3)); a 142 bp fragment of OsERF62 gene (forward primer: 5'-ATGGCTTGCTTGATTACCGAA-3' (SEQ ID NO:53) (corresponding to nucleotides 1203 to 1223 of SEQ ID NO 16); reverse primer: 5'-AGACCCCG-TAAAAGTAGCCCA-3' (SEQ ID NO:54) (corresponding to nucleotides 1324 to 1344 of SEQ ID NO: 16)); and a 255 bp fragment (255 bp) of the Nipponbare Actin gene (forward primer: 5'-ATTTGGCACCACACATTCTAC-3' (SEQ ID NO:55); reverse primer: 5'-ATAACCTTCGTAGAT-TGGGACT-3') (SEQ ID NO:56), which was used as an internal reference for real-time quantitative analysis.

Real-time fluorescence quantitative PCR was carried out on a real-time fluorescence quantitative PCR apparatus (Applied Biosystems® 7500 Real Time PCR system, Life Technologies, Grand Island, N.Y., USA); one parallel experiment was performed with three repetitions. The relative expression levels of OsCOBL4, OsERF62, and Actin were calculated by the method reported by Livak K J and Schmittgen T D (*Analysis of relative gene expression data using real-time quantitative PCR and the 2(−Delta Delta C (T)) Method*, METHODS 25(4):402 (2001).

Figure 3A:
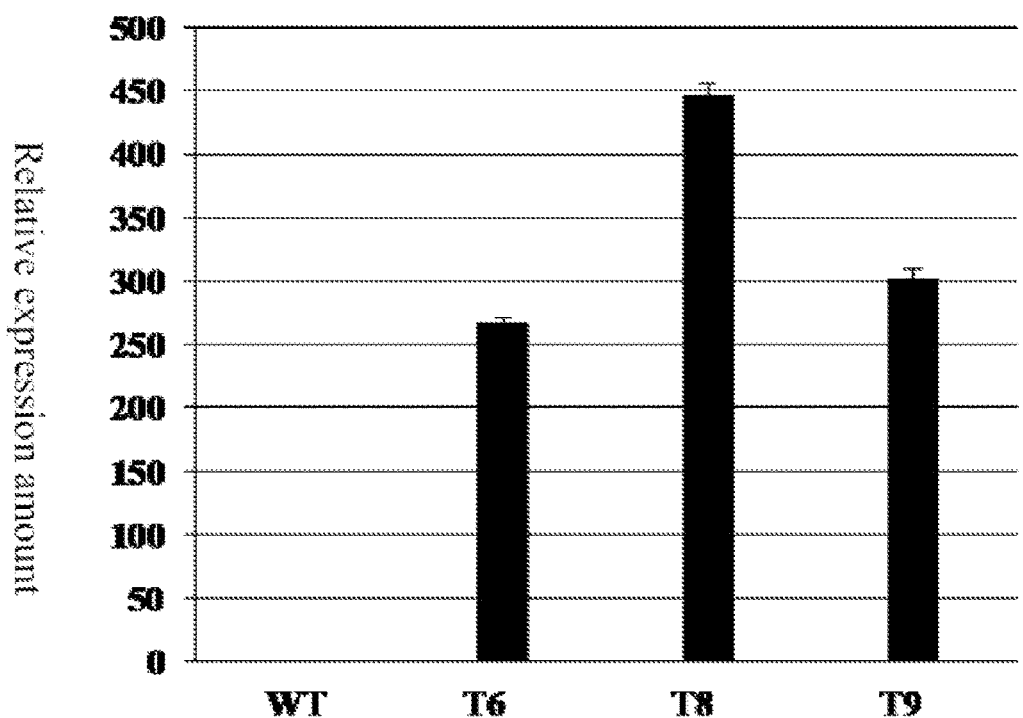
FIG. 3A is a graph showing the relative expression levels of OsCOBL4 in wild-type Nipponbare rice plants (WT) and $T_2$-generation OsCOBL4$_{IRAT109}$ transgenic Nipponbare rice plants (T6, T8, T9).
Figure 3B:
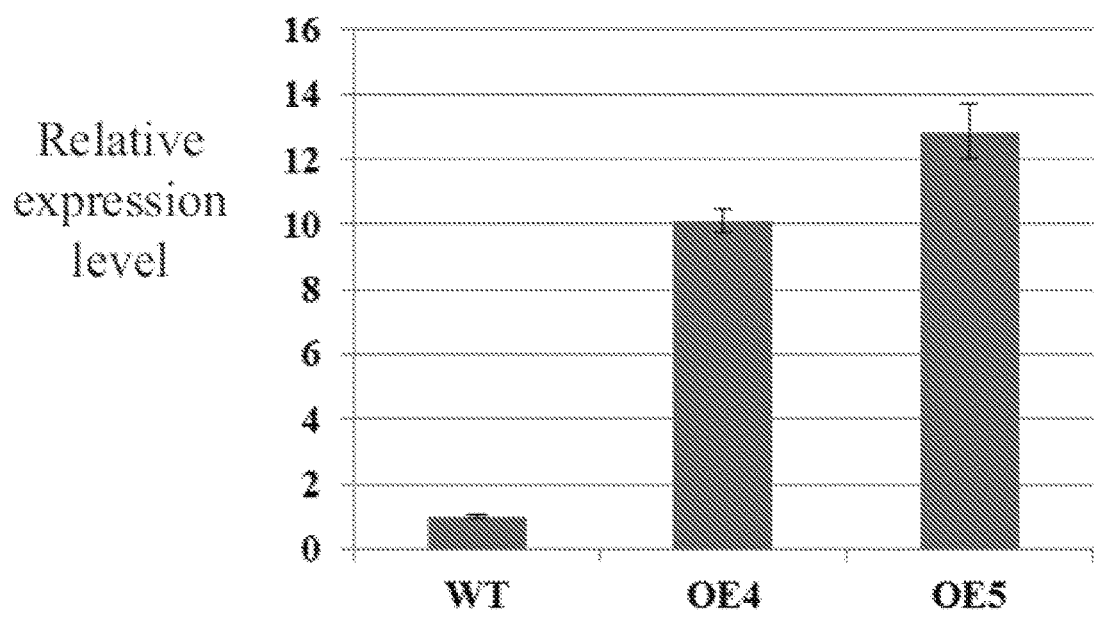
FIG. 3B is a graph showing the relative expression levels of OsERF62 in wild-type Nipponbare rice plants (WT) and $T_2$-generation OsERF62$_{IRAT109}$ transgenic Nipponbare rice plants (OE4, OE5).

As shown in FIGS. 3A-3B, respectively, the expression of OsCOBL4 and OsERF62 in the $T_2$-generation OsCOBL4$_{IRAT109}$ transgenic Nipponbare rice lines (T6, T8, T9) and $T_2$-generation OsERF62$_{IRAT109}$ transgenic Nipponbare rice lines (T6, T8, T9) were significantly higher than in the WT lines.

Part VII. Overexpression of OsCOBL4 and OsERF62 Gave Rise to Enhanced Abiotic Stress Tolerance in Rice Plants Grown Under Simulated Drought Stress Conditions Wild-type lowland rice variety Nipponbare lines (WT) were subjected to PEG-simulated drought stress conditions, along with two $T_2$-generation OsCOBL4$_{IRAT109}$ transgenic Nipponbare rice lines (T6 and T8) and two $T_2$-generation OsERF62$_{IRAT109}$ transgenic Nipponbare rice lines (OE4 and OE5), each of which were positively identified by PCR in Step 5 of Part V. Seeds of individual plant lines were sterilized with 20% NaClO. Seeds of the $T_2$-generation OsCOBL4$_{IRAT109}$ transgenic Nipponbare rice lines (T6 and T8) and the $T_2$-generation OsERF62$_{IRAT109}$ transgenic Nipponbare rice lines (OE4 and OE5) were soaked in sterile water containing 50 mg/L hygromycin for 2 days. WT seeds were soaked in sterile water free of hygromycin for 2 days. The soaked seeds were washed with sterile water containing 50 mg/L hygromycin, and forced to germinate for 2-3 days after excess water was removed.

Seeds having the same (or substantially the same) growth potential under normal growth conditions were selected and transferred to PCR plates, the bottom of which were hollowed out. Thirty T6, T8, OE4 or OE5 plants were planted on each PCR plate, using WT plants as controls, and cultured with a Hoagland nutrient fluid (1.43 mM NH$_4$NO$_3$, 0.27 mM NaH$_2$PO$_4$.2H$_2$O, 0.51 mM K$_2$SO$_4$, 1.0 mM CaCl$_2$, 1.46 mM MnSO$_4$.7H$_2$O, 0.19 mM Na$_2$SiO$_3$, 9.5 µM MnCl$_2$.4H$_2$O, 7.5×10$^{-2}$ µM (NH$_4$)$_6$Mo$_7$O$_{24}$.4H$_2$O, 18.8 µM H$_3$BO$_3$, 0.15 µM ZnSO$_4$.7H$_2$O, 0.16 µM CuSO$_4$.5H$_2$O, 35.6 µM FeCl$_3$.6H$_2$O, pH 5.5-6.0) in an illuminated culture room until they grew to the two-leaf one-apical bud stage, at which point the PCR plates were transferred into an aqueous solution containing 200 g/L PEG6000 for 3 days and then transferred to sterile water for 7 days. The number of surviving plants was counted, and the survival rates (i.e., the percentage of the number of surviving plants to the total number of plants subjected to the stress treatment) were calculated.

Figure 4A:
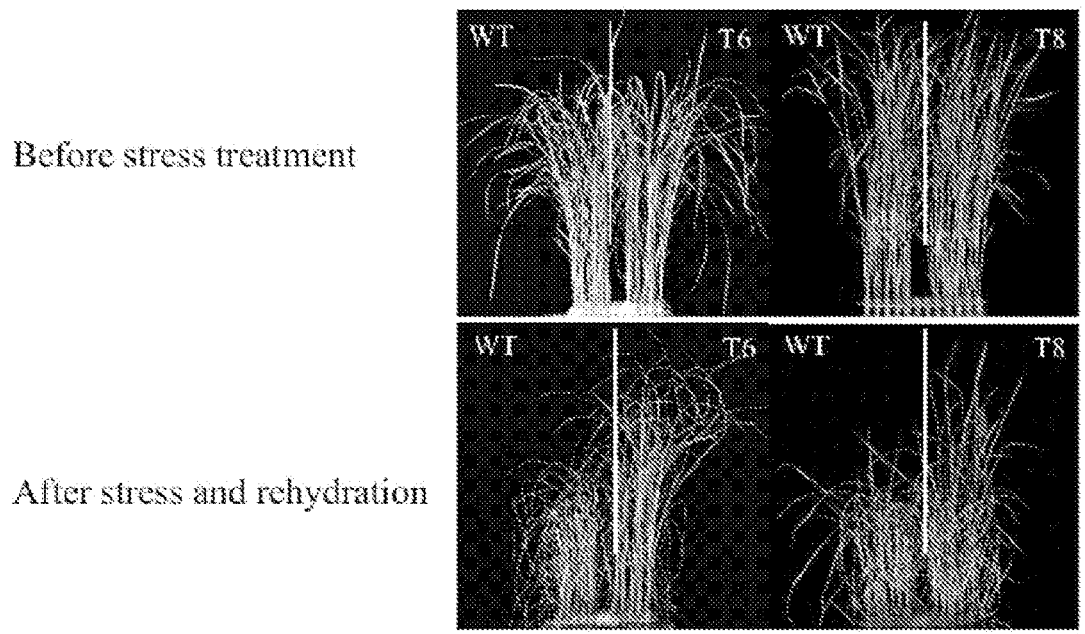
FIGS. 4A-4B shows wild-type Nipponbare rice plants (WT), $T_2$-generation OsCOBL4$_{IRAT109}$ transgenic Nipponbare rice plants (T6, T8) and $T_2$-generation OsERF62$_{IRAT109}$ transgenic Nipponbare rice plants (OE4, OE5) before and after PEG-simulated drought stress treatment.
Figure 4B:
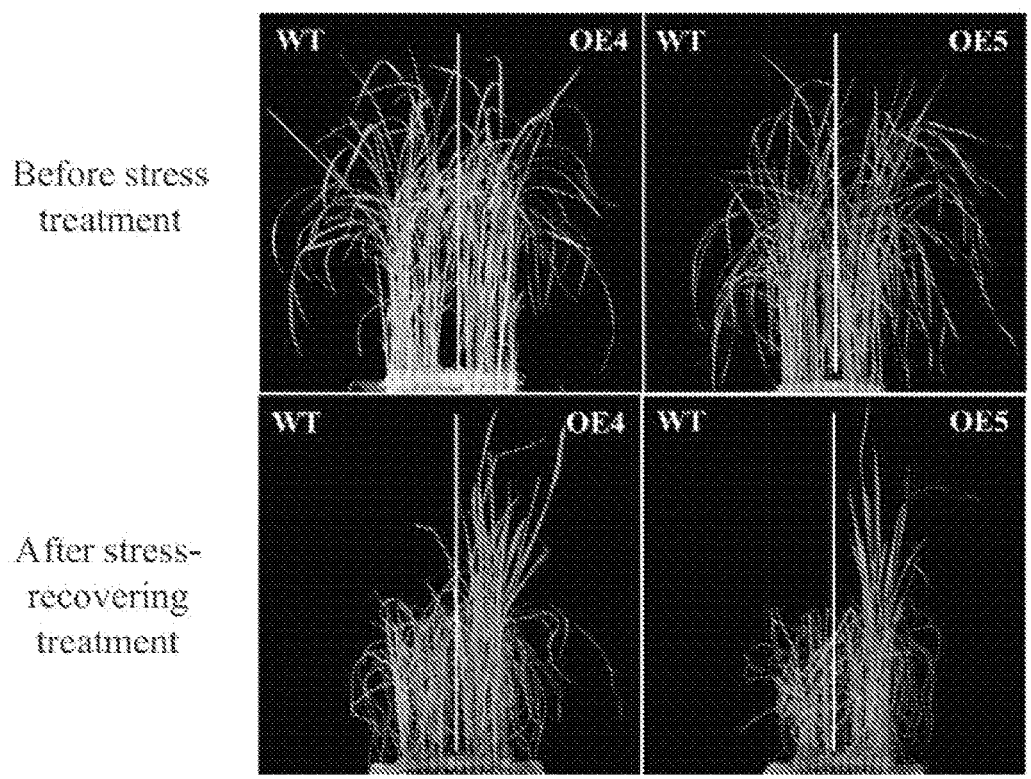

As shown in FIGS. 4A-4B and Table 1, the survival rates of OsCOBL4$_{IRAT109}$ transgenic Nipponbare rice lines and OsERF62$_{IRAT109}$ transgenic Nipponbare rice lines were significantly higher than that of WT Nipponbare rice lines, indicating that overexpression of OsCOBL4 and/or OsERF62 gave rise to enhanced abiotic stress tolerance (more particularly, enhanced drought stress tolerance).

TABLE 1

Survival rates of seedlings grown under
PEG-simulated drought stress conditions.

|  | Plant Line | Survival Rate |
|---|---|---|
| Group 1 | T6 | 92.96 ± 3.53** |
|  | WT | 46.67 ± 3.33 |
| Group 2 | T8 | 66.69 ± 2.17** |
|  | WT | 35.56 ± 2.22 |
| Group 3 | OE4 | 100 ± 0** |
|  | WT | 33.33 ± 6.67 |
| Group 4 | OE5 | 62.22 ± 6.19** |
|  | WT | 10 ± 5.57 |

** = significance at $p < 0.01$ as compared with WT.

Part VIII. Overexpression of OsCOBL4 and OsERF62 Gave Rise to Enhanced Abiotic Stress Tolerance in Rice Plants Grown Under Osmotic Stress Conditions Wild-type lowland rice variety Nipponbare lines (WT) were subjected to osmotic stress conditions, along with three $T_2$-generation OsCOBL4$_{IRAT109}$ transgenic Nipponbare rice lines (T6, T8, T9) and two $T_2$-generation OsERF62$_{IRAT109}$ transgenic Nipponbare rice lines (OE4 and OE5), each of which were positively identified by PCR in Step 5 of Part V.

Seeds of individual plant lines were dehulled and sterilized with 20% NaClO. Seeds of the $T_2$-generation OsCOBL4$_{IRAT109}$ transgenic Nipponbare rice lines (T6, T8, T9) and the $T_2$-generation OsERF62$_{IRAT109}$ transgenic Nipponbare rice lines (OE4 and OE5) were allowed to germinate on ½ MS media containing 50 mg/L hygromycin at 28° C. with a light rhythm of 12-hour illumination and 12-hour darkness every day. WT seeds were allowed to germinate on a ½ MS medium free of hygromycin at 28° C. with a light rhythm of 12-hour illumination and 12-hour darkness every day.

Germinated seeds having the same or substantially the same growth potential under normal conditions were selected and transferred to ½ MS media containing 0 mmol/L or 200 mmol/L mannitol and cultured at 28° C. for 7-10 days with a light rhythm of 12-hour illumination and 12-hour darkness every day. The heights and fresh weights of the plants were measured, the percentage of the heights of the plants treated with 200 mmol/L mannitol to the heights of the plants treated with 0 mmol/L mannitol were calculated and recorded as relative plant heights (%), and the percentages of the fresh weights of the plants treated with 200 mmol/L mannitol to the fresh weights of the plants treated with 0 mmol/L mannitol were calculated and recorded as relative fresh weights (%).

Figure 5A:
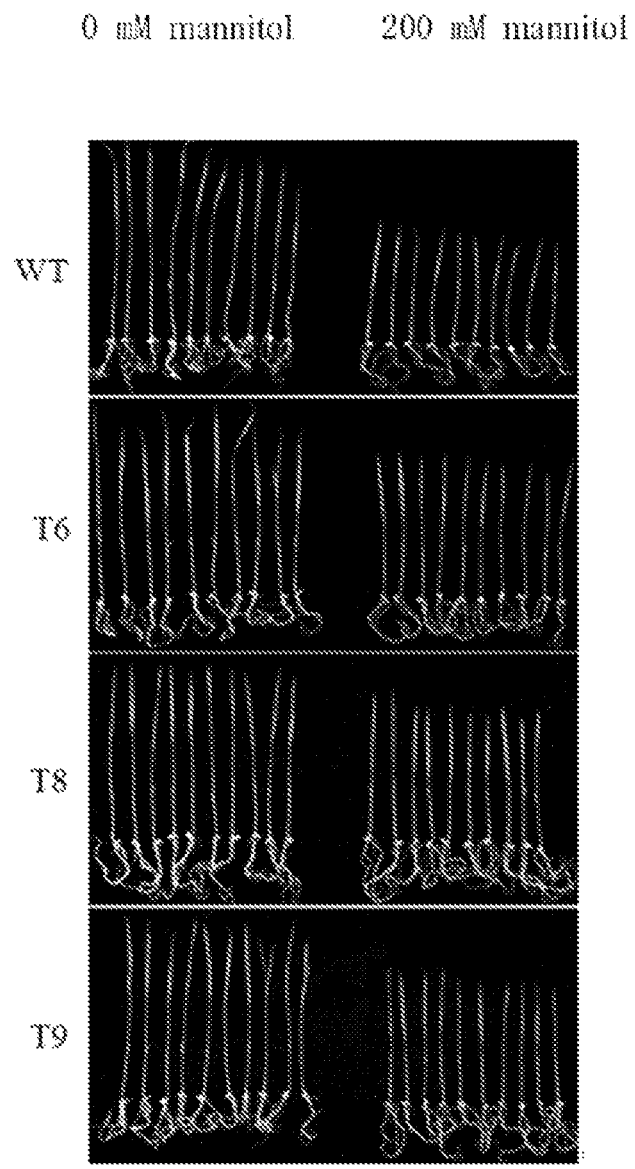
FIG. 5A-5B shows wild-type Nipponbare rice plants (WT), $T_2$-generation OsCOBL4$_{IRAT109}$ transgenic Nipponbare rice plants (T6, T8, T9) and $T_2$-generation OsERF62$_{IRAT109}$ transgenic Nipponbare rice plants (OE4, OE5) before and after mannitol-induced osmotic stress treatment.
Figure 5B:
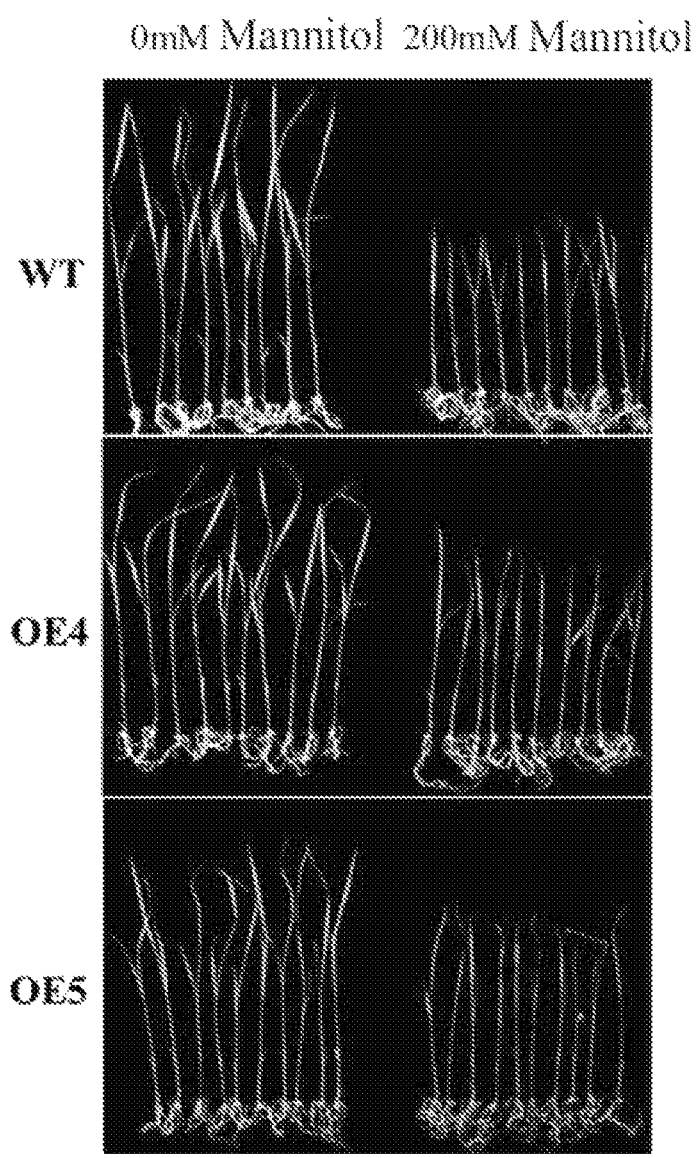

As shown in FIGS. 5A-5B and Table 2 below, the plant heights and fresh weights of the OsCOBL4$_{IRAT109}$ transgenic Nipponbare rice lines and the OsERF62$_{IRAT109}$ transgenic Nipponbare rice lines exposed to 200 mmol/L mannitol were significantly higher than that of WT Nipponbare rice lines, indicating that overexpression of OsCOBL4 and/or OsERF62 gave rise to enhanced abiotic stress tolerance (more particularly, enhanced osmotic stress tolerance).

TABLE 2

Growth of seedlings grown under mannitol-
induced osmotic stress conditions.

|  | Plant Line | Relative Height | Relative Weight |
|---|---|---|---|
| Group 1 | WT | 68.03 ± 1.15 | 72.79 ± 2.85 |
|  | T6 | 81.90 ± 1.86** | 91.93 ± 4.10** |
|  | T8 | 76.95 ± 1.93** | 94.78 ± 3.61** |
|  | T9 | 75.18 ± 1.41** | 97.73 ± 2.72** |
| Group 2 | WT | 58.72 ± 1.19 | 76.93 ± 3.74 |
|  | OE4 | 63.22 ± 1.78** | 88.15 ± 3.67** |
|  | OE5 | 75.90 ± 3.07** | 97.96 ± 5.17** |

** = significance at $p < 0.01$ as compared with WT.

Part IX. Overexpression of OsCOBL4 and OsERF62 Gave Rise to Enhanced Abiotic Stress Tolerance in Rice Plants Grown Under Drought Stress Conditions Wild-type lowland rice variety Nipponbare lines (WT) were subjected to drought stress conditions, along with three $T_2$-generation OsCOBL4$_{IRAT109}$ transgenic Nipponbare rice lines (T6, T8, T9) and two $T_2$-generation OsERF62$_{IRAT109}$ transgenic Nipponbare rice lines (OE4 and OE5), each of which were positively identified by PCR in Step 5 of Part V.

Seeds of individual plant lines were sterilized with 20% NaClO. Seeds of the $T_2$-generation OsCOBL4$_{IRAT109}$ transgenic Nipponbare rice lines (T6, T8, T9) and the $T_2$-generation OsERF62$_{IRAT109}$ transgenic Nipponbare rice lines (OE4 and OE5) were soaked in sterile water containing 50 mg/L hygromycin for 2 days. WT seeds were soaked in sterile water free of hygromycin for 2 days. The soaked seeds were washed with sterile water containing 50 mg/L hygromycin, and forced to germinate for 2-3 days after excess water was removed. The soaked seeds were washed with sterile water containing 50 mg/L hygromycin, and forced to germinate for 3-4 days after excess water was removed.

Seeds having the same or substantially the same growth potential under normal conditions were selected and transplanted into flower pots. Fifteen WT, T6, T8, T9, OE4 or OE5 plants were planted in each pot and grown under normal conditions unto they grew to the four-leaf stage, at which point the plants were subjected to a water shortage (i.e., were not watered) for one week and then rehydration for 10 days. The number of surviving plants was counted, and the survival rates (i.e., the percentage of the number of surviving plants to the total number of plants subjected to the stress treatment) were calculated.

Figure 6A:
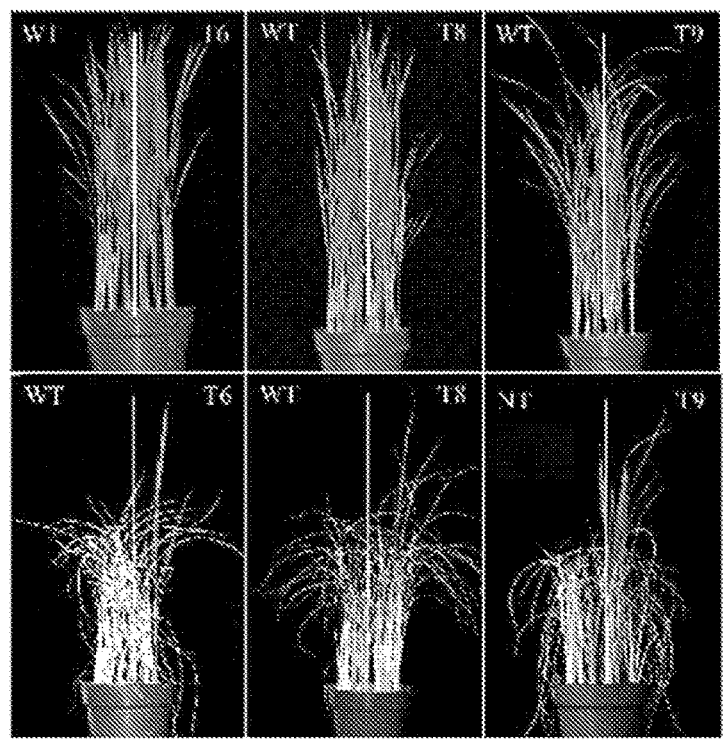
FIG. 6A-6B show wild-type Nipponbare rice plants (WT), $T_2$-generation OsCOBL4$_{IRAT109}$ transgenic Nipponbare rice plants (T6, T8, T9) and $T_2$-generation OsERF62$_{IRAT109}$ transgenic Nipponbare rice plants (OE4, OE5) before and after drought stress treatment.
Figure 6B:
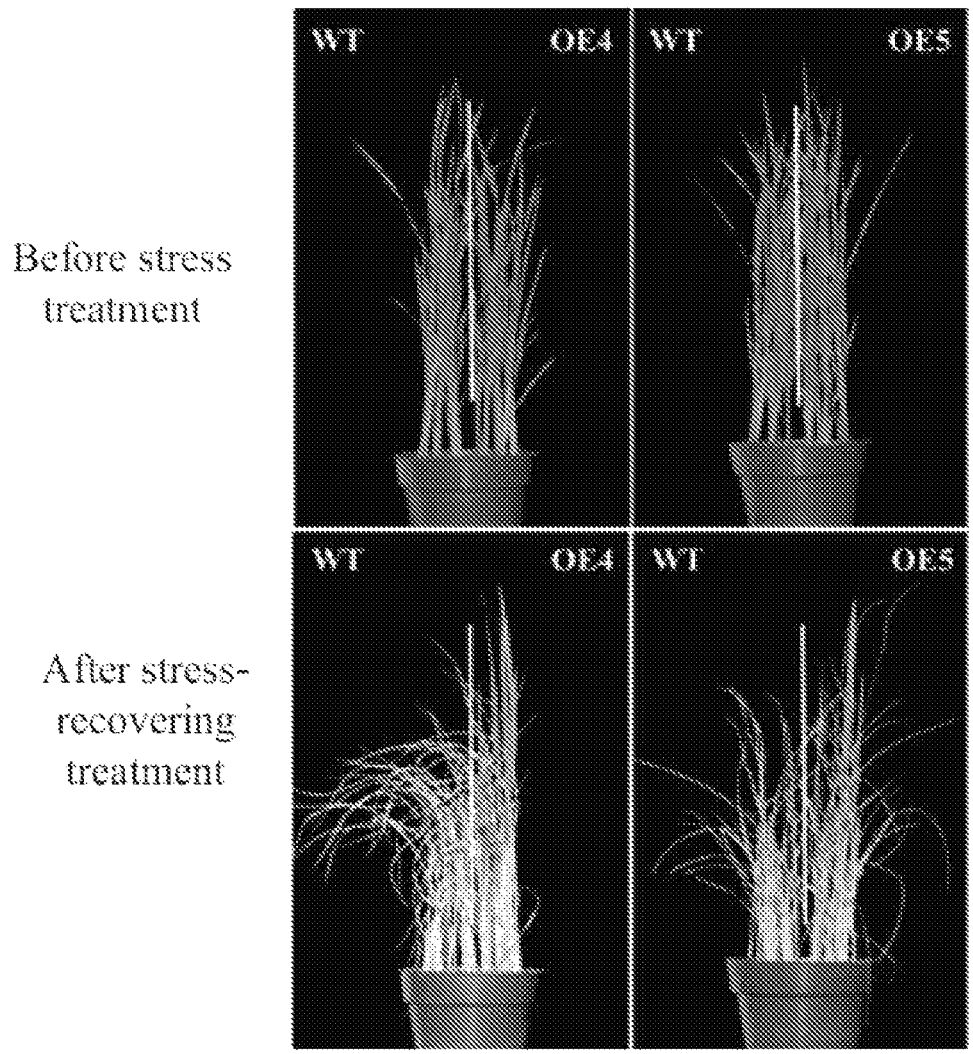

As shown in FIGS. 6A-6B and Table 3 below, the survival rates of OsCOBL4$_{IRAT109}$ transgenic Nipponbare rice lines and OsERF62$_{IRAT109}$ transgenic Nipponbare rice lines were significantly higher than that of WT Nipponbare rice lines, indicating that overexpression of OsCOBL4 and/or OsERF62 gave rise to enhanced abiotic stress tolerance (more particularly, enhanced drought stress tolerance).

TABLE 3

Survival rates of seedlings grown
under drought stress conditions.

|  | Plant Line | Survival Rate |
|---|---|---|
| Group 1 | T6 | 41.67 ± 10.14* |
|  | WT | 6.67 ± 6.67 |
| Group 2 | T8 | 43.33 ± 3.33** |
|  | WT | 13.33 ± 6.67 |
| Group 3 | T9 | 56.67 ± 3.33** |
|  | WT | 21.67 ± 1.67 |

TABLE 3-continued

Survival rates of seedlings grown under drought stress conditions.

| | Plant Line | Survival Rate |
|---|---|---|
| Group 4 | OE4 | 93.33 ± 6.67** |
| | WT | 28.33 ± 6.01 |
| Group 5 | OE5 | 46.67 ± 21.67* |
| | WT | 21.67 ± 1.67 |

\* = significance at p < 0.05 as compared with WT.
\*\* = significance at p < 0.01 as compared with WT.

Thus, it was shown that both OsCOBL4 and OsERF62 give rise to enhanced abiotic stress tolerance (more particularly, enhanced drought tolerance and enhanced osmotic stress tolerance).

Example 2

Over-expression of OsCOBL4 Enhances Abiotic Stress Tolerance

As shown in FIGS. 13A-17C, overexpression of $OsCOBL4_{IRAT109}$ or $OsCOBL4_{Nipponbare}$ gave rise to enhanced abiotic stress tolerance in transgenic rice plants.

Part I. Bioinformatic Analysis of OsCOBL4

Figure 7:
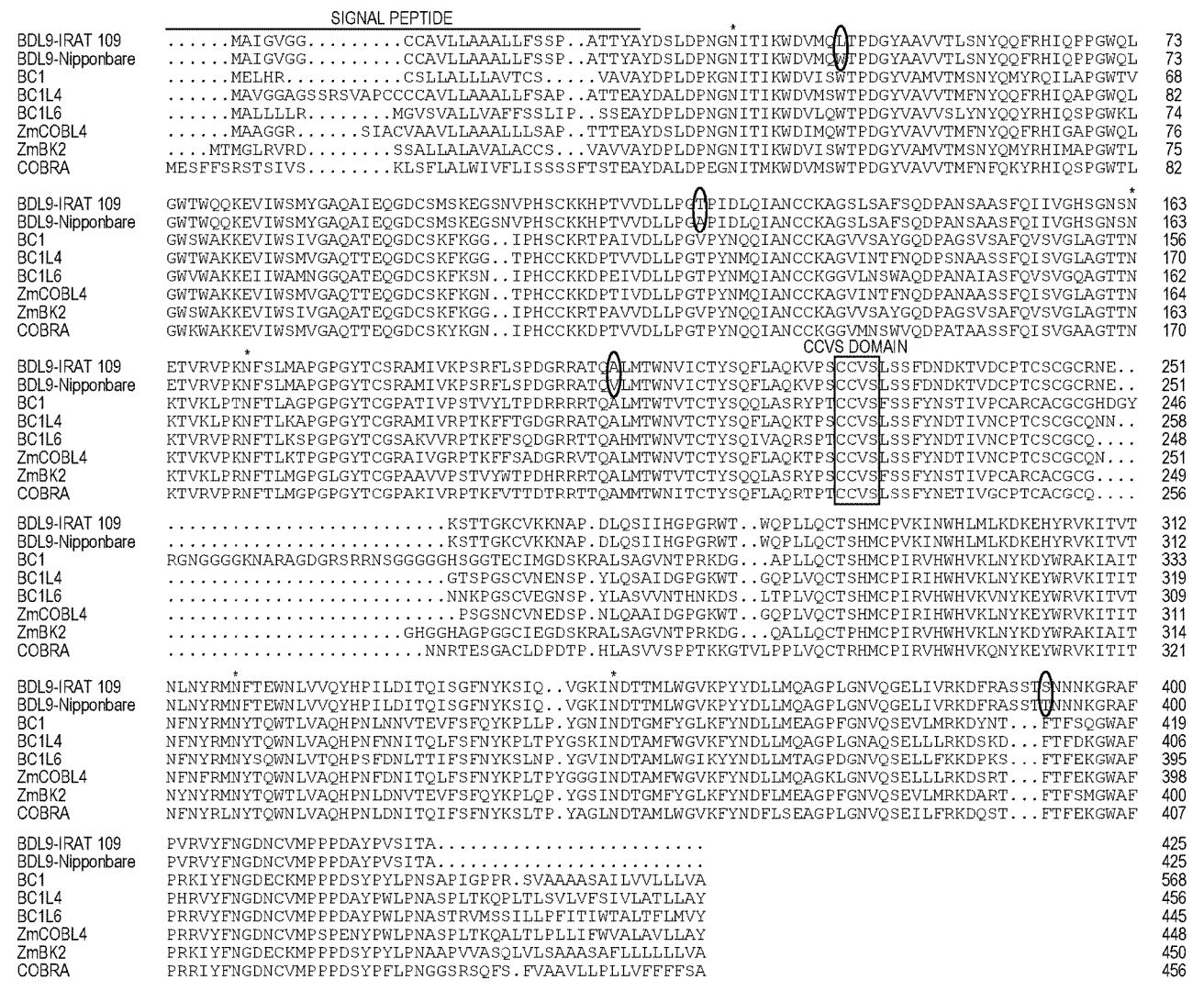
Figure 8:
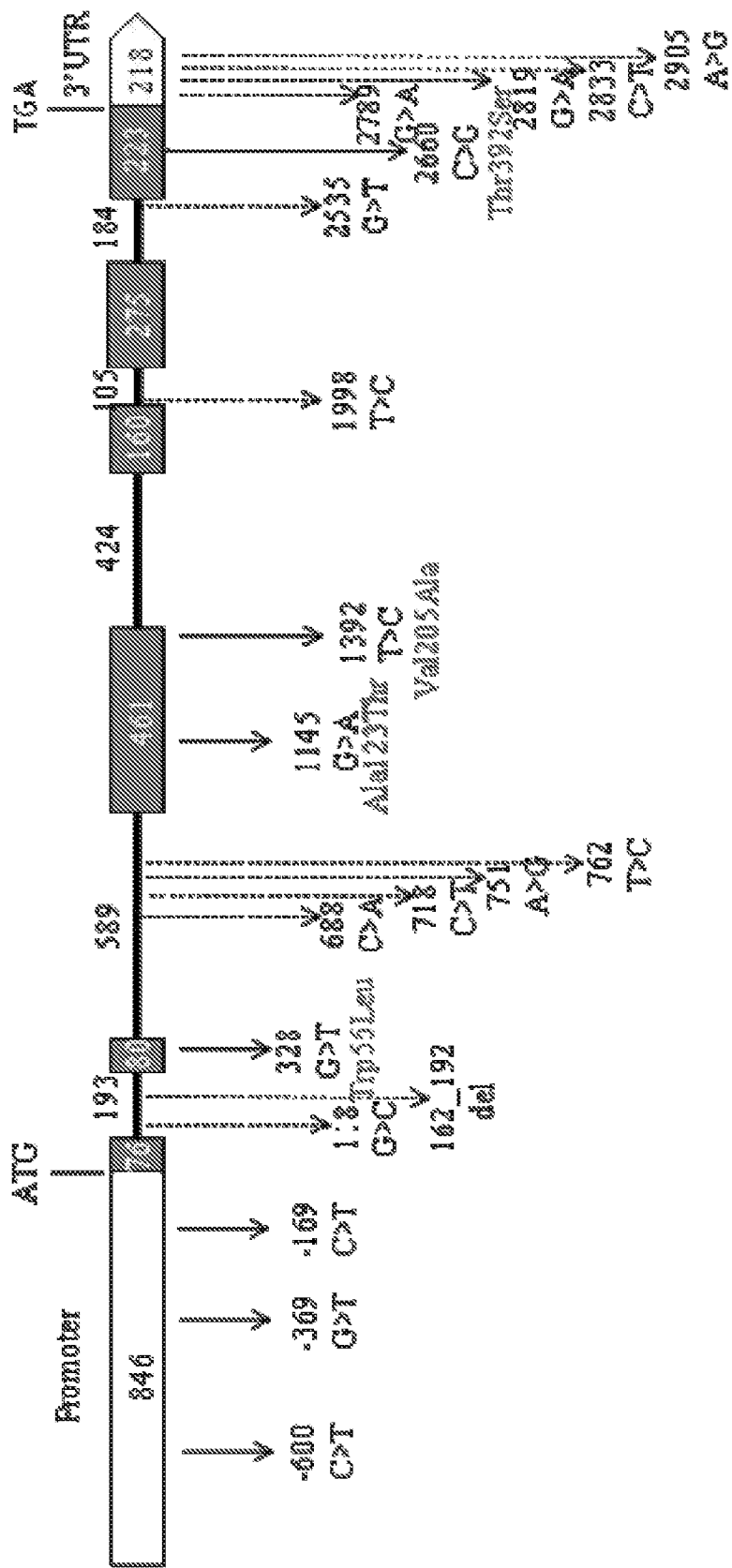
FIG. 8 shows the variation between OsCOBL4$_{IRAT109}$ and OsCOBL4$_{Nipponbare}$.

OsCOBL4 encodes a protein that comprises 425 amino acids and that has an N-terminal signal peptide sequence and a CCVS domain, which are both typical of proteins belonging to the COBRA family. FIG. 7. Both the nucleotide and amino acid sequences of OsCOBL4 vary between typical upland rice varieties (e.g., IRAT109 and Haogelao) and lowland rice varieties (e.g., Nipponbare and Yuefu): three SNPs in the promoter region; four SNPs in the exon region, which lead to the variation of four amino acids; seven SNPs and 1 Indel in the introns; and four SNPs in the 3'UTR. FIG. 8.

Figure 9A:
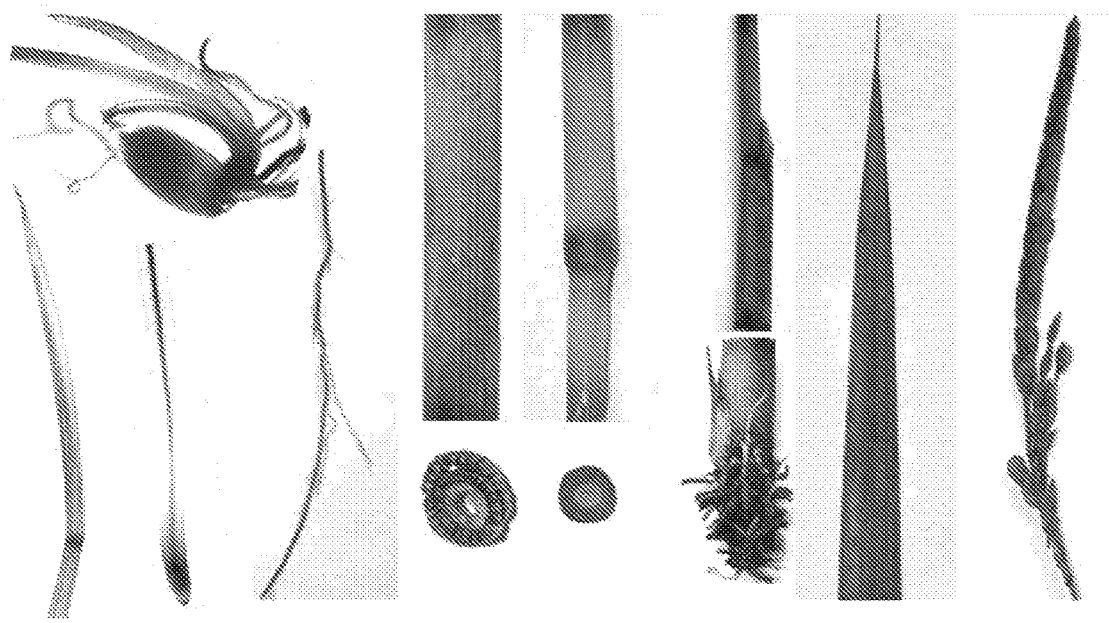
FIG. 9A shows tissues from Pro$_{COBL4-IRAT109}$::GUS transgenic IRAT109 rice plants and Pro$_{COBL4-IRAT109}$::GUS transgenic Nipponbare rice plants following GUS staining.
Figure 9B:
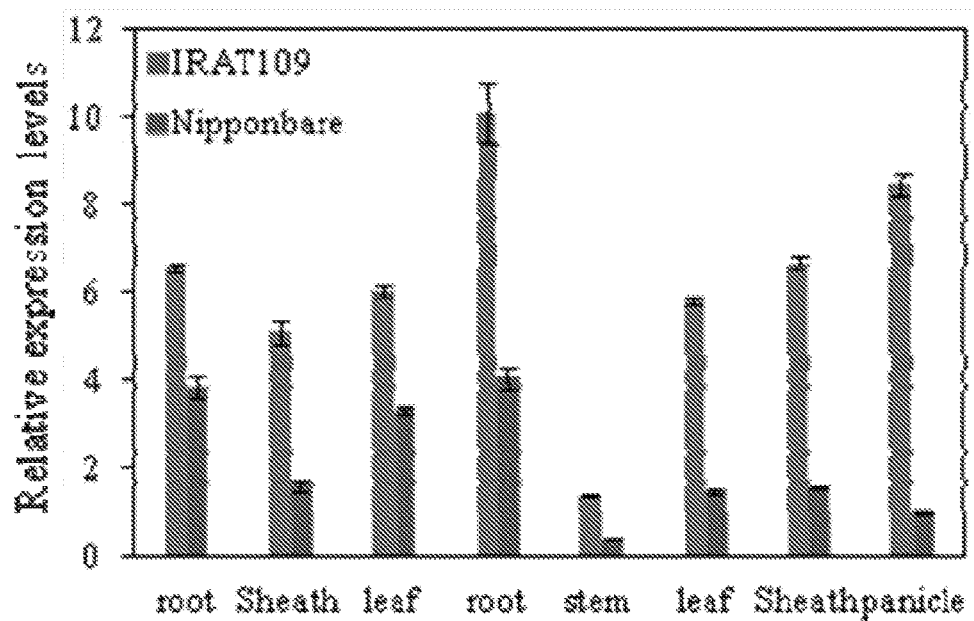
FIG. 9B is a graph showing the results of real-time fluorescence quantitative PCR analyses of the relative expression levels of OsCOBL4 in Pro$_{COBL4-IRAT109}$::GUS transgenic IRAT109 rice plants and Pro$_{COBL4-IRAT109}$::GUS transgenic Nipponbare rice plants. The standard error bars shown therein are based on three replicates.
Figure 10:
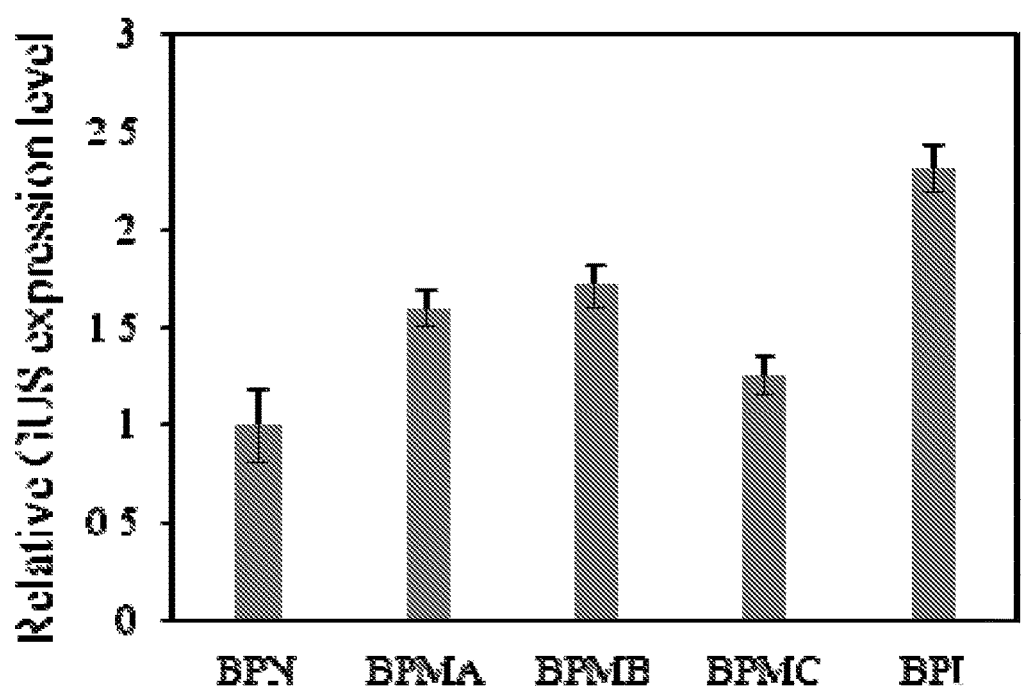
FIG. 10 is a graph showing the results of real-time fluorescence quantitative PCR analyses of the relative expression levels of GUS in Pro$_{Nipponbare}$::GUS transgenic Nipponbare rice plants (BPN), Pro$_{IRAT109e}$::GUS transgenic Nipponbare rice plants (BPI), Pro$_{Nipponbare\ (-600C>T)}$::GUS transgenic Nipponbare rice plants (BPMA), Pro$_{Nipponbare\ (-369G>T)}$::GUS transgenic Nipponbare rice plants (BPMB), and Pro$_{Nipponbare\ (-169C>T)}$::GUS transgenic Nipponbare rice plants (BPMC).

Part II. Expression Pattern of $OsCOBL4_{IRAT109}$ in Various Tissues and Organs of Plants GUS staining was performed on various tissues and organs of $Pro_{COBL4IRAT109}$::GUS transgenic IRAT rice plants and $Pro_{COBL4IRAT109}$::GUS transgenic Nipponbare rice plants. As shown in FIG. 9A, $OsCOBL4_{IRAT109}$ was expressed at the seedling stage in the root, sheath, and leaf, and at the reproductive stage in the root, sheath, vascular bundle, stem, node, ligule, leaf and panicle. As shown in FIG. 9B, the expression of $OsCOBL4_{IRAT109}$ in IRAT109 was relatively low in the stem at the productive stage, was more highly expressed in the root, sheath, and leaf at the seedling stage, and in the root, leaf, sheath, and panicle at the productive stage. Also as shown in FIG. 9B, the expression of $OsCOBL4_{IRAT109}$ in Nipponbare was generally lower than in IRAT109, with higher expression in the root and leaf at the seedling stage and in the root at the productive stage, with low expression in the stem at the productive stage. Thus, it was observed that OsCOBL4 was constitutively expressed in various tissues and organs of IRAT109 and Nipponbare, that expression levels differed with respect to both tissue and reproductive stage, and that expression was generally higher in IRAT109 that in Nipponbare.

Part III. Differences in the Expression Patterns of $OsCOBL4_{IRAT109}$ and $OsCOBL4_{Nipponbare}$ May be Explained by Differences in their Respective Promoter Regions As noted in Part I above, the promoter region of OsCOBL4 varies contains three SNPs with respect to upland rice variety IRAT109 and lowland rice variety Nipponbare. In order to determine whether those three SNPs were responsible for the differences in expression levels seen in Part III, five Pro:: GUS vectors were constructed: BPN ($Pro_{Nipponbare}$::GUS), BPI ($Pro_{IRAT109}$::GUS), BPMA ($Pro_{Nipponbare\ (-600C>T)}$::GUS), BPMB ($Pro_{Nipponbare\ (-369G>T)}$::GUS), and BPMC ($Pro_{Nipponbare\ (-169C>T)}$::GUS). The five vectors were transferred into Nipponbare through Agrobacterium-mediated transformation, and single copies of homozygous $T_2$ generation line were obtained. Quantitative PCR analysis of the expression level of the GUS gene was performed to reflect the initiation capabilities of the five promoters by the magnitude of the expression of the GUS gene. The results showed that the expression level of GUS in the BPI transgenic plants was the highest, followed by that of BPMB, BPMA, and BPMC, and GUS is lowest expressed in BPN. FIG. 9. It was postulated that the three SNP variations in the promoter region led to the different expression level of the OsCOBL4 between the upland rice variety IRAT109 and lowland rice variety Nipponbare and that each contributed to the increase of the expression to some degree.

Part IV. Subcellular Localization of $OsCOBL4_{IRAT109}$

Figure 11:
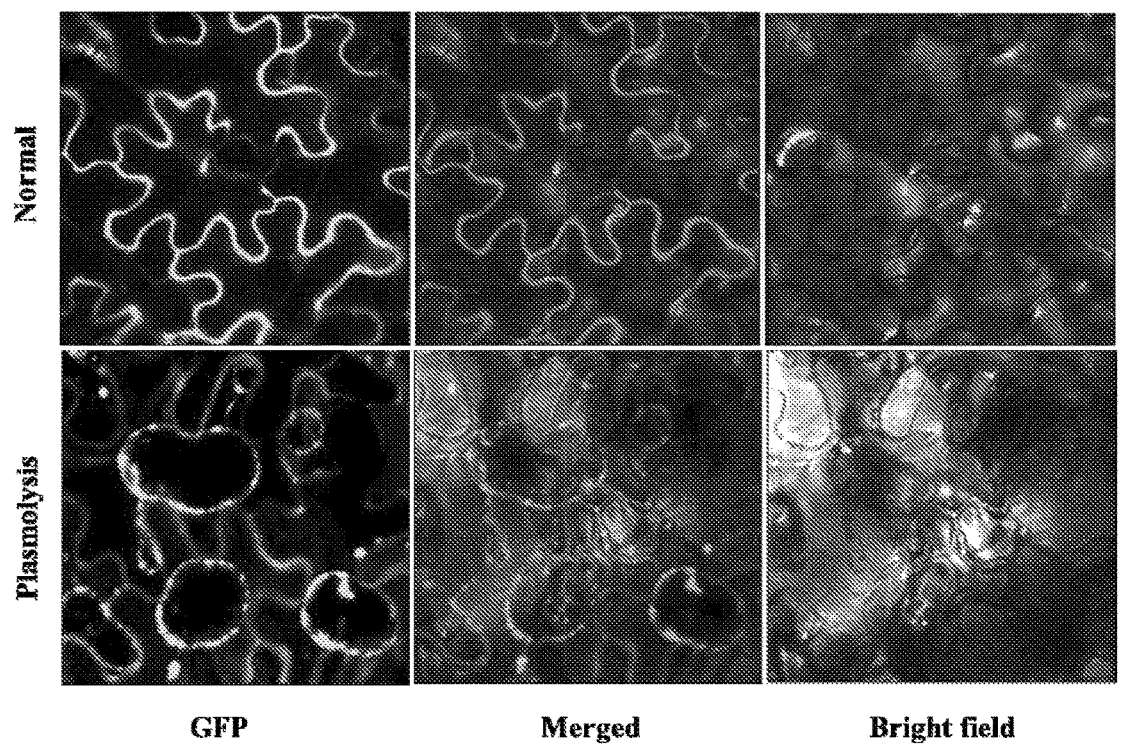
FIG. 11 shows the subcellular localization of GFP-fusedI-RAT109 OsCOBL4$_{IRAT109}$ in N. benthamiana leaves following Agrobacterium-mediated transformation. Leaves were treated with 10% NaCl to separate cell walls and protoplasts.

For determining the subcellular localization of COBL4, $OsCOBL4_{IRAT109}$ was ligated into a pMDC83 vector to produce a GFP-$OsCOBL4_{IRAT109}$ expression vector. The GFP-$OsCOBL4_{IRAT109}$ expression vector transferred into tobacco plants through Agrobacterium-mediated transformation. As shown in FIG. 11, GFP-$OsCOBL4_{IRAT109}$ was expressed in the cell membranes and cell walls of the tobacco plants.

Figure 12:
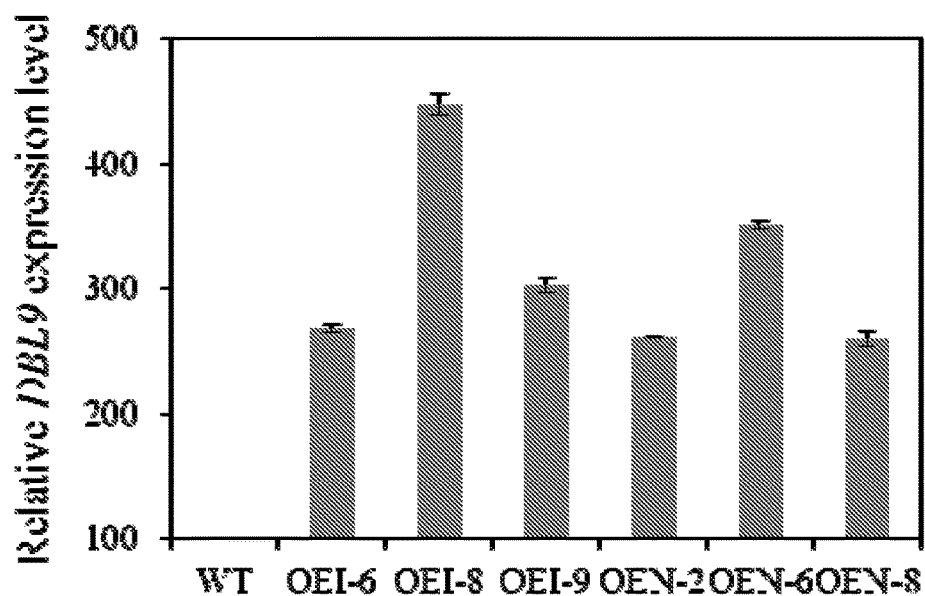
FIG. 12 is a graph showing the relative expression levels of OsCOBL4 (referred to as DBL9 I the figure legend) in wild-type Nipponbare rice plants (WT), IRAT109 OsCOBL4$_{IRAT109}$ transgenic Nipponbare rice plants (OEI-6, OEI-8, OEI-9) and OsCOBL4$_{Nipponbare}$ transgenic Nipponbare rice plants (OEN-2, OEN-6, OEN-8).

Part V. Overexpression of $OsCOBL4_{IRAT109}$ and $OsCOBL4_{Nipponbare}$ Gave Rise to Enhanced Abiotic Stress Tolerance in Rice Plants Grown Under Abiotic Stress Conditions $OsCOBL4_{IRAT109}$ and $OsCOBL4_{Nipponbare}$ were isolated and amplified as described in Example 1, Part II, ligated into a pMDC32 vector as described in Example 1, Part III, transformed into Agrobacterium tumefaciens EHA105 as described in Example I, Part IV, and introduced into Nipponbare rice plants as described in Example I, Part V. FIG. 12 shows the relative OsCOBL4 expression levels in wild-type Nipponbare rice plants (WT), $OsCOBL4_{IRAT109}$ transgenic Nipponbare rice plants (OEI-6, OEI-8, OEI-9) and $OsCOBL4_{Nipponbare}$ transgenic Nipponbare rice plants (OEN-2, OEN-6, OEN-8).

Figure 13A:
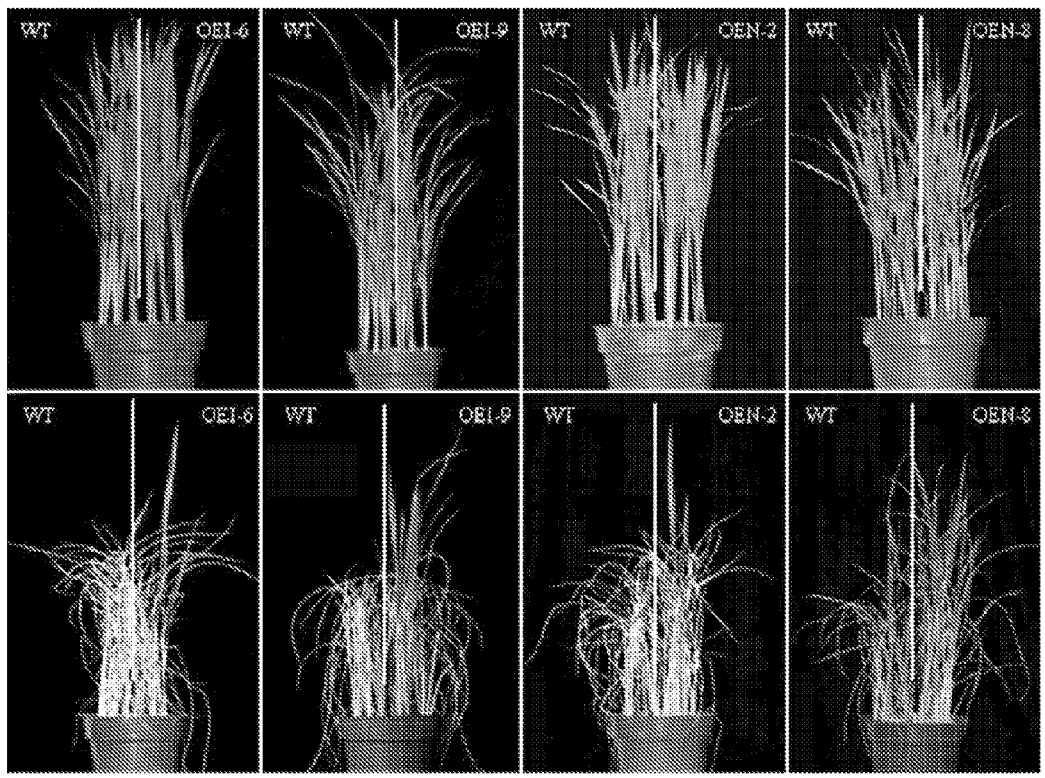
FIG. 13A shows wild-type Nipponbare rice plants (WT), IRAT109 OsCOBL4$_{IRAT109}$ transgenic Nipponbare rice plants (OEI-6, OEI-9) and OsCOBL4$_{Nipponbare}$ transgenic Nipponbare rice plants (OEN-2, OEN-8) before (upper panels) and after (lower panels) drought stress treatment.
Figure 13B:
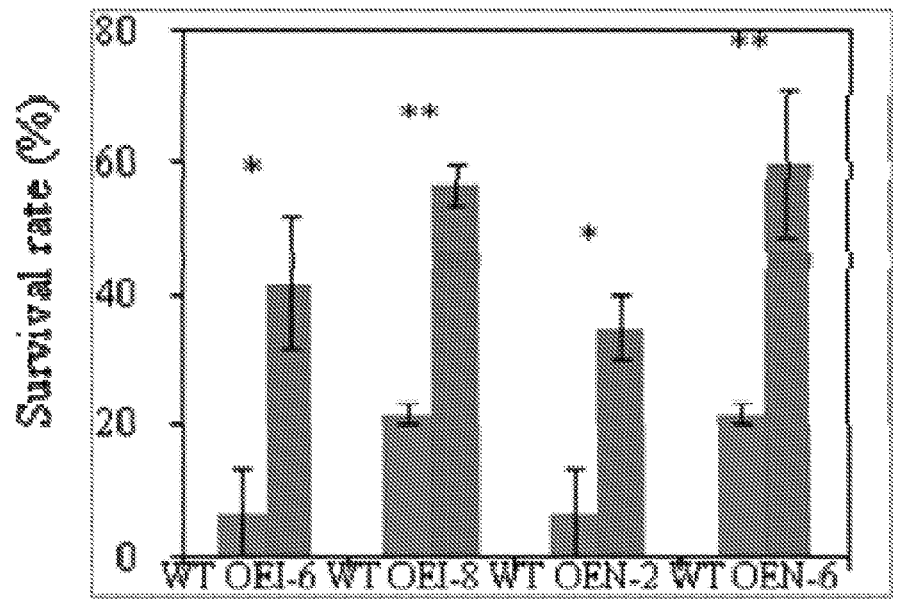
FIG. 13B is a graph showing the survival rates of wild-type Nipponbare rice plants (WT), IRAT109 OsCOBL4$_{IRAT109}$ transgenic Nipponbare rice plants (OEI-6, OEI-8) and OsCOBL4$_{Nipponbare}$ transgenic Nipponbare rice plants (OEN-2, OEN-6) following drought stress treatment. The standard error bars shown therein are based on three replicates. *=significance at p<0.05. **=significance at p<0.01.

Overexpression of $OsCOBL4_{IRAT109}$ and $OsCOBL4_{Nipponbare}$ Gave Rise to Enhanced Abiotic Stress Tolerance in Rice Plants Grown Under Drought Stress Conditions Wild-type Nipponbare lines (WT), $T_2$-generation $OsCOBL4_{IRAT109}$ transgenic Nipponbare rice lines (OEI) and $T_2$-generation $OsCOBL4_{Nipponbare}$ are transgenic Nipponbare rice lines (OEN) were subjected to drought stress conditions as described in Example 1, Part IX. As shown in FIG. 13 and Table 4 below, the survival rates of the OEI and OEN lines were significantly higher than that of WT lines, indicating that overexpression of both $OsCOBL4_{IRAT109}$ and $OsCOBL4_{Nipponbare}$ gives rise to enhanced abiotic stress tolerance (more particularly, enhanced drought stress tolerance).

TABLE 4

Survival rates of seedlings grown under drought stress conditions.

| | Plant Line | Survival Rate |
|---|---|---|
| Group 1 | OEI | 56.67%-68%** |
| | WT | 6.67%-15% |
| Group 2 | OEN | 43.33%-80%** |
| | WT | 6.67%-28.33% |

\* = significance at $p < 0.05$ as compared with WT.
\*\* = significance at $p < 0.01$ as compared with WT.

Figure 14A:
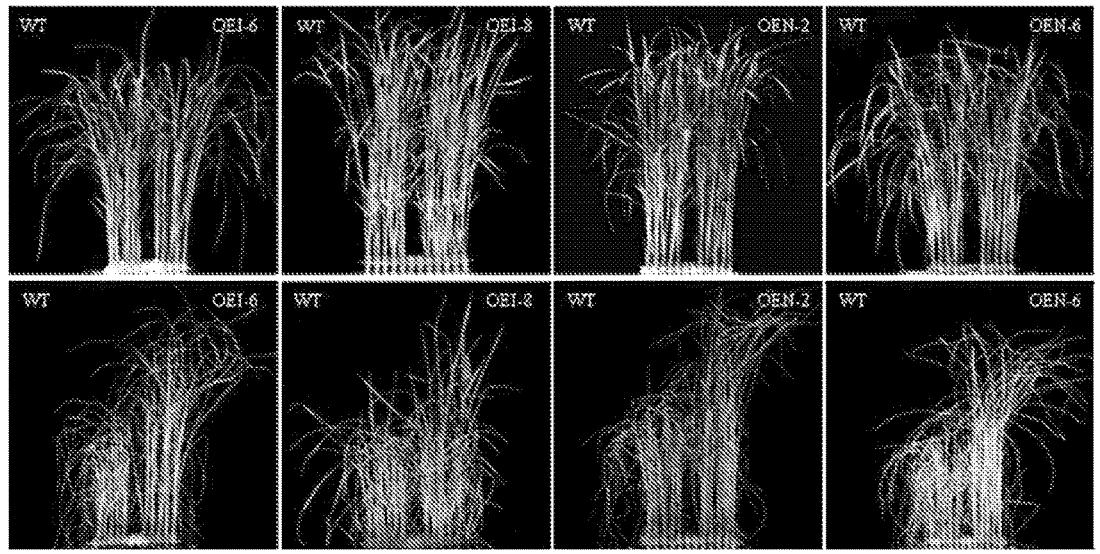
FIG. 14A shows wild-type Nipponbare rice plants (WT), OsCOBL4$_{IRAT109}$ transgenic Nipponbare rice plants (OEI-6, OEI-8) and OsCOBL4$_{Nipponbare}$ transgenic Nipponbare rice plants (OEN-2, OEN-6) before and after physiological dehydration stress treatment.
Figure 14B:
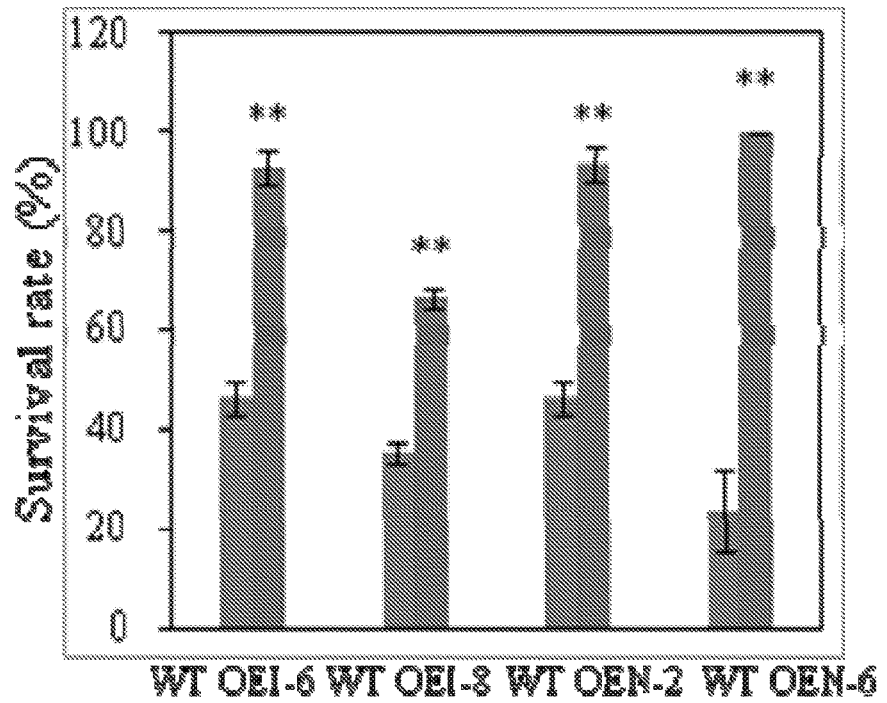
FIG. 14B is a graph showing the survival rates of wild-type Nipponbare rice plants (WT), OsCOBL4$_{IRAT109}$ transgenic Nipponbare rice plants (OEI-6, OEI-8) and OsCOBL4$_{Nipponbare}$ transgenic Nipponbare rice plants (OEN-2, OEN-6) following physiological dehydration drought stress treatment. The standard error bars shown therein are based on three replicates. *=significance at p<0.05. **=significance at p<0.01.

Overexpression of OsCOBL4$_{IRAT109}$ and OsCOBL4$_{Nipponbare}$ Gave Rise to Enhanced Abiotic Stress Tolerance in Rice Plants Grown Under Simulated Drought Stress Conditions Wild-type Nipponbare lines (WT), T$_2$-generation OsCOBL4$_{IRAT109}$ transgenic Nipponbare rice lines (OEI) and T$_2$-generation OsCOBL4$_{Nipponbare}$ are transgenic Nipponbare rice lines (OEN) were subjected to PEG-simulated drought stress conditions as described in Example 1, Part VII. As shown in FIG. 14 and Table 5 below, the survival rates of the OEI and OEN lines were significantly higher than that of WT lines, indicating that overexpression of both OsCOBL4$_{IRAT109}$ and OsCOBL4$_{Nipponbare}$ gave rise to enhanced abiotic stress tolerance (more particularly, enhanced drought stress tolerance).

TABLE 5

Survival rates of seedlings grown under PEG-simulated drought stress conditions.

| | Plant Line | Survival Rate |
|---|---|---|
| Group 1 | OEI | 66.39%-92.96%** |
| | WT | 35.55%-46.67% |
| Group 2 | OEN | 93.33%-100%** |
| | WT | 23.77%-46.67% |

\*\* = significance at $p < 0.01$ as compared with WT.

Figure 15:
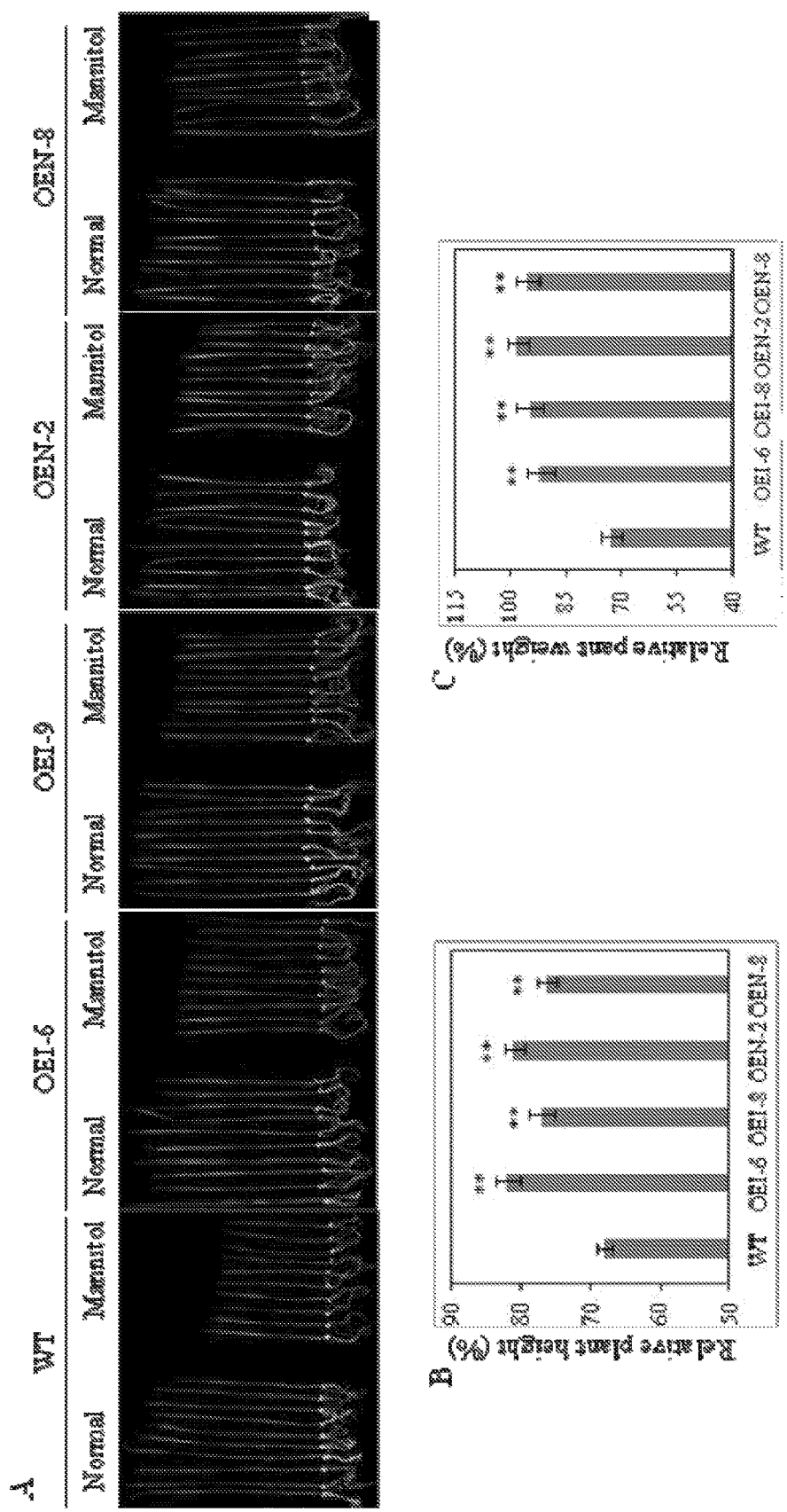
FIG. 15A shows wild-type Nipponbare rice plants (WT), OsCOBL4$_{IRAT109}$ transgenic Nipponbare rice plants (OEI-6, OEI-9) and OsCOBL4Nipponbare transgenic Nipponbare rice plants (OEN-2, OEN-8) following a control treatment (Normal) or an osmotic stress treatment (Mannitol).
FIG. 15B is a graph showing the relative heights of wild-type Nipponbare rice plants (WT), OsCOBL4$_{IRAT109}$ transgenic Nipponbare rice plants (OEI-6, OEI-8) and OsCOBL4$_{Nipponbare}$ transgenic Nipponbare rice plants (OEN-2, OEN-8) following an osmotic stress treatment. The standard error bars shown therein are based on three replicates. *=significance at p<0.05. **=significance at p<0.01.
FIG. 15C is a graph showing the relative weights of wild-type Nipponbare rice plants (WT), OsCOBL4$_{IRAT109}$ transgenic Nipponbare rice plants (OEI-6, OEI-8) and OsCOBL4$_{Nipponbare}$ transgenic Nipponbare rice plants (OEN-2, OEN-8) following an osmotic stress treatment. The standard error bars shown therein are based on three replicates. *=significance at p<0.05. **=significance at p<0.01.

Overexpression of OsCOBL4$_{IRAT109}$ and OsCOBL4$_{Nipponbare}$ Gave Rise to Enhanced Abiotic Stress Tolerance in Rice Plants Grown Under Osmotic Stress Conditions Wild-type Nipponbare lines (WT), T$_2$-generation OsCOBL4$_{IRAT109}$ transgenic Nipponbare rice lines (OEI) and T$_2$-generation OsCOBL4 Nipponbare transgenic Nipponbare rice lines (OEN) were subjected to drought stress conditions as described in Example 1, Part VIII. As shown in FIG. 15 and Table 6 below, the plant heights and fresh weights of the OEI and OEN lines were significantly higher than that of WT lines, indicating that overexpression of both OsCOBL4$_{IRAT109}$ and OsCOBL4$_{Nipponbare}$ gave rise to enhanced abiotic stress tolerance (more particularly, enhanced osmotic stress tolerance).

TABLE 6

Growth of seedlings grown under mannitol-induced osmotic stress conditions.

| Plant Line | Relative Height | Relative Weight |
|---|---|---|
| WT | 68.03% | 72.8% |
| OEI6 | 81.91%** | 91.93%** |
| OEI8 | 76.95%** | 94.78%** |
| OEN2 | 81.03%** | 98.03%** |
| OEN8 | 76.39%** | 95.34%** |

\*\* = significance at $p < 0.01$ as compared with WT.

Figure 16:
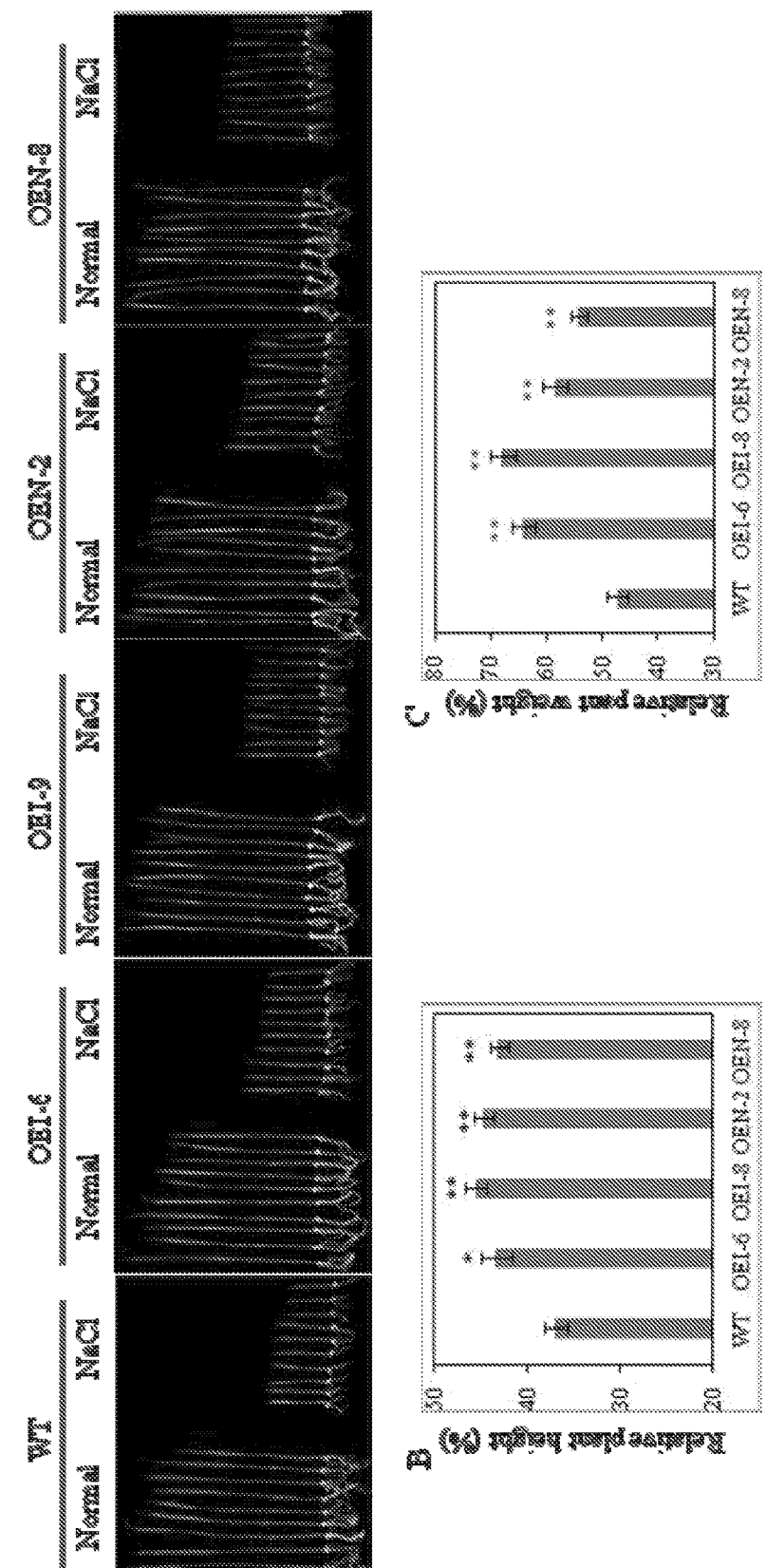
FIG. 16A shows wild-type Nipponbare rice plants (WT), OsCOBL4$_{IRAT109}$ transgenic Nipponbare rice plants (OEI-6, OEI-9) and OsCOBL4$_{Nipponbare}$ transgenic Nipponbare rice plants (OEN-2, OEN-8) following a control treatment (Normal) or a salt stress treatment (NaCl).
FIG. 16B is a graph showing the relative heights of wild-type Nipponbare rice plants (WT), OsCOBL4$_{IRAT109}$ transgenic Nipponbare rice plants (OEI-6, OEI-8) and OsCOBL4$_{Nipponbare}$ transgenic Nipponbare rice plants (OEN-2, OEN-8) following salt stress treatment. The standard error bars shown therein are based on three replicates. *=significance at p<0.05. **=significance at p<0.01.
FIG. 16C is a graph showing the relative weights of wild-type Nipponbare rice plants (WT), OsCOBL4$_{IRAT109}$ transgenic Nipponbare rice plants (OEI-6, OEI-8) and OsCOBL4$_{Nipponbare}$ transgenic Nipponbare rice plants (OEN-2, OEN-8) following salt stress treatment. The standard error bars shown therein are based on three replicates. *=significance at p<0.05. **=significance at p<0.01.

Overexpression of OsCOBL4$_{IRAT109}$ and OsCOBL4$_{Nipponbare}$ Gave Rise to Enhanced Abiotic Stress Tolerance in Rice Plants Grown Under Salt Stress Conditions Wild-type Nipponbare lines (WT), T$_2$-generation OsCOBL4$_{IRAT109}$ transgenic Nipponbare rice lines (OEI) and T$_2$-generation OsCOBL4 Nipponbare transgenic Nipponbare rice lines (OEN) were subjected to salt stress conditions as follows: Seedlings that normally germinated for 2-3 days and had uniform growth were transferred to a ½ MS medium containing 0 and 150 mmol/L NaCl, respectively. The plants were grown for 7 d in a light incubator, and then measured for the shoot length and fresh weight. The relative shoot length and fresh weight prior and post stress treatment were used as evaluation criteria. As shown in FIG. 16 and Table 7 below, the plant heights and fresh weights of the OEI and OEN lines were significantly higher than that of WT lines, indicating that overexpression of both OsCOBL4$_{IRAT109}$ and OsCOBL4$_{Nipponbare}$ gave rise to enhanced abiotic stress tolerance (more particularly, enhanced salt stress tolerance).

TABLE 7

Growth of seedlings grown under salt stress conditions.

| Plant Line | Relative Height | Relative Weight |
|---|---|---|
| WT | 36.93% | 47.32% |
| OEI6 | 43.3%** | 64.08%** |
| OEI8 | 45.48%** | 67.88%** |
| OEN2 | 44.68%** | 58.43%** |
| OEN8 | 43.05%** | 54.3%** |

\* = significance at $p < 0.05$ as compared with WT.
\*\* = significance at $p < 0.01$ as compared with WT.

Figure 17:
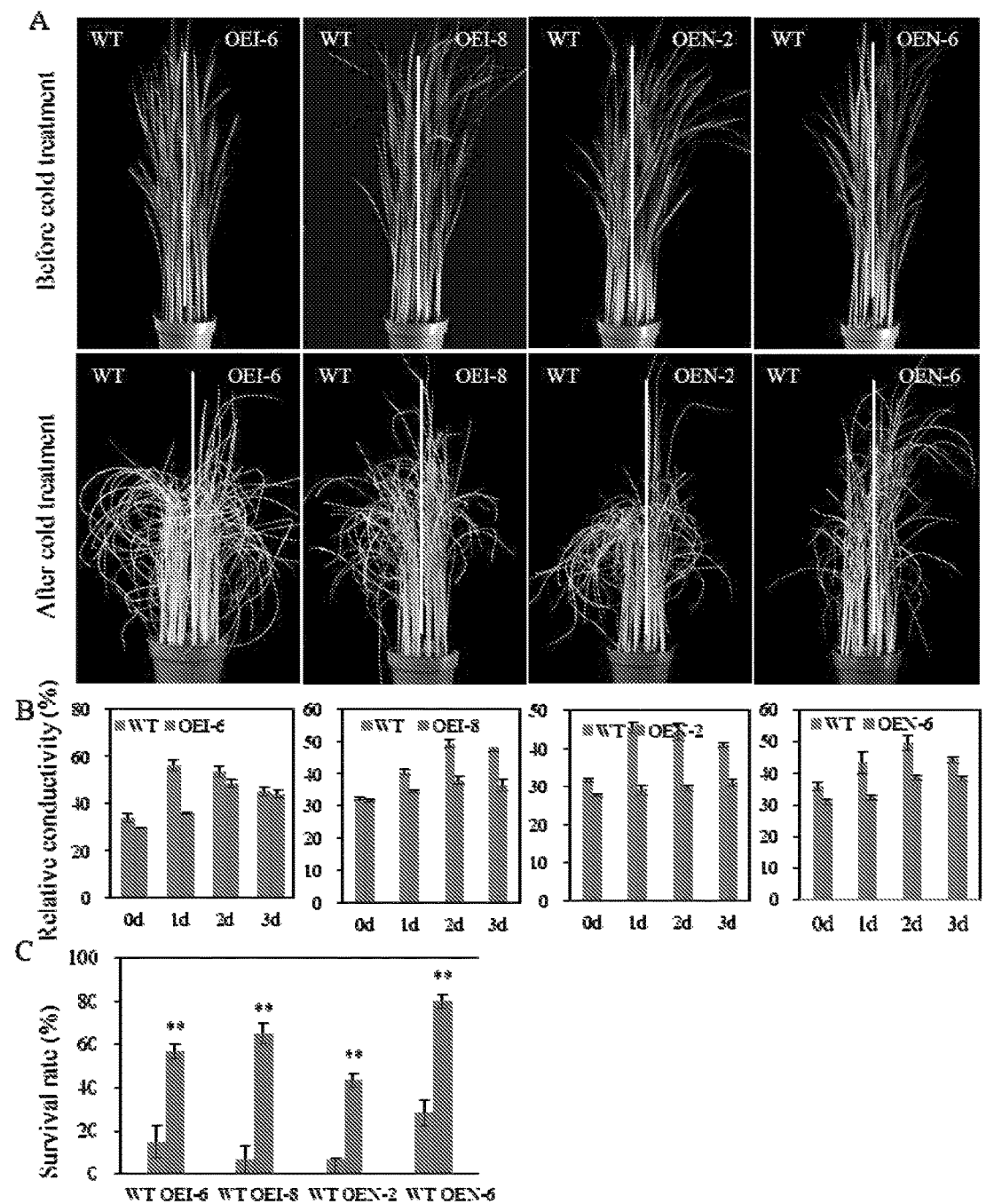
FIG. 17A shows wild-type Nipponbare rice plants (WT), OsCOBL4$_{IRAT109}$ transgenic Nipponbare rice plants (OEI-6, OEI-8) and OsCOBL4$_{Nipponbare}$ transgenic Nipponbare rice plants (OEN-2, OEN-6) before and after low-temperature stress treatment.
FIG. 17B is a graph showing the relative membrane permeativities of wild-type Nipponbare rice plants (WT), OsCOBL4$_{IRAT109}$ transgenic Nipponbare rice plants (OEI-6, OEI-8) and OsCOBL4$_{Nipponbare}$ transgenic Nipponbare rice plants (OEN-2, OEN-6) following low-temperature stress treatment. The standard error bars shown therein are based on three replicates. *=significance at $p<0.05$. **=significance at $p<0.01$.
FIG. 17C is a graph showing the survival rates of wild-type Nipponbare rice plants (WT), OsCOBL4$_{IRAT109}$ transgenic Nipponbare rice plants (OEI-6, OEI-8) and OsCOBL4$_{Nipponbare}$ transgenic Nipponbare rice plants (OEN-2, OEN-6) following a low-temperature stress treatment. The standard error bars shown therein are based on three replicates. *=significance at $p<0.05$. **=significance at $p<0.01$.

Overexpression of OsCOBL4$_{IRAT109}$ and OsCOBL4$_{Nipponbare}$ Gave Rise to Enhanced Abiotic Stress Tolerance in Rice Plants Grown Under Low-Temperature Stress Conditions Wild-type Nipponbare lines (WT), T$_2$-generation OsCOBL4$_{IRAT109}$ transgenic Nipponbare rice lines (OEI) and T$_2$-generation OsCOBL4$_{Nipponbare}$ transgenic Nipponbare rice lines (OEN) were subjected to drought stress conditions. WT, OEI and OEN seeds were sterilized, germination promoted, and then cultivated in pots, each pot having 15 transgenic plants and 15 WT controls. After growing to 4-leaf stage in a light incubator under normal conditions, the pot was transferred to an artificial climate chamber of 4° C. for low-temperature stress treatment, during which the performance was observed, and the change in the membrane permeability was detected. After 3 days of stressing, the normal growth conditions were recovered, and the survival rate was calculated after 7 days. As shown in FIG. 17, during the low temperature treatment, the membrane permeability of the WT lines rose more quickly than that of the OEI and OEN lines. Survival rate analysis showed that the survival rate of the OE16 plants was 56.67%, compared to 15% of that of the WT plants; the survival rate of the OE18 plants was 65%, compared to 6.67% of that of the WT plants; the survival rate of the OEN2 plants was 43.33%, compared to 6.67% of that of the WT plants; and the survival of the OEN6 plants was 80%, compared to 28.33% of that of the WT plants, indicating that overexpression of both OsCOBL4$_{IRAT109}$ and OsCOBL4$_{Nipponbare}$ gave rise to enhanced abiotic stress tolerance (more particularly, enhanced low-temperature stress tolerance).

Thus, it was shown that both OsCOBL4$_{IRAT109}$ and OsCOBL4$_{Nipponbare}$ give rise to enhanced abiotic stress tolerance (more particularly, enhanced drought tolerance, enhanced osmotic stress tolerance, enhanced salt stress tolerance and enhanced low-temperature stress tolerance). It was therefore postulated that the genetic differences between OsCOBL4$_{IRAT109}$ and OsCOBL4$_{Nipponbare}$ are do not significantly influence the anti-abiotic stress properties/performance of the resultant proteins.

Figure 18:
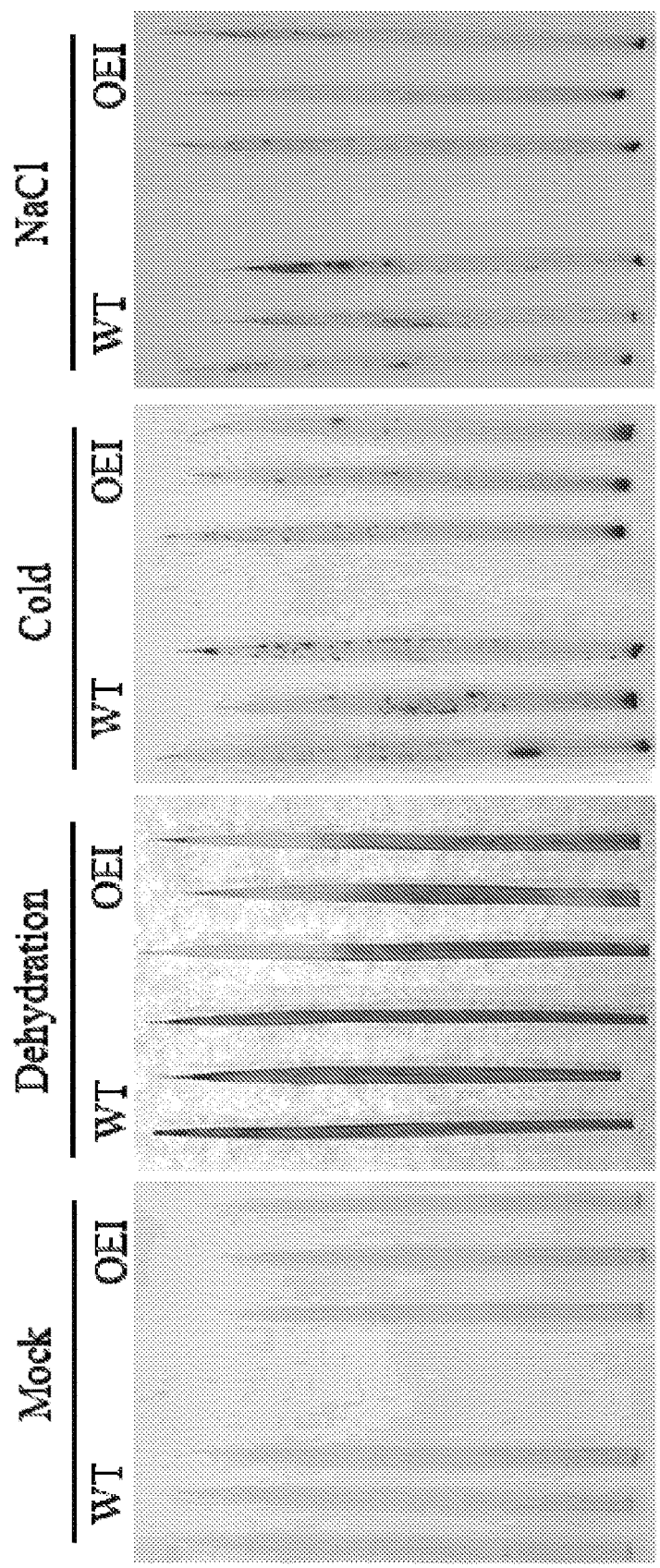
FIG. 18 shows the accumulation of reactive oxygen species in leaves taken from wild-type Nipponbare rice plants (WT) and OsCOBL4$_{IRAT109}$ transgenic Nipponbare rice plants (OH) following control treatment (Mock), dehydration stress treatment (Dehydration), low-temperature stress treatment (Cold) or salt stress treatment (NaCl). Reactive oxygen species were detected using DAB staining.

Part VI. Analysis of Reactive Oxygen Species (ROS) Accumulation in OsCOBL4 Transgenic Plants Wild-type Nipponbare lines (WT) and OsCOBL4$_{IRAT109}$ transgenic Nipponbare rice lines (OEI) were grown in a nutrient solution for 3 weeks were treated with dehydration for 8 h, with 4° C. cold for 24 h, or with 150 mmol/L NaCl for 24 h, and then analyzed for ROS accumulation by DAB staining. As shown in FIG. 18, after dehydration, low temperature and high salt stress treatments, ROS accumulation in the OEI lines was lower than in the WT lines, indicating that overexpression of OsCOBL4$_{IRAT109}$ gave rise to a more potent ROS scavenger system, as compared to WT plants.

Part VII. Ingredient Analysis of Cell Wall of COBL4 Transgenic Plants

Figure 19:
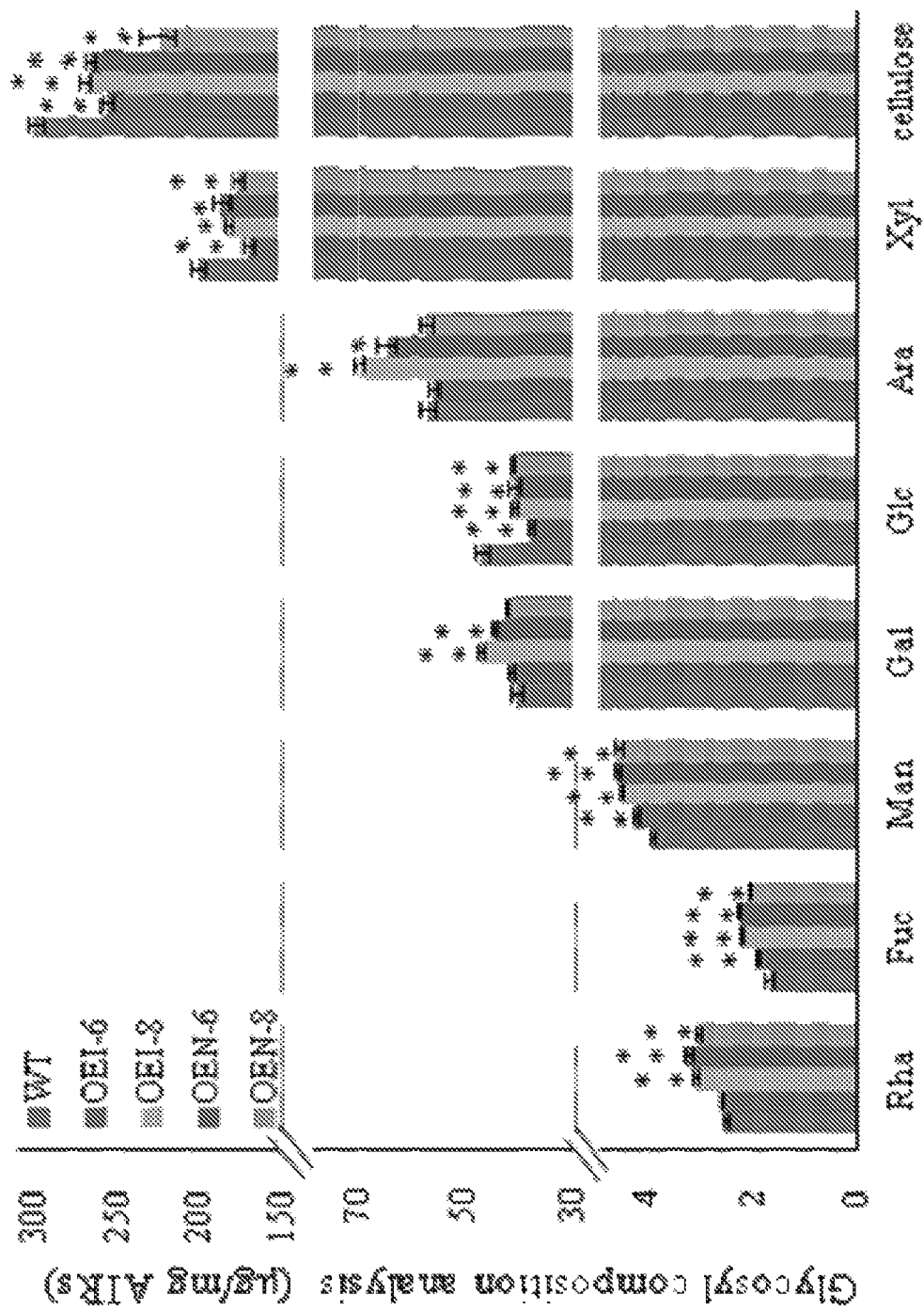
FIG. 19 is a graph showing the sugar composition of cell walls taken from wild-type Nipponbare rice plants (WT), OsCOBL4$_{IRAT109}$ transgenic Nipponbare rice plants (OH) and OsCOBL4$_{Nipponbare}$ transgenic Nipponbare rice plants (OEN). The values shown therein are means+/−standard error. *=significance at $p<0.05$. **=significance at $p<0.01$.

It was previously reported that the members of the COBRA gene family are involved in the formation of plant cell walls and the synthesis of cellulose. In order to ascertain whether OsCOBL4 is involved in the synthesis of plant cell walls, cell walls in the roots of seedlings of wild-type Nipponbare lines (WT) were analyzed, along with cell walls in the roots of seedlings of two $T_2$-generation OsCOBL4$_{IRAT109}$ transgenic Nipponbare rice lines (OEI6, OEI8) and two $T_2$-generation OsCOBL4$_{Nipponbare}$ transgenic Nipponbare rice lines (OEN6, OEN8) at seedling stage were analyzed. As shown in FIG. 19, glucose (Glc), Xylose (Xyl), and cellulose levels were decreased in both OEI plants and OEN plants, whereas the levels of rhamnose (Rha), fucose (Fuc), mannose (Man), galactose (Gal), and arabinose (Ara) were increased, indicating that OsCOBL4 overexpression may enhance abiotic stress tolerance by effecting the monosaccharide content of plant cell walls.

Example 3

Over-expression of OsERF62 Enhances Abiotic Stress Tolerance

As shown in FIGS. 26A-36, overexpression of OsERF62 gave rise to enhanced abiotic stress tolerance in transgenic rice plants.

Part I. Bioinformatic Analysis of OsERF62

Figure 20:
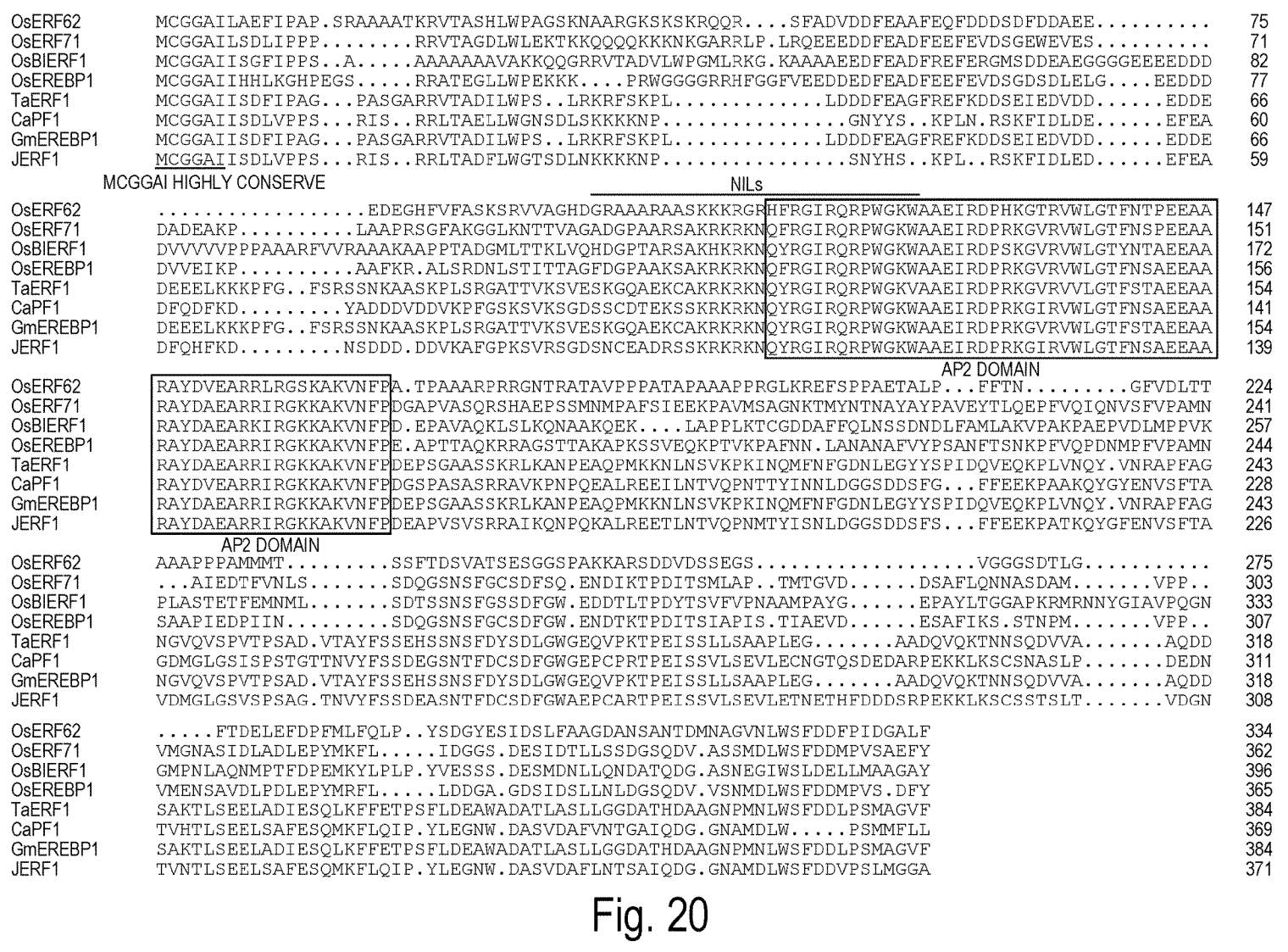

OsERF62 encodes a protein that comprises 335 amino acids and that has a molecular weight of 35760.44 Da and an isoelectric point of 6.0764. Comparison and analysis of protein homology showed that OsERF62 has a conservative AP2 domain in the region from positions 110 to 167, which is quite highly homologous to previously reported ERF transcription factors. FIG. 20. The amino acids at positions 14 and 19 in the conservative domain are alanine (A) and aspartic acid (D), respectively, which is a feature typical of ERF transcription factors.

Part II. OsERF62 Expression was Upregulated in Rice Exposed to Abiotic Stress Conditions Water-cultured three-week-old seedlings of upland rice variety IRAT109 and lowland rice variety Nipponbare were subjected to the following abiotic stress treatments: PEG treatment (roots were soaked in 200 g/L polyethylene glycol (PEG6000) aqueous solution for 1, 2, 4, 6, 9, 12 or 24 hours); dehydration treatment (roots were left in the air for 1, 2, 4, 6, 9, 12 or 24 hours); salt treatment (roots were soaked in 200 mM NaCl for 1, 2, 4, 6, 9, 12 or 24 hours); cold treatment (seedlings were transferred to an artificial climate chamber of 4° C. for 1, 2, 4, 6, 9, 12 or 24 hours); $H_2O_2$ treatment (roots were soaked in 1 mM $H_2O_2$ solution and left in the air 1, 2, 4, 6, 9, 12 or 24 hours); ABA treatment (roots were soaked in 100 μM ABA solution and cultured under illumination for 1, 2, 4, 6, 9, 12 or 24 hours); ethylene treatment (roots were soaked in 1 mM ethylene for 1, 2, 4, 6, 9, 12 or 24 hours); GA treatment (roots were soaked in 100 μM GA for 1, 2, 4, 6, 9, 12 or 24 hours); or control treatment (roots remained in water culture). Following treatment, leaves were collected and quickly frozen using liquid nitrogen and stored at −80° C. for further use.

Total RNA was extracted from the harvested leaves and the relative expression levels of OsERF62 and Actin were calculated as described above in Example 1, Part I.

Figure 21:
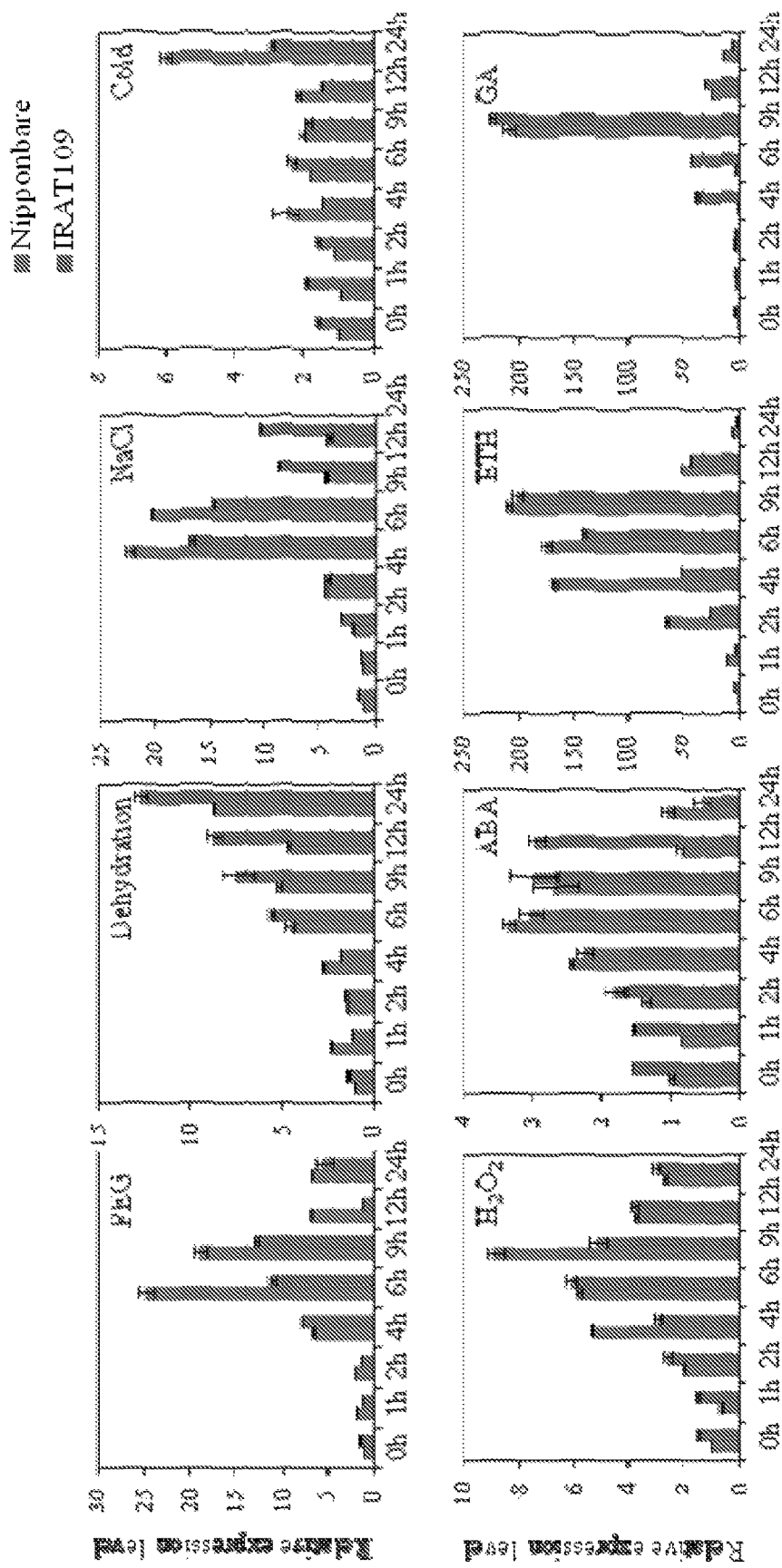
FIG. 21 shows the results of real-time fluorescence quantitative PCR analyses of the relative expression levels of native OsERF62 in IRAT109 rice plants and Nipponbare rice plants at various time points during PEG-simulated drought stress treatment, physiological dehydration drought stress treatment, low-temperature stress treatment, $H_2O_2$ treatment, ethylene treatment, ABA treatment, or GA treatment. The standard error bars shown therein are based on three replicates.

As shown in FIG. 21, the expression of OsERF62 in both IRAT109 and Nipponbare rice plants was upregulated in response to each of the abiotic stress treatments, indicating that OsERF62 is associated with one or more abiotic stress responses. OsERF62 expression gradually increased in both Nipponbare and IRAT109 4 h after stress treatment with 20% PEG, and reached the highest respectively at 6 h in Nipponbare (24.86 times) and at 9 h in IRAT109 (12.72 times). OsERF62 expression gradually increased in both Nipponbare and IRAT109 4 h after dehydration stress treatment, and reached the highest at 8 h (8.69 times in Nipponbare and 12.71 times in IRAT109). OsERF62 expression gradually increased in both Nipponbare and IRAT109 2 h after stress treatment with NaCl, and reached the highest at 6 h (22.29 times in Nipponbare and 16.74 times in IRAT109). OsERF62 expression increased in both Nipponbare and IRAT109 2 h after stress treatment with $H_2O_2$, reached a peak at 9 h in Nipponbare (8.89 times) followed by a gradual decrease, and reached a peak at 6 h in IRAT109 followed by a gradual decrease (6.12 times). OsERF62 expression gradually increased in both Nipponbare and IRAT109 2 h after treatment with ABA, and reached the highest at 6 h (3.35 times in Nipponbare and 3.02 times in IRAT109). OsERF62 expression in Nipponbare was up-regulated 1 h after treatment with ethylene, and reached the highest at 9 h (209.54 times), and increased at 2 h in IRAT109 and reached the highest at 9 h (202.19 times). Under treatment with GA, the expression was remarkably up-regulated at 9 h in Nipponbare (209.95 times), and was started to inductively express at 4 h, and reached the highest at 9 h (225.41 times) in IRAT109. These results suggest that OsERF62 is strongly inductively expressed in both Nipponbare and IRAT109 in response to abiotic stress conditions, particularly drought stress conditions, osmotic stress conditions and salt stress conditions.

Part III. Expression Analysis of OsERF62 in Various Tissues of Plants

Figure 22:
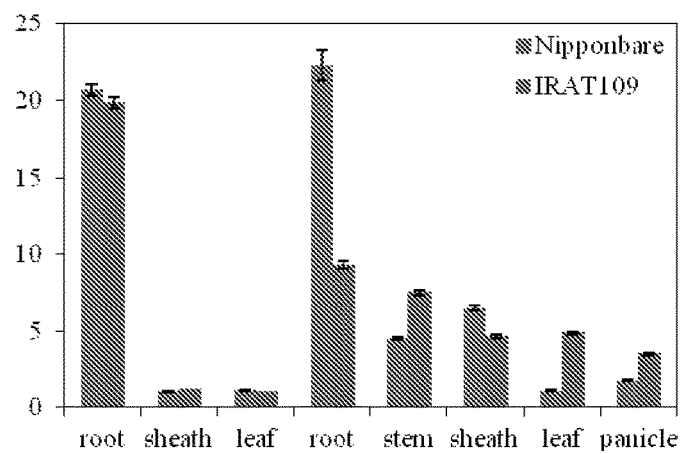
FIG. 22 is a graph showing the results of real-time fluorescence quantitative PCR analyses of the relative expression levels of native OsERF62 in tissues from IRAT109 rice plants and Nipponbare rice plants.

Reverse transcription of RNA extracted from the roots, stems, sheaths, leaves and panicles of upland rice variety IRAT109 and lowland rice variety Nipponbare showed that OsERF62 was maximally expressed in the root at both the seedling and reproductive stages, and was minimally expressed in the sheath and leaf at the seedling stage. FIG. 22.

Part IV. Subcellular Localization Analysis of OsERF62

Figure 23:
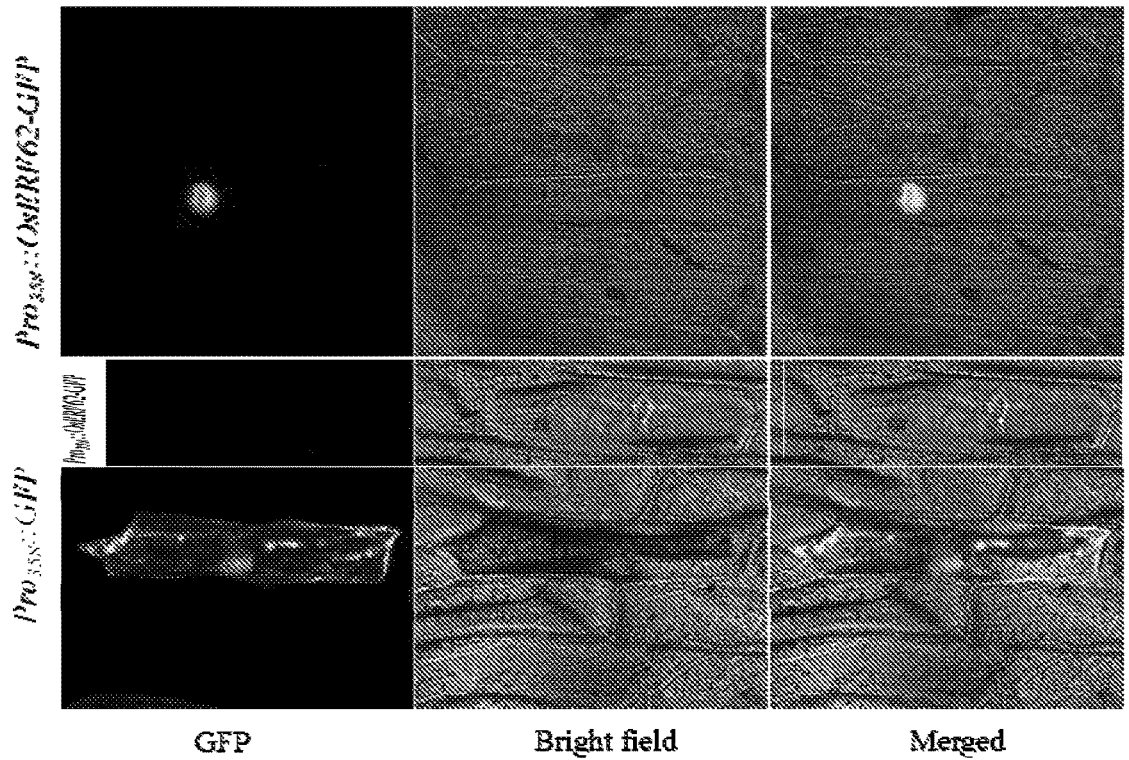
FIG. 23 shows the subcellular localization of GFP-fused ERF62 in onion epithelium following particle bombardment-mediated transformation. Leaves were treated with 10% NaCl to separate cell walls and protoplasts.

OsERF62 was ligated into a pMDC83 vector to produce an OsERF62-GFP expression vector. GFP was located at C-terminus of the OsERF62 protein. The vector was transformed into onion epithelial cells through particle bombardment. A relatively strong fluorescence signal was observed in the nuclei under confocal laser scanning microscope (FIG. 23), indicating that OsERF62 is a nuclei protein, which is consistent with its proposed role as a transcription factor.

Part V. Analysis of Transactivation Activity and Domain of OsERF62 Protein

Figure 24:
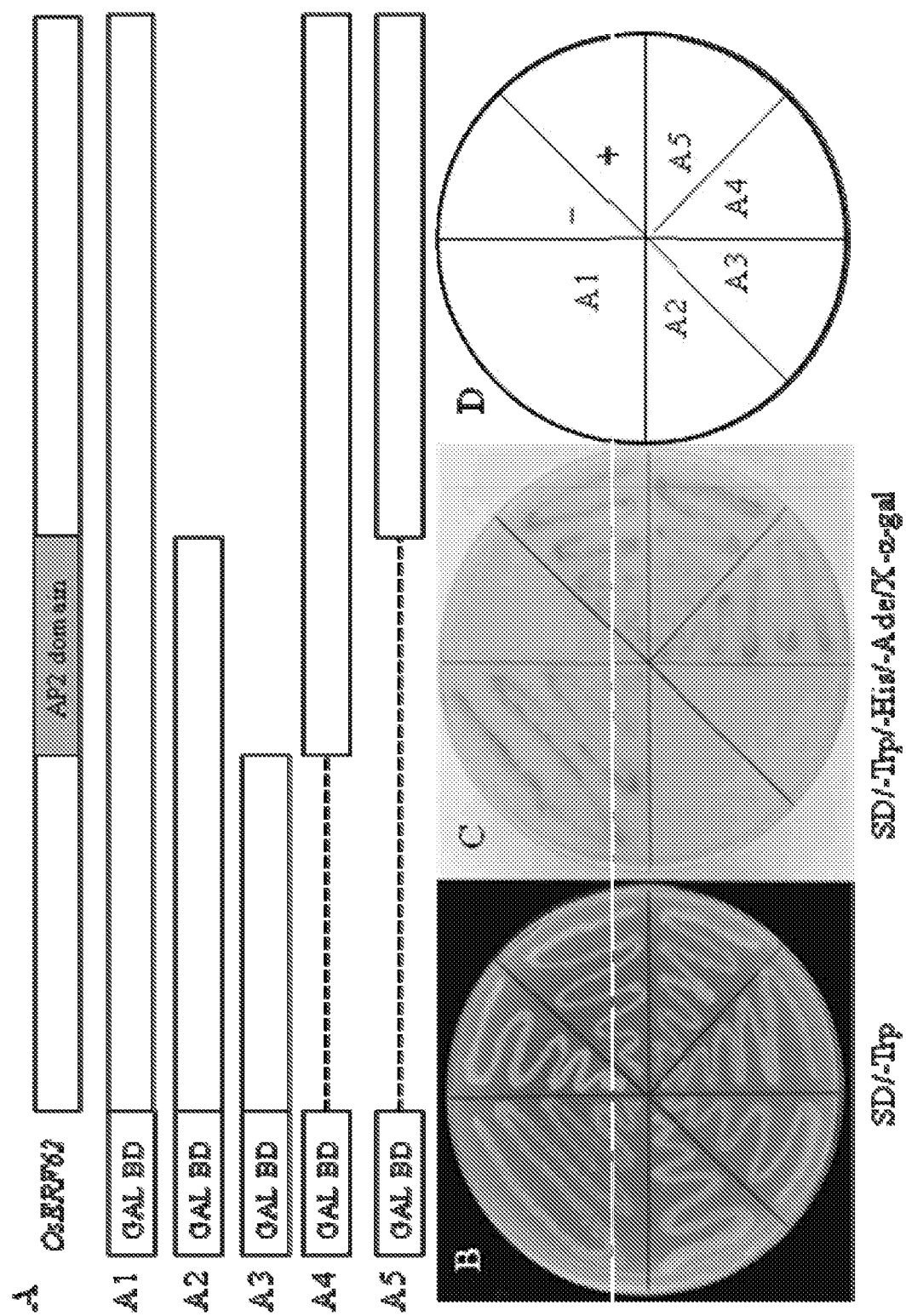
FIG. 24A shows maps of various GAL4BD yeast expression vectors used to test the transaction activity of OsERF62: A1=full-length OsERF62 fused to GAL4BD; A2=amino acids 1-167 of OsERF62 fused to GAL4BD; A3=amino acids 1-106 of OsERF62 fused to GAL4BD; A4=amino acids 162-335 of OsERF62 fused to GAL4BD; A5=amino acids 230-335 of GAL4BD fused to GAL4BD.
FIG. 24B-D show the results of an in vivo yeast assay using the GAL4BD yeast expression vectors depicted in FIG. 24A. +=positive control. −=negative control.

For analyzing the transactivation activity and domain of OsERF62 protein, full-length and deletion ORF fragments of OsERF62 were constructed into a yeast expression vector pGBKT7, and for determining the activation domain of OsERF62 protein, the AP2 domain of OsERF62 was divided into five regions based on the positions thereof—A1: full-length, 335 aa; A2: 1-106 aa; A3: 1-167 aa; A4: 162-335 aa: A5: 230-335aa—which were fused to the yeast GAL4BD fusion expression vector pGBKT7, and then used to transform the yeast strain AH109. FIG. 24A. As shown in FIGS. 24B-24D, yeasts transformed with A1, A4, A5 and positive vectors grew normally on SD/-Trp-His-Ade/X-α-gal plate and developed a blue appearance, while the yeasts transformed with A2, A3, and negative control failed to grow normally. These results suggest that OsERF62 had transactivation activity and that the transactivation domain of OsERF62 is located in a region from positions 230 to 335 at C-terminus of the protein sequence.

Figure 25:
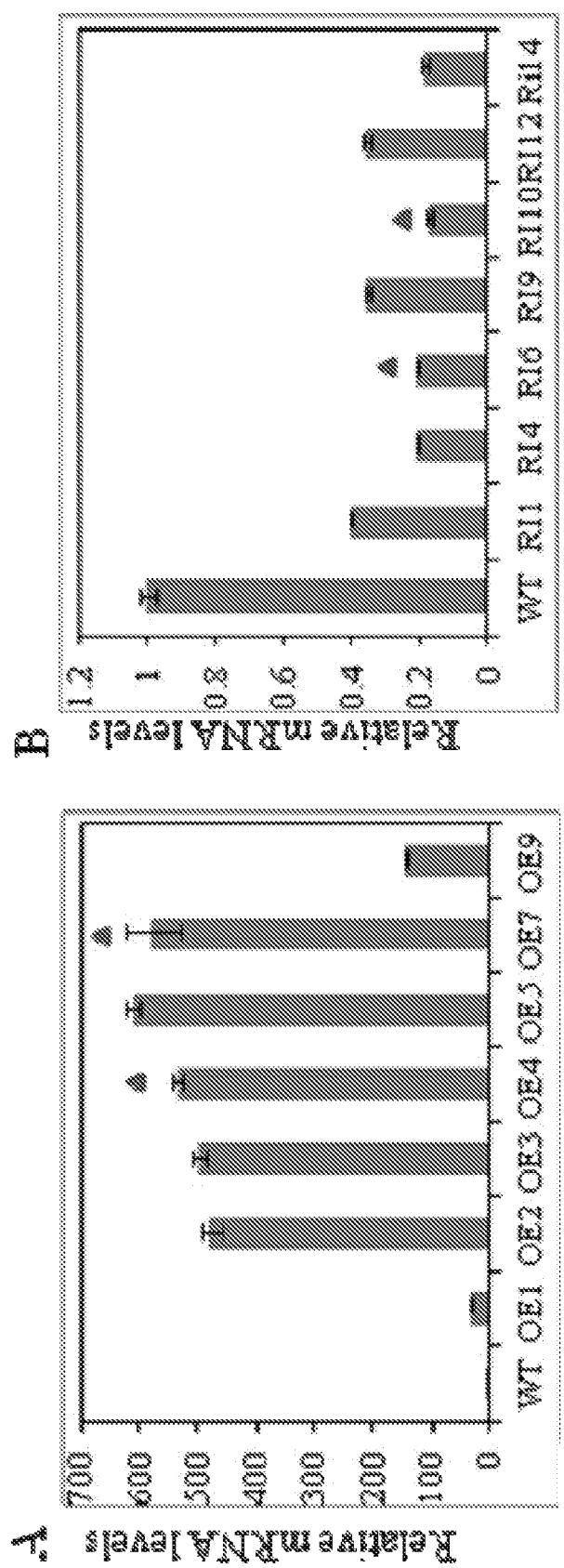
FIG. 25A is a graph showing the relative expression levels of OsERF62 in wild-type Nipponbare rice plants (WT) and OsERF62 transgenic Nipponbare rice plants (OE1, OE2, OE3, OE4, OE5, OE7, OE9). The standard error bars shown therein are based on three replicates. Triangle=line used for further analysis.
FIG. 25B is a graph showing the relative expression levels of OsERF62 in wild-type Nipponbare rice plants (WT) and transgenic Nipponbare rice plants expressing an RNA interference molecule directed at OsERF62 (RI1, RI4, RI6, RI9, RI10, RI12, RI14). The standard error bars shown therein are based on three replicates. Triangle=line used for further analysis.

Part VI. Response of OsERF62 OE and Suppression Expression Transgenic Plants to Abiotic Stress For further determining the role and functions of OsERF62 under abiotic stress conditions, OsERF62 over-expression and OsERF62 RNAi vectors were constructed and transformed into the lowland rice variety Nipponbare through *Agrobacterium*-mediated transformation to produce OsERF62 transgenic Nipponbare rice lines (OE) and OsERF62 RNAi transgenic Nipponbare rice lines (RI). Quantitative PCR analysis showed that five transformation events of significantly increased expression occurred in ten individual OE transgenic plants (FIG. 25A), and that seven transformation events of significantly decreased expression occurred in 14 individual RNA-interference plants (FIG. 25B). The OE plants having the highest expression (OE4, OE7) and the RNA-interference plants having the lowest expression (RI6, RI10) were selected for subsequent experimental analysis.

Figure 26A:
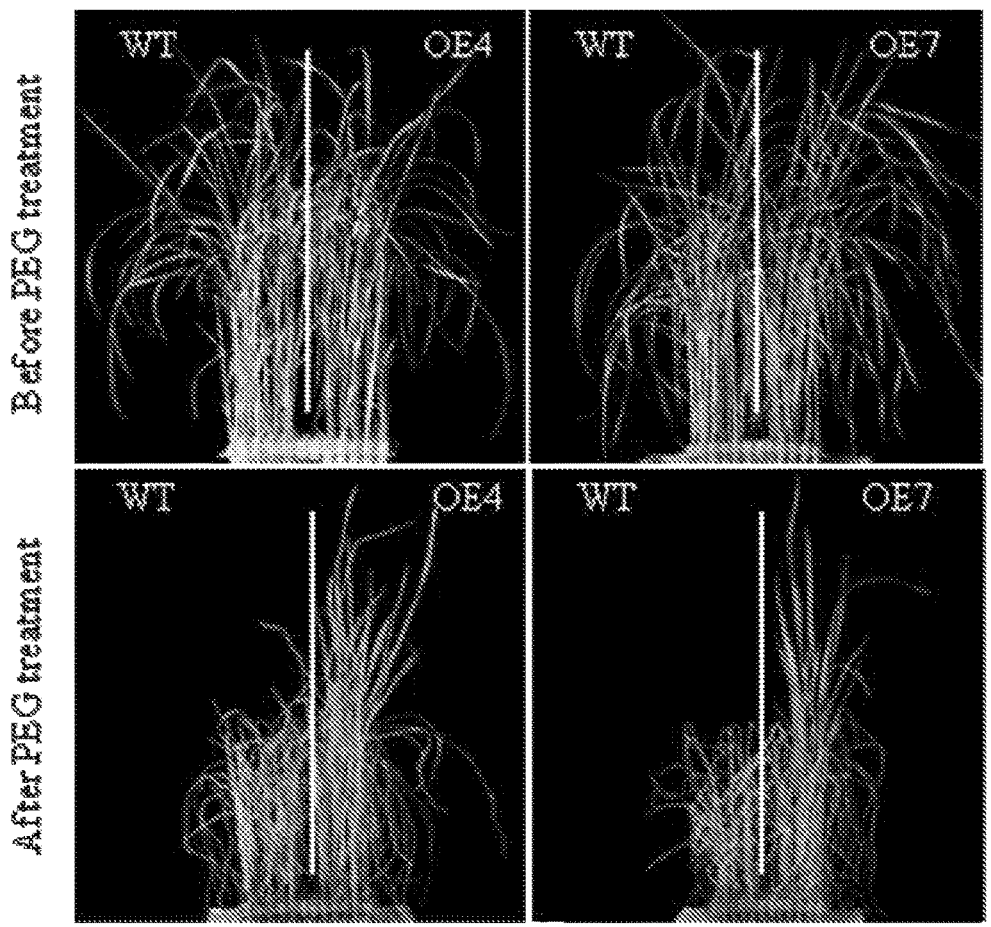
FIG. 26A shows wild-type Nipponbare rice plants (WT) and OsERF62 transgenic Nipponbare rice plants (OE4, OE7) before and after physiological dehydration stress treatment.
Figure 26B:
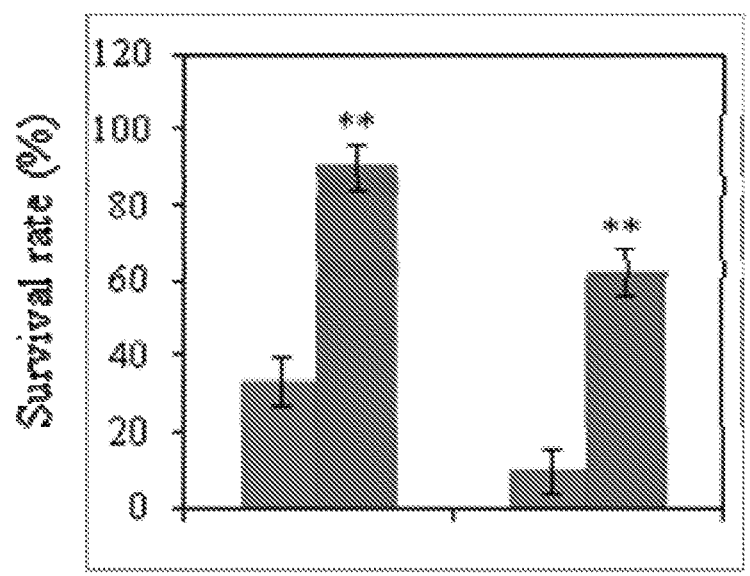
FIG. 26B is a graph showing the survival rates of wild-type Nipponbare rice plants (WT) and OsERF62 transgenic Nipponbare rice plants (OE4, OE7) following physiological dehydration drought stress treatment. The standard error bars shown therein are based on three replicates. **=significance at $p<0.01$.
Figure 27:
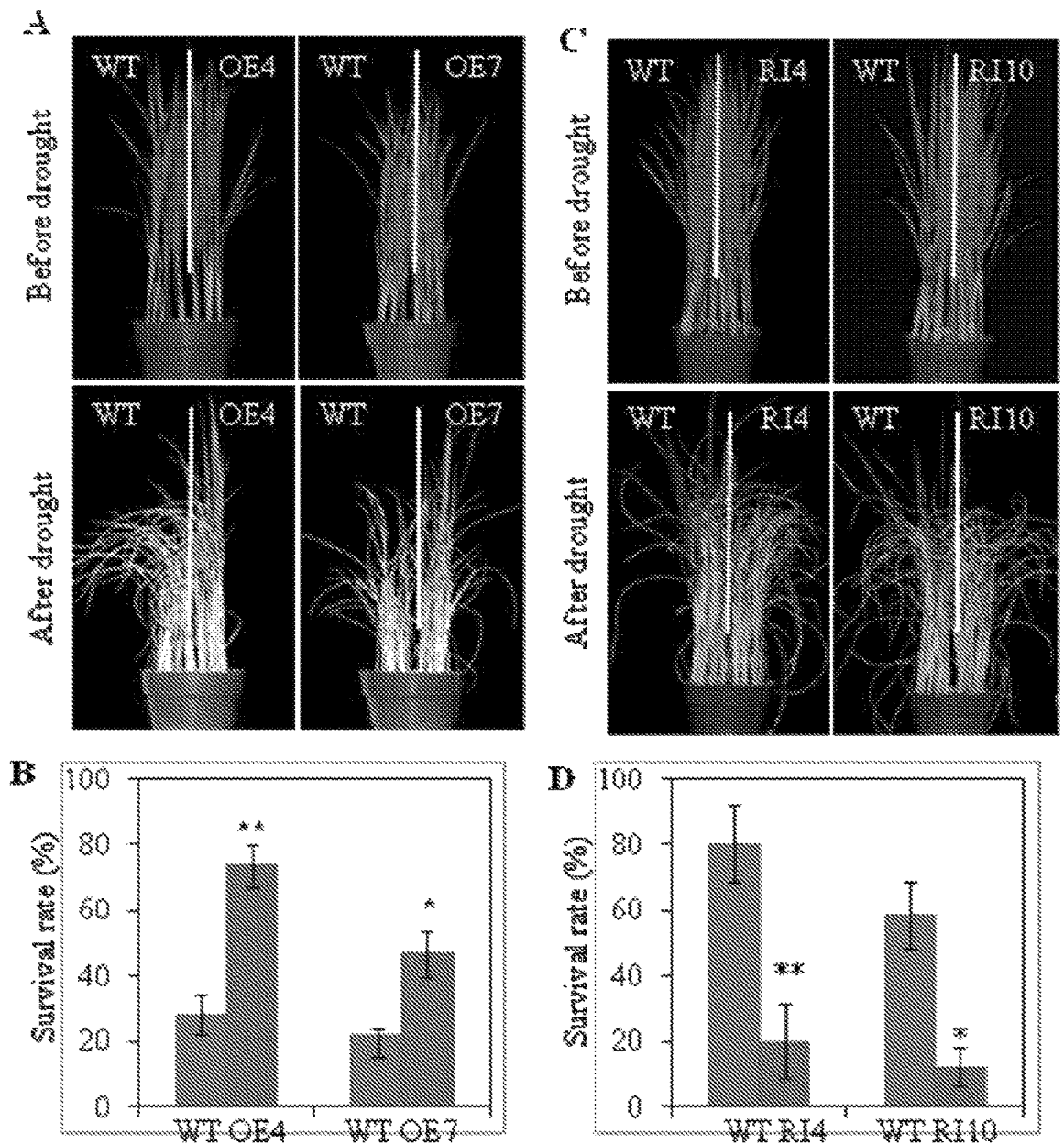
FIG. 27A shows wild-type Nipponbare rice plants (WT) and OsERF62 transgenic Nipponbare rice plants (OE4, OE7) before and after drought stress treatment.
FIG. 27B is a graph showing the survival rates of wild-type Nipponbare rice plants (WT) and OsERF62 transgenic Nipponbare rice plants (OE4, OE7) following drought stress treatment. The standard error bars shown therein are based on three replicates. *=significance at $p<0.05$. **=significance at $p<0.01$.
FIG. 27C shows wild-type Nipponbare rice plants (WT) and transgenic Nipponbare rice plants expressing an RNA interference molecule directed at OsERF62 (RI4, RI10) before and after drought stress treatment.
FIG. 27D is a graph showing the survival rates of wild-type Nipponbare rice plants (WT) and transgenic Nipponbare rice plants expressing an RNA interference molecule directed at OsERF62 (RI4, RI10) following drought stress treatment. The standard error bars shown therein are based on three replicates. *=significance at $p<0.05$. **=significance at $p<0.01$.
Figure 28:
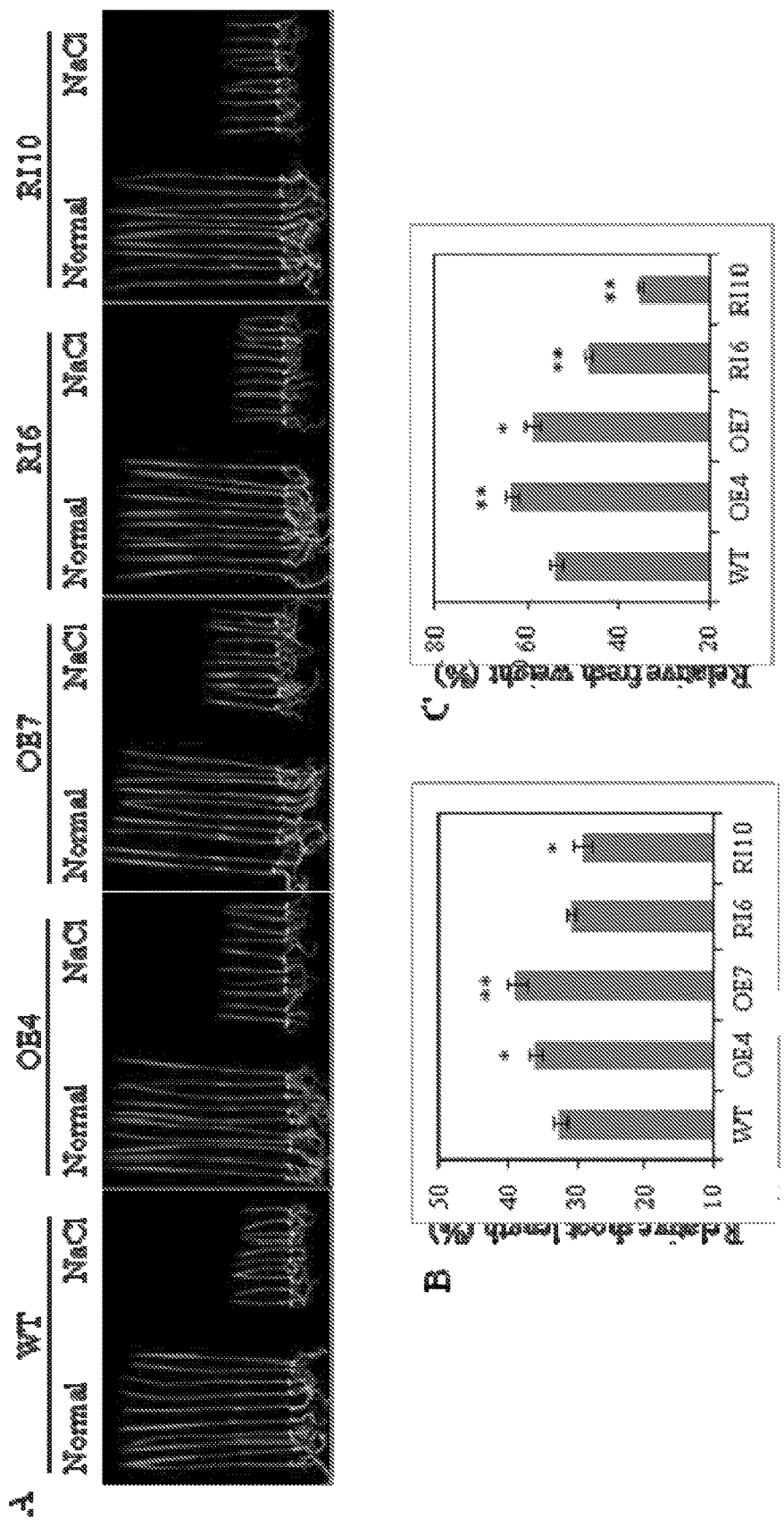
FIG. 28A shows wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10) following control treatment (Normal) or salt stress treatment (NaCl).
FIG. 28B is a graph showing the relative shoot lengths of wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10) following salt stress treatment. The standard error bars shown therein are based on three replicates. *=significance at $p<0.05$. **=significance at $p<0.01$.
FIG. 28C is a graph showing the relative weights of wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10) following salt stress treatment. The standard error bars shown therein are based on three replicates. *=significance at $p<0.05$. **=significance at $p<0.01$.
Figure 29:
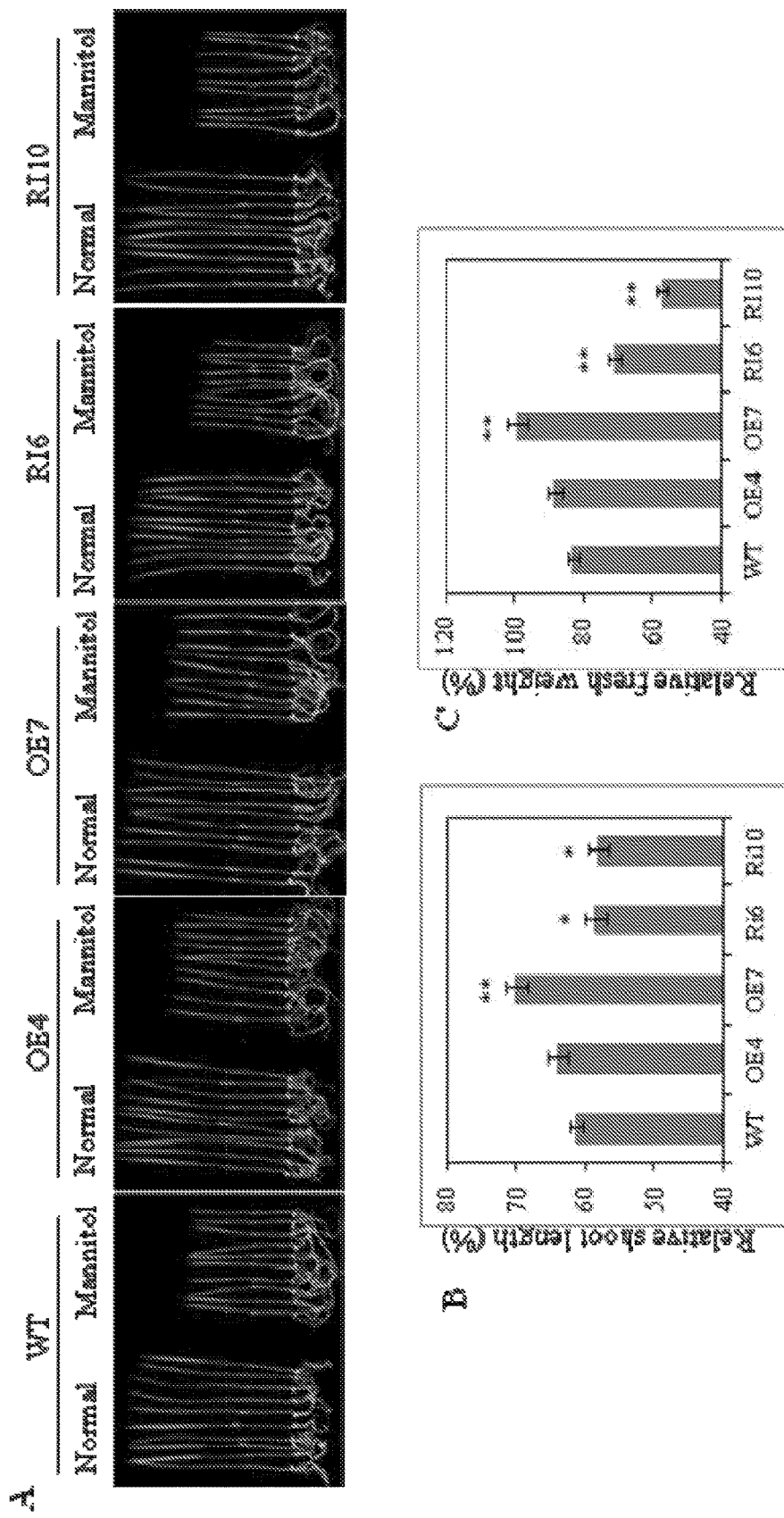
FIG. 29A shows wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10) following control treatment (Normal) or osmotic stress treatment (Mannitol).
FIG. 29B is a graph showing the relative shoot lengths of wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10) following osmotic stress treatment. The standard error bars shown therein are based on three replicates. *=significance at p<0.05. **=significance at p<0.01.
FIG. 29C is a graph showing the relative weights of wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10) following osmotic stress treatment. The standard error bars shown therein are based on three replicates. *=significance at p<0.05. **=significance at p<0.01.
Figure 30:
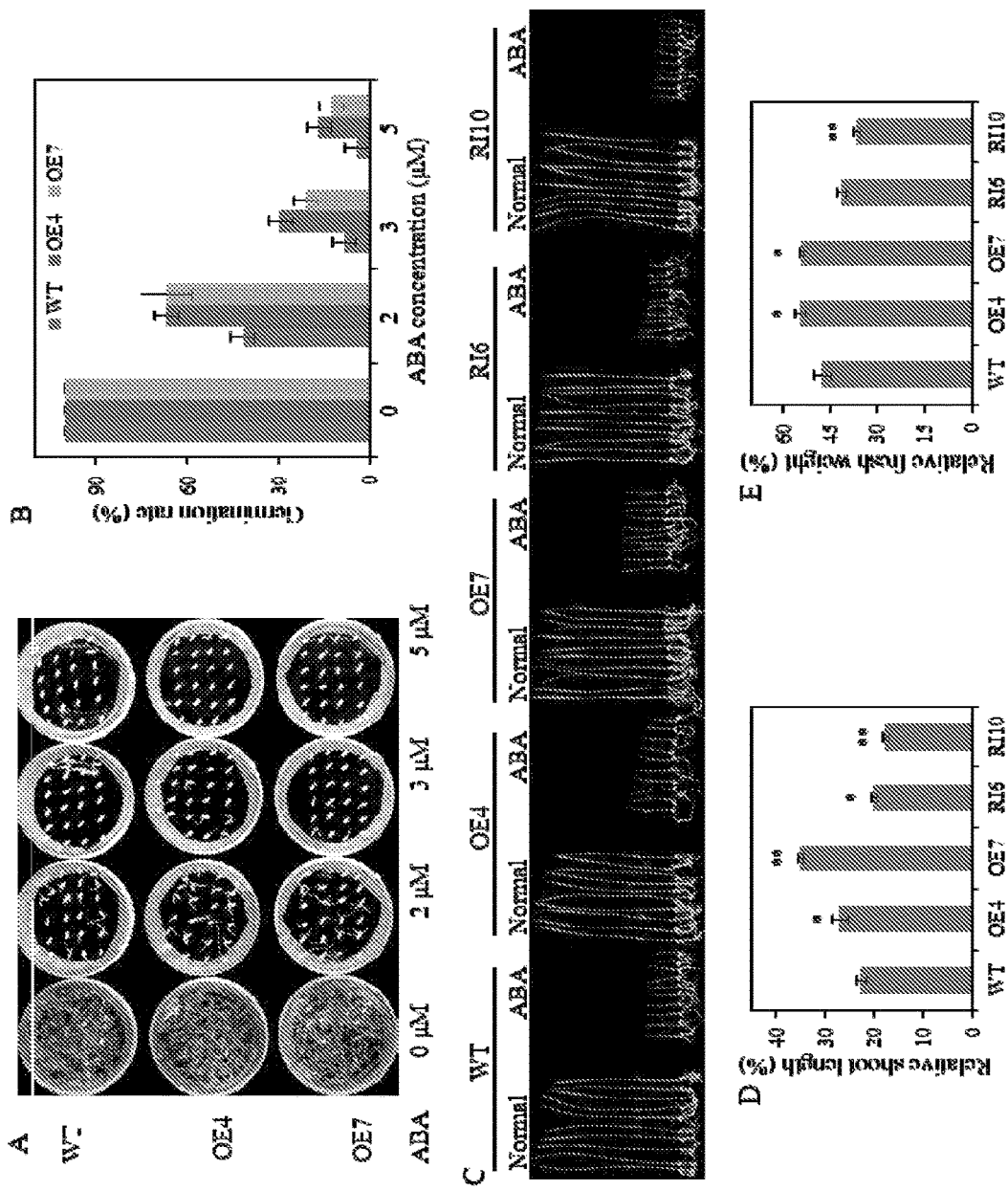
FIG. 30A shows the germination performance of wild-type Nipponbare rice plants (WT) and OsERF62 transgenic Nipponbare rice plants (OE4, OE7) grown on medium comprising 0, 2, 3, or 5 µM ABA.
FIG. 30B is a graph showing the germination rates of wild-type Nipponbare rice plants (WT) and OsERF62 transgenic Nipponbare rice plants (OE4, OE7) grown on medium comprising 0, 2, 3, or 5 µM ABA. The standard error bars shown therein are based on three replicates.
FIG. 30C shows wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10) grown on medium comprising 0 µM ABA (Normal) or 3 µM ABA (ABA).
FIG. 30D is a graph showing the relative shoot lengths of wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10) grown on medium comprising 3 µM ABA. The standard error bars shown therein are based on three replicates. *=significance at p<0.05. **=significance at p<0.01.
FIG. 30E is a graph showing the relative weights of wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10) grown on medium comprising 3 µM ABA. The standard error bars shown therein are based on three replicates. *=significance at p<0.05. **=significance at p<0.01.

Overexpression of OsERF62 Gave Rise to Enhanced Abiotic Stress Tolerance in Rice Plants Grown Under Simulated Drought Stress Conditions Wild-type Nipponbare lines (WT) and $T_2$-generation OsERF62 transgenic Nipponbare rice lines (OE) were subjected to PEG-simulated drought stress conditions as described in Example 1, Part VII. As shown in FIGS. 26A-26B and Table 8 below, the survival rates of the OE lines were significantly higher than that of WT lines, indicating that overexpression of OsERF62 gave rise to enhanced abiotic stress tolerance (more particularly, enhanced drought stress tolerance).

TABLE 8

Survival rates of seedlings grown under PEG-simulated drought stress conditions.

| Plant Line | Survival Rate |
| --- | --- |
| OE4 | 90%** |
| WT | 33.33%% |
| OE7 | 62.22%** |
| WT | 10% |

** = significance at $p < 0.01$ as compared with WT.

Drought Stress Tolerance of OsERF62 OE and RNAi Transgenic Plants at Seedling Stage Wild-type Nipponbare lines (WT), $T_2$-generation OsERF62 transgenic Nipponbare rice lines (OE) and $T_2$-generation OsERF62-RNAi transgenic Nipponbare rice lines (RI) were subjected to drought stress conditions as described in Example 1, Part IX. As shown in FIGS. 27A-27D and Table 9 below, the survival rates of the OE lines were significantly higher than that of WT lines, while the survival rates of the RI lines were significantly lower than that of the WT lines, indicating that overexpression of OsERF62 gave rise to enhanced abiotic stress tolerance (more particularly, enhanced drought stress tolerance). These results suggest that suppression of OsERF62 expression may attenuate a plant's drought stress response(s).

TABLE 9

Survival at rates of seedlings grown under drought stress conditions.

|  | Plant Line | Survival Rate |
| --- | --- | --- |
| Group 1 | OE4 | 73.33%** |
|  | WT | 28.33% |
| Group 2 | OE7 | 46.637%* |
|  | WT | 21.67% |
| Group 3 | RI4 | 20%** |
|  | WT | 80% |
| Group 4 | RI10 | 12.22% |
|  | WT | 58.33% |

* = significance at $p < 0.05$ as compared with WT.
** = significance at $p < 0.01$ as compared with WT.

Salt Stress Tolerance Assay of OsERF62 OE and RNAi Transgenic Plants

Wild-type Nipponbare lines (WT), $T_2$-generation OsERF62 transgenic Nipponbare rice lines (OE) and $T_2$-generation OsERF62-RNA/transgenic Nipponbare rice lines (RI) were subjected to salt stress conditions as described in Example 2, Part V. As shown in FIGS. 28A-28C and Table 10 below, both the plant heights and fresh weights of the OE lines were significantly higher than that of WT lines and RI lines, indicating that overexpression of OsERF62 gave rise to enhanced abiotic stress tolerance (more particularly, enhanced drought stress tolerance). These results suggest that suppression of OsERF62 expression may attenuate a plant's salt stress response(s).

TABLE 10

Growth of seedlings grown under salt stress conditions.

| Plant Line | Relative Height | Relative Weight |
| --- | --- | --- |
| WT | 32.38% | 53.53% |
| OE4 | 36.01%* | 63.29%** |
| OE7 | 38.86%** | 58.77%* |
| RI6 | 30.84% | 46.63%** |
| RI10 | 29.18%* | 35.2%** |

\* = significance at p < 0.05 as compared with WT.
\*\* = significance at p < 0.01 as compared with WT.

High Osmotic Stress Tolerance Assay of OsERF62 OE, and RNA/Transgenic Plants

Wild-type Nipponbare lines (WT), $T_2$-generation OsERF62 transgenic Nipponbare rice lines (OE) and $T_2$-generation OsERF62-RNA/transgenic Nipponbare rice lines (RI) were subjected to osmotic stress conditions as described in Example 1, Part VIII. As shown in FIGS. 29A-29C and Table 11 below, both the plant heights and fresh weights of the OE lines were significantly higher than that of WT lines and RI lines, indicating that overexpression of OsERF62 gave rise to enhanced abiotic stress tolerance (more particularly, enhanced osmotic stress tolerance). These results suggest that suppression of OsERF62 expression may attenuate a plant's osmotic stress response(s).

TABLE 11

Growth of seedlings grown under mannitol-induced osmotic stress conditions.

| Plant Line | Relative Height | Relative Weight |
| --- | --- | --- |
| WT | 61.35% | 83.04% |
| OE4 | 63.97% | 88.24% |
| OE7 | 70.03%** | 99.15%** |
| RI6 | 58.51%* | 71.11%** |
| RI10 | 55.54%* | 57.22%** |

\*\* = significance at p < 0.01 as compared with WT.

ABA Sensitivity Assay of OsERF62 OE and RNAi Transgenic Plants at Seedling Stage It was observed that the expression of OsERF62 was induced by ABA. Therefore, for analyzing the function of OsERF62 in ABA signaling pathway, ABA sensitivity tests of wild-type Nipponbare lines (WT), $T_2$-generation OsCOBL4$_{IRAT109}$ transgenic Nipponbare rice lines (OE) and were conducted at seedling stage. The seeds of WT plants and homozygous OE plants were unshelled and sterilized, then cultivated in ½ MS medium containing 0, 2, 3, and 5 μM ABA for 7 d. The germination rates were calculated. In the presence of ABA, the germination rate of the OsERF62-OE plants was higher than that of the control. FIG. 30A-30C. The seedlings of WT plants, OE plants and RI plants that were normally germinated in ½MS medium for 2-3 d and had the uniform growth status were transferred to ½ MS medium containing 0 and 3 μM ABA, grown in a light incubator for 7 d, and then measured for the shoot length and fresh weight. As shown in FIG. 30B, at 0 μM ABA, there was no obvious difference in growing performances between the WT plants and the OE plants. However, in the medium containing 3 μM ABA, the relative shoot length of the OsERF62-OE plants was 20.78%-25.87%, and the relative fresh weight was 33.75%-42.21%; while the relative shoot length of the WT was 29.78%, and the relative fresh weight was 44.84%; and the relative shoot length of the OsERF62-RI plants was 20.78%-25.87%, and the relative fresh weight was 33.75%-42.21%. These results suggest that overexpression of OsERF62 may reduce the sensitivity of plants to ABA at germination stage, and that suppression of OsERF62 expression may increase the sensitivity of transgenic plants to ABA.

Water Loss Assay of OsERF62 OE, and RNAi Transgenic Plants

Figure 31:
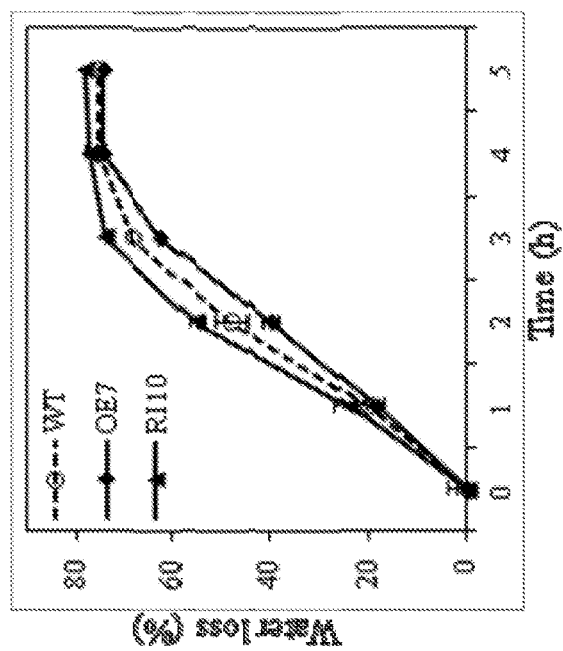
FIG. 31 is a graph showing water loss of leaves taken from wild-type Nipponbare rice plants (WT), OsERF62 transgenic Nipponbare rice plants (OE7), and transgenic Nipponbare rice plants expressing an RNA interference molecule directed at OsERF62 (RI10). The standard error bars shown therein are based on three replicates.

A direct behavior in response of the plants to drought stress is to effectively reduce the water loss in plants under drought conditions. For further analyzing the contribution of OsERF62 to abiotic stress tolerance (particularly drought stress tolerance), water loss was analyzed in detached leaves of wild-type Nipponbare lines (WT), $T_2$-generation OsERF62 transgenic Nipponbare rice lines (OE) and $T_2$-generation OsERF62-RNAi transgenic Nipponbare rice lines (RI). As shown in FIG. 31, water loss was lowest in the leaves of OE plants and highest in the leaves of RI plants. The ability to reduce water loss might partly account for the contribution of OsERF62 to enhanced abiotic stress tolerance (particularly, enhanced drought stress tolerance) in plants.

Figure 32:
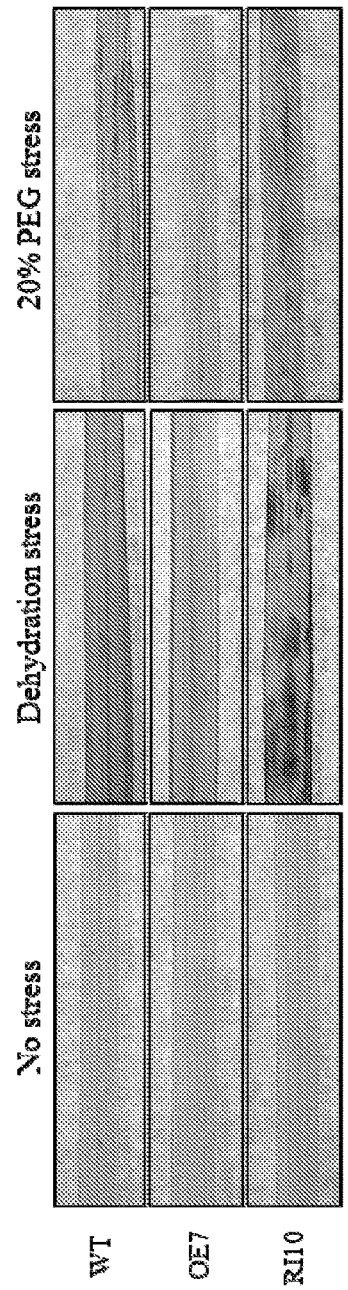
FIG. 32 shows the accumulation of reactive oxygen species in leaves taken from wild-type Nipponbare rice plants (WT), OsERF62 transgenic Nipponbare rice plants (OE7), and transgenic Nipponbare rice plants expressing an RNA interference molecule directed at OsERF62 (RI10) following control treatment (No Stress), dehydration stress treatment (Dehydration stress), or simulated drought stress treatment (20% PEG stress). Reactive oxygen species were detected using DAB staining.

Part VII. Oxidative Stress Tolerance Assay of OsERF62 OE and Suppression Expression Transgenic Plants Under drought stress, reactive oxygen species (ROS) such as $O^-$ and $H_2O_2$ were accumulated in plants, and excessive accumulation of ROS could lead to oxidative stress (Miller et al., 2010; Zhu, 2001). OsERF62 was strongly induced to express by $H_2O_2$, and the tolerance to drought stress of transgenic plants over-expressing OsERF62 was improved. In order to analyze the effect of OsERF62 on ROS accumulation, ROS accumulations in wild-type Nipponbare lines (WT), $T_2$-generation OsERF62 transgenic Nipponbare rice plants (OE) and $T_2$-generation OsERF62-RNAi transgenic Nipponbare rice plants (RI) were detected under dehydration and simulated stress with 20% PEG treatment. Plants normally grown for 3 weeks were dehydrated for 6 h, and then treated in a nutrient solution containing 20% PEG for 24 h. After treatment, the leaves were subjected to DAB staining, then decolored, and observed. Untreated plants were used as a control. As shown in FIG. 32, in the absence of stress, all the background levels of $H_2O_2$ in the WT, OE and RI plants were quite low, and after dehydration and stress treatment with 20% PEG, the leaves of the RI plants were deepest colored and the leaves of OE plants were least colored. These results suggest that that overexpression of OsERF62 may reduce the accumulation of ROS under abiotic stress conditions (particularly drought stress conditions), thereby reducing harm to the plant.

Excessive accumulation of $H_2O_2$ could lead to oxidative stress, thereby destroying the life cycle of the cells. The results above showed that overexpression of OsERF62 may reduce the accumulation of $H_2O_2$ in plants under abiotic stress conditions (particularly drought stress conditions), thereby avoiding serious damage caused by ROS.

Figure 33:
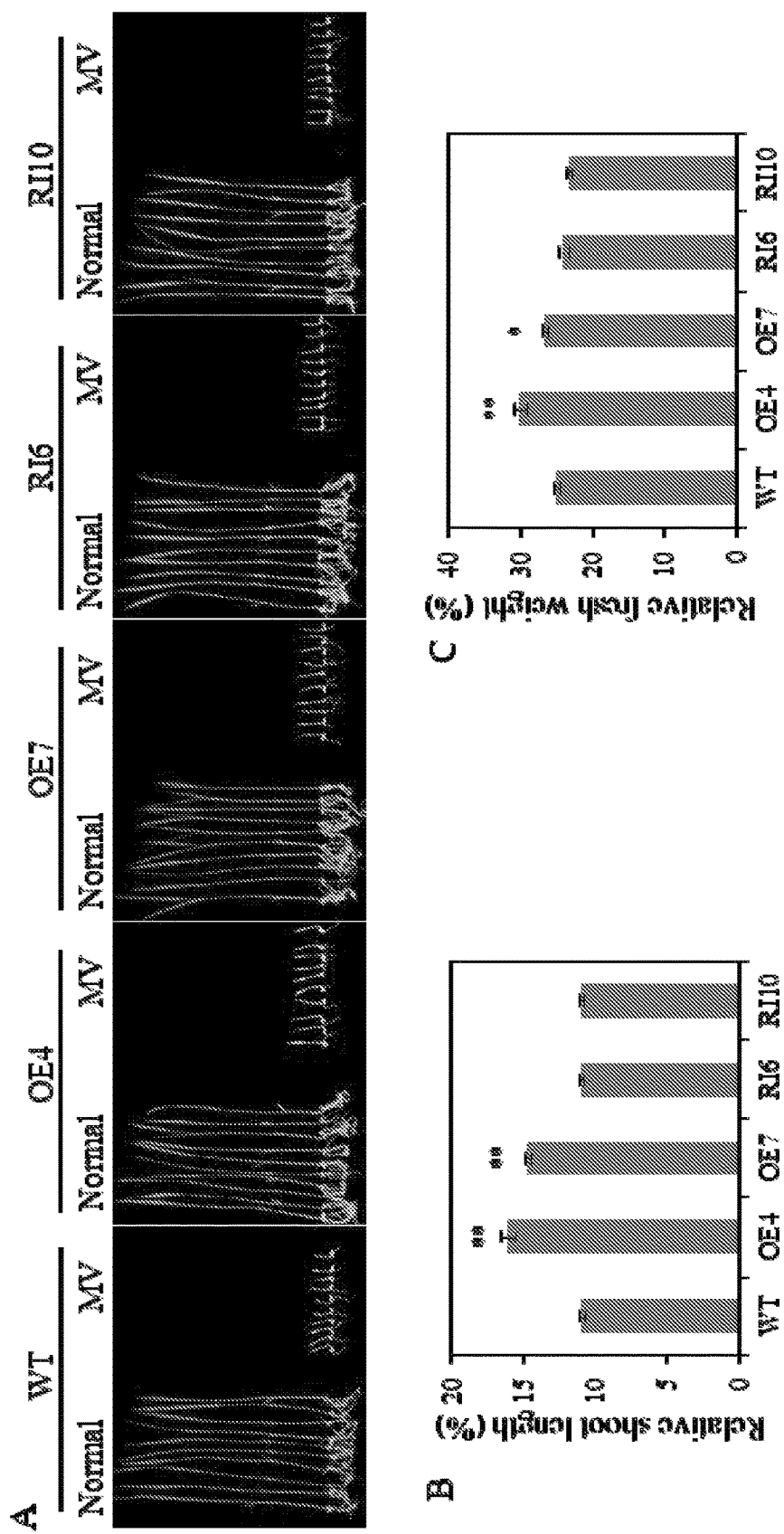
FIG. 33A shows wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10) following control treatment (Normal) or oxidative stress treatment (MV).
FIG. 33B is a graph showing the relative shoot lengths of wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10) following oxidative stress treatment (MV). The standard error bars shown therein are based on three replicates. **=significance at p<0.01.
FIG. 33C is a graph showing the relative weights of wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10) following oxidative stress treatment (MV). The standard error bars shown therein are based on three replicates. *=significance at p<0.05. **=significance at p<0.01.

To find out what role OsERF62 plays in oxidative stress, the performance of OE plants and RI plants under oxidative stress was also investigated. Seedlings of WT plants, OE plants, and RI plants that were normally germinated in ½MS MS medium for 2-3 d and had uniform growth status were transferred to ½MS medium containing 0 or 2 μM MV and grown for 7 d. Then the shoot length and fresh weight were measured. As shown in FIG. 33, under treatment with MV, the relative shoot length of OE plants was higher than that of WT and RI plants; likewise, the relative fresh weight of OE plants was also significantly higher than that of WT and RI plants, indicating that overexpression of OsERF62 gave rise to enhanced abiotic stress tolerance (more particularly, enhanced oxidative stress tolerance).

Figure 34:
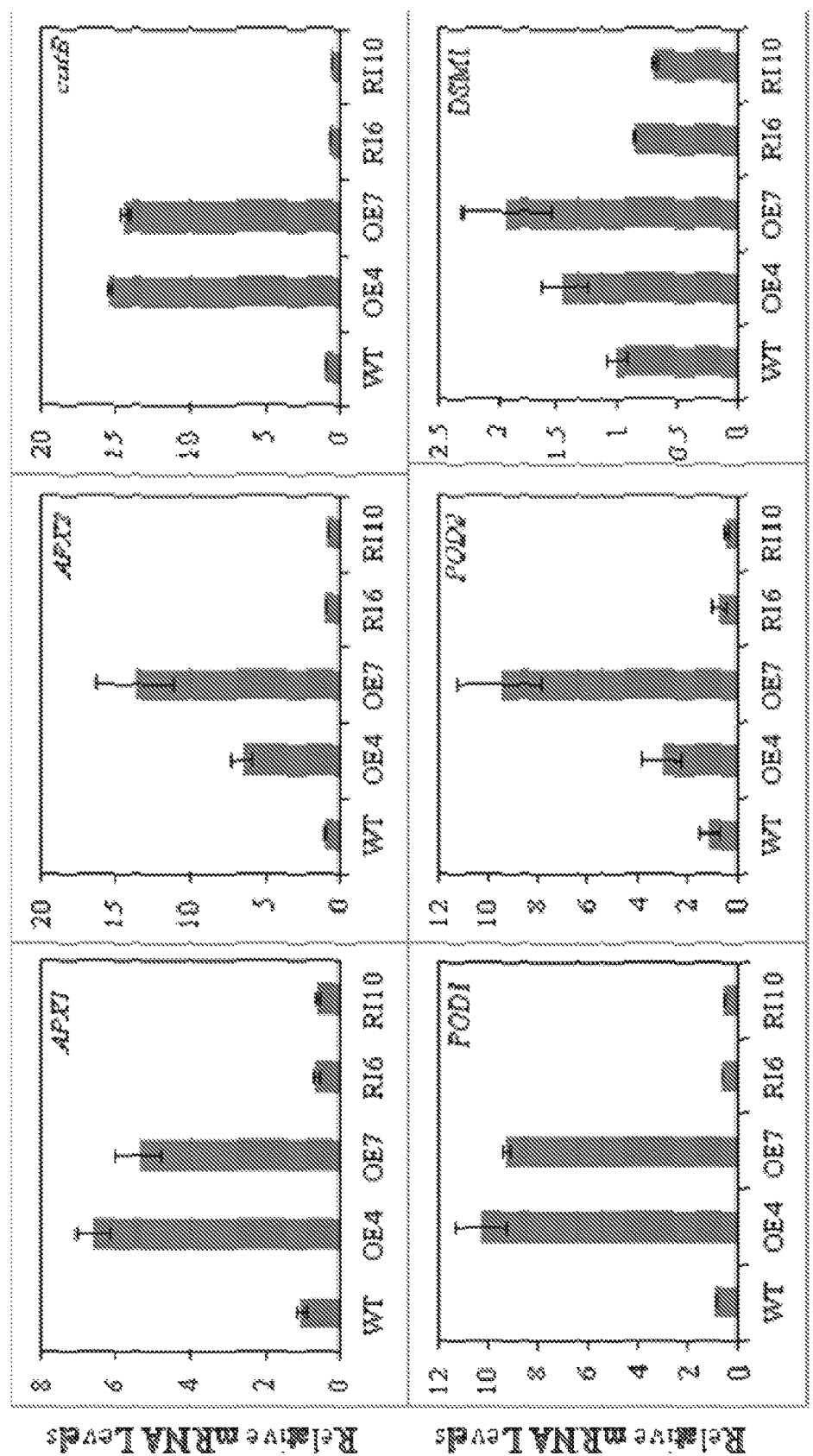
FIG. 34 shows the relative mRNA levels of genes associated with reactive oxygen species scavenging (APX1, APX2, catB, POD1, POD2, and DSM1) in wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10). The standard error bars shown therein are based on three replicates.

Under drought stress, the ROS content accumulated in OE transgenic plants is lower than that in WT plants, and is higher in RI plants than that in WT plants. Therefore, it was postulated that OsERF62 reduced the ROS accumulated in the plants by regulating the expression of one or more ROS scavenge-related genes. To verify the postulation, ROS scavenge related genes were analyzed, including APX1, APX2, catB, DSM, POD1 and POD2. As shown in FIG. 34, although there was no significant change in DSM 1 expression, the expression levels of APX1, APX2, catB, POD1, and POD2 in OE plants were significantly higher than in WT plants, and were slightly lower in RI plants than that in WT plants. These results suggest that overexpression of OsERF62 may reduce the accumulation of ROS in plants by regulating the expression of ROS scavenge related gene, thereby alleviating the damage of drought stress to plants.

Part VIII. OsERF62 Affected Emission of Ethylene from Rice

Ethylene plays an important role in regulating the drought tolerance of plants. OsERF62 expression was strongly induced by ethylene (Example 3, Part II), and previously reported ERF genes, such as OsERF3, DERF1, and SERF1, respond to ethylene. To determine whether the improvements in abiotic stress tolerance caused by OsERF62 overexpression are correlated with the anti-drought pathway regulated by ethylene, the ethylene emissions from wild-type Nipponbare lines (WT), $T_2$-generation OsERF62 transgenic Nipponbare rice plants (OE) and $T_2$-generation OsERF62-RNAi transgenic Nipponbare rice plants (RI) were analyzed.

Figure 35:
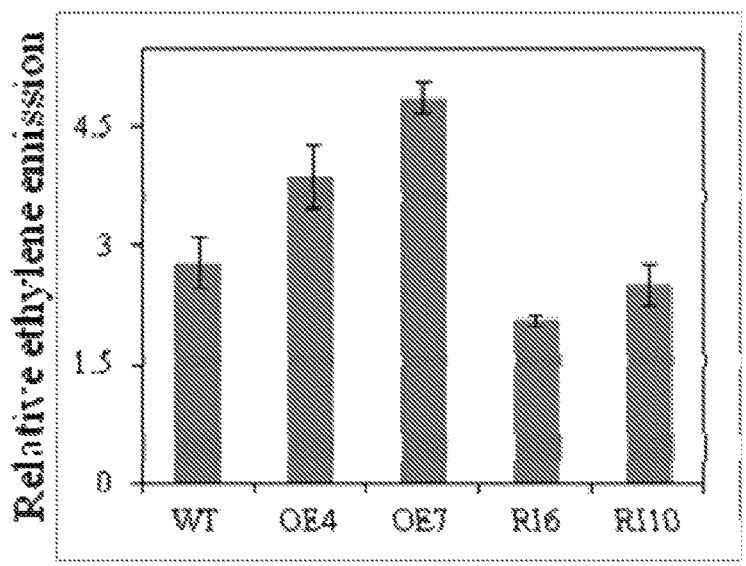
FIG. 35 is a graphing showing the relative ethylene emissions of wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10). The standard error bars shown therein are based on three replicates.

Seedlings germinated for 3 d in a normal medium were transferred to a glass tube (diameter: 4.8 cm; height: 14.8 cm) containing 50 mol ½ MS medium (10 plants each), grown for 7 d, and then sealed for 24 h. The emission of ethylene from the plants was determined by high resolution gas chromatography. An empty tube without rice was used as a control. For more intuitively expressing the difference in the biosynthesis of ethylene between WT and the transgenic plants, the biosynthesis of ethylene in WT was designated as a reference value of 100, with which the biosynthesis of ethylene from the transgenic plants was compared, the production of ethylene from the plants being represented by relative ethylene biosynthesis. As shown in FIG. 35, the emission of ethylene from OE plants was higher than that of WT plants, and the emission of ethylene from RI plants was lower than that of WT plants. The relative emissions of ethylene from OE4 and OE7 transgenic plants were 139.22 and 174.6, and were 73.9 and 89.66 from RI6 and RI10 suppression expression plants, indicating that OsERF62 is involved in the regulation of the biosynthesis of ethylene in rice.

Figure 36:
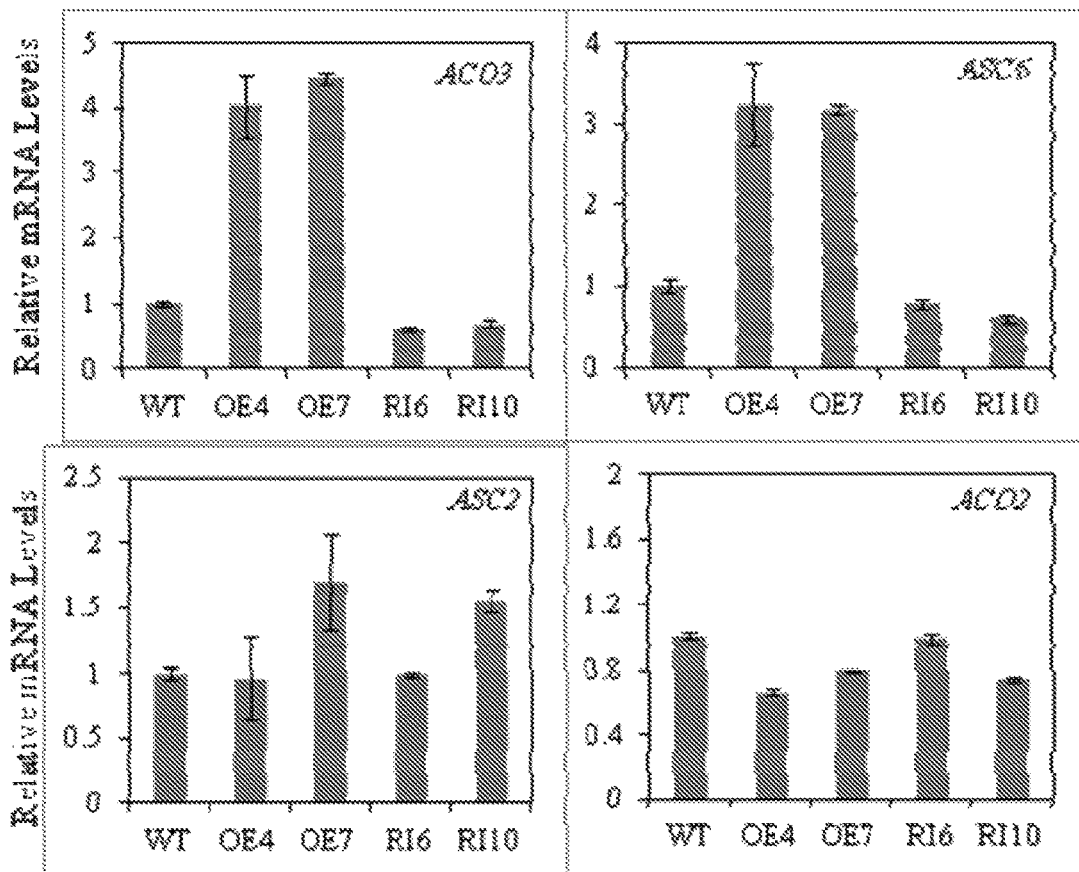
FIG. 36 shows the relative mRNA levels of genes associated with ethylene biosynthesis (ACO3, ASC6, ASC2, ACO2) in wild-type Nipponbare rice plants (WT), OsERF62 transgenic Nipponbare rice plants (OE4, OE7), and transgenic Nipponbare rice plants expressing an RNA interference molecule directed at OsERF62 (RI6, RI10). The standard error bars shown therein are based on three replicates.

Because OsERF62 was strongly induced to express in both Nipponbare and IRAT109 by ethylene, and because over expression of OsERF62 could improve the emission of ethylene from the transgenic plants, the expression of ethylene biosynthesis related genes ACO2, ACO3, ASC2, and ASC6 were analyzed. As shown in FIG. 36, the expressions of ACO3 and ASC6 in OE plants were improved, and were decreased in RI. These results suggest that OsERF62 might affect the biosynthesis of ethylene by regulating the expressions of ethylene biosynthesis related genes ACO3 and ASC6, thereby regulating the drought tolerance of the plant.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of the present invention.

The invention claimed is:

1. A recombinant nucleic acid, comprising:
   (a) the nucleotide sequence SEQ ID NO:1; or
   (b) a nucleotide sequence that encodes a polypeptide comprising the amino acid sequence SEQ ID NO:28, wherein each of the nucleotide sequences of (a) and (b) is operably linked to a heterologous promoter.

2. An expression cassette comprising the recombinant nucleic acid of claim 1.

3. A vector comprising the expression cassette of claim 2.

4. A plant, plant part or plant cell comprising the recombinant nucleic acid of claim 1.

5. A recombinant bacteria or a recombinant virus comprising the recombinant nucleic acid of claim 1.

6. A method of identifying, a plant or plant part having enhanced drought stress tolerance, salt stress tolerance and/or cold stress tolerance as compared to a control plant or plant part, comprising:
   detecting, in the plant or plant part, the recombinant nucleic acid of claim 1, thereby identifying a plant or plant part having enhanced drought stress tolerance, salt stress tolerance and/or cold stress tolerance.

7. A method of producing a plant having enhanced drought stress tolerance, salt stress tolerance and/or cold stress tolerance, comprising:
   introducing an exogenous nucleic acid into a plant part, wherein the exogenous nucleic acid comprises the recombinant nucleic acid of claim 1 to produce a transgenic plant part; and
   growing the transgenic plant part into a transgenic plant that expresses the exogenous nucleic acid and that has enhanced drought stress tolerance, salt stress tolerance and/or cold stress tolerance as compared to a control plant of the same species that has not been transformed with the exogenous nucleic acid grown under the same environmental conditions.

8. A method of producing a plant having enhanced drought stress tolerance, salt stress tolerance and/or cold stress tolerance, comprising:
   crossing a first parent plant or plant part with a second parent plant or plant part, wherein the first parent plant or plant part comprises within its genome an exogenous nucleic acid that comprises the recombinant nucleic acid of claim 1;
   thereby producing a progeny generation,
   wherein the progeny generation comprises at least one plant that comprises the exogenous nucleic acid within its genome and that exhibits enhanced drought stress tolerance, salt stress tolerance and/or cold stress tolerance as compared to a control plant of the same species grown under the same environmental conditions.

9. The method of claim 7, further comprising:
   selecting for a plant having increased seed yield and/or increased biomass, its compared to the control plant.

10. The method of claim 7, wherein the plant is a monocot, optionally a rice, maize, wheat, barley, oats, rye, millet, sorghum, triticale, secale, einkorn, spelt, emmer, teff, milo, fax gramma grass, *Tripsacion* sp. or teosinte plant.

11. The plant, plant part or plant cell of claim 4, wherein the plant part is a seed.

12. A plant grown from the seed of claim 11.

13. A crop comprising a plurality of the plant of claim 4.

14. A plant produced according to the method of claim 7.

15. A plant produced according to the method of claim 8.

16. The method of claim 7, wherein the plant is a dicot, optionally a cotton, potato, soybean, sugar beet, sunflower, tobacco or tomato plant.

17. A method of producing a transgenie plant, comprising introducing into a plant the recombinant nucleic acid of claim 1, thereby producing the transgenic plant.

18. The method of claim 17, wherein the transgenic plant is a monocot, optionally a rice, maize, wheat, barley, oats, rye, millet, sorghum, triticale, secale, einkorn, spelt, miner, teff, milo, flax gramma grass, *Tripsacum* sp. or teosinte plant.

19. The method of claim 17, wherein the transgenic plant is a dicot, optionally a cotton, potato, soybean, sugar beet, sunflower, tobacco or tomato plant.

20. A method of producing a transgenic plant, comprising introducing into a plant cell the recombinant nucleic acid of claim 1, thereby producing a transgenic plant cell; and
regenerating the transgenic plant cell into a transgenic plant, thereby producing a transgenic plant.

21. The method of claim 20, wherein the transgenic plant is a monocot, optionally a rice, maize, wheat, barley, oats, rye, millet, sorghum, triticale, sectile, einkorn, spelt, emmer, teff, milo, flax gramma grass, *Tripsacum* sp. or teosinte plant.

22. The method of claim 20, wherein the transgenic plant is a dicot, optionally a cotton, potato, soybean, sugar beet, sunflower, tobacco or tomato plant.

\* \* \* \* \*

UNITED STATES PATENT AND TRADEMARK OFFICE
CERTIFICATE OF CORRECTION

PATENT NO. : 10,190,133 B2  
APPLICATION NO. : 14/908219  
DATED : January 29, 2019  
INVENTOR(S) : Li et al.

Page 1 of 2

It is certified that error appears in the above-identified patent and that said Letters Patent is hereby corrected as shown below:

On the Title Page

Item (30) Foreign Application Priority Data: Please correct "2013 1 0322316" to read -- 2013 1 0322316.8 --

Item (30) Foreign Application Priority Data: Please correct "2013 1 0322634" to read -- 2013 1 0322634.4 --

In the Specification

Column 7, Line 24: Please correct "(OH)" to read -- (OEI) --

Column 7, Line 30: Please correct "(OH)" to read -- (OEI) --

Column 47, Line 27: Please correct "5'-TTGGCGCGCCA-" to read -- 5'-TTGGCGCGCCA- --

Column 47, Line 31: Please correct "5'-CCTTAATTAACCCCTGCCACGAATCTGCTAT-3'" to read -- 5'-CCTTAATTAACCCCTGCCACGAATCTGCTAT-3' --

Column 47, Lines 34-35: Please correct "5'-CGGGGTACCAAAGGCATTCGCAACACACA-3'" to read -- 5'-CGGGGTACCAAAGGCATTCGCAACACACA-3' --

Column 47, Line 38: Please correct "5'-CCTTAATTAACCAAAATACATTACGACTGGAC-3'" to read -- 5'-CCTTAATTAACCAAAATACATTACGACTGGAC-3' --

Column 50, Line 32: Please insert a paragraph break between the words "Part V." and "Seeds"

Column 53, Line 42: Please correct "Pro$_{COBL4IRAT109}$" to read -- Pro$_{COBL4IRAT109}$ --

Signed and Sealed this  
Twenty-fifth Day of June, 2019

Andrei Iancu  
*Director of the United States Patent and Trademark Office*

Column 61, Line 16: Please correct "RNA/" to read -- RNAi --

Column 61, Line 20: Please correct "RNA/" to read -- RNAi --

In the Claims

Column 157, Line 50, Claim 6: Please correct "identifying, a" to read -- identifying a --

Column 158, Line 57, Claim 9: Please correct "its" to read -- as --

Column 158, Line 61, Claim 10: Please correct "Tripsacion" to read -- Tripsacum --

Column 159, Line 9, Claim 18: Please correct "miner" to read -- emmer --

Column 159, Line 22, Claim 21: Please correct "sectile" to read -- secale --

SEQUENCE LISTING

```
<160> NUMBER OF SEQ ID NOS: 62

<210> SEQ ID NO 1
<211> LENGTH: 1278
<212> TYPE: DNA
<213> ORGANISM: Oryza sativa

<400> SEQUENCE: 1
atggcgattg gtgttggtgg ctgctgcgcc gtgctgctcg cggcggcgct gctcttctcc      60
tctccggcca ccacatatgc ttatgattcc ctggatccaa acggcaacat cacgataaaa     120
tgggatgtga tgcaattgac tcctgatggc tatgctgccg ttgtcacact gtccaactac     180
cagcaattcc ggcacatcca gccaccgggg tggcagctgg ggtggacatg gcagcagaag     240
gaggtgatct ggtccatgta cggcgcgcag gccatcgagc agggcgactg ctccatgtcc     300
aaggagggca gcaatgtccc ccacagctgc aagaagcatc ccaccgtcgt cgacctcctc     360
ccgggcaccc aatcgacct gcagatcgcc aactgctgca aggctggatc actgagcgca     420
ttcagccagg acccggcaaa ttctgccgcg tcgtttcaga tcattgtagg ccattctggg     480
aacagcaatg agactgttag ggtgccgaag aacttcagtc ttatggcgcc tggtccgggg     540
tatacctgta gccgtgctat gattgtgaag cctagtaggt ttttaagtcc ggatgggagg     600
```

| | |
|---|---|
| agggcgactc aagctctgat gacatggaat gtgatctgca catactccca atttcttgca | 660 |
| caaaaggttc catcctgctg tgtttctctc tcgtcgttcg acaatgacaa aactgttgac | 720 |
| tgcccaacat gctcttgtgg ctgccgaaat gaaaaatcta ctacaggaaa atgtgtaaag | 780 |
| aagaatgcac ctgatttgca atccatcatt cacggccctg gcagatggac ctggcagcct | 840 |
| cttctccagt gcacttcaca catgtgccca gtgaaaatta actggcactt gatgctcaaa | 900 |
| gacaaggaac actacagagt gaaaatcact gtcactaact gaactaccg catgaatttc | 960 |
| accgaatgga acctggttgt tcagtatcat cccatcctcg atatcaccca gatatctggc | 1020 |
| ttcaattaca agtcaatcca agtcggcaaa ataaatgata ctacgatgct atggggagta | 1080 |
| aagccctact atgatttgct catgcaagct ggtccgcttg gaaatgtgca aggagaactg | 1140 |
| attgtgagaa aggatttcag ggcttcttcc actagtaaca ataacaaggg aagggccttc | 1200 |
| ccagtccgtg tgtacttcaa cggtgataac tgtgtgatgc cgcctccgga tgcatatcca | 1260 |
| gttagtatta cggcttag | 1278 |

<210> SEQ ID NO 2
<211> LENGTH: 1569
<212> TYPE: DNA
<213> ORGANISM: Oryza sativa

<400> SEQUENCE: 2

| | |
|---|---|
| acacaccgag tcatcgctcg ccggagttag agttcgtagc ggcgaaggat atagccatat | 60 |
| attatagatg gcgattggtg ttggtggctg ctgcgccgtg ctgctcgcgg cggcgctgct | 120 |
| cttctcctct ccggccacca catatgctta tgattccctg gatccaaacg gcaacatcac | 180 |
| gataaaatgg gatgtgatgc aattgactcc tgatggctat gctgccgttg tcacactgtc | 240 |
| caactaccag caattccggc acatccagcc accggggtgg cagctggggt ggacatggca | 300 |
| gcagaaggag gtgatctggt ccatgtacgg cgcgcaggcc atcgagcagg gcgactgctc | 360 |
| catgtccaag gagggcagca atgtccccca cagctgcaag aagcatccca ccgtcgtcga | 420 |
| cctcctcccg ggcacccaa tcgacctgca gatcgccaac tgctgcaagg ctggatcact | 480 |
| gagcgcattc agccaggacc cggcaaattc tgccgcgtcg tttcagatca ttgtaggcca | 540 |
| ttctgggaac agcaatgaga ctgttagggt gccgaagaac ttcagtctta tggcgcctgg | 600 |
| tccgggtat acctgtagcc gtgctatgat tgtgaagcct agtaggtttt taagtccgga | 660 |
| tgggaggagg gcgactcaag ctctgatgac atggaatgtg atctgcacat actcccaatt | 720 |
| tcttgcacaa aaggttccat cctgctgtgt ttctctctcg tcgttcgaca atgacaaaac | 780 |
| tgttgactgc ccaacatgct cttgtggctg ccgaaatgaa aaatctacta caggaaaatg | 840 |
| tgtaagaag aatgcacctg atttgcaatc catcattcac ggccctggca gatggacctg | 900 |
| gcagcctctt ctccagtgca cttcacacat gtgcccagtg aaaattaact ggcacttgat | 960 |
| gctcaaagac aaggaacact acagagtgaa atcactgtc actaacttga actaccgcat | 1020 |
| gaatttcacc gaatggaacc tggttgttca gtatcatccc atcctcgata tcacccagat | 1080 |
| atctggcttc aattacaagt caatccaagt cggcaaaata atgatacta cgatgctatg | 1140 |
| gggagtaaag ccctactatg atttgctcat gcaagctggt ccgcttggaa atgtgcaagg | 1200 |
| agaactgatt gtgagaaagg atttcagggc ttcttccact agtaacaata caagggaag | 1260 |
| ggccttccca gtccgtgtgt acttcaacg tgataactgt gtgatgccgc tccggatgc | 1320 |
| atatccagtt agtattacgg cttagaggcg atcgtcaaga tgattgtatc acattactat | 1380 |

| atttatgggg tcatgaataa agtgtgttgt cttgtctatt gaagattaga agtaactata | 1440 |
| attaaattga atctccaact agtattaaga ttgtcagagg tctgttgttt tgcttgtaga | 1500 |
| taaaattctg cctatgttaa cttcgatggt gtcaaagata tcaaatccat agcagattcg | 1560 |
| tggcaggggg | 1569 |

<210> SEQ ID NO 3
<211> LENGTH: 1589
<212> TYPE: DNA
<213> ORGANISM: Oryza sativa

<400> SEQUENCE: 3

| ttggcgcgcc acacaccgag tcatcgctcg ccggagttag agttcgtagc ggcgaaggat | 60 |
| atagccatat attatagatg gcgattggtg ttggtggctg ctgcgccgtg ctgctcgcgg | 120 |
| cggcgctgct cttctcctct ccggccacca catatgctta tgattccctg gatccaaacg | 180 |
| gcaacatcac gataaaatgg gatgtgatgc aattgactcc tgatggctat gctgccgttg | 240 |
| tcacactgtc caactaccag caattccggc acatccagcc accggggtgg cagctggggt | 300 |
| ggacatggca gcagaaggag gtgatctggt ccatgtacgg cgcgcaggcc atcgagcagg | 360 |
| gcgactgctc catgtccaag gagggcagca atgtccccca cagctgcaag aagcatccca | 420 |
| ccgtcgtcga cctcctcccg ggcaccccaa tcgacctgca gatcgccaac tgctgcaagg | 480 |
| ctggatcact gagcgcattc agccaggacc cggcaaattc tgccgcgtcg tttcagatca | 540 |
| ttgtaggcca ttctgggaac agcaatgaga ctgttagggt gccgaagaac ttcagtctta | 600 |
| tggcgcctgg tccgggtat acctgtagcc gtgctatgat tgtgaagcct agtaggtttt | 660 |
| taagtccgga tgggaggagg gcgactcaag ctctgatgac atggaatgtg atctgcacat | 720 |
| actcccaatt tcttgcacaa aaggttccat cctgctgtgt ttctctctcg tcgttcgaca | 780 |
| atgacaaaac tgttgactgc ccaacatgct cttgtggctg ccgaaatgaa aaatctacta | 840 |
| caggaaaatg tgtaaagaag aatgcacctg atttgcaatc catcattcac ggccctggca | 900 |
| gatggacctg gcagcctctt ctccagtgca cttcacacat gtgcccagtg aaaattaact | 960 |
| ggcacttgat gctcaaagac aaggaacact acagagtgaa atcactgtc actaacttga | 1020 |
| actaccgcat gaatttcacc gaatggaacc tggttgttca gtatcatccc atcctcgata | 1080 |
| tcacccagat atctggcttc aattacaagt caatccaagt cggcaaaata aatgatacta | 1140 |
| cgatgctatg gggagtaaag ccctactatg atttgctcat gcaagctggt ccgcttggaa | 1200 |
| atgtgcaaga agaactgatt gtgagaaagg atttcagggc ttcttccact agtaacaata | 1260 |
| acaagggaag ggccttccca gtccgtgtgt acttcaacgg tgataactgt gtgatgccgc | 1320 |
| ctccggatgc atatccagtt agtattacgg cttagaggcg atcgtcaaga tgattgtatc | 1380 |
| acattactat atttatgggg tcatgaataa agtgtgttgt cttgtctatt gaagattaga | 1440 |
| agtaactata attaaattga atctccaact agtattaaga ttgtcagagg tctgttgttt | 1500 |
| tgcttgtaga taaaattctg cctatgttaa cttcgatggt gtcaaagata tcaaatccat | 1560 |
| agcagattcg tggcaggggt taattaagg | 1589 |

<210> SEQ ID NO 4
<211> LENGTH: 3024
<212> TYPE: DNA
<213> ORGANISM: Oryza sativa

<400> SEQUENCE: 4

| acacaccgag tcatcgctcg ccggagttag agttcgtagc ggcgaaggat atagccatat | 60 |

```
attatagatg cgcgattggtg ttggtggctg ctgcgccgtg ctgctcgcgg cggcgctgct      120
cttctcctct ccggccacca catgtaagca cgcccatctt cttcttcttc ttttttttct      180
tctttctttt ttttttggaaa tgagccgcag ctgacaaaaa gatcactcaa tgcctaagcc     240
attttgtttt cttgttttgg attttctctt ttatgtgtat cacttttgct tgttgctctt     300
gcagatgctt atgattccct ggatccaaac ggcaacatca cgataaaatg ggatgtgatg     360
caattgactc ctgatggcta tgctgtaagt agcggtggca gtacaccaac atctctacct     420 ttatttttcgt ctcaacctgt acatttacac tatcttgttc tactacctct aataaaaaaa   480
tatatttgat gttttaaaat ctattaagtt ctagagatta ggaaagctac acatggtttt    540
atgttttgat actattaagt agtatatttt ataagttata ttgaaggctg gggtttcaaa    600
agtttgacta cactagatct tattcaaagc gtcaatgat tactgaacgg aggaagtatg     660
aacttataga cttgaagtta aacagcatag ccacatctct tcatgtatac ttcatccgtt    720
tcatattata agattttcta gcattatcca catttatata tatgttaatg aatctagaca    780
tatatgtgcg tctagattca ttaatatcta tatgaattgg gcaatgctat aaaatcttat    840
aacctgaaaa acggagggag tatgtcgcaa acaacaacaa caataacaac gagcaaaatc    900
tatatcgaat ccggtttccc tcttgtaact gtatcaaaga tctgtcctct gaaacgtccc    960
ctgttcatca ggccgttgtc acactgtcca actaccagca attccggcac atccagccac   1020
cggggtggca gctggggtgg acatggcagc agaaggaggt gatctggtcc atgtacggcg   1080
cgcaggccat cgagcagggc gactgctcca tgtccaagga gggcagcaat gtcccccaca   1140
gctgcaagaa gcatcccacc gtcgtcgacc tcctcccggg caccccaatc gacctgcaga   1200
tcgccaactg ctgcaaggct ggatcactga gcgcattcag ccaggacccg gcaaattctg   1260
ccgcgtcgtt tcagatcatt gtaggccatt ctgggaacag caatgagact gttagggtgc   1320
cgaagaactt cagtcttatg gcgcctggtc cggggtatac ctgtagccgt gctatgattg   1380
tgaagcctag taggtttta gtccggatg ggaggagggc gactcaagct ctgagtaagt     1440
agtccatctg ttgttctttt tctgaattgc tgcttgatgc ccaattgctt gtatgtcatg   1500
tggaaatgca ttaggaacat agactcagtt gtgatttctt aatgctaagt tggattaggc   1560
ataggtttag tgaggaaggg acaggagttg gtcacctaag actggttgat ctgatattag   1620
ttgaaaacaa gttacagcat gctaggcttt acaaggctga gcctacttaa caaatgttgt   1680
catctttttt ttaatcaatt ttgttatcta gcaactaata catgtcaaat tcagacagac   1740
atccccatga ttacatatag gacttgttgt ttgttttgag ttctatagta gaaaaaattc   1800
ctatattcag tactactagt agtacttctt aacaaaaagg aaatctctat tcacagtgac   1860
atggaatgtg atctgcacat actcccaatt tcttgcacaa aaggttccat cctgctgtgt   1920
ttctctctcg tcgttcgaca atgacaaaac tgttgactgc ccaacatgct cttgtggctg   1980
ccgaaatgaa aaatctacta caggaaaatg tgtaaagtga gttaatataa ctgtcactga   2040
tcttaactac aatttccact gggatcctag cttcttgttt tcaccaaaaa attgtaacaa   2100
tttcctttgc atttgacagg aagaatgcac ctgatttgca atccatcatt cacggccctg   2160
gcagatggac ctggcagcct cttctccagt gcacttcaca catgtgccca gtgaaaatta   2220
actggcactt gatgctcaaa gacaaggaac actacagagt gaaaatcact gtcactaact   2280
tgaactaccg catgaatttc accgaatgga acctggttgt tcagtatcat cccatcctcg   2340
atatcaccca gatatctggc ttcaattaca agtcaatcca agtcggcaaa ataagtaagt   2400
```

| | |
|---|---|
| caatctggaa ccatccttt ttgataaaaa aaaatgcatg tgtatgtgtg tgtatatata | 2460 |
| cttctgacct atgtctagat tcgtagccaa aatttatttt ttttaaggac agaaggtgta | 2520 |
| tataccatct ctctatcttt tgctcacgaa gttttttttt tctccttgta ttttagatga | 2580 |
| tactacgatg ctatggggag taaagccta ctatgatttg ctcatgcaag ctggtccgct | 2640 |
| tggaaatgtg caaggagaac tgattgtgag aaaggatttc agggcttctt ccactagtaa | 2700 |
| caataacaag ggaagggcct cccagtccg tgtgtacttc aacggtgata actgtgtgat | 2760 |
| gccgcctccg gatgcatatc cagttagtat tacggcttag aggcgatcgt caagatgatt | 2820 |
| gtatcacatt actatattta tggggtcatg aataaagtgt gttgtcttgt ctattgaaga | 2880 |
| ttagaagtaa ctataattaa attgaatctc caactagtat taagattgtc agaggtctgt | 2940 |
| tgttttgctt gtagataaaa ttctgcctat gttaacttcg atggtgtcaa agatatcaaa | 3000 |
| tccatagcag attcgtggca gggg | 3024 |

<210> SEQ ID NO 5
<211> LENGTH: 1278
<212> TYPE: DNA
<213> ORGANISM: Oryza sativa

<400> SEQUENCE: 5

| | |
|---|---|
| atggcgattg gtgttggtgg ctgctgcgcc gtgctgctcg cggcggcgct gctcttctcc | 60 |
| tctccggcca ccacatatgc ttatgattcc ctggatccaa acggcaacat acgataaaa | 120 |
| tgggatgtga tgcaatggac tcctgatggc tatgctgccg ttgtcacact gtccaactac | 180 |
| cagcaattcc ggcacatcca gccaccgggg tggcagctgg ggtggacatg gcagcagaag | 240 |
| gaggtgatct ggtccatgta cggcgcgcag gccatcgagc agggcgactg ctccatgtcc | 300 |
| aaggagggca gcaatgtccc ccacagctgc aagaagcatc ccaccgtcgt cgacctcctc | 360 |
| ccgggcgccc aatcgacct gcagatcgcc aactgctgca aggctggatc actgagcgca | 420 |
| ttcagccagg acccggcaaa ttctgccgcg tcgtttcaga tcattgtagg ccattctggg | 480 |
| aacagcaatg agactgttag ggtgccgaag aacttcagtc ttatggcgcc tggtccgggg | 540 |
| tatacctgta gccgtgctat gattgtgaag cctagtaggt ttttaagtcc ggatgggagg | 600 |
| agggcgactc aagttctgat gacatggaat gtgatctgca catactccca atttcttgca | 660 |
| caaaaggttc catcctgctg tgttctctc tcgtcgttcg acaatgacaa aactgttgac | 720 |
| tgcccaacat gctcttgtgg ctgccgaaat gaaaaatcta ctacaggaaa atgtgtaaag | 780 |
| aagaatgcac ctgatttgca atccatcatt cacggccctg gcagatggac ctggcagcct | 840 |
| cttctccagt gcacttcaca catgtgccca gtgaaaatta ctggcactt gatgctcaaa | 900 |
| gacaaggaac actacagagt gaaaatcact gtcactaact tgaactaccg catgaatttc | 960 |
| accgaatgga acctggttgt tcagtatcat cccatcctcg atatcaccca gatatctggc | 1020 |
| ttcaattaca agtcaatcca gtcggcaaa ataaatgata ctacgatgct atggggagta | 1080 |
| aagccctact atgatttgct catgcaagct ggtccgcttg gaaatgtgca aggagaactg | 1140 |
| attgtgagaa aggatttcag ggcttcttcc actactaaca ataacaaggg aagggccttc | 1200 |
| ccagtccgtg tgtacttcaa cggtgataac tgtgtgatgc cgcctccgga tgcatatcca | 1260 |
| gttagtatta cggcttag | 1278 |

<210> SEQ ID NO 6
<211> LENGTH: 1569
<212> TYPE: DNA
<213> ORGANISM: Oryza sativa

<400> SEQUENCE: 6

```
acacaccgag tcatcgctcg ccggagttag agttcgtagc ggcgaaggat atagccatat    60
attatagatg gcgattggtg ttggtggctg ctgcgccgtg ctgctcgcgg cggcgctgct   120
cttctcctct ccggccacca catatgctta tgattccctg gatccaaacg gcaacatcac   180
gataaaatgg gatgtgatgc aatggactcc tgatggctat gctgccgttg tcacactgtc   240
caactaccag caattccggc acatccagcc accggggtgg cagctggggt ggacatggca   300
gcagaaggag gtgatctggt ccatgtacgg cgcgcaggcc atcgagcagg gcgactgctc   360
catgtccaag gagggcagca atgtccccca cagctgcaag aagcatccca ccgtcgtcga   420
cctcctcccg ggcgccccaa tcgacctgca gatcgccaac tgctgcaagg ctggatcact   480
gagcgcattc agccaggacc cggcaaattc tgccgcgtcg tttcagatca ttgtaggcca   540
ttctgggaac agcaatgaga ctgttagggt gccgaagaac ttcagtctta tggcgcctgg   600
tccggggtat acctgtagcc gtgctatgat tgtgaagcct agtaggtttt taagtccgga   660
tgggaggagg gcgactcaag ttctgatgac atggaatgtg atctgcacat actcccaatt   720
tcttgcacaa aaggttccat cctgctgtgt ttctctctcg tcgttcgaca atgacaaaac   780
tgttgactgc ccaacatgct cttgtggctg ccgaaatgaa aaatctacta caggaaaatg   840
tgtaaagaag aatgcacctg atttgcaatc catcattcac ggccctggca gatggacctg   900
gcagcctctt ctccagtgca cttcacacat gtgcccagtg aaaattaact ggcacttgat   960
gctcaaagac aaggaacact acagagtgaa aatcactgtc actaacttga actaccgcat  1020
gaatttcacc gaatggaacc tggttgttca gtatcatccc atcctcgata tcacccagat  1080
atctggcttc aattacaagt caatccaagt cggcaaaata aatgatacta cgatgctatg  1140
gggagtaaag ccctactatg atttgctcat gcaagctggt ccgcttggaa atgtgcaagg  1200
agaactgatt gtgagaaagg atttcagggc ttcttccact actaacaata caagggaag   1260
ggccttccca gtccgtgtgt acttcaacgg tgataactgt gtgatgccgc ctccggatgc  1320
atatccagtt agtattacgg cttagaggcg atcgtcaaga tgattgtatc gcattactat  1380
atttatgggg tcatgaataa agtgtattgt cttgcctatt gaagattaga agtaactata  1440
attaaattga atctccaact agtattaaga ttgtcagagg tctgttattt tgcttgtaga  1500
taaaattctg cctatgttaa cttcgatggt gtcaaagata tcaaatccat agcagattcg  1560
tggcagggg                                                          1569
```

<210> SEQ ID NO 7
<211> LENGTH: 3054
<212> TYPE: DNA
<213> ORGANISM: Oryza sativa

<400> SEQUENCE: 7

```
acacaccgag tcatcgctcg ccggagttag agttcgtagc ggcgaaggat atagccatat    60
attatagatg gcgattggtg ttggtggctg ctgcgccgtg ctgctcgcgg cggcgctgct   120
cttctcctct ccggccacca catgtaagca cgcccatctt cttcttcttc ttttttctt    180
tctttgtttt ttttttggaaa tgagccgcag ctgacaaaaa gatcactcac acatggatac   240
actgtcgtga cactaaccaa tgcctaagcc attttgtttt cttgttttgg attttttctt   300
ttatgtgtat cacttttgct tgttgctctt gcagatgctt atgattccct ggatccaaac   360
ggcaacatca cgataaaatg ggatgtgatg caatggactc ctgatggcta tgctgtaagt   420
```

-continued

```
agcggtggca gtacaccaac atctctacct ttatttcgt ctcaacctgt acatttacac       480
tatcttgttc tactacctct aataaaaaaa tatatttgat gttttaaaat ctattaagtt       540
ctagagatta ggaaagctac acatggtttt atgttttgat actattaagt agtatatttt       600
ataagttata ttgaaggctg gggtttcaaa agtttgacta cactagatct tattcaaagc       660
gtctaatgat tactgaacgg aggaagtatg aacttataga cttgaagtta aacagcatag       720
ccacatctct tcatgtatac ttcatccgtt tcatcttata agattttcta gcattatcca       780
cattcatata tatgttaatg aatctagaca tatatgtacg tctagattta ttaatatcta       840
tatgaattgg gcaatgctat aaaatcttat aacctgaaaa acggagggag tatgtcgcaa       900
acaacaacaa caataacaac gagcaaaatc tatatcgaat ccggtttccc tcttgtaact       960
gtatcaaaga tctgtcctct gaaacgtccc ctgttcatca ggccgttgtc acactgtcca      1020
actaccagca attccggcac atccagccac cggggtggca gctggggtgg acatggcagc      1080
agaaggaggt gatctggtcc atgtacggcg cgcaggccat cgagcagggc gactgctcca      1140
tgtccaagga gggcagcaat gtcccccaca gctgcaagaa gcatcccacc gtcgtcgacc      1200
tcctcccggg cgccccaatc gacctgcaga tcgccaactg ctgcaaggct ggatcactga      1260
gcgcattcag ccaggacccg gcaaattctg ccgcgtcgtt tcagatcatt gtaggccatt      1320
ctgggaacag caatgagact gttagggtgc cgaagaactt cagtcttatg gcgcctggtc      1380
cggggtatac ctgtagccgt gctatgattg tgaagcctag taggttttta agtccggatg      1440
ggaggagggc gactcaagtt ctgagtaagt agtccatctg ttgttctttt tctgaattgc      1500
tgcttgatgc ccaattgctt gtatgtcatg tggaaatgca ttaggaacat agactcagtt      1560
gtgatttctt aatgctaagt tggattaggc ataggtttag tgaggaaggg acaggagttg      1620
gtcacctaag actggttgat ctgatattag ttgaaaacaa gttacagcat gctaggcttt      1680
acaaggctga gcctacttaa caaatgttgt catctttttt ttaatcaatt ttgttatcta      1740
gcaactaata catgtcaaat tcagacagac atccccatga ttacatatag gacttgttgt      1800
ttgttttgag ttctatagta gaaaaaattc ctatattcag tactactagt agtacttctt      1860
aacaaaaagg aaatctctat tcacagtgac atggaatgtg atctgcacat actcccaatt      1920
tcttgcacaa aaggttccat cctgctgtgt ttctctctcg tcgttcgaca atgacaaaac      1980
tgttgactgc ccaacatgct cttgtggctg ccgaaatgaa aaatctacta caggaaaatg      2040
tgtaaagtga gttaatataa ctgttactga tcttaactac aatttccact gggatcctag      2100
cttcttgttt tcaccaaaaa attgtaacaa tttccttttgc atttgacagg aagaatgcac      2160
ctgatttgca atccatcatt cacggccctg gcagatggac ctggcagcct cttctccagt      2220
gcacttcaca catgtgccca gtgaaaatta actggcactt gatgctcaaa gacaaggaac      2280
actacagagt gaaaatcact gtcactaact tgaactaccg catgaatttc accgaatgga      2340
acctggttgt tcagtatcat cccatcctcg atatcaccca gatatctggc ttcaattaca      2400
agtcaatcca agtcggcaaa ataagtaagt caatctggaa ccatcctttt ttgataaaaa      2460
aaaatgcatg tgtatgtgtg tgtatatata cttctgacct atgtctagat tcgtagccaa      2520
aatttatttt tttaaggac agaaggtgta tataccatct ctctatcttt tgctcacgaa      2580
gttttttttt tctccttgta tgttagatga tactacgatg ctatggggag taaagcccta      2640
ctatgatttg ctcatgcaag ctggtccgct tggaaatgtg caaggagaac tgattgtgag      2700
aaaggatttc agggcttctt ccactactaa caataacaag ggaagggcct tcccagtccg      2760
tgtgtacttc aacggtgata actgtgtgat gccgcctccg gatgcatatc cagttagtat      2820
```

```
tacggcttag aggcgatcgt caagatgatt gtatcgcatt actatattta tggggtcatg    2880
aataaagtgt attgtcttgc ctattgaaga ttagaagtaa ctataattaa attgaatctc    2940
caactagtat taagattgtc agaggtctgt tattttgctt gtagataaaa ttctgcctat    3000
gttaacttcg atggtgtcaa agatatcaaa tccatagcag attcgtggca gggg          3054

<210> SEQ ID NO 8
<211> LENGTH: 2765
<212> TYPE: DNA
<213> ORGANISM: Oryza sativa

<400> SEQUENCE: 8
gagcgccatg cccgcatatg cacgggacga acccaagatt cacggcatgt taaccatgtc      60
ggagaggtgg cgctgagcca tcacccttc cgtcatgcaa tgagtcctcc tcaagaaacc      120
caaccgacga tcaatccatc gaggtgtgac gcgccatctc gccgctcggt ggcttcttct     180
tcttctacct tctcctccct cttcctggcc agccagtgca cgccttctca ttcaattccc     240
tgctcacctc gatcgagtag ctgctgctgc tgtgctagct tgctcgccgg ccggtgaggt     300
cgacgatgga gctgcacaga tgctctctcc tcgctctgct cctcgccgtg acatgctcgg     360
ttgcaggtta attacttctt cgatcttctt gcccattatt cctaattaaa ttatacttt     420 gctgttgatt aatcaatcat gcatgtgtgt gtgcttgcag tggcgtatga tccgctggac     480
ccgaagggga acatcacgat aaagtgggac gtgatatcgt ggacgcccga cgggtacgtg    540
gcgatggtga cgatgagcaa ctaccagatg taccggcaga tcctggcgcc cgggtggaca    600
gtggggtggt cgtgggccaa gaaggaggtc atctggtcca tcgtggggc ccaggccacc     660 gagcagggcg actgctccaa gttcaagggc ggcatccccc acagctgcaa gcgcaccccg    720
gccatcgtcg acctcctccc cggcgtcccc tacaaccagc agatcgccaa ctgctgcaag    780
gccggcgtcg tctccgccta cggccaggac cccgccggat ccgtctccgc cttccaggtc    840
tccgtcggcc tcgccggcac caccaacaag accgtcaagc tacccaccaa cttcaccctc    900
gccggcccgg gacccgggta cacgtgtggc ccggccacca tcgtcccttc caccgtctac    960 ctcacccgg accggcgccg ccgcacccag gcgctcatga cgtggaccgt cacctgcacc   1020
tactcccagc agctggcgtc gcgctacccg acctgctgcg tctccttctc ctccttctac   1080
aacagcacca tcgtgccgtg cgccaggtgc gcctgcgggt gcggcacga cggctaccgc   1140 ggcaacggcg gcggcgggaa gaacgcccgc gccggcgacg gacgcagcag acgcaacagc   1200
ggcggcggcg gagggcacag cggcggcacc gagtgcatca tggcgactc gaagcgggcg   1260 ctgtcggcgg gggtgaacac gccgcgcaag gacggggcgc cgctgctgca gtgcacgtcg   1320
cacatgtgcc cgatccgcgt gcactggcac gtcaagctca actacaagga ctactggcgc   1380
gccaagatcg ccatcacaaa cttcaactac cgcatgaact acacccagtg gacgctcgtc   1440
gcccagcacc ccaacctcaa caacgtcacc gaggtcttca gcttccagta caagcccctc   1500
ctcccctacg gcaacatcag taagctctct accacaacct cttattcctc ctctccgaca   1560
tcgttctcgc tttcatatct ataccctgtac taattggacg acaccacggc catggtatat   1620
tgcagacgac accggcatgt tctacgggct caagttctac aacgacctgc tcatggaggc   1680
agggccgttc ggcaacgtgc agtcggaggt gctgatgcga aaggactaca acaccttcac   1740
cttcagccag ggctgggcgt tcccgcgcaa gatctacttc aacggcgacg agtgcaagat   1800
gccgccgccg gactcctacc cctacctacc caactccgct ccgatcgggc cgccgcgttc   1860
```

| | |
|---|---|
| cgtggccgcc gccgcctcgg cgatcttggt ggtgctcctc ctggtggcat gatcagaaaa | 1920 |
| atgtccccctt ttgctttgtc ttcttgataa ttcccacatg tttggagagc agtgtaggta | 1980 |
| ggggcatttt ggtctattca tactggatat tcagtcaaag aggaaatctg tgatattgtg | 2040 |
| ttaactttga aattgcctga tagatctcca taatgtacaa cacaatcagg ctggaagagt | 2100 |
| tttggtcagt ccccagttag gccagccctg agaaatcaca ccacaaactt ttctgcaaat | 2160 |
| tctgttgtga ctacaaatat gtatgcaggt attgaccttg aattgagagg aaaaaagaaa | 2220 |
| caatttccac atttactgac caactacaaa atgcaatttc ttgcaatcag atgagatggc | 2280 |
| aaacatttct ctagacaatt aatgttggga cttggggttc tcaattagtc ttcacacttc | 2340 |
| agaccaagaa tacacaccat cagaatgtac aacccaaact ttaatgattt cgaggaacct | 2400 |
| aaacttacaa cctaaatcaa acgcgaatta gcttttcatg caagagcaca ccctaaactt | 2460 |
| ccaaaagact cagtatgtca acagccaatg cccaatgtgg tcagcacttt ccacagtttt | 2520 |
| tgtctaaaac taggtggttg tgcaagaatg ctaatgttcc acaaaccagg aatgacatga | 2580 |
| gaaggaatac agtcctaaat ctaggagtag aagagggggg taaccatggg tacagatctg | 2640 |
| gtgaaggcat gacacaactt tcgccattga agtatatgcg ccttggaaaa gcccaaccct | 2700 |
| tgtcaaaggt gaaggttgac cggtccttcc ggaatagaag ctcggattgg acatttccat | 2760 |
| ctggc | 2765 |

<210> SEQ ID NO 9
<211> LENGTH: 3644
<212> TYPE: DNA
<213> ORGANISM: Oryza sativa

<400> SEQUENCE: 9

| | |
|---|---|
| ggcgagccga gtgccaccga cagaaagagg gaggagaggc tctgtcacct gcgccttttt | 60 |
| tattcccccg cggtagtgtc ggtttcccct tgccttgcct ggcggttggc gcgtcgcatc | 120 |
| taccctgct actagtagta ccacttctcg cggcagaaaa atgccgcaat atatttgctt | 180 |
| ccaccgaggc gcagagcgga ggagagtgac gagctgacgc acgcggcgcg gcggaccagc | 240 |
| tcaatttgcc tgccgctcct cgtcttccgg tggggcggag gagggggacg ccgggcgggc | 300 |
| gggcgctcgc attccggagc ggggagcgcg agctcgatcg ggcggggata tggcggtggg | 360 |
| gggagccggg agctccagat ccgtggcgcc gtgctgctgc tgcgccgtgc tgctcgcggc | 420 |
| ggcgctgctc ttctccgcgc cggccaccac aggtttcccc ggctctcgct ccttctctct | 480 |
| ctctctctct gtttgcgcct gccagctcgt gccgtgccgg tctcagatcc atgcgccggc | 540 |
| ccgatcgccg aggctctcga ctaactttca cgagttgtga ccacgagatt tgggcaatgc | 600 |
| gatcccctcc tgactgtgtc ggtggctcca gttcggtgtg tcgtggcttt ttttttttt | 660 |
| tttgaattcc gattcgtttc atcagtaatt cagttcgttt cgctcctgct tttgccagaa | 720 |
| ttcttggagc agattaggta gcagtaattc agttcgtttc gctcccgctt gaccggattc | 780 |
| ttggatcagg ttaggtagct tagatccatt gagaggagcc cgcatggagc ttccttccca | 840 |
| cactaatcag tgcccaaggt gatagatctg atcaggagag gcgaattcga aaaaaaattc | 900 |
| ccttccagat cgaaatcggg atcacgatat aactaactca tggggcttat tcatctgccg | 960 |
| aactgctaat ttaccccccat ttcgtttccc ttgttcagga tcttgatatg caactctttt | 1020 |
| ttgtttttcct cttgcagagg cttatgatgc gctggatcca aatggaaaca tcacgataaa | 1080 |
| atgggacgtt atgtcgtgga ctcctgatgg ctatgttgta agtagcaacc ccacaccaaa | 1140 |
| aaatgcatct tgtattgttc gttcaaaaaa atccatctgc atcttgtttc cccaactatt | 1200 |

```
attaggccat aatttattt tattgatac tactacaagt tgtctttgaa gtacaaagtt    1260
gatagcataa ccagcagctg gtcagaaaca tatgcagcaa ttaacaataa taaacacgag    1320
ttttatgtca gcatattatg gatactctga ttatcttgta tatgtgtgtc atgattccc    1380 cccaaaatgt ttcttgtgca ggctgtggtc acgatgttca actatcaaca attccggcac    1440
atccaggcac ctgggtggca gctggggtgg acatgggcaa agaaggaggt catttggtcg    1500
atggttggag cacagaccac tgagcagggc gattgctcaa agttcaaggg tggcacgccc    1560
cactgctgca agaaggatcc cacagttgtt gatctgcttc cgggcacccc atacaacatg    1620
caaatcgcta attgctgcaa agctggagtt ataaatacat ttaaccagga cccatcaaat    1680
gctgcttctt ccttccagat cagtgtaggt cttgctggga ctaccaacaa gacagttaag    1740
ttgcctaaga acttcactct taaggcccca ggtcctgggt acacgtgcgg gcgtgctatg    1800
attgtcaggc ctactaagtt tttcaccggg gatgggcgca gagcaaccca agctctaagt    1860
aagtagctca tctgttgttc tttaatgttt aataccaatt gctttcattc tttgaggaaa    1920
tgcatttgca gcctaaacaa caattgcatg gttgaactag gttaccttat gtgtagggtt    1980
agtaagaaga tgtaatctgt tgaagggaaa gagattgttc tcaaagtgag atgagtccaa    2040
ctgtgaataa tagttgataa taggttatat tacttggcat gttggcctaa tagaatacag    2100
ctaattcagt taatattatt ctctagcaaa taatattcgt caaatgcaga catgcatcat    2160
agtggctcca tatagaagtt aaatttgtca aaatcttata ccataaagtt cattttttgtt    2220 ttttgtttct taacaaaaat aaaatctgtt gcagtgaca tggaatgtga cctgcacata    2280
ctcccaattt cttgctcaga agactccttc ctgctgtgta tctctctcat cattttataa    2340
tgacacaatt gtgaactgcc caacatgctc ttgtggctgc caaaacaatg ggacaagtcc    2400
tggaagctgt gtaaagtgag ttaataaaac caaaactctt acttcgcttc ttgttgaggc    2460 ccaactttc tgcaaaattg ctaacaagtt ccatgcattt ccacagtgag aattcacctt    2520
atttacaatc tgccattgat ggccctggca aatggaccgg tcagcctctt gtccaatgta    2580
cttctcacat gtgcccgatc agaatccact ggcatgtgaa actcaactat aaggaatatt    2640
ggagagtgaa gatcacgatt acgaacttca actaccgcat gaattacaca cagtggaatt    2700
tggtcgctca acatcctaac ttcaataata tcacccagct gtttagcttc aactacaagc    2760
cacttactcc atatggaagc aagataagta agtcaattta caaactgttc tcctttatttt    2820 aagaaaattg gagtgcactt gtaatacgtt cctttatctc tctctctctc tctctttctc    2880
tgatgaagtt tattccttct attttagatg atactgcgat gttctgggga gttaagttct    2940
ataacgattt gctcatgcaa gctggtccac ttggaaatgc acagtcagaa cttcttctgc    3000
gtaaggattc caaggacttc acctttgaca agggatgggc cttcccacac cgcgtgtact    3060
tcaatggtga taattgtgtc atgccacctc cggatgcata tccatggttg cctaatgcaa    3120
gtcctctgac aaaacaacca ttgacactct cggttttggt attttcgatt gtgttggcta    3180
ctttgctggc ttatgcatga tgagtgaaac caagaaattc ggtgagcttc aagttgtcag    3240
gttccatggt gtgcactgca acagatcatt tgttcattca gttccacggt tgcatagaag    3300
agaagatgtc acgctgagga aagctgatat gtgtgtgtgt gttgtatgtt aaaagaaggc    3360
caaaatgtat ttctttttttg gtatatatac tggccacagc attttggtga acttagttac    3420
tgcaaactag ataattacag ttgcaccttt tgtatgttat agcaaccaga aattcaattg    3480
aattatatga cttcccttct tgtagtacat gtatagactc cgtaataatg ttctgtatga    3540
```

```
ttttgtgaac agaaaggatg ctgttgattg agatcattta gttttgtttc ttgtttcatc    3600
aggtgtattg agctaagtaa tcgaattaac tgatgcttat gttc                     3644

<210> SEQ ID NO 10
<211> LENGTH: 3810
<212> TYPE: DNA
<213> ORGANISM: Oryza sativa

<400> SEQUENCE: 10
tggaaagaaa gaagaaaaac aagaggagga tttcccccac aagaatagct caaacctgtc      60
tgcatgcatg tctgtctgca ctctgcatcc atccatccat ccatccatcc ccgggcagac     120
acggattcag acgcgcaaga aatctccctc acctttactt gcaaacatat acccacaaat     180
ctctctctct cgcccgcttg tcttgtctga cttcttgttg cctcttgcct ccttcttctt     240
cttcttcgtc ttcgtcgtcg cgaaatacag gcgtgtgggg cgagagtgat caggtggcag     300
ctgggtgttt cttcttcttc ttcttcagct cgagttcttc cttagccatg gcgctcctgc     360
tgctgcgtat gggcgtctcc gtcgcgctgc tcgtcgcctt cttctcctct ctgattccgt     420
cgtcaggtcg gtgcctgtgc ctgtgcctct gcatttccca ttggttcttg cagtactatt     480
tggatttcgg ttcttggttc tcaggttgtt cttctccggt tgattcattc acgcctaaat     540
ttttgcgtct tttttttggg tgccgtgtgc tgtatgattc gtctgtaagg attccggagt     600
tttttttttt ttggtgttgt ttttttttttc ttcttatttt actctattcg gagaaaattt     660 ctcttccccca tcgtagcgcg attatcgtga tcaaaatgga tgtgacaata aaggaatgag     720 ctgtttttccg tttacctcat taaagatttt aatttggtgt ttatgacctt tccaaaatgg     780
acaattaaga gtcatgaata ccaaatttaa attttatttg ttgtatatgc gtggtgcgat     840
gggttttgct catagtatat gtttgtttgt ttcggatcat atgtcaaaac aaactatttc     900
tgtttagttc atgatcaggt tttaatccat ttttccaaaa aaaaatgtca aagcaaactg     960
aacatgtagc gagtgtgtgc atattatttc tgttagagct cagagcgaag aatcagcctt    1020
atgtgtcgcg tcatgctaca atcgtgatct tttcttgtta cgtactacta tatgttgtta    1080
acacaaatat tataatcact gaagctattg gcacaaatca ctattatgtt tcatgtatgt    1140
ctattcatct gaactgtgat cctgatcatg cacaagatga taaagttcga tcctttatct    1200
tcacatgcat gattaaccat caaagatgag atgtgcccta ccaaaacgtt cttcaatctg    1260
gatgtatcac taaattctga cttgtttctt gatacattat gcagaggcat acgatccgct    1320
tgatccaaat gggaacataa caatcaagtg ggatgtgctg caatggactc cagatggata    1380
tgttgtgagt aaaccttaat ttactattat gtgtctgtaa ctactttatt accattatca    1440
tctatcaacc aactcaatgc atgtcgctgt tgccacatga gtccacatct gctttcatca    1500
atctctgcac attagtactc tgtcttgttg gcagattgac gcttcactgt ctctcttttg    1560
taactgaaac actgaaagta gtggcctttc gttaaatttc cattcatgcc acttttttag    1620
cttttgactt tcttgataaa cttacaactg gcatgaccaa atactggtgc atcgatgctt    1680
gcaatccatg gttgctggtc aaagacatga catcacgaca caaatctatt ttctttgtat    1740
ttatctattt tatctgttag actgttactt ataggtgctc tgaactgttg atcttgatta    1800
atatcagtac tcacaagaca taacacaaac cttacataaa ctcaattttg ttgcattttg    1860
aactagtcaa gaccaaatct ttgcactatc tcttatcttc agtgtatttt tacacaattc    1920
agaaaactgt caacctgcac aaaattccct tcctgccttc ctggttcaca ggacttgtga    1980
ttagttgctg agataatgtt aaaaatccat tttctccagg ctgttgtttc actatacaac    2040
```

| | |
|---|---:|
| tatcagcagt atcgacacat tcaatcaccc ggatggaaac tcggatgggt gtgggcaaag | 2100 |
| aaggagataa tctgggcgat gaacggcggc caagcgacgg agcaaggcga ctgctcaaag | 2160 |
| ttcaaatcaa atatcccaca ttgctgcaag aaagatcctg agatcgtgga cctgctcccg | 2220 |
| ggaacccctt acaacatgca gattgccaac tgctgcaagg gaggagtgct caactcgtgg | 2280 |
| gcacaggacc ctgcaaatgc catagcatca ttccaagtca gtgttggtca ggcagggacg | 2340 |
| acgaacaaga cggtgcgggt gccgagaaat tcaccctga atctccagg tccagggtat | 2400 |
| acctgtggca gtgccaaggt tgtgagacct accaagtttt tttcgcagga tggaaggaga | 2460 |
| acaactcagg ctcacagtaa gatttttttc tgaagtttcc atgatcttag tatttgccgt | 2520 |
| gcaaagtagt tcagggatga gcttacaatc tattgcaaca gattcagaat tgttcttgtt | 2580 |
| tcgatactgc cttttcgtgc atcatcggtg accgcttgat ttcttttgtg cagtgacatg | 2640 |
| gaatgtgact tgcacatatt cacagattgt cgcgcaaaga tctccgacgt gctgcgtttc | 2700 |
| gctctcgtct ttttacaatg ataccatagt taactgccca acatgctcat gtggctgcca | 2760 |
| gaataataaa ccaggaagct gtgtagagta agttacatta acatgacaaa actactcaaa | 2820 |
| atcagtttta tgttcagtta acatgactgt tgcaacgtac tgtttgacag ggaaattct | 2880 |
| ccttatttgg cttctgttgt gaacacccat aacaaggaca gcttgacacc tctagtccag | 2940 |
| tgcacttctc atatgtgccc aataagagtt cattggcatg tgaaggttaa ctacaaggag | 3000 |
| tactggaggg tcaagatcac agtgacaaac ttcaattaca ggatgaacta ctctcagtgg | 3060 |
| aacctagtca ctcagcaccc cagttttgac aatctgacaa ccattttcag cttcaactac | 3120 |
| aaatctttga acccatatgg agtaataagt aagccctgaa acaattcta ctcatgtggt | 3180 |
| taattatttt tcagatattt actgtttctt ttttcagatg ataccgcgat gttatgggga | 3240 |
| atcaagtact acaatgactt gctcatgacg gcgggtccag atggaaatgt tcagtctgag | 3300 |
| cttctgttca agaaggaccc caagagtttc acctttgaga aaggctgggc cttcccaaga | 3360 |
| cgtgtatact tcaatggtga caactgtgtg atgccaccac cagatgcata tccatggctg | 3420 |
| ccaaatgctt caacaagagt gatgtcttca attctccttc cattcattac catttggaca | 3480 |
| gcactgacat tcttgatggt ttacgcatag tgaaaggaaa tcgtaatttt acgtattcag | 3540 |
| gaaagttttg accttgttgt gcattacaaa gttttagatg atatgttgca tgaagagaag | 3600 |
| attcagtgca gataccctaac cataaaccgt cgttgatcat tgtataaact tacttgtata | 3660 |
| catttaatct cagacaagat aagatgcaaa cacagtactt cttaaggaat tttatcctct | 3720 |
| cttcctttat gaaccttcac acatttatca gatgagcatg tactgcaaaa tgaagttagt | 3780 |
| tgatttttcc tatgatcata tatgaaaact | 3810 |

<210> SEQ ID NO 11
<211> LENGTH: 2102
<212> TYPE: DNA
<213> ORGANISM: Zea mays

<400> SEQUENCE: 11

| | |
|---|---:|
| ggaaagcagc gctgcggagc agagtgtgtc gcttcgctgt aaaaacaggg gagagggaga | 60 |
| cgcgcccgct gccagtgcct gccgcacacg cgtttagcgt ttaagttcca ctcctcgccg | 120 |
| ccccagatct ccgccctcct caccactgcc cctcattccc cggcgcccag cacccggcgg | 180 |
| ccgcaaccgc cgcagtccgg agcaagatcg gcgggtagac ggacggacgg acgggcgaca | 240 |
| ggcgggcggg cgcggctctg tctgtatcta tctgttggtg ggagaccggt tgtgtcggtt | 300 |

```
aggcggcggc gggtgggaag gaagaatggc ggcgggcggc agatccatcg cgtgctttgc     360
cgccgtgctg ctcgcggccg cgctgctcct ctccgcaccg accaccacag aggcctacga     420
ttcgctggat ccaaacggca acatcactat aaaatgggat atcatgcagt ggactcctga     480
cggatatgtc gctgttgtca caatgttcaa ttatcaacaa tttcggcaca tcggggcacc     540
tggatggcag cttgggtgga catgggcaaa aaaggaggtt atatggtcaa tggttggggc     600
tcagaccact gaacagggtg actgctcaaa gttcaagggc aacaccccc attgctgcaa      660 gaaagatcca acaattgttg atttacttcc aggcactcca tacaacatgc aaattgccaa     720
ttgctgcaag gcaggagtta taaatacctt taaccaggac ccagcaaatg ctgcttcctc     780
cttccagatc agtgttggtc ttgctggaac taccaataaa actgttaagg tgccgaagaa     840
tttcactctt aagactccag gccctgggta cacatgtggg cgtgctattg ttggcaggcc     900
aacgaagttt ttctctgcag atgggcgcag ggtaacccaa gctctaatga catggaatgt     960
gacctgcaca tattcccaat tcttgctca gaagactcca tcctgctgtg tatctctctc     1020
atcattttat aatgacacaa ttgtgaactg cccgacatgc tcatgtggct gccagaaccc     1080
aagtgggtca aactgtgtga acgaggattc acctaatcta caagccgcaa ttgatggtcc     1140
tggtaaatgg actggccagc tcttgtaca atgcacttct cacatgtgcc caataagaat      1200
ccactggcat gtgaagctca actacaagga atactggaga gtgaaaatca ctatcacgaa     1260
cttcaacttc cgcatgaatt acacacagtg aacttagtt gctcagcatc caaactttga      1320
taatatcact cagttgttca gcttcaacta caaaccactt actccatatg ggggtggcat     1380 aaaatgatacg gcaatgttct ggggtgtaaa gttctacaat gatttgctga tgcaagccgg    1440
caaacttggg aatgtgcaat cagaactgct ctccgcaag gactcacgga ctttcacatt      1500
cgaaaaggga tgggccttcc cacgccgagt gtacttcaat ggtgataatt gtgtcatgcc     1560
atctcctgaa aattatccat ggctgccgaa tgcaagccct ctaacaaaac aagcattgac     1620
actcccactc ttgatattct gggttgcctt ggctgttctg ttggcttatg catgatgagt     1680
gggatcaaga tgtttagcaa gcttcaagtt gatgtcggat ccatgaggt gcactgcaac      1740 gggatattta ttcattcaat tccatagcgg cacaggagag atgaggcgaa gccagagaaa     1800
agtggatgtg tgtgtgtgtg tgtttgtaag ttaaaggcc aaaatgtatt tcttgtctgg      1860
tagtatatag cagctctaca acactttggt gaacttagtt actgcaaatt aggcaattac     1920
agttgcacct tttgtatttt atagcaaacc cagacttcta ttggattcta tgactgcccc     1980
tcttgtagta aacgcaaggc ttcactggta ctcctgttta aagattggtc aaatagaaga     2040
gacgacggtg attgtcaaaa aaaaaaaaaa aaaaaaaaaa aaaaaaaaaa aaaaaaaaaa     2100
aa                                                                    2102
```

<210> SEQ ID NO 12
<211> LENGTH: 1784
<212> TYPE: DNA
<213> ORGANISM: Zea mays

<400> SEQUENCE: 12

```
gatcggagct tgtgctgcta ctgctactat accagcgcta gctagcagca gccgccggcc      60
ggctcgcgca agctaaggaa gggtcgacat gacgatgggg ctccgcgtcc gcgactcctc     120
cgcgctgctg gctctggccg tcgcgctcgc ctgctgctcc gttgcagtgg tggcctacga    180
ccccctggac ccgaacggca acatcaccat caagtgggac gtgatctcgt ggacgcccga    240
cgggtacgtg gcgatggtga cgatgagcaa ctaccagatg taccggcaca tcatggcgcc    300
```

```
cgggtggacg ttggggtggt cgtgggccaa aaggaggtg atctggtcca tcgtgggggc    360
gcaggccacg gagcagggg actgctccaa gttcaagggc ggcatcccgc actgctgcaa    420
gcgcaccccg ccgtggtgg acctcctccc ggggtgccc tacaaccagc agatcgccaa     480
ctgctgcaag gccggcgtgg tgtcggcgta cgggcaggac ccggcggggt ccgtctccgc    540
gttccaggtc tccgtcggcc tggccggtac caccaacaag acggtgaagc tgcccaggaa    600
cttcacgctc atggggcccg ggctgggcta cctgcggg cccgccgccg tggtgccgtc      660
caccgtgtac tggacgcccg accaccggcg ccggacgcag cgctcatga cgtggacggt     720 gacctgcacc tactcgcagc agctggcgtc ccggtacccg tcctgctgcg tctccttctc    780
ctccttctac aacagcacca tcgtgccgtg cgcccggtgc gcgtgcggct gcggcggcca    840
cggcggccac gcgggtccgg gcggctgcat cgagggggac tccaagcgcg cgctgtcggc    900
cggggtgaac acgccgcgca aggacggcca ggcgctgctg cagtgcacgc cgcacatgtg    960
ccccatccgg gtgcactggc acgtcaagct caactacaag gactactggc gcgccaagat   1020
cgccatcacc aactacaact acaggatgaa ctacacgcag tggacgctgg tggcgcagca   1080
ccccaacctg gacaacgtca ccgaggtctt cagcttccag tacaagccgc tgcaaccata   1140
cgggagcatc aatgacactg gcatgttcta cgggctcaag ttctacaacg actttctcat   1200
ggaggccggc ccgttcggca acgtgcagtc ggaggtgctc atgcgcaagg acgcaaggac   1260
cttcaccttc agcatgggct gggcgttccc gcgcaagatc tacttcaacg gcgacgagtg   1320
caagatgccg ccgccggact cctacccta cctgcccaac gccgcgcccg tcgtcgcctc    1380
gcagctggtc ctgtccgccg ccgcctcggc gttcctactg ttgctgctcc tggtggcatg   1440
accgtgaccg aaccaaggc aaggcctccg ttttgttttc ccgtctcgtc ccgtgggcag    1500
ggagcagact tcagtaggca gggcatttta tttggtttt tgccaagga ttcaacactt     1560 gggttttcgt cagaggaaaa ctgtcgtgta tgtagtgtga gttgcaggtc gtcggatccc   1620
cacgtacaag acaatctttg gatctagaat atgcaaaacg tgaatcagca cgccaggatc   1680
atcgtctcct acaagattgg cagaaaaaaa atctcatgat gagtgatgtg tcaacagacc   1740
tatatatatg tgataatcac tggtttcaaa aaaaaaaaaa aaaa                    1784
```

<210> SEQ ID NO 13
<211> LENGTH: 2934
<212> TYPE: DNA
<213> ORGANISM: Oryza sativa

<400> SEQUENCE: 13

```
caaaaatgtc tcattgcttc tctcgttcta aaaaaatct tgctgctatc tctctataag     60
tccactcctc cttcaagcaa agcaccttcc tcttcttttt gctcctctga gattggttta   120
agattaaacc agacccatct aagggatctg gaacaagctt cgtctctggt tccactctga   180
tcatcagagt attaaaaatg gagtctttct ctccagatc cacctccatc gtctccaaat    240
tgagtttctt ggccttatgg atcgtcttct tgatttcttc atcttctttt acttcgacag    300
gttactttct tattcccatt atcaccaatt attctgcttc ttggttctgt ttctttgtct    360
cagagctttt tcaacttcca atcttgctcc ttgatcggta tttcacttt cagagttaag    420 atcgtgaaat tgttcatttt tcttaaattt agactatgtt tttgcatctg agtatcttca    480
attgtaactg atttgtttgt tgaaattgat aaagagaggt gataatatga atcgtgtatt    540
gtgtggtgtt ggcagttcat gatccatttt aaaaaaaaac tcttttgtag atctttcctc   600
```

```
aattagtgag atgataattg cttgctcact gttcaagtct tttttataga gttcagatcc    660
taaaatcaat acgtcaattt ccatattagt gcttcatatg tagatcagtg gattttgctt    720
atataaggaa acaccaaagt ttcaagtttt ctgatctaaa attagtaact ttctgatatt    780
ttctataagt agaaaacttg atgcacactt gtgagttata agcagttaac actttggtct    840
attttctaca aaccaaataa ttagtagttt taagattgaa gcaatcacaa tgtcggtgtg    900
gatcaggata aacaaagttc tgacttttgg taaatccttt tgcagaagca tatgatgcgc    960
ttgatccaga aggcaacatt acaatgaaat gggatgttat gagctggact cctgatggct   1020
atgttgtaag ttcaagaacc tgaagtagaa aatattaggc cttgtttacc ggttttgat    1080
tcatctaaac tgtttgtttg ttcgatctag gccgtggtta cgatgttcaa cttccagaaa   1140
tacagacaca ttcaatctcc aggatgggaca ttaggttgga atgggcaaa gaaggaagtt   1200
atatggagta tggttggagc acaaacaact gaacaaggta actaattgtt tcaggttcca   1260
ttactttatg ttttaattgc gaattatctg gatatgaatt atagacaaaa tggttttaca   1320
ggtgattgtt caaagtacaa aggaaacata ccacattgtt gtaagaagga tccaacagtt   1380
gtagacttgc ttccagggac tccttataat cagcagattg ctaattgctg caagggtggt   1440
gttatgaact catgggttca agaccctgcc actgcggcta gctccttcca gattagtgtt   1500
ggtgctgctg gaaccacaaa caaaaccgtt agggtcccaa gaaacttcac tctcatggga   1560
cctggtccag gttacacttg tggtccagca aagattgtca gaccaacaaa atttgtcacg   1620
actgacacac gcagaaccac tcaagctatg agtaagaacc catgactgca attcgacatt   1680
ttttaaacca taatgttagt taacattgtt tctcatctaa cagaccggtt aaatgtttct   1740
ctttgaatta ctgcagtgac atggaacatt acgtgcacat actcgcagtt ccttgctcaa   1800
agaactccaa cttgctgtgt ttctttatct tctttctaca atgaaaccat tgttggatgt   1860
ccaacttgtg cttgcggatg tcaaaacaac agaacagaat ccggtgcctg cctcgagtaa   1920
gtagttcaaa tcaatattca gtttcctcct cttgttctct gttcagtttt caatcataaa   1980
gtcccacact ttttatgtat ttgcagcccg acacaccac acttagcctc ggttgtgtca    2040
ccaccaacaa agaaaggaac ggttttacca ccattagtgc aatgcacgag acacatgtgc   2100
ccgatcagag tgcattggca tgtaaagcag aactacaaag agtattggcg tgtgaagatc   2160
acaatcacaa acttcaacta tcgcttgaac tacacacaat ggaaccttgt tgctcaacat   2220
ccaaatctcg acaacatcac tcaaatcttc agcttcaact acaaatctct tactccttac   2280
gctggactaa gtaagtacac acacacacac acacacaaag cccctctctt ctctttatgc   2340
cagcttatct caaagattta acatttttggt tttgcagacg atacggcgat gttatgggga   2400
gtgaagttct acaacgattt cttatcagaa gcaggtcctc ttgggaatgt tcaatcagag   2460
attttgttcc gtaaagacca atcaaccttc acattcgaga aaggttgggc ttttccacga   2520
aggatttact ttaatggaga caattgcgtc atgcctcctc cagactctta cccttttctt   2580
cccaacggtg gttcccggtc acaattctca ttcgtcgccg ccgtgctcct ccctcttctt   2640
gtcttttcct tcttctctgc ctaatctcgg atttacggtt ttgccactgg tttgcttagg   2700
gttacggcgg agtggtataa acgtttattt atgattcttt tgtgtcccac aaaaattata   2760
atcttttgat acttttaaa aatataaata gttttcaact tccttgtttt taaaagaaat   2820
ttatatcctt gtgttctgtt ggtccgtcgt tgtagaatat cgggaaaaaa aaaaaaagat   2880
gttagatact gtaaactttg ttttccgaac gttatatact ttacttttc tgtt          2934
```

<210> SEQ ID NO 14
<211> LENGTH: 1005
<212> TYPE: DNA
<213> ORGANISM: Oryza sativa

<400> SEQUENCE: 14

| | | | | | |
|---|---|---|---|---|---|
| atgtgtggag | cgccatcct | cgccgagttc | atcccggcgc | cgtcgcgcgc | cgcggcggcg | 60 |
| accaagcggg | tgaccgccag | ccacctgtgg | ccggccggct | ccaagaacgc | cgcccgcggc | 120 |
| aagagcaaga | gcaagaggca | gcagaggagc | ttcgccgacg | tcgacgactt | cgaggccgcc | 180 |
| ttcgagcagt | tcgacgatga | ctccgacttc | gacgacgcgg | aggaagaaga | cgaaggacac | 240 |
| ttcgtgttcg | cgtccaaatc | tcgtgtcgtc | gccgggcacg | acgggcgcgc | ggcggcgagg | 300 |
| gcggcgagca | agaagaagcg | ggggcggcac | ttccgaggca | tccggcagcg | gccatggggg | 360 |
| aagtgggcgg | cggagatccg | cgaccccgca | caagggcacg | cgcgtctggct | cggcacgttc | 420 |
| aacaccccgg | aggaggccgc | acgcgcctac | gacgtcgagg | cgcgccgcct | ccgcggcagc | 480 |
| aaggccaagg | tcaacttccc | cgccacgccc | gccgccgcgc | gcccacgccg | cggcaacacg | 540 |
| agagccaccg | ccgtgccacc | gccggcgaca | gcacccgccg | ccgccccgcc | gcgcggactg | 600 |
| aagcgagaat | tctcgccgcc | tgctgagacc | gcgctacctt | tcttcaccaa | cggcttcgtc | 660 |
| gacctgacga | ccgccgcggc | gccgccaccg | gccatgatga | tgacgagctc | cttcaccgac | 720 |
| agcgtcgcca | cgtcggagtc | cggcgggagc | ccgccaagaa | aggcgaggtc | cgacgacgtc | 780 |
| gactcgtccg | agggcagcgt | cggcggcggc | agcgacacgc | tgggtttcac | cgacgagctg | 840 |
| gagttcgacc | cgttcatgct | gttccagctc | ccctactccg | acggctacga | gtccatcgac | 900 |
| agcctcttcg | ccgccggcga | cgccaacagc | gcgaacaccg | acatgaacgc | cggcgtcaac | 960 |
| ctgtggagct | tcgacgactt | cccaatcgac | ggcgcccttt | tctga | | 1005 |

<210> SEQ ID NO 15
<211> LENGTH: 1561
<212> TYPE: DNA
<213> ORGANISM: Oryza sativa

<400> SEQUENCE: 15

| | | | | | |
|---|---|---|---|---|---|
| aaaggcattc | gcaacacaca | cttgaagaaa | aaaaacacga | cgaacacgtt | aaaaaaaggt | 60 |
| cgaagagaag | tgggagaccc | aaaccgcgaa | caatgtgtgg | aggcgccatc | ctcgccgagt | 120 |
| tcatcccggc | gccgtcgcgc | gccgcggcgg | cgaccaagcg | ggtgaccgcc | agccacctgt | 180 |
| ggccggccgg | ctccaagaac | gccgcccgcg | gcaagagcaa | gagcaagagg | cagcagagga | 240 |
| gcttcgccga | cgtcgacgac | ttcgaggccg | ccttcgagca | gttcgacgat | gactccgact | 300 |
| tcgacgacgc | ggaggaagaa | gacgaaggac | acttcgtgtt | cgcgtccaaa | tctcgtgtcg | 360 |
| tcgccgggca | cgacgggcgc | gcggcggcga | ggcggcgagc | aagaagaagc | ggggggcggc | 420 |
| acttccgagg | catccggcag | cggccatggg | ggaagtgggc | ggcggagatc | cgcgaccccg | 480 |
| caagggcac | gcgcgtctgg | ctcggcacgt | tcaacacccc | ggaggaggcc | gcacgcgcct | 540 |
| acgacgtcga | ggcgcgccgc | ctccgcggca | gcaaggccaa | ggtcaacttc | ccgccacgc | 600 |
| ccgccgccgc | gcgcccacgc | cgcggcaaca | cgagagccac | cgccgtgcca | ccgccggcga | 660 |
| cagcacccgc | cgccgccccg | ccgcgcggac | tgaagcgaga | attctcgccg | cctgctgaga | 720 |
| ccgcgctacc | tttcttcacc | aacggcttcg | tcgacctgac | gaccgccgcg | gcgccgccac | 780 |
| cggccatgat | gatgacgagc | tccttcaccg | acagcgtcgc | cacgtcggag | tccggcggga | 840 |
| gcccgccaa | gaaggcgagg | tccgacgacg | tcgactcgtc | cgagggcagc | gtcggcggcg | 900 |

```
gcagcgacac gctgggtttc accgacgagc tggagttcga cccgttcatg ctgttccagc    960
tcccctactc cgacggctac gagtccatcg acagcctctt cgccgccggc gacgccaaca   1020
gcgcgaacac cgacatgaac gccggcgtca acctgtggag cttcgacgac ttcccaatcg   1080
acggcgccct tttctgatgt actcctccat tgatgcagtt tgtgcactca attgttaatc   1140
acgtcgtcgt tgatgaatgt taaccggag gatgatgggg tgcagctgat atcatggctt    1200
gcttgattac cgaattatat tgcggtgttt gtgtttgtca attagattct gaatctgtac   1260
tactgccgat cttatgatca aaactatata ttaagtttat gtactcttaa tttgtgggct   1320
acttttacgg ggtcttcgta ctgctggtca aatagtccta tgaaatcgat catgtcggca   1380
atatcgtcgt caattatcgt ggtcgtggtt gttaatgatg tcaaataagt ctatgaaaac   1440
ctggtcctct tggtgtttat gtaccactga tcgatccatc atttgatctc tgtcatgttg   1500
agatggatcg tgtaagaata tcataatttg ctggattcag ccagtcgta atgtattttg    1560
g                                                                   1561

<210> SEQ ID NO 16
<211> LENGTH: 1580
<212> TYPE: DNA
<213> ORGANISM: Oryza sativa

<400> SEQUENCE: 16
cggggtacca aaggcattcg caacacacac ttgaagaaaa aaaacacgac gaacacgtta     60
aaaaaaggtc gaagagaagt gggagaccca accgcgaac aatgtgtgga ggcgccatcc    120
tcgccgagtt catcccggcg ccgtcgcgcg ccgcggcggc gaccaagcgg gtgaccgcca   180
gccacctgtg gccggccggc tccaagaacg ccgcccgcgg caagagcaag agcaagaggc   240
agcagaggag cttcgccgac gtcgacgact tcgaggccgc cttcgagcag ttcgacgatg   300
actccgactt cgacgacgcg gaggaagaag acgaaggaca cttcgtgttc gcgtccaaat   360
ctcgtgtcgt cgccgggcac gacgggcgcg cggcggcgag ggcggcgagc aagaagaagc   420
gggggcggca cttccgaggc atccggcagc ggccatgggg gaagtgggcg gcggagatcc   480
gcgacccgca aagggcacg cgcgtctggc tcggcacgtt caacaccccg gaggaggccg    540
cacgcgccta cgacgtcgag gcgcgccgcc tccgcggcag caaggccaag gtcaacttcc   600
ccgccacgcc cgccgccgcg cgcccacgcc cggcaacac gagagccacc gccgtgccac    660
cgccggcgac agcacccgcc gccgccccgc cgcgcggact gaagcgagaa ttctcgccgc   720
ctgctgagac cgcgctacct ttcttcacca acggcttcgt cgacctgacg accgccgcgg   780
cgccgccacc ggccatgatg atgacgagct ccttcaccga cagcgtcgcc acgtcggagt   840
ccggcgggag ccccgccaag aaggcgaggt ccgacgacgt cgactcgtcc gagggcagcg   900
tcggcggcgg cagcgacacg ctgggtttca ccgacgagct ggagttcgac ccgttcatgc   960
tgttccagct cccctactcc gacggctacg agtccatcga cagcctcttc gccgccggcg  1020
acgccaacag cgcgaacacc gacatgaacg ccggcgtcaa cctgtggagc ttcgacgact  1080
tcccaatcga cggcgccctt ttctgatgta ctcctccatt gatgcagttt gtgcactcaa  1140
ttgttaatca cgtcgtcgtt gatgaatgtt aaccggagg atgatgggt gcagctgata   1200
tcatggcttg cttgattacc gaattatatt gcggtgtttg tgtttgtcaa ttagattctg  1260
aatctgtact actgccgatc ttatgatcaa aactatatat taagtttatg tactcttaat  1320
ttgtgggcta cttttacggg gtcttcgtac tgctggtcaa atagtccat gaaatcgatc    1380
atgtcggcaa tatcgtcgtc aattatcgtg gtcgtggttg ttaatgatgt caaataagtc  1440
```

```
tatgaaaacc tggtcctctt ggtgtttatg taccactgat cgatccatca tttgatctct   1500
gtcatgttga gatggatcgt gtaagaatat cataatttgc tggattcagt ccagtcgtaa   1560
tgtatttggg ttaattaagg                                                1580

<210> SEQ ID NO 17
<211> LENGTH: 1089
<212> TYPE: DNA
<213> ORGANISM: Oryza sativa

<400> SEQUENCE: 17
atgtgcggcg cgccatcct ctccgacctc atcccgccgc cgcggcgggt caccgccggc     60
gacctctggc tggagaagac caagaagcag cagcagcaga agaagaagaa caagggcgcg   120
aggaggctgc cactgcgcca agaggaggag gatgatttcg aggccgactt cgaggagttc   180
gaggtggatt ccggcgagtg ggaggtggag tccgacgccg acgaggccaa gccgctcgcc   240
gcgccccgga gcggcttcgc taaaggtgga ttgaaaaaca ctactgttgc tggtgctgat   300
gggcctgcag caaggtctgc taaaaggaag agaaagaacc aattcagggg tatccgccag   360
cggccatggg gcaaatgggc tgcggaaatc agagatcctc gcaaaggtgt ccgcgtctgg   420
cttggcacct tcaactctcc tgaggaagct gccagagctt atgatgctga agcacgaagg   480
attcgaggca agaaggccaa ggtcaatttc ccagatgggg ctccagtggc ttctcagagg   540
agtcatgctg agccctcctc catgaacatg cctgctttca gcatcgaaga agccggcc    600 gtcatgtcag caggcaacaa aaccatgtac aacacaaatg cttatgccta ccctgctgtt   660
gagtacacct tacaggagcc atttgtgcag attcagaatg tctcatttgt tcctgcaatg   720
aacgcgattg aggatacttt cgtgaacctg tcctctgatc aagggagcaa ctcctttggt   780
tgctcggact ttagccagga gaatgatatc aagacccctg acataacttc catgcttgca   840
ccgaccatga caggtgttga tgactccgca ttcctccaga acaatgccag tgatgcaatg   900
gtacctcctg tgatggggaa tgctagcatt gatcttgctg acctggagcc gtacatgaaa   960
tttctgatcg atggtggttc ggatgagtcg attgacaccc ttctgagctc tgatggatct  1020
caggatgtgg ccagtagcat ggacctttgg agcttcgatg acatgcccgt gtcggccgag  1080
ttctactga                                                          1089

<210> SEQ ID NO 18
<211> LENGTH: 2582
<212> TYPE: DNA
<213> ORGANISM: Oryza sativa

<400> SEQUENCE: 18
actctctgta aaacaagca aacaaagaaa gaaaagcatc acaaatctca cgcactgtct     60
ctcgttcgcg caaagcacgc tgcttttctc cgctttgcga gcaccatagc ctagcccacc   120
atgtgcggcg cgccatcct ctccgacctc atcccgccgc cgcggcgggt caccgccggc   180
gacctctggc tggagaagac caagaagcag cagcagcaga agaagaagaa caagggcgcg   240
aggaggctgc cactgcgcca agaggaggag gatgatttcg aggccgactt cgaggagttc   300
gaggtggatt ccggcgagtg ggaggtggag tccgacgccg acgaggccaa gccgctcgcc   360
gcgccccgga gcggcttcgc taaaggtaaa acaagaacgc gagatttggg agataaaagc   420
gagctgtttc ttgattttgg ttggcccaga ttttttttt tgcttgcggt cagtggggag    480
attagtaggt gaggagaagg atgcctttt tttttctatt gttctgtagg aaatttaatg    540
```

| | |
|---|---|
| tctgcaaatc tgaaaattcc acctaattat tgttgcagtt agtgcttgct tatcatgcta | 600 |
| ggttgctgct gccgggttag ctttattacc ttattgatta atcttaagga atattattat | 660 |
| atctcagttt tagaaatcag ggcctatgtt atgatgaatc atcatgtcct gtgatggctc | 720 |
| ctacgattca tggatggagc ttccatacaa cacaatttgg agaagaagtt tctgagagtt | 780 |
| tgcccaaatt ggatcagatc tatgtttttt cgtgttaatt actgtactca agtaatcccg | 840 |
| tatgaagaat cttggatccg acactgggcg tatagaatct tgacatttct gaacaaagtt | 900 |
| aggactcaag cagatccatg ttctgaagaa atatctgttt ttttttctat accatgtgat | 960 |
| tggactgaac atgtacagta ttttcttcac tgttttttaat atattctctt ctgttttctt | 1020 |
| ttcttaatgc ttattggcca gcagttctta tgttaaagtg ttcgattctc aatgcttctt | 1080 |
| tgtgtatgct actgattcaa aaggttgaag gataataagt ttttaccata ttaaaattta | 1140 |
| tacaccgatc ttgttccttg cttcaggtgg attgaaaaac actactgttg ctggtgctga | 1200 |
| tgggcctgca gcaaggtctg ctaaaaggaa gagaaagaac caattcaggg gtatccgcca | 1260 |
| gcggccatgg ggcaaatggg ctgcggaaat cagagatcct cgcaaaggtg tccgcgtctg | 1320 |
| gcttggcacc ttcaactctc ctgaggaagc tgccagagct tatgatgctg aagcacgaag | 1380 |
| gattcgaggc aagaaggcca aggtcaattt cccagatggg gctccagtgg cttctcagag | 1440 |
| gagtcatgct gagccctcct ccatgaacat gcctgctttc agcatcgaag agaagccggc | 1500 |
| cgtcatgtca gcaggcaaca aaaccatgta caacacaaat gcttatgcct accctgctgt | 1560 |
| tgagtacacc ttacaggagc catttgtgca gattcagaat gtctcatttg ttcctgcaat | 1620 |
| gaacgcgatt gaggatactt tcgtgaacct gtcctctgat caagggagca actcctttgg | 1680 |
| ttgctcggac tttagccagg agaatgatat caagacccct gacataactt ccatgcttgc | 1740 |
| accgaccatg acaggtgttg atgactccgc attcctccag aacaatgcca gtgatgcaat | 1800 |
| ggtacctcct gtgatgggga atgctagcat tgatcttgct gacctggagc cgtacatgaa | 1860 |
| atttctgatc gatggtggtt cggatgagtc gattgacacc cttctgagct ctgatggatc | 1920 |
| tcaggatgtg gccagtagca tggacctttg gagcttcgat gacatgcccg tgtcggccga | 1980 |
| gttctactga ggggtttggg gtgtagcaac tggtgcctgt atatataagg acaaatggta | 2040 |
| agcatcagca atgtgaaaac ggctaactct ttgtgacatt tcgatctcca tttctctgat | 2100 |
| ctttctccgc ctctcgtttc aggaataaac attctggaca tccaagaagc ggcatgtgtc | 2160 |
| tgtcgggcgc ttcagttgc gctatatagc tatgttagta tgttagtatg tgctgtgtct | 2220 |
| agcttagatg ctgaagtctc aagtactatt tggcagtgaa actatctatc tgtaactgct | 2280 |
| atatgaggct ggaacaagtt acttagcttc taccttatct gtacttgcta tagtggctgt | 2340 |
| gaaccttgtg gatctgaact ctgaagccaa tgtttactat ataatgtggt tggttttata | 2400 |
| aactctagtt gatttggacc cctgtcaatg gtcatgctat ggctggggat aagaaccatt | 2460 |
| gatgatcata tttgactaga aacgctgctt ccaaaatatc ccataaagta aagctgaact | 2520 |
| tgtactaatg ttcttgcaca agttgcaata atgttgcctt atggaaaaac agtttccgga | 2580 |
| cc | 2582 |

<210> SEQ ID NO 19
<211> LENGTH: 1191
<212> TYPE: DNA
<213> ORGANISM: Oryza sativa

<400> SEQUENCE: 19

| | |
|---|---|
| atgtgcggcg gagcaatcat ctccgggttc atcccgccgt cggccgctgc ggcggcggcg | 60 |

```
gctgcggtgg ccaagaagca gcagggcagg agggtcacgg ccgacgtgct gtggccgggg      120
atgctgcgga aggggaaggc ggcggcggcg gaggaggact tgaggccga cttccgcgag       180 ttcgagcgtg gcatgagcga cgacgaggcg gaggggggcg gcggcgagga ggaggaggac      240
gacgacgacg tggtcgtggt ggtccccccg ccggcggcgg cgaggttcgt cgtccgtgcc      300
gcggccaagg cggcgccccc aactgcagat gggatgttga ctacaaagct tgtccaacat     360
gatggaccta ctgctagatc agcaaagcac aagaggaaga atcagtacag ggggatccgc    420
cagcgtccct ggggcaaatg ggcagctgaa atccgagacc ccagcaaggg tgtccgtgtt   480
tggcttggaa catataacac tgctgaggag gcagctaggg catatgacgc tgaagcccgc    540
aagatccgtg gcaagaaagc caaggtcaac tttcctgatg aaccagctgt tgctcagaag     600
ctctccctga gcaaaacgc tgccaagcaa gagaaactag ctccacctct gaagacctgt     660
ggcgatgatg ctttctttca gctaaacagt tcagacaatg atttgtttgc aatgcttgca    720
aaggtgcctg caaagccggc agagcctgtt gatctcatgc ctccagtcaa acctcttgct   780
tccactgaga cattcgagat gaacatgctc tctgatacga gcagcaactc atttggctct    840
tcagactttg gttgggagga tgacaccctg accccagact acacttcagt cttcgttcct     900
aatgctgcca tgccagcata tggtgaacct gcttacctga caggtggagc gccaaagaga  960
atgaggaaca actatggtat cgccgtgccc cagggaaatg gcatgcctaa tctcgcacaa   1020
aacatgccca ccttcgatcc cgagatgaag tatttgccat taccttatgt tgagagcagc   1080
tcagatgaat caatggacaa ccttctgcaa aatgatgcta cacaagacgg ggcaagcaac  1140
gagggcatct ggagccttga tgagctgctc atggcagctg gtgcctactg a            1191

<210> SEQ ID NO 20
<211> LENGTH: 3652
<212> TYPE: DNA
<213> ORGANISM: Oryza sativa

<400> SEQUENCE: 20
ctcttcctcc attttttttt cttttctttt tatttgatta cgccgtcgct gtcgagtagc       60
gcgtcagctg catccgcggt tataagtagc ggccaccacc caccaccccc ggcttcctct     120
cccactgcgc cctccgcgtg agcggcagca agtgttcact gcgttcttct tctcgattta     180
tctttcttgg tttcttgatc tgtagcttat tagcggccat gtgcggcgga gcaatcatct    240
ccgggttcat cccgccgtcg gccgctgcgg cggcggcggc tgcggtggcc aagaagcagc    300
agggcaggag ggtcacggcc gacgtgctgt ggccggggat gctgcggaag gggaaggcgg     360
cggcggcgga ggaggacttt gaggccgact ccgcgagtt cgagcgtggc atgagcgacg     420
acgaggcgga ggggggcggc ggcgaggagg aggaggacga cgacgacgtg gtcgtggtgg    480 tcccccgcc ggcggcggcg aggttcgtcg tccgtgccgc ggccaaggcg gcgcccccaa    540
ctgcaggtga aaaataacg cataaagcta gctctttttc ccccttttct cgttagacga     600
gcgcaagatg cggccttttt tctgggtccg tttcttgcgt tcttcgtgtg atttggggag    660
agaattgggg tctcatgggg tagctgccaa atggggcttc atcaggttgc gccatggatt   720
tgatcttgat gcgaaccatg gacggcact gtgtagtata gtttttttt ttcaatctca   780 gcgtgttatt agttcttaac ttcattaata cctgtgtacg taaacttgct agcgaatctg   840 gttctttag atgatagca tctgtaggtt tggtggttta cgaatttaca ctacgaaata    900
ggaattcaac tttgtcctag attctactct tctttctttt cctgaattg gagtagcaaa   960
```

```
gagagagtga tgagttttag atatttattc ttgtgatttc gcagtgtcat tatgtgtttt    1020
aatcactaat atttgtgttg gattagagaa aatttggctt tgtagagttg tagtatgttc    1080
ttggattaac ctatgtttat ggatgctctt ctgtcgctgg atttacttgc tttgtttcta    1140
ataagtgatc tagtagtgta attacgcaaa acttaatggc ctttttttt tccttggcaa     1200 agtttcatct gtgccaccat ctcatcttga gatttggagt actctttgag gcatattttt    1260
ttcttgtact cttgatttat catatttagc tgttagtttt cagagtatga tgggttctgt    1320
agtattatct aaaaataaaa aaaatgatgg gttctttagt tgttccactc tttatataga    1380
ttgttagatg catgtcaaag ctcccttctt ttttttcttg ttaattctaa acagaagaaa    1440
ctttaggtga tgctgtcaaa gctcccttct tttttttttc ttgttaattc taaacagaag    1500
aaactttagg ttgttaattt gaactttgtt ggtgatctcg tactctcatt caagggatac    1560
gaatttaaag aattatttta ttttttttaaa aaaactaacg aatataagga actctaattt   1620
agtagtttgt acagttgatt ttgagctaca tcaaaatata ccctcagagg gacctcgtta    1680
gttttatgca tctgagatct cattcctgga tagaacgttg caggtgagta gatgactact    1740
gtagacagta tatgtagatt attatctatt gttaatcata gggcaagtga gtagttctac    1800
actttgacag tgcttacacc atatgcttgc tatattcatg gactttaaga tttcttatat    1860
atgtcatgat ttatttgaga agtgatcaat tgaactgatt catgtctcaa cctctctgtg    1920
aacatccagt ataacttcat cttcatgttg cttgagagtg tattgtgtaa cttacagttt    1980
atagctatga tatttccttt atatccttct tccaaatctg tttgttgaga tgtatactaa    2040
caaataagct ttcgtgtaga tgggatgttg actacaaagc ttgtccaaca tgatggacct    2100
actgctagat cagcaaagca caagaggaag aatcagtaca gggggatccg ccagcgtccc    2160
tggggcaaat gggcagctga atccgagac cccagcaagg gtgtccgtgt ttggcttgga     2220
acatataaca ctgctgagga ggcagctagg gcatatgacg ctgaagcccg caagatccgt    2280
ggcaagaaag ccaaggtcaa ctttcctgat gaaccagctg ttgctcagaa gctctccctg    2340
aagcaaaacg ctgccaagca agagaaacta gctccacctc tgaagacctg tggcgatgat    2400
gctttctttc agctaaacag ttcagacaat gatttgtttg caatgcttgc aaaggtgcct    2460
gcaaagccgg cagagcctgt tgatctcatg cctccagtca aacctcttgc ttccactgag    2520
acattcgaga tgaacatgct ctctgatacg agcagcaact catttggctc ttcagacttt    2580
ggttgggagg atgacaccct gaccccagac tacacttcag tcttcgttcc taatgctgcc    2640
atgccagcat atggtgaacc tgcttacctg acaggtggag cgccaaagag aatgaggaac    2700
aactatggta tcgccgtgcc ccagggaaat ggcatgccta atctcgcaca aaacatgccc    2760
accttcgatc ccgagatgaa gtatttgcca ttaccttatg ttgagagcag ctcagatgaa    2820
tcaatggaca accttctgca aaatgatgct acacaagacg gggcaagcaa cgagggcatc    2880
tggagccttg atgagctgct catggcagct ggtgcctact gaggagacga atgttctgg     2940 tcagtgtggt ctgtcactag caaaccatgt aaggcactcc acactaccta ctattttgat    3000
ttcttgtaga tacatttttca tgtacagatt acatatgttg taaaatggga tatggttttc    3060
ttgtcaggtt gaatgtgtat ggccaagatg aagagctggt gatgtctgct atgttttgta    3120
gagggatgct accaaagtaa tgctagaata ttacaagctg ctatcagctg tactctctat    3180
gacaatgttt atactatgtt tgctgtatgg tgtggtctat gatttgaagt atgttggaga    3240
ctgattcaaa taactgcctt ggccatgtgt gtgctgtaat gtgcttatta agttatatag    3300
ttgtgctcat attgcgtatc tacaatctgc aactttgaaa gtgctcgctt tcgctttcct    3360
```

```
gtgcagttct gcttttctgg aatgtcaaca gctagtgtgt gacatcagaa atctagagaa    3420
atcaagacag aatcaagctt acatgttaac gatgtatgag cttatttgtc ttgcccagct    3480
tacttgttgg gaatgatttg tgtctcattc cagcaatgta tattctgagc agtcggtggt    3540
taaggcataa gctgattttt ggcttttctt tcgtgctata tttatacttt gatgctgaag    3600
atttaatact ggggcagttg attggctaca ggactgtgac ctgaaaaaaa aa            3652
```

<210> SEQ ID NO 21
<211> LENGTH: 1098
<212> TYPE: DNA
<213> ORGANISM: Oryza sativa

<400> SEQUENCE: 21

```
atgtgcggcg cgccatcat ccaccacctg aagggcacc cggaggggtc gcgccgggcg       60
acggaggggc tcctgtggcc cgagaagaag aagcccaggt ggggcggcgg cgggaggcgc    120
cacttcgggg ggtcgtgga ggaggacgac gaggacttcg aggccgactt cgaggagttc     180
gaggtggact ccggggactc ggatttggag ctcggggagg aggacgacga tgacgtcgtc    240
gagatcaagc cggccgcctt caagagggcc ctctccagag ataacttgag caccattacc    300
actgccggat ttgatggtcc tgctgcaaag tctgccaaaa gaaagagaaa gaaccaattc    360 agggggcatcc gccagcgccc ttggggtaag tgggctgctg aaatcagaga tcctcgcaag    420
ggtgttcgtg tctggcttgg cactttcaac agtgctgaag aagctgcaag agcttatgat    480
gctgaagcac gcaggattcg tggcaagaag gccaaggtga atttccaga ggctccaaca     540 actgctcaga gcgtcgtgc tggctccacc actgctaaag cacccaagtc aagtgtggaa     600
cagaagccta ctgtcaaacc agcattcaac aatcttgcca atgcaaatgc gtttgtctac    660
ccatctgcta acttcacttc aaacaagccg tttgttcagc ctgataacat gccatttgtt    720
cctgcaatga actctgctgc tcctattgag gaccctatca tcaactctga ccagggaagc    780
aactcatttg gctgctctga cttggctgg gagaatgata ccaagacacc agatattaca     840
tcaattgctc ccatttcaac catagctgaa gtcgatgaat ctgcattcat taagagcagt    900
accaacccaa tggtccctcc tgttatggag aacagtgctg ttgatctgcc tgatttagaa    960
ccctacatga ggttccttct ggatgatggt gctggtgact caattgatag ccttctcaac   1020
ctggatggat cacaggatgt tgtcagcaac atggacctct ggagctttga tgacatgccc   1080
gttagcgatt tctattga                                                 1098
```

<210> SEQ ID NO 22
<211> LENGTH: 2881
<212> TYPE: DNA
<213> ORGANISM: Oryza sativa

<400> SEQUENCE: 22

```
gcttctctcc aatattttgt cgaaccgatt gagggaaaaa aaaagagaaa aagaaaagaa     60 aaaaagaag aagaagagag aactcgaact ctcgcctacc atttcgcccc cctccgcaag    120
caatccacca ctgcatcggc ggcgagggct caccggcggc gagccatgtg cggcggcgcc    180
atcatccacc acctgaaggg gcacccggag ggtcgcgcc gggcgacgga ggggctcctg    240
tggcccgaga agaagaagcc caggtggggc ggcggcggga ggcgccactt cgggggttc     300 gtggaggagg acgacgagga cttcgaggcc gacttcgagg agttcgaggt ggactccggg    360
gactcggatt tggagctcgg ggaggaggac gacgatgacg tcgtcgagat caagccggcc    420
```

```
gccttcaaga gggccctctc cagaggtatg ggcgtcgctg ggagcggctt gatttgtgta    480
gtttacttgt tcttcaggga ttgattgctg ttgtaaatcg ttagttctac ggccgattgg    540
gaattttttt ggggatcgag gacgctcggt ggatggattg ggaggaaaaa aagggggatag    600
ataattttag ggggttgatcc tgagagatca gatttgggggt gatactcctg tttaattggt    660
gatttagggt ggaatgatgt gcctccatgt cttatttgtg gtgatcaggg cttcatgtgc    720
tgattctgtc tgctaggatt ttagagatgc catttcagct cttgcactgt tcgatctttt    780
ttttttctttt ttctaaattg cgcaatccat atgattacct ttttctccaa ggagttgaat    840
tcgcagtaaa ggggaaatta ttctccgttc tctttggagg tctccccatc tgggttctta    900
gttgttagat ggatgaccct agtatcgctt gatgtggttg tatgattgcg agaggattgt    960
tccggacgta attcaactat tagtcgaagt aaaggatttt tatgatgttg actgtcaagt   1020
cctacatgcc ttagcatata ctcctggctg tttagtcgtc ctggtgcctg tttttggttc   1080
tatctttcgg tcaatagcgt caaatcattt ttttgtggtc tttgttggcc tcttttgctt   1140
agacatacta gttcattta tttatgggga tgttacctct tgtgtaaatt gtctaaatcg   1200
gttgtatcta gtcagtcgtg tgagctaaac cacagatctt tgttgaagtg ttgcaactca   1260
gttttggtgt tccttgttta caattaatgt tgctgcagca tattgatgtt agtccgtaaa   1320
gcacaacttt agactgcaat tgcagaaatg atgaggtcca ttcatgggtt ttttttccta   1380
caatcttgaa tttcatgatt tgagatatgc tttcctaaaa tttgaatgtt tatacgcatg   1440
gttgcatgtt ccaacttcat gtttgtgacc aaaagaaaat aacatcagca agagaagttc   1500
atctgtgtaa tttcttgcca ttgatgttga ccttccattg cagataactt gagcaccatt   1560
accactgccg gatttgatgg tcctgctgca aagtctgcca aagaaagag aaagaaccaa   1620
ttcagggggca tccgccagcg cccttgggggt aagtgggctg ctgaaaatcag gatcctcgc   1680
aagggtgttc gtgtctggct tggcactttc aacagtgctg aagaagctgc aagagcttat   1740
gatgctgaag cacgcaggat tcgtggcaag aaggccaagg tgaattttcc agaggctcca   1800
acaactgctc agaagcgtcg tgctggctcc accactgcta aagcacccaa gtcaagtgtg   1860
gaacagaagc ctactgtcaa accagcattc aacaatcttg ccaatgcaaa tgcgtttgtc   1920
tacccatctg ctaacttcac ttcaaacaag ccgtttgttc agcctgataa catgccattt   1980
gttcctgcaa tgaactctgc tgctcctatt gaggacccta tcatcaactc tgaccaggga   2040
agcaactcat ttggctgctc tgactttggc tgggagaatg ataccaagac accagatatt   2100
acatcaattg ctcccatttc aaccatagct gaagtcgatg aatctgcatt cattaagagc   2160
agtaccaacc caatggtccc tcctgttatg gagaacagtg ctgttgatct gcctgattta   2220
gaaccctaca tgaggttcct tctggatgat ggtgctggtg actcaattga tagccttctc   2280
aacctggatg gatcacagga tgttgtcagc aacatggacc tctggagctt tgatgacatg   2340
cccgttagcg atttctattg aggaattcga agtcttctag tcggagcatg tacacaggga   2400
aaaaaaggt aaggattatc aatttgattt tttctctctg aatatgcacg atttttaca   2460
ttgctctaat tttgcttgtg ttttttcagga ataaatacta ttggagattg ggaggcacct   2520
gcatggcacc ttgggggtag catatcgtta tgtttagctt agatgcaaaa ggctgcatcc   2580
tgaaactctt tggtgattgg acctgttccc tatccgctgt ctatgtatgg cagccatcta   2640
tgagactcaa gaactgcttt tttttttccg ttctagtttt ctgtcgttgc tacctgtata   2700
tggctatgaa catcgtgaat ccatggccat tatgttttaa tctatgttgt tgactgctct   2760
ttctttcggt ctttgctgtg ctgcgctatg ttggtgataa ctagctacca tattgatttt   2820
```

```
ctgtacataa ttcatttgtt gaatccgaaa ttaaatagtg cattgactat atatttatat    2880
a                                                                    2881
```

<210> SEQ ID NO 23
<211> LENGTH: 1403
<212> TYPE: DNA
<213> ORGANISM: Triticum aestivum

<400> SEQUENCE: 23

```
ctctccaccc gcggccccac gtgctcccag ccatgtgcgg cggcgccatc ctctccgaca      60
tcatcccgcc gccgcgccgg gccaccggcg gcaacgtctg gcgggcggac aagaagagga    120
gggccaggcc cgacgccgcc gcggggaggc cccgccgcgt gcccgaggag gagttccagg    180
aggaggaggg cgacgcggag ttcgaggccg acttcgaggg gttcgtggag gcggaggagg    240
agtccgacgg cgaggccaag cccttccccg tccgcaggac cggcttctcc ggagatggac    300
tgaaggcaac tgctgctggt gatgatgact gtgcctcagg gtctgctaaa ggaagagaa     360
agagccagtt caggggcatc cgccgccgcc cttggggtaa atgggctgct gaaataagag    420
atcctcgcaa gggtgtccgt gtctggcttg gcacttacaa ctctgctgag gaagctgcca    480
gagcctatga tgttgaagcc cgcagaattc gtggcaagaa ggcaaaggtc aatttcccag    540
aagaagctcc catggatcct cagcaacgct gcgctaccte tgtgaaggtg cccgagttca    600
acaccgaaca gaagccagta ctcaacacca tgggcaacac agatgtgtat tcctgccctg    660
ctgttgacta caccttaaat cagcaatttg tgcagcctca gaacatgtcg tttgtgccta    720
cagtgaatgc agttgaggct cctttcatga atttttcctc tgaccagggg agcaactcct    780
ttagttgctc agacttcagc tgggagaatg atatcaagac ccctgacata acttctgtgc    840
ttgcatccat tcccacctca actgaggtca atgaatctgc atttctccag aacaatggca    900
ttaattcaac ggtacctcct gtgatgggtg atgctaatgt tgatcttgcc gacttggagc    960
catacatgaa gttcctgatg gacgatggtt cagatgagtc aattgacagc attctaagct   1020
gtgatgtacc gcaggacgtt gtcggcaaca tgggcctttg gacctttgat gacatgccct   1080
tgtctgctgg tttctactga gggaatcgag gtcgctgggt gcctgtatat atagacaaag   1140
gaataagtat tctggacatc aacaagtgct tgtgtctggt gcctctagaa tcgagcagta   1200
gcgacgtcag tctatggtta tgtctagctt aaatggtcag gagacctaag tcttttgcaa   1260
tagacctctg tcttgtgccc ccagactata ttatatctat atatgaaacc agtatgtgat   1320
gggaactgct tattttgtat tcctgttttct accttattgt aattgctaca agtggctgta   1380
aaccttttaa ctttgaaaaa aaa                                            1403
```

<210> SEQ ID NO 24
<211> LENGTH: 1110
<212> TYPE: DNA
<213> ORGANISM: Capsicum annuum

<400> SEQUENCE: 24

```
atgtgtggtg gtgcaattat ctccgatttg gtacctccta gccggatttc ccgccggcta     60
accgccgagt tgctatgggg taactctgat ctgagcaaaa agaagaaaaa tccagggaat    120
tattactcaa agcctttgaa caggtctaag tttattgacc ttgatgagga atttgaagct    180
gactttcagg acttcaagga ctatgccgat gacgatgttg atgatgttaa gcccttcggt    240
tccaaatctg tgaaatctgg cgattcaagc tgcgatactg aaaaatcttc caagagaaag    300
```

| | |
|---|---|
| aggaagaatc agtaccgggg atcagacag cgtccttggg gtaagtgggc agctgaaatt | 360 |
| cgtgatccga ggaaagggat tcgagtttgg cttggaactt tcaattctgc ggaagaagca | 420 |
| gctagagctt atgatgttga ggcacgaagg atcagaggca agaaggctaa ggtgaacttt | 480 |
| cctgatggat ctccagcttc tgcttcaaga cgtgctgtta agccaaatcc tcaggaggca | 540 |
| cttcgcgagg aaatcttgaa cacagttcag ccgaacacaa cttatatcaa caacttggac | 600 |
| ggcggatctg atgattcgtt tggcttttc gaagagaaac cagcagcaaa gcagtatggc | 660 |
| tatgagaatg tttcttttac tgctggagat atgggactgg gttcaatttc cccttcaact | 720 |
| ggtacaacaa atgtttactt cagttctgat gaaggaagca acacctttga ctgctctgat | 780 |
| ttcggttggg gtgaaccatg tccgaggact ccagagatct catctgttct gtcagaagtt | 840 |
| ctagaatgta atggtactca atctgatgaa gatgctagac cagagaaaaa actgaagtcg | 900 |
| tgttccaacg cttccttgcc agatgaggat aacactgtgc acacgctatc tgaagagcta | 960 |
| tcggcttttg aatcccagat gaagttcttg cagatcccat atcttgaggg aaattgggat | 1020 |
| gcatcagttg atgcctttgt caacacaggc gcaattcagg atggcggaaa tgcgatggat | 1080 |
| ctctggcctt cgatgatgtt ccttcttta | 1110 |

<210> SEQ ID NO 25
<211> LENGTH: 1155
<212> TYPE: DNA
<213> ORGANISM: Glycine max

<400> SEQUENCE: 25

| | |
|---|---|
| atgtgtggtg gtgcgattat ctccgacttc ataccggcag gtcccgccag cggggcgcgg | 60 |
| cgcgtgaccg ccgacatcct gtggccgagt ttgaggaagc gcttctcgaa gccgctgctg | 120 |
| gacgatgatt tcgaggctgg gttcagagaa ttcaaggatg attcggaaat cgaggatgtt | 180 |
| gatgacgagg acgatgaaga cgaggaggag ttgaagaaga agcccttgg gttctctcgc | 240 |
| tccagcaaca aggctgcttc taagcctctc tctcgtggag caacaactgt gaaatctgtg | 300 |
| gaatcaaagg ggcaagctga agtgtgcc aagagaaaga ggaagaacca gtatcgcgga | 360 |
| atccgccagc gtccatgggg aaagtgggct gctgagattc gcgacccaag aaaggggtt | 420 |
| cgtgtttggc ttggaacttt cagcactgct gaagaagctg caagagctta cgatgctgaa | 480 |
| gcaaggagga tccgtggcaa gaaagccaag gtgaatttcc ctgatgagcc ttcaggcgct | 540 |
| gcttcctcaa aacgtctcaa ggcgaatcca gaggctcagc caatgaagaa aaatctgaac | 600 |
| tctgtgaagc cgaaaataaa ccagatgttc aattttggtg acaatcttga gggctactac | 660 |
| agccctatag atcaggtgga acagaaacca ctggttaacc agtatgttaa ccgtgccccg | 720 |
| tttgctggaa atggagttca agtctcacct gttactccat ctgctgatgt tactgcttac | 780 |
| ttcagctctg agcattcgag caactcgttt gattattctg accttggatg gggtgaacaa | 840 |
| gtccccaaga cccccgagat ctcatccttg ctttctgctg ctcctttgga gggtgctgct | 900 |
| gatcaggttc agaagaccaa caactcgcag gatgtggtgg ctgcacaaga tgattctgca | 960 |
| aaaacccttt ccgaagagct tgcagacatt gaatcccagc tcaagttctt tgagacccct | 1020 |
| tcttttcttg atgaagcctg ggctgatgct acattggcgt ctttgctcgg cggagacgca | 1080 |
| actcatgacg ccgccggaaa ccctatgaac ctttggagct tcgacgacct gccttccatg | 1140 |
| gcaggagtct tctga | 1155 |

<210> SEQ ID NO 26
<211> LENGTH: 1119

```
<212> TYPE: DNA
<213> ORGANISM: Solanum lycopersicum

<400> SEQUENCE: 26
atgtgtggtg gtgcaattat ctccgatttg gtacctccta gccggatttc tcgccggtta      60
accgctgatt ttctatgggg tacatccgat ctgaacaaga agaagaagaa ccctagtaat     120
taccactcaa agcccttgag gtctaagttt attgaccttg aagatgaatt tgaagctgac     180
tttcagcact tcaaggataa ttctgatgat gatgatgatg tgaaggcatt tggccccaaa     240
tccgtgagat ctggtgattc aaactgcgaa gctgacagat cctccaagag aaagaggaag     300
aatcagtacc gggggatcag acagcgtcct tggggtaagt gggcagctga atacgtgat      360
ccaaggaaag gtattcgagt ctggcttggt actttcaatt cagccgaaga ggcagccaga     420
gcttatgatg ctgaggcgcg aaggatcaga ggcaagaaag ctaaggtgaa ctttcctgat     480
gaagctccag tgtctgtttc aagacgtgct attaagcaaa atccccaaaa ggcacttcgt     540
gaggaaaccc tgaacacagt tcagcccaac atgacttata ttagtaactt ggatggtgga     600
tctgatgatt cgttcagttt tttcgaagag aaaccagcaa ccaagcagta cggcttcgag     660
aatgtgtctt ttactgctgt agatatggga ctgggctcag tttccccttc agctggtaca     720
aatgtttact tcagctctga tgaagcaagt aacacttttg actgctctga tttcggttgg     780
gctgaaccgt gtgcaaggac tccagagatc tcatctgttc tgtcggaagt tctgaaaacc     840
aatgagactc attttgatga tgattccaga ccagagaaaa aactgaagtc ctgttccagc     900
acttcattga cagttgacgg taacactgtg aacacgctat ctgaagagct atcggctttt     960
gaatcccaga tgaagttctt gcagatccca tatctcgagg gaaattggga tgcatcggtt    1020
gatgccttcc tcaatacaag tgcaattcag gatggtggaa acgccatgga cctttggtcc    1080
ttcgatgatg taccttcttt aatgggaggt gcctactaa                           1119

<210> SEQ ID NO 27
<211> LENGTH: 1296
<212> TYPE: DNA
<213> ORGANISM: Arabidopsis thaliana

<400> SEQUENCE: 27
atgaggctcc tcttcagctt ctgcttcttc ttcttcatga tcatctttac cgcaactgct      60
tatgatccat tagatcctag tggtaacatt acaatcaaat gggatattat gtcctggacg     120
gcagatggct atgtggctac ggtaactatg aacaacttcc aaatctaccg gcacatacaa     180
aaccctggtt ggacattagg ttggacatgg gcaaagaaag aggtgatttg gtcaatggtt     240
ggtgcacaaa caacagaaca aggagactgt tccaagttta agggaaatgt acctcattgc     300
tgtaagaaaa ccectacagt tgttgatctc ttgccaggtg tgccttataa tcaacagttc     360
tcaaactgtt gcaaaggagg tgtaattgga gcttggggtc aagatccatc agccgctgta     420
tcccagtttc aggttagtgc tggtttagct ggaactacaa acaagactgt caagcttcct     480
aagaacttca ctttgcttgg tcccggccct ggttacactt gcggtcctgc caaaatcgtg     540
ccctctaccg ttttctcac aactgacaaa cggcgaaaaa cacaagcttt gatgacatgg     600
aatgttacct gcacatactc acagttttta gcaagaaagc atccaagctg ttgtgtctcc     660
ttctcttctt tctacaacga caccataact ccttgcccgt cttgtgcctg ggctgcgag      720
aacaaaaaga gctgcgtcaa ggctgattct aagattctaa ccaagaaagg tctcaacaca     780
ccaaaaaagg acaacactcc tttgttgcaa tgcacacatc acatgtgccc tgttagagtc     840
```

```
cactggcacg ttaaaactaa ctacaaagac tattggcgag tgaagatagc aatcacaaat        900
ttcaattacc ggatgaatca tacactctgg actttagcaa ttcagcatcc aaatctcaac        960
aatgtgactc aagttttcag ctttgactac aaaccagtct ctccttacgg atccataaat       1020
gatactggaa tgttctatgg aacgaagttt tacaatgatt tattaatgga agctggacct       1080
tcagggaatg tgcaatcaga ggttttgcta cagaaagatc aaaagacttt tactttcaag       1140
caaggttggg cttttcctag aaaagtttac tttaatggtg atgaatgtat gttacctcca       1200
ccagattcat acccttttct accaaactct gcacaaggga actttgcttc gttctcactc       1260
accattcttc ttctcctatt catctcaata tggtga                                 1296
```

<210> SEQ ID NO 28
<211> LENGTH: 425
<212> TYPE: PRT
<213> ORGANISM: Oryza sativa

<400> SEQUENCE: 28

```
Met Ala Ile Gly Val Gly Gly Cys Cys Ala Val Leu Leu Ala Ala
1               5                   10                  15

Leu Leu Phe Ser Ser Pro Ala Thr Thr Tyr Ala Tyr Asp Ser Leu Asp
                20                  25                  30

Pro Asn Gly Asn Ile Thr Ile Lys Trp Asp Val Met Gln Leu Thr Pro
            35                  40                  45

Asp Gly Tyr Ala Ala Val Val Thr Leu Ser Asn Tyr Gln Gln Phe Arg
        50                  55                  60

His Ile Gln Pro Pro Gly Trp Gln Leu Gly Trp Thr Trp Gln Lys
65                  70                  75                  80

Glu Val Ile Trp Ser Met Tyr Gly Ala Gln Ala Ile Glu Gln Gly Asp
                85                  90                  95

Cys Ser Met Ser Lys Glu Gly Ser Asn Val Pro His Ser Cys Lys Lys
            100                 105                 110

His Pro Thr Val Val Asp Leu Leu Pro Gly Thr Pro Ile Asp Leu Gln
        115                 120                 125

Ile Ala Asn Cys Cys Lys Ala Gly Ser Leu Ser Ala Phe Ser Gln Asp
130                 135                 140

Pro Ala Asn Ser Ala Ala Ser Phe Gln Ile Ile Val Gly His Ser Gly
145                 150                 155                 160

Asn Ser Asn Glu Thr Val Arg Val Pro Lys Asn Phe Ser Leu Met Ala
                165                 170                 175

Pro Gly Pro Gly Tyr Thr Cys Ser Arg Ala Met Ile Val Lys Pro Ser
            180                 185                 190

Arg Phe Leu Ser Pro Asp Gly Arg Ala Thr Gln Ala Leu Met Thr
        195                 200                 205

Trp Asn Val Ile Cys Thr Tyr Ser Gln Phe Leu Ala Gln Lys Val Pro
210                 215                 220

Ser Cys Cys Val Ser Leu Ser Ser Phe Asp Asn Asp Lys Thr Val Asp
225                 230                 235                 240

Cys Pro Thr Cys Ser Cys Gly Cys Arg Asn Glu Lys Ser Thr Gly
                245                 250                 255

Lys Cys Val Lys Lys Asn Ala Pro Asp Leu Gln Ser Ile Ile His Gly
            260                 265                 270

Pro Gly Arg Trp Thr Trp Gln Pro Leu Leu Gln Cys Thr Ser His Met
        275                 280                 285

Cys Pro Val Lys Ile Asn Trp His Leu Met Leu Lys Asp Lys Glu His
```

```
              290                 295                 300
Tyr Arg Val Lys Ile Thr Val Thr Asn Leu Asn Tyr Arg Met Asn Phe
305                 310                 315                 320

Thr Glu Trp Asn Leu Val Val Gln Tyr His Pro Ile Leu Asp Ile Thr
                325                 330                 335

Gln Ile Ser Gly Phe Asn Tyr Lys Ser Ile Gln Val Gly Lys Ile Asn
                340                 345                 350

Asp Thr Thr Met Leu Trp Gly Val Lys Pro Tyr Tyr Asp Leu Leu Met
            355                 360                 365

Gln Ala Gly Pro Leu Gly Asn Val Gln Gly Glu Leu Ile Val Arg Lys
        370                 375                 380

Asp Phe Arg Ala Ser Ser Thr Ser Asn Asn Asn Lys Gly Arg Ala Phe
385                 390                 395                 400

Pro Val Arg Val Tyr Phe Asn Gly Asp Asn Cys Val Met Pro Pro Pro
                405                 410                 415

Asp Ala Tyr Pro Val Ser Ile Thr Ala
                420                 425
```

<210> SEQ ID NO 29
<211> LENGTH: 425
<212> TYPE: PRT
<213> ORGANISM: Oryza sativa

<400> SEQUENCE: 29

```
Met Ala Ile Gly Val Gly Gly Cys Cys Ala Val Leu Ala Ala Ala
1               5                   10                  15

Leu Leu Phe Ser Ser Pro Ala Thr Thr Tyr Ala Tyr Asp Ser Leu Asp
                20                  25                  30

Pro Asn Gly Asn Ile Thr Ile Lys Trp Asp Val Met Gln Trp Thr Pro
            35                  40                  45

Asp Gly Tyr Ala Ala Val Val Thr Leu Ser Asn Tyr Gln Gln Phe Arg
        50                  55                  60

His Ile Gln Pro Pro Gly Trp Gln Leu Gly Trp Thr Trp Gln Gln Lys
65                  70                  75                  80

Glu Val Ile Trp Ser Met Tyr Gly Ala Gln Ala Ile Glu Gln Gly Asp
                85                  90                  95

Cys Ser Met Ser Lys Glu Gly Ser Asn Val Pro His Ser Cys Lys Lys
                100                 105                 110

His Pro Thr Val Val Asp Leu Leu Pro Gly Ala Pro Ile Asp Leu Gln
            115                 120                 125

Ile Ala Asn Cys Cys Lys Ala Gly Ser Leu Ser Ala Phe Ser Gln Asp
        130                 135                 140

Pro Ala Asn Ser Ala Ala Ser Phe Gln Ile Ile Val Gly His Ser Gly
145                 150                 155                 160

Asn Ser Asn Glu Thr Val Arg Val Pro Lys Asn Phe Ser Leu Met Ala
                165                 170                 175

Pro Gly Pro Gly Tyr Thr Cys Ser Arg Ala Met Ile Val Lys Pro Ser
                180                 185                 190

Arg Phe Leu Ser Pro Asp Gly Arg Arg Ala Thr Gln Val Leu Met Thr
            195                 200                 205

Trp Asn Val Ile Cys Thr Tyr Ser Gln Phe Leu Ala Gln Lys Val Pro
        210                 215                 220

Ser Cys Cys Val Ser Leu Ser Ser Phe Asp Asn Asp Lys Thr Val Asp
225                 230                 235                 240
```

```
Cys Pro Thr Cys Ser Cys Gly Cys Arg Asn Glu Lys Ser Thr Thr Gly
                245                 250                 255

Lys Cys Val Lys Lys Asn Ala Pro Asp Leu Gln Ser Ile Ile His Gly
            260                 265                 270

Pro Gly Arg Trp Thr Trp Gln Pro Leu Leu Gln Cys Thr Ser His Met
        275                 280                 285

Cys Pro Val Lys Ile Asn Trp His Leu Met Leu Lys Asp Lys Glu His
    290                 295                 300

Tyr Arg Val Lys Ile Thr Val Thr Asn Leu Asn Tyr Arg Met Asn Phe
305                 310                 315                 320

Thr Glu Trp Asn Leu Val Val Gln Tyr His Pro Ile Leu Asp Ile Thr
                325                 330                 335

Gln Ile Ser Gly Phe Asn Tyr Lys Ser Ile Gln Val Gly Lys Ile Asn
                340                 345                 350

Asp Thr Thr Met Leu Trp Gly Val Lys Pro Tyr Tyr Asp Leu Leu Met
            355                 360                 365

Gln Ala Gly Pro Leu Gly Asn Val Gln Gly Glu Leu Ile Val Arg Lys
        370                 375                 380

Asp Phe Arg Ala Ser Ser Thr Thr Asn Asn Lys Gly Arg Ala Phe
385                 390                 395                 400

Pro Val Arg Val Tyr Phe Asn Gly Asp Asn Cys Val Met Pro Pro Pro
                405                 410                 415

Asp Ala Tyr Pro Val Ser Ile Thr Ala
                420                 425

<210> SEQ ID NO 30
<211> LENGTH: 468
<212> TYPE: PRT
<213> ORGANISM: Oryza sativa

<400> SEQUENCE: 30

Met Glu Leu His Arg Cys Ser Leu Leu Ala Leu Leu Leu Ala Val Thr
1               5                   10                  15

Cys Ser Val Ala Val Ala Tyr Asp Pro Leu Asp Pro Lys Gly Asn Ile
            20                  25                  30

Thr Ile Lys Trp Asp Val Ile Ser Trp Thr Pro Asp Gly Tyr Val Ala
        35                  40                  45

Met Val Thr Met Ser Asn Tyr Gln Met Tyr Arg Gln Ile Leu Ala Pro
    50                  55                  60

Gly Trp Thr Val Gly Trp Ser Trp Ala Lys Lys Glu Val Ile Trp Ser
65                  70                  75                  80

Ile Val Gly Ala Gln Ala Thr Glu Gln Gly Asp Cys Ser Lys Phe Lys
                85                  90                  95

Gly Gly Ile Pro His Ser Cys Lys Arg Thr Pro Ala Ile Val Asp Leu
            100                 105                 110

Leu Pro Gly Val Pro Tyr Asn Gln Gln Ile Ala Asn Cys Cys Lys Ala
        115                 120                 125

Gly Val Val Ser Ala Tyr Gly Gln Asp Pro Ala Gly Ser Val Ser Ala
    130                 135                 140

Phe Gln Val Ser Val Gly Leu Ala Gly Thr Thr Asn Lys Thr Val Lys
145                 150                 155                 160

Leu Pro Thr Asn Phe Thr Leu Ala Gly Pro Gly Pro Gly Tyr Thr Cys
                165                 170                 175

Gly Pro Ala Thr Ile Val Pro Ser Thr Val Tyr Leu Thr Pro Asp Arg
            180                 185                 190
```

-continued

Arg Arg Arg Thr Gln Ala Leu Met Thr Trp Thr Val Thr Cys Thr Tyr
        195                 200                 205

Ser Gln Gln Leu Ala Ser Arg Tyr Pro Thr Cys Cys Val Ser Phe Ser
    210                 215                 220

Ser Phe Tyr Asn Ser Thr Ile Val Pro Cys Ala Arg Cys Ala Cys Gly
225                 230                 235                 240

Cys Gly His Asp Gly Tyr Arg Gly Asn Gly Gly Gly Lys Asn Ala
                245                 250                 255

Arg Ala Gly Asp Gly Arg Ser Arg Arg Asn Ser Gly Gly Gly Gly
            260                 265                 270

His Ser Gly Gly Thr Glu Cys Ile Met Gly Asp Ser Lys Arg Ala Leu
        275                 280                 285

Ser Ala Gly Val Asn Thr Pro Arg Lys Asp Gly Ala Pro Leu Leu Gln
        290                 295                 300

Cys Thr Ser His Met Cys Pro Ile Arg Val His Trp His Val Lys Leu
305                 310                 315                 320

Asn Tyr Lys Asp Tyr Trp Arg Ala Lys Ile Ala Ile Thr Asn Phe Asn
                325                 330                 335

Tyr Arg Met Asn Tyr Thr Gln Trp Thr Leu Val Ala Gln His Pro Asn
            340                 345                 350

Leu Asn Asn Val Thr Glu Val Phe Ser Phe Gln Tyr Lys Pro Leu Leu
        355                 360                 365

Pro Tyr Gly Asn Ile Asn Asp Thr Gly Met Phe Tyr Gly Leu Lys Phe
    370                 375                 380

Tyr Asn Asp Leu Leu Met Glu Ala Gly Pro Phe Gly Asn Val Gln Ser
385                 390                 395                 400

Glu Val Leu Met Arg Lys Asp Tyr Asn Thr Phe Thr Phe Ser Gln Gly
                405                 410                 415

Trp Ala Phe Pro Arg Lys Ile Tyr Phe Asn Gly Asp Glu Cys Lys Met
            420                 425                 430

Pro Pro Pro Asp Ser Tyr Pro Tyr Leu Pro Asn Ser Ala Pro Ile Gly
        435                 440                 445

Pro Pro Arg Ser Val Ala Ala Ala Ser Ala Ile Leu Val Val Leu
    450                 455                 460

Leu Leu Val Ala
465

<210> SEQ ID NO 31
<211> LENGTH: 457
<212> TYPE: PRT
<213> ORGANISM: Oryza sativa

<400> SEQUENCE: 31

Met Ala Val Gly Gly Ala Gly Ser Ser Arg Ser Val Ala Pro Cys Cys
1               5                   10                  15

Cys Cys Ala Val Leu Leu Ala Ala Leu Leu Phe Ser Ala Pro Ala
            20                  25                  30

Thr Thr Glu Ala Tyr Asp Ala Leu Asp Pro Asn Gly Asn Ile Thr Ile
            35                  40                  45

Lys Trp Asp Val Met Ser Trp Thr Pro Asp Gly Tyr Val Ala Val Val
        50                  55                  60

Thr Met Phe Asn Tyr Gln Gln Phe Arg His Ile Gln Ala Pro Gly Trp
65              70                  75                  80

Gln Leu Gly Trp Thr Trp Ala Lys Lys Glu Val Ile Trp Ser Met Val

```
                    85                  90                  95
Gly Ala Gln Thr Thr Glu Gln Gly Asp Cys Ser Lys Phe Lys Gly Gly
                100                 105                 110

Thr Pro His Cys Cys Lys Lys Asp Pro Thr Val Val Asp Leu Leu Pro
            115                 120                 125

Gly Thr Pro Tyr Asn Met Gln Ile Ala Asn Cys Cys Lys Ala Gly Val
        130                 135                 140

Ile Asn Thr Phe Asn Gln Asp Pro Ser Asn Ala Ala Ser Ser Phe Gln
145                 150                 155                 160

Ile Ser Val Gly Leu Ala Gly Thr Thr Asn Lys Thr Val Lys Leu Pro
                165                 170                 175

Lys Asn Phe Thr Leu Lys Ala Pro Gly Pro Gly Tyr Thr Cys Gly Arg
            180                 185                 190

Ala Met Ile Val Arg Pro Thr Lys Phe Phe Thr Gly Asp Gly Arg Arg
        195                 200                 205

Ala Thr Gln Ala Leu Met Thr Trp Asn Val Thr Cys Thr Tyr Ser Gln
210                 215                 220

Phe Leu Ala Gln Lys Thr Pro Ser Cys Cys Val Ser Leu Ser Ser Phe
225                 230                 235                 240

Tyr Asn Asp Thr Ile Val Asn Cys Pro Thr Cys Ser Cys Gly Cys Gln
                245                 250                 255

Asn Asn Gly Thr Ser Pro Gly Ser Cys Val Asn Glu Asn Ser Pro Tyr
            260                 265                 270

Leu Gln Ser Ala Ile Asp Gly Pro Gly Lys Trp Thr Gly Gln Pro Leu
        275                 280                 285

Val Gln Cys Thr Ser His Met Cys Pro Ile Arg Ile His Trp His Val
290                 295                 300

Lys Leu Asn Tyr Lys Glu Tyr Trp Arg Val Lys Ile Thr Ile Thr Asn
305                 310                 315                 320

Phe Asn Tyr Arg Met Asn Tyr Thr Gln Trp Asn Leu Val Ala Gln His
                325                 330                 335

Pro Asn Phe Asn Asn Ile Thr Gln Leu Phe Ser Phe Asn Tyr Lys Pro
            340                 345                 350

Leu Thr Pro Tyr Gly Ser Lys Ile Asn Asp Thr Ala Met Phe Trp Gly
        355                 360                 365

Val Lys Phe Tyr Asn Asp Leu Leu Met Gln Ala Gly Pro Leu Gly Asn
370                 375                 380

Ala Gln Ser Glu Leu Leu Leu Arg Lys Asp Ser Lys Asp Phe Thr Phe
385                 390                 395                 400

Asp Lys Gly Trp Ala Phe Pro His Arg Val Tyr Phe Asn Gly Asp Asn
                405                 410                 415

Cys Val Met Pro Pro Asp Ala Tyr Pro Trp Leu Pro Asn Ala Ser
            420                 425                 430

Pro Leu Thr Lys Gln Pro Leu Thr Leu Ser Val Leu Val Phe Ser Ile
        435                 440                 445

Val Leu Ala Thr Leu Leu Ala Tyr Ala
450                 455

<210> SEQ ID NO 32
<211> LENGTH: 446
<212> TYPE: PRT
<213> ORGANISM: Oryza sativa

<400> SEQUENCE: 32
```

```
Met Ala Leu Leu Leu Leu Arg Met Gly Val Ser Val Ala Leu Leu Val
1               5                   10                  15

Ala Phe Phe Ser Ser Leu Ile Pro Ser Ser Glu Ala Tyr Asp Pro Leu
            20                  25                  30

Asp Pro Asn Gly Asn Ile Thr Ile Lys Trp Asp Val Leu Gln Trp Thr
            35                  40                  45

Pro Asp Gly Tyr Val Ala Val Ser Leu Tyr Asn Tyr Gln Gln Tyr
    50                  55                  60

Arg His Ile Gln Ser Pro Gly Trp Lys Leu Gly Trp Val Trp Ala Lys
65                  70                  75                  80

Lys Glu Ile Ile Trp Ala Met Asn Gly Gln Ala Thr Glu Gln Gly
                85                  90                  95

Asp Cys Ser Lys Phe Lys Ser Asn Ile Pro His Cys Cys Lys Lys Asp
            100                 105                 110

Pro Glu Ile Val Asp Leu Leu Pro Gly Thr Pro Tyr Asn Met Gln Ile
            115                 120                 125

Ala Asn Cys Cys Lys Gly Gly Val Leu Asn Ser Trp Ala Gln Asp Pro
            130                 135                 140

Ala Asn Ala Ile Ala Ser Phe Gln Val Ser Val Gly Gln Ala Gly Thr
145                 150                 155                 160

Thr Asn Lys Thr Val Arg Val Pro Arg Asn Phe Thr Leu Lys Ser Pro
            165                 170                 175

Gly Pro Gly Tyr Thr Cys Gly Ser Ala Lys Val Val Arg Pro Thr Lys
            180                 185                 190

Phe Phe Ser Gln Asp Gly Arg Arg Thr Thr Gln Ala His Met Thr Trp
            195                 200                 205

Asn Val Thr Cys Thr Tyr Ser Gln Ile Val Ala Gln Arg Ser Pro Thr
            210                 215                 220

Cys Cys Val Ser Leu Ser Ser Phe Tyr Asn Asp Thr Ile Val Asn Cys
225                 230                 235                 240

Pro Thr Cys Ser Cys Gly Cys Gln Asn Asn Lys Pro Gly Ser Cys Val
            245                 250                 255

Glu Gly Asn Ser Pro Tyr Leu Ala Ser Val Val Asn Thr His Asn Lys
            260                 265                 270

Asp Ser Leu Thr Pro Leu Val Gln Cys Thr Ser His Met Cys Pro Ile
            275                 280                 285

Arg Val His Trp His Val Lys Val Asn Tyr Lys Glu Tyr Trp Arg Val
            290                 295                 300

Lys Ile Thr Val Thr Asn Phe Asn Tyr Arg Met Asn Tyr Ser Gln Trp
305                 310                 315                 320

Asn Leu Val Thr Gln His Pro Ser Phe Asp Asn Leu Thr Thr Ile Phe
            325                 330                 335

Ser Phe Asn Tyr Lys Ser Leu Asn Pro Tyr Gly Val Ile Asn Asp Thr
            340                 345                 350

Ala Met Leu Trp Gly Ile Lys Tyr Tyr Asn Asp Leu Leu Met Thr Ala
            355                 360                 365

Gly Pro Asp Gly Asn Val Gln Ser Glu Leu Leu Phe Lys Lys Asp Pro
            370                 375                 380

Lys Ser Phe Thr Phe Glu Lys Gly Trp Ala Phe Pro Arg Arg Val Tyr
385                 390                 395                 400

Phe Asn Gly Asp Asn Cys Val Met Pro Pro Asp Ala Tyr Pro Trp
            405                 410                 415

Leu Pro Asn Ala Ser Thr Arg Val Met Ser Ser Ile Leu Leu Pro Phe
```

```
                420             425             430
Ile Thr Ile Trp Thr Ala Leu Thr Phe Leu Met Val Tyr Ala
            435             440             445

<210> SEQ ID NO 33
<211> LENGTH: 449
<212> TYPE: PRT
<213> ORGANISM: Zea mays

<400> SEQUENCE: 33

Met Ala Ala Gly Gly Arg Ser Ile Ala Cys Val Ala Ala Val Leu Leu
1               5                   10                  15

Ala Ala Ala Leu Leu Leu Ser Ala Pro Thr Thr Thr Glu Ala Tyr Asp
            20                  25                  30

Ser Leu Asp Pro Asn Gly Asn Ile Thr Ile Lys Trp Asp Ile Met Gln
        35                  40                  45

Trp Thr Pro Asp Gly Tyr Val Ala Val Val Thr Met Phe Asn Tyr Gln
    50                  55                  60

Gln Phe Arg His Ile Gly Ala Pro Gly Trp Gln Leu Gly Trp Thr Trp
65                  70                  75                  80

Ala Lys Lys Glu Val Ile Trp Ser Met Val Gly Ala Gln Thr Thr Glu
                85                  90                  95

Gln Gly Asp Cys Ser Lys Phe Lys Gly Asn Thr Pro His Cys Cys Lys
            100                 105                 110

Lys Asp Pro Thr Ile Val Asp Leu Leu Pro Gly Thr Pro Tyr Asn Met
        115                 120                 125

Gln Ile Ala Asn Cys Cys Lys Ala Gly Val Ile Asn Thr Phe Asn Gln
    130                 135                 140

Asp Pro Ala Asn Ala Ala Ser Ser Phe Gln Ile Ser Val Gly Leu Ala
145                 150                 155                 160

Gly Thr Thr Asn Lys Thr Val Lys Val Pro Lys Asn Phe Thr Leu Lys
                165                 170                 175

Thr Pro Gly Pro Gly Tyr Thr Cys Gly Arg Ala Ile Val Gly Arg Pro
            180                 185                 190

Thr Lys Phe Phe Ser Ala Asp Gly Arg Arg Val Thr Gln Ala Leu Met
        195                 200                 205

Thr Trp Asn Val Thr Cys Thr Tyr Ser Gln Phe Leu Ala Gln Lys Thr
    210                 215                 220

Pro Ser Cys Cys Val Ser Leu Ser Ser Phe Tyr Asn Asp Thr Ile Val
225                 230                 235                 240

Asn Cys Pro Thr Cys Ser Cys Gly Cys Gln Asn Pro Ser Gly Ser Asn
                245                 250                 255

Cys Val Asn Glu Asp Ser Pro Asn Leu Gln Ala Ala Ile Asp Gly Pro
            260                 265                 270

Gly Lys Trp Thr Gly Gln Pro Leu Val Gln Cys Thr Ser His Met Cys
        275                 280                 285

Pro Ile Arg Ile His Trp His Val Lys Leu Asn Tyr Lys Glu Tyr Trp
    290                 295                 300

Arg Val Lys Ile Thr Ile Thr Asn Phe Asn Phe Arg Met Asn Tyr Thr
305                 310                 315                 320

Gln Trp Asn Leu Val Ala Gln His Pro Asn Phe Asp Asn Ile Thr Gln
                325                 330                 335

Leu Phe Ser Phe Asn Tyr Lys Pro Leu Thr Pro Tyr Gly Gly Gly Ile
            340                 345                 350
```

-continued

```
Asn Asp Thr Ala Met Phe Trp Gly Val Lys Phe Tyr Asn Asp Leu Leu
            355                 360                 365

Met Gln Ala Gly Lys Leu Gly Asn Val Gln Ser Glu Leu Leu Leu Arg
    370                 375                 380

Lys Asp Ser Arg Thr Phe Thr Phe Glu Lys Gly Trp Ala Phe Pro Arg
385                 390                 395                 400

Arg Val Tyr Phe Asn Gly Asp Asn Cys Val Met Pro Ser Pro Glu Asn
                405                 410                 415

Tyr Pro Trp Leu Pro Asn Ala Ser Pro Leu Thr Lys Gln Ala Leu Thr
                420                 425                 430

Leu Pro Leu Leu Ile Phe Trp Val Ala Leu Ala Val Leu Leu Ala Tyr
                435                 440                 445

Ala

<210> SEQ ID NO 34
<211> LENGTH: 450
<212> TYPE: PRT
<213> ORGANISM: Zea mays

<400> SEQUENCE: 34

Met Thr Met Gly Leu Arg Val Arg Asp Ser Ser Ala Leu Leu Ala Leu
1               5                   10                  15

Ala Val Ala Leu Ala Cys Cys Ser Val Ala Val Ala Tyr Asp Pro
            20                  25                  30

Leu Asp Pro Asn Gly Asn Ile Thr Ile Lys Trp Asp Val Ile Ser Trp
            35                  40                  45

Thr Pro Asp Gly Tyr Val Ala Met Val Thr Met Ser Asn Tyr Gln Met
    50                  55                  60

Tyr Arg His Ile Met Ala Pro Gly Trp Thr Leu Gly Trp Ser Trp Ala
65                  70                  75                  80

Lys Lys Glu Val Ile Trp Ser Ile Val Gly Ala Gln Ala Thr Glu Gln
                85                  90                  95

Gly Asp Cys Ser Lys Phe Lys Gly Gly Ile Pro His Cys Cys Lys Arg
            100                 105                 110

Thr Pro Ala Val Val Asp Leu Leu Pro Gly Val Pro Tyr Asn Gln Gln
            115                 120                 125

Ile Ala Asn Cys Cys Lys Ala Gly Val Val Ser Ala Tyr Gly Gln Asp
130                 135                 140

Pro Ala Gly Ser Val Ser Ala Phe Gln Val Ser Val Gly Leu Ala Gly
145                 150                 155                 160

Thr Thr Asn Lys Thr Val Lys Leu Pro Arg Asn Phe Thr Leu Met Gly
                165                 170                 175

Pro Gly Leu Gly Tyr Thr Cys Gly Pro Ala Ala Val Val Pro Ser Thr
            180                 185                 190

Val Tyr Trp Thr Pro Asp His Arg Arg Thr Gln Ala Leu Met Thr
    195                 200                 205

Trp Thr Val Thr Cys Thr Tyr Ser Gln Gln Leu Ala Ser Arg Tyr Pro
210                 215                 220

Ser Cys Cys Val Ser Phe Ser Ser Phe Tyr Asn Ser Thr Ile Val Pro
225                 230                 235                 240

Cys Ala Arg Cys Ala Cys Gly Cys Gly Gly His Gly His Ala Gly
            245                 250                 255

Pro Gly Gly Cys Ile Glu Gly Asp Ser Lys Arg Ala Leu Ser Ala Gly
            260                 265                 270
```

```
Val Asn Thr Pro Arg Lys Asp Gly Gln Ala Leu Leu Gln Cys Thr Pro
            275                 280                 285

His Met Cys Pro Ile Arg Val His Trp His Val Lys Leu Asn Tyr Lys
    290                 295                 300

Asp Tyr Trp Arg Ala Lys Ile Ala Ile Thr Asn Tyr Asn Tyr Arg Met
305                 310                 315                 320

Asn Tyr Thr Gln Trp Thr Leu Val Ala Gln His Pro Asn Leu Asp Asn
                325                 330                 335

Val Thr Glu Val Phe Ser Phe Gln Tyr Lys Pro Leu Gln Pro Tyr Gly
            340                 345                 350

Ser Ile Asn Asp Thr Gly Met Phe Tyr Gly Leu Lys Phe Tyr Asn Asp
        355                 360                 365

Phe Leu Met Glu Ala Gly Pro Phe Gly Asn Val Gln Ser Glu Val Leu
    370                 375                 380

Met Arg Lys Asp Ala Arg Thr Phe Thr Phe Ser Met Gly Trp Ala Phe
385                 390                 395                 400

Pro Arg Lys Ile Tyr Phe Asn Gly Asp Glu Cys Lys Met Pro Pro Pro
                405                 410                 415

Asp Ser Tyr Pro Tyr Leu Pro Asn Ala Ala Pro Val Val Ala Ser Gln
            420                 425                 430

Leu Val Leu Ser Ala Ala Ala Ser Ala Phe Leu Leu Leu Leu Leu Leu
        435                 440                 445

Val Ala
    450

<210> SEQ ID NO 35
<211> LENGTH: 456
<212> TYPE: PRT
<213> ORGANISM: Arabidopsis thaliana

<400> SEQUENCE: 35

Met Glu Ser Phe Phe Ser Arg Ser Thr Ser Ile Val Ser Lys Leu Ser
1               5                   10                  15

Phe Leu Ala Leu Trp Ile Val Phe Leu Ile Ser Ser Ser Ser Phe Thr
            20                  25                  30

Ser Thr Glu Ala Tyr Asp Ala Leu Asp Pro Glu Gly Asn Ile Thr Met
        35                  40                  45

Lys Trp Asp Val Met Ser Trp Thr Pro Asp Gly Tyr Val Ala Val Val
    50                  55                  60

Thr Met Phe Asn Phe Gln Lys Tyr Arg His Ile Gln Ser Pro Gly Trp
65                  70                  75                  80

Thr Leu Gly Trp Lys Trp Ala Lys Lys Glu Val Ile Trp Ser Met Val
                85                  90                  95

Gly Ala Gln Thr Thr Glu Gln Gly Asp Cys Ser Lys Tyr Lys Gly Asn
            100                 105                 110

Ile Pro His Cys Cys Lys Lys Asp Pro Thr Val Val Asp Leu Leu Pro
        115                 120                 125

Gly Thr Pro Tyr Asn Gln Gln Ile Ala Asn Cys Cys Lys Gly Gly Val
    130                 135                 140

Met Asn Ser Trp Val Gln Asp Pro Ala Thr Ala Ala Ser Ser Phe Gln
145                 150                 155                 160

Ile Ser Val Gly Ala Ala Gly Thr Thr Asn Lys Thr Val Arg Val Pro
                165                 170                 175

Arg Asn Phe Thr Leu Met Gly Pro Gly Pro Gly Tyr Thr Cys Gly Pro
            180                 185                 190
```

```
Ala Lys Ile Val Arg Pro Thr Lys Phe Val Thr Thr Asp Thr Arg Arg
        195                 200                 205

Thr Thr Gln Ala Met Met Thr Trp Asn Ile Thr Cys Thr Tyr Ser Gln
    210                 215                 220

Phe Leu Ala Gln Arg Thr Pro Thr Cys Cys Val Ser Leu Ser Ser Phe
225                 230                 235                 240

Tyr Asn Glu Thr Ile Val Gly Cys Pro Thr Cys Ala Cys Gly Cys Gln
                245                 250                 255

Asn Asn Arg Thr Glu Ser Gly Ala Cys Leu Asp Pro Asp Thr Pro His
                260                 265                 270

Leu Ala Ser Val Val Ser Pro Pro Thr Lys Gly Thr Val Leu Pro
        275                 280                 285

Pro Leu Val Gln Cys Thr Arg His Met Cys Pro Ile Arg Val His Trp
        290                 295                 300

His Val Lys Gln Asn Tyr Lys Glu Tyr Trp Arg Val Lys Ile Thr Ile
305                 310                 315                 320

Thr Asn Phe Asn Tyr Arg Leu Asn Tyr Thr Gln Trp Asn Leu Val Ala
                325                 330                 335

Gln His Pro Asn Leu Asp Asn Ile Thr Gln Ile Phe Ser Phe Asn Tyr
                340                 345                 350

Lys Ser Leu Thr Pro Tyr Ala Gly Leu Asn Asp Thr Ala Met Leu Trp
        355                 360                 365

Gly Val Lys Phe Tyr Asn Asp Phe Leu Ser Glu Ala Gly Pro Leu Gly
        370                 375                 380

Asn Val Gln Ser Glu Ile Leu Phe Arg Lys Asp Gln Ser Thr Phe Thr
385                 390                 395                 400

Phe Glu Lys Gly Trp Ala Phe Pro Arg Arg Ile Tyr Phe Asn Gly Asp
                405                 410                 415

Asn Cys Val Met Pro Pro Pro Asp Ser Tyr Pro Phe Leu Pro Asn Gly
                420                 425                 430

Gly Ser Arg Ser Gln Phe Ser Phe Val Ala Ala Val Leu Leu Pro Leu
        435                 440                 445

Leu Val Phe Phe Phe Phe Ser Ala
        450                 455

<210> SEQ ID NO 36
<211> LENGTH: 334
<212> TYPE: PRT
<213> ORGANISM: Oryza sativa

<400> SEQUENCE: 36

Met Cys Gly Gly Ala Ile Leu Ala Glu Phe Ile Pro Ala Pro Ser Arg
1               5                   10                  15

Ala Ala Ala Ala Thr Lys Arg Val Thr Ala Ser His Leu Trp Pro Ala
                20                  25                  30

Gly Ser Lys Asn Ala Ala Arg Gly Lys Ser Lys Ser Lys Arg Gln Gln
        35                  40                  45

Arg Ser Phe Ala Asp Val Asp Phe Glu Ala Ala Phe Glu Gln Phe
    50                  55                  60

Asp Asp Asp Ser Asp Phe Asp Ala Glu Glu Asp Glu Gly His
65                  70                  75              80

Phe Val Phe Ala Ser Lys Ser Arg Val Val Ala Gly His Asp Gly Arg
                85                  90                  95

Ala Ala Ala Arg Ala Ala Ser Lys Lys Lys Arg Gly Arg His Phe Arg
```

```
                    100                 105                 110
Gly Ile Arg Gln Arg Pro Trp Gly Lys Trp Ala Ala Glu Ile Arg Asp
                115                 120                 125

Pro His Lys Gly Thr Arg Val Trp Leu Gly Thr Phe Asn Thr Pro Glu
            130                 135                 140

Glu Ala Ala Arg Ala Tyr Asp Val Glu Ala Arg Arg Leu Arg Gly Ser
145                 150                 155                 160

Lys Ala Lys Val Asn Phe Pro Ala Thr Pro Ala Ala Arg Pro Arg
                165                 170                 175

Arg Gly Asn Thr Arg Ala Thr Ala Val Pro Pro Ala Thr Ala Pro
            180                 185                 190

Ala Ala Ala Pro Pro Arg Gly Leu Lys Arg Glu Phe Ser Pro Pro Ala
            195                 200                 205

Glu Thr Ala Leu Pro Phe Phe Thr Asn Gly Phe Val Asp Leu Thr Thr
            210                 215                 220

Ala Ala Ala Pro Pro Ala Met Met Met Thr Ser Ser Phe Thr Asp
225                 230                 235                 240

Ser Val Ala Thr Ser Glu Ser Gly Gly Ser Pro Ala Lys Lys Ala Arg
                245                 250                 255

Ser Asp Asp Val Asp Ser Ser Glu Gly Ser Val Gly Gly Ser Asp
                260                 265                 270

Thr Leu Gly Phe Thr Asp Glu Leu Glu Phe Asp Pro Phe Met Leu Phe
            275                 280                 285

Gln Leu Pro Tyr Ser Asp Gly Tyr Glu Ser Ile Asp Ser Leu Phe Ala
            290                 295                 300

Ala Gly Asp Ala Asn Ser Ala Asn Thr Asp Met Asn Ala Gly Val Asn
305                 310                 315                 320

Leu Trp Ser Phe Asp Asp Phe Pro Ile Asp Gly Ala Leu Phe
                325                 330

<210> SEQ ID NO 37
<211> LENGTH: 362
<212> TYPE: PRT
<213> ORGANISM: Oryza sativa

<400> SEQUENCE: 37

Met Cys Gly Gly Ala Ile Leu Ser Asp Leu Ile Pro Pro Arg Arg
1               5                   10                  15

Val Thr Ala Gly Asp Leu Trp Leu Glu Lys Thr Lys Lys Gln Gln Gln
                20                  25                  30

Gln Lys Lys Lys Asn Lys Gly Ala Arg Arg Leu Pro Leu Arg Gln Glu
            35                  40                  45

Glu Glu Asp Asp Phe Glu Ala Asp Phe Glu Glu Phe Glu Val Asp Ser
        50                  55                  60

Gly Glu Trp Glu Val Glu Ser Asp Ala Asp Glu Ala Lys Pro Leu Ala
65                  70                  75                  80

Ala Pro Arg Ser Gly Phe Ala Lys Gly Gly Leu Lys Asn Thr Thr Val
                85                  90                  95

Ala Gly Ala Asp Gly Pro Ala Ala Arg Ser Ala Lys Arg Lys Arg Lys
            100                 105                 110

Asn Gln Phe Arg Gly Ile Arg Gln Arg Pro Trp Gly Lys Trp Ala Ala
        115                 120                 125

Glu Ile Arg Asp Pro Arg Lys Gly Val Arg Val Trp Leu Gly Thr Phe
    130                 135                 140
```

Asn Ser Pro Glu Glu Ala Arg Ala Tyr Asp Ala Glu Ala Arg Arg
145                 150                 155                 160

Ile Arg Gly Lys Lys Ala Lys Val Asn Phe Pro Asp Gly Ala Pro Val
                165                 170                 175

Ala Ser Gln Arg Ser His Ala Glu Pro Ser Ser Met Asn Met Pro Ala
            180                 185                 190

Phe Ser Ile Glu Glu Lys Pro Ala Val Met Ser Ala Gly Asn Lys Thr
        195                 200                 205

Met Tyr Asn Thr Asn Ala Tyr Ala Tyr Pro Ala Val Glu Tyr Thr Leu
    210                 215                 220

Gln Glu Pro Phe Val Gln Ile Gln Asn Val Ser Phe Val Pro Ala Met
225                 230                 235                 240

Asn Ala Ile Glu Asp Thr Phe Val Asn Leu Ser Ser Asp Gln Gly Ser
                245                 250                 255

Asn Ser Phe Gly Cys Ser Asp Phe Ser Gln Glu Asn Asp Ile Lys Thr
            260                 265                 270

Pro Asp Ile Thr Ser Met Leu Ala Pro Thr Met Thr Gly Val Asp Asp
        275                 280                 285

Ser Ala Phe Leu Gln Asn Asn Ala Ser Asp Ala Met Val Pro Pro Val
    290                 295                 300

Met Gly Asn Ala Ser Ile Asp Leu Ala Asp Leu Glu Pro Tyr Met Lys
305                 310                 315                 320

Phe Leu Ile Asp Gly Gly Ser Asp Glu Ser Ile Asp Thr Leu Leu Ser
                325                 330                 335

Ser Asp Gly Ser Gln Asp Val Ala Ser Ser Met Asp Leu Trp Ser Phe
            340                 345                 350

Asp Asp Met Pro Val Ser Ala Glu Phe Tyr
        355                 360

<210> SEQ ID NO 38
<211> LENGTH: 396
<212> TYPE: PRT
<213> ORGANISM: Oryza sativa

<400> SEQUENCE: 38

Met Cys Gly Gly Ala Ile Ile Ser Gly Phe Ile Pro Pro Ser Ala Ala
1               5                   10                  15

Ala Ala Ala Ala Ala Val Ala Lys Lys Gln Gln Gly Arg Arg Val
                20                  25                  30

Thr Ala Asp Val Leu Trp Pro Gly Met Leu Arg Lys Gly Lys Ala Ala
            35                  40                  45

Ala Ala Glu Glu Asp Phe Glu Ala Asp Phe Arg Glu Phe Glu Arg Gly
        50                  55                  60

Met Ser Asp Asp Glu Ala Glu Gly Gly Gly Glu Glu Glu Asp
65                  70                  75                  80

Asp Asp Asp Val Val Val Val Pro Pro Ala Ala Arg Phe
                85                  90                  95

Val Val Arg Ala Ala Ala Lys Ala Ala Pro Thr Ala Asp Gly Met
            100                 105                 110

Leu Thr Thr Lys Leu Val Gln His Asp Gly Pro Thr Ala Arg Ser Ala
        115                 120                 125

Lys His Lys Arg Lys Asn Gln Tyr Arg Gly Ile Arg Gln Arg Pro Trp
    130                 135                 140

Gly Lys Trp Ala Ala Glu Ile Arg Asp Pro Ser Lys Gly Val Arg Val
145                 150                 155                 160

Trp Leu Gly Thr Tyr Asn Thr Ala Glu Glu Ala Ala Arg Ala Tyr Asp
            165                 170                 175

Ala Glu Ala Arg Lys Ile Arg Gly Lys Lys Ala Lys Val Asn Phe Pro
            180                 185                 190

Asp Glu Pro Ala Val Ala Gln Lys Leu Ser Leu Lys Gln Asn Ala Ala
            195                 200                 205

Lys Gln Glu Lys Leu Ala Pro Pro Leu Lys Thr Cys Gly Asp Asp Ala
            210                 215                 220

Phe Phe Gln Leu Asn Ser Ser Asp Asn Asp Leu Phe Ala Met Leu Ala
225                 230                 235                 240

Lys Val Pro Ala Lys Pro Ala Glu Pro Val Asp Leu Met Pro Pro Val
            245                 250                 255

Lys Pro Leu Ala Ser Thr Glu Thr Phe Glu Met Asn Met Leu Ser Asp
            260                 265                 270

Thr Ser Ser Asn Ser Phe Gly Ser Ser Asp Phe Gly Trp Glu Asp Asp
            275                 280                 285

Thr Leu Thr Pro Asp Tyr Thr Ser Val Phe Val Pro Asn Ala Ala Met
            290                 295                 300

Pro Ala Tyr Gly Glu Pro Ala Tyr Leu Thr Gly Gly Ala Pro Lys Arg
305                 310                 315                 320

Met Arg Asn Asn Tyr Gly Ile Ala Val Pro Gln Gly Asn Gly Met Pro
            325                 330                 335

Asn Leu Ala Gln Asn Met Pro Thr Phe Asp Pro Glu Met Lys Tyr Leu
            340                 345                 350

Pro Leu Pro Tyr Val Glu Ser Ser Asp Glu Ser Met Asp Asn Leu
            355                 360                 365

Leu Gln Asn Asp Ala Thr Gln Asp Gly Ala Ser Asn Glu Gly Ile Trp
            370                 375                 380

Ser Leu Asp Glu Leu Leu Met Ala Ala Gly Ala Tyr
385                 390                 395

<210> SEQ ID NO 39
<211> LENGTH: 365
<212> TYPE: PRT
<213> ORGANISM: Oryza sativa

<400> SEQUENCE: 39

Met Cys Gly Gly Ala Ile Ile His His Leu Lys Gly His Pro Glu Gly
1               5                   10                  15

Ser Arg Arg Ala Thr Glu Gly Leu Leu Trp Pro Glu Lys Lys Lys Pro
            20                  25                  30

Arg Trp Gly Gly Gly Arg Arg His Phe Gly Gly Phe Val Glu Glu
            35                  40                  45

Asp Asp Glu Asp Phe Glu Ala Asp Phe Glu Glu Phe Glu Val Asp Ser
            50                  55                  60

Gly Asp Ser Asp Leu Glu Leu Gly Glu Glu Asp Asp Asp Val Val
65                  70                  75                  80

Glu Ile Lys Pro Ala Ala Phe Lys Arg Ala Leu Ser Arg Asp Asn Leu
            85                  90                  95

Ser Thr Ile Thr Thr Ala Gly Phe Asp Gly Pro Ala Ala Lys Ser Ala
            100                 105                 110

Lys Arg Lys Arg Lys Asn Gln Phe Arg Gly Ile Arg Gln Arg Pro Trp
            115                 120                 125

Gly Lys Trp Ala Ala Glu Ile Arg Asp Pro Arg Lys Gly Val Arg Val

```
                    130                 135                 140
Trp Leu Gly Thr Phe Asn Ser Ala Glu Glu Ala Ala Arg Ala Tyr Asp
145                 150                 155                 160

Ala Glu Ala Arg Arg Ile Arg Gly Lys Lys Ala Lys Val Asn Phe Pro
                165                 170                 175

Glu Ala Pro Thr Thr Ala Gln Lys Arg Arg Ala Gly Ser Thr Thr Ala
                180                 185                 190

Lys Ala Pro Lys Ser Ser Val Glu Gln Lys Pro Thr Val Lys Pro Ala
                195                 200                 205

Phe Asn Asn Leu Ala Asn Ala Asn Ala Phe Val Tyr Pro Ser Ala Asn
            210                 215                 220

Phe Thr Ser Asn Lys Pro Phe Val Gln Pro Asp Asn Met Pro Phe Val
225                 230                 235                 240

Pro Ala Met Asn Ser Ala Ala Pro Ile Glu Asp Pro Ile Ile Asn Ser
                245                 250                 255

Asp Gln Gly Ser Asn Ser Phe Gly Cys Ser Asp Phe Gly Trp Glu Asn
                260                 265                 270

Asp Thr Lys Thr Pro Asp Ile Thr Ser Ile Ala Pro Ile Ser Thr Ile
                275                 280                 285

Ala Glu Val Asp Glu Ser Ala Phe Ile Lys Ser Ser Thr Asn Pro Met
                290                 295                 300

Val Pro Pro Val Met Glu Asn Ser Ala Val Asp Leu Pro Asp Leu Glu
305                 310                 315                 320

Pro Tyr Met Arg Phe Leu Leu Asp Asp Gly Ala Gly Asp Ser Ile Asp
                325                 330                 335

Ser Leu Leu Asn Leu Asp Gly Ser Gln Asp Val Val Ser Asn Met Asp
                340                 345                 350

Leu Trp Ser Phe Asp Asp Met Pro Val Ser Asp Phe Tyr
                355                 360                 365

<210> SEQ ID NO 40
<211> LENGTH: 355
<212> TYPE: PRT
<213> ORGANISM: Triticum aestivum

<400> SEQUENCE: 40

Met Cys Gly Gly Ala Ile Leu Ser Asp Ile Ile Pro Pro Arg Arg
1               5                   10                  15

Ala Thr Gly Gly Asn Val Trp Arg Ala Asp Lys Lys Arg Arg Ala Arg
                20                  25                  30

Pro Asp Ala Ala Ala Gly Arg Pro Arg Arg Val Pro Glu Glu Phe
            35                  40                  45

Gln Glu Glu Glu Gly Asp Ala Glu Phe Glu Ala Asp Phe Glu Gly Phe
    50                  55                  60

Val Glu Ala Glu Glu Ser Asp Gly Glu Ala Lys Pro Phe Pro Val
65                  70                  75                  80

Arg Arg Thr Gly Phe Ser Gly Asp Gly Leu Lys Ala Thr Ala Ala Gly
                85                  90                  95

Asp Asp Asp Cys Ala Ser Gly Ser Ala Lys Arg Lys Lys Ser Gln
                100                 105                 110

Phe Arg Gly Ile Arg Arg Arg Pro Trp Gly Lys Trp Ala Ala Glu Ile
        115                 120                 125

Arg Asp Pro Arg Lys Gly Val Arg Val Trp Leu Gly Thr Tyr Asn Ser
    130                 135                 140
```

```
Ala Glu Glu Ala Ala Arg Ala Tyr Asp Val Glu Ala Arg Arg Ile Arg
145                 150                 155                 160

Gly Lys Lys Ala Lys Val Asn Phe Pro Glu Glu Ala Pro Met Asp Pro
                165                 170                 175

Gln Gln Arg Cys Ala Thr Ser Val Lys Val Pro Glu Phe Asn Thr Glu
            180                 185                 190

Gln Lys Pro Val Leu Asn Thr Met Gly Asn Thr Asp Val Tyr Ser Cys
        195                 200                 205

Pro Ala Val Asp Tyr Thr Leu Asn Gln Gln Phe Val Gln Pro Gln Asn
    210                 215                 220

Met Ser Phe Val Pro Thr Val Asn Ala Val Glu Ala Pro Phe Met Asn
225                 230                 235                 240

Phe Ser Ser Asp Gln Gly Ser Asn Ser Phe Ser Cys Ser Asp Phe Ser
                245                 250                 255

Trp Glu Asn Asp Ile Lys Thr Pro Asp Ile Thr Ser Val Leu Ala Ser
                260                 265                 270

Ile Pro Thr Ser Thr Glu Val Asn Glu Ser Ala Phe Leu Gln Asn Asn
                275                 280                 285

Gly Ile Asn Ser Thr Val Pro Pro Val Met Gly Asp Ala Asn Val Asp
290                 295                 300

Leu Ala Asp Leu Glu Pro Tyr Met Lys Phe Leu Met Asp Asp Gly Ser
305                 310                 315                 320

Asp Glu Ser Ile Asp Ser Ile Leu Ser Cys Asp Val Pro Gln Asp Val
                325                 330                 335

Val Gly Asn Met Gly Leu Trp Thr Phe Asp Asp Met Pro Leu Ser Ala
                340                 345                 350

Gly Phe Tyr
        355

<210> SEQ ID NO 41
<211> LENGTH: 369
<212> TYPE: PRT
<213> ORGANISM: Capsicum annuum

<400> SEQUENCE: 41

Met Cys Gly Gly Ala Ile Ile Ser Asp Leu Val Pro Pro Ser Arg Ile
1               5                   10                  15

Ser Arg Arg Leu Thr Ala Glu Leu Leu Trp Gly Asn Ser Asp Leu Ser
                20                  25                  30

Lys Lys Lys Lys Asn Pro Gly Asn Tyr Tyr Ser Lys Pro Leu Asn Arg
            35                  40                  45

Ser Lys Phe Ile Asp Leu Asp Glu Glu Phe Glu Ala Asp Phe Gln Asp
        50                  55                  60

Phe Lys Asp Tyr Ala Asp Asp Val Asp Val Lys Pro Phe Gly
65                  70                  75                  80

Ser Lys Ser Val Lys Ser Gly Asp Ser Ser Cys Asp Thr Glu Lys Ser
                85                  90                  95

Ser Lys Arg Lys Arg Lys Asn Gln Tyr Arg Gly Ile Arg Gln Arg Pro
            100                 105                 110

Trp Gly Lys Trp Ala Ala Glu Ile Arg Asp Pro Arg Lys Gly Ile Arg
        115                 120                 125

Val Trp Leu Gly Thr Phe Asn Ser Ala Glu Glu Ala Ala Arg Ala Tyr
    130                 135                 140

Asp Val Glu Ala Arg Arg Ile Arg Gly Lys Lys Ala Lys Val Asn Phe
145                 150                 155                 160
```

-continued

```
Pro Asp Gly Ser Pro Ala Ser Ala Ser Arg Arg Ala Val Lys Pro Asn
            165                 170                 175

Pro Gln Glu Ala Leu Arg Glu Ile Leu Asn Thr Val Gln Pro Asn
        180                 185                 190

Thr Thr Tyr Ile Asn Asn Leu Asp Gly Gly Ser Asp Asp Ser Phe Gly
            195                 200                 205

Phe Phe Glu Glu Lys Pro Ala Ala Lys Gln Tyr Gly Tyr Glu Asn Val
210                 215                 220

Ser Phe Thr Ala Gly Asp Met Gly Leu Gly Ser Ile Ser Pro Ser Thr
225                 230                 235                 240

Gly Thr Thr Asn Val Tyr Phe Ser Ser Asp Glu Gly Ser Asn Thr Phe
                245                 250                 255

Asp Cys Ser Asp Phe Gly Trp Gly Glu Pro Cys Pro Arg Thr Pro Glu
                260                 265                 270

Ile Ser Ser Val Leu Ser Glu Val Leu Glu Cys Asn Gly Thr Gln Ser
            275                 280                 285

Asp Glu Asp Ala Arg Pro Glu Lys Lys Leu Lys Ser Cys Ser Asn Ala
        290                 295                 300

Ser Leu Pro Asp Glu Asp Asn Thr Val His Thr Leu Ser Glu Glu Leu
305                 310                 315                 320

Ser Ala Phe Glu Ser Gln Met Lys Phe Leu Gln Ile Pro Tyr Leu Glu
                325                 330                 335

Gly Asn Trp Asp Ala Ser Val Asp Ala Phe Val Asn Thr Gly Ala Ile
                340                 345                 350

Gln Asp Gly Gly Asn Ala Met Asp Leu Trp Pro Ser Met Met Phe Leu
            355                 360                 365

Leu
```

<210> SEQ ID NO 42
<211> LENGTH: 384
<212> TYPE: PRT
<213> ORGANISM: Glycine max

<400> SEQUENCE: 42

```
Met Cys Gly Gly Ala Ile Ile Ser Asp Phe Ile Pro Ala Gly Pro Ala
1               5                   10                  15

Ser Gly Ala Arg Arg Val Thr Ala Asp Ile Leu Trp Pro Ser Leu Arg
            20                  25                  30

Lys Arg Phe Ser Lys Pro Leu Leu Asp Asp Asp Phe Glu Ala Gly Phe
        35                  40                  45

Arg Glu Phe Lys Asp Asp Ser Glu Ile Glu Asp Val Asp Asp Glu Asp
50                  55                  60

Asp Glu Asp Glu Glu Glu Leu Lys Lys Lys Pro Phe Gly Phe Ser Arg
65                  70                  75                  80

Ser Ser Asn Lys Ala Ala Ser Lys Pro Leu Ser Arg Gly Ala Thr Thr
                85                  90                  95

Val Lys Ser Val Glu Ser Lys Gly Gln Ala Glu Lys Cys Ala Lys Arg
            100                 105                 110

Lys Arg Lys Asn Gln Tyr Arg Gly Ile Arg Gln Arg Pro Trp Gly Lys
        115                 120                 125

Trp Ala Ala Glu Ile Arg Asp Pro Arg Lys Gly Val Arg Val Trp Leu
    130                 135                 140

Gly Thr Phe Ser Thr Ala Glu Glu Ala Ala Arg Ala Tyr Asp Ala Glu
145                 150                 155                 160
```

```
Ala Arg Arg Ile Arg Gly Lys Lys Ala Lys Val Asn Phe Pro Asp Glu
                165                 170                 175

Pro Ser Gly Ala Ala Ser Ser Lys Arg Leu Lys Ala Asn Pro Glu Ala
            180                 185                 190

Gln Pro Met Lys Lys Asn Leu Asn Ser Val Lys Pro Lys Ile Asn Gln
        195                 200                 205

Met Phe Asn Phe Gly Asp Asn Leu Glu Gly Tyr Tyr Ser Pro Ile Asp
    210                 215                 220

Gln Val Glu Gln Lys Pro Leu Val Asn Gln Tyr Val Asn Arg Ala Pro
225                 230                 235                 240

Phe Ala Gly Asn Gly Val Gln Val Ser Pro Val Thr Pro Ser Ala Asp
                245                 250                 255

Val Thr Ala Tyr Phe Ser Ser Glu His Ser Ser Asn Ser Phe Asp Tyr
            260                 265                 270

Ser Asp Leu Gly Trp Gly Glu Gln Val Pro Lys Thr Pro Glu Ile Ser
        275                 280                 285

Ser Leu Leu Ser Ala Ala Pro Leu Glu Gly Ala Ala Asp Gln Val Gln
    290                 295                 300

Lys Thr Asn Asn Ser Gln Asp Val Val Ala Ala Gln Asp Ser Ala
305                 310                 315                 320

Lys Thr Leu Ser Glu Glu Leu Ala Asp Ile Glu Ser Gln Leu Lys Phe
                325                 330                 335

Phe Glu Thr Pro Ser Phe Leu Asp Glu Ala Trp Ala Asp Ala Thr Leu
            340                 345                 350

Ala Ser Leu Leu Gly Gly Asp Ala Thr His Asp Ala Ala Gly Asn Pro
        355                 360                 365

Met Asn Leu Trp Ser Phe Asp Asp Leu Pro Ser Met Ala Gly Val Phe
    370                 375                 380

<210> SEQ ID NO 43
<211> LENGTH: 372
<212> TYPE: PRT
<213> ORGANISM: Solanum lycopersicum

<400> SEQUENCE: 43

Met Cys Gly Gly Ala Ile Ile Ser Asp Leu Val Pro Pro Ser Arg Ile
1               5                   10                  15

Ser Arg Arg Leu Thr Ala Asp Phe Leu Trp Gly Thr Ser Asp Leu Asn
            20                  25                  30

Lys Lys Lys Lys Asn Pro Ser Asn Tyr His Ser Lys Pro Leu Arg Ser
        35                  40                  45

Lys Phe Ile Asp Leu Glu Asp Glu Phe Glu Ala Asp Phe Gln His Phe
    50                  55                  60

Lys Asp Asn Ser Asp Asp Asp Asp Val Lys Ala Phe Gly Pro Lys
65                  70                  75                  80

Ser Val Arg Ser Gly Asp Ser Asn Cys Glu Ala Asp Arg Ser Ser Lys
                85                  90                  95

Arg Lys Arg Lys Asn Gln Tyr Arg Gly Ile Arg Gln Arg Pro Trp Gly
            100                 105                 110

Lys Trp Ala Ala Glu Ile Arg Asp Pro Arg Lys Gly Ile Arg Val Trp
        115                 120                 125

Leu Gly Thr Phe Asn Ser Ala Glu Glu Ala Ala Arg Ala Tyr Asp Ala
    130                 135                 140

Glu Ala Arg Arg Ile Arg Gly Lys Lys Ala Lys Val Asn Phe Pro Asp
```

```
                145                 150                 155                 160
        Glu Ala Pro Val Ser Val Ser Arg Arg Ala Ile Lys Gln Asn Pro Gln
                            165                 170                 175

Lys Ala Leu Arg Glu Glu Thr Leu Asn Thr Val Gln Pro Asn Met Thr
                            180                 185                 190

Tyr Ile Ser Asn Leu Asp Gly Gly Ser Asp Asp Ser Phe Ser Phe Phe
                            195                 200                 205

Glu Glu Lys Pro Ala Thr Lys Gln Tyr Gly Phe Glu Asn Val Ser Phe
                210                 215                 220

Thr Ala Val Asp Met Gly Leu Gly Ser Val Ser Pro Ser Ala Gly Thr
        225                 230                 235                 240

Asn Val Tyr Phe Ser Ser Asp Glu Ala Ser Asn Thr Phe Asp Cys Ser
                            245                 250                 255

Asp Phe Gly Trp Ala Glu Pro Cys Ala Arg Thr Pro Glu Ile Ser Ser
                            260                 265                 270

Val Leu Ser Glu Val Leu Glu Thr Asn Glu Thr His Phe Asp Asp
                            275                 280                 285

Ser Arg Pro Glu Lys Lys Leu Lys Ser Cys Ser Ser Thr Ser Leu Thr
                290                 295                 300

Val Asp Gly Asn Thr Val Asn Thr Leu Ser Glu Glu Leu Ser Ala Phe
        305                 310                 315                 320

Glu Ser Gln Met Lys Phe Leu Gln Ile Pro Tyr Leu Glu Gly Asn Trp
                            325                 330                 335

Asp Ala Ser Val Asp Ala Phe Leu Asn Thr Ser Ala Ile Gln Asp Gly
                            340                 345                 350

Gly Asn Ala Met Asp Leu Trp Ser Phe Asp Asp Val Pro Ser Leu Met
                            355                 360                 365

Gly Gly Ala Tyr
                    370

<210> SEQ ID NO 44
<211> LENGTH: 431
<212> TYPE: PRT
<213> ORGANISM: Arabidopsis thaliana

<400> SEQUENCE: 44

Met Arg Leu Leu Phe Ser Phe Cys Phe Phe Phe Met Ile Ile Phe
        1               5                   10                  15

Thr Ala Thr Ala Tyr Asp Pro Leu Asp Pro Ser Gly Asn Ile Thr Ile
                            20                  25                  30

Lys Trp Asp Ile Met Ser Trp Thr Ala Asp Gly Tyr Val Ala Thr Val
                        35                  40                  45

Thr Met Asn Asn Phe Gln Ile Tyr Arg His Ile Gln Asn Pro Gly Trp
                50                  55                  60

Thr Leu Gly Trp Thr Trp Ala Lys Lys Glu Val Ile Trp Ser Met Val
        65                  70                  75                  80

Gly Ala Gln Thr Thr Glu Gln Gly Asp Cys Ser Lys Phe Lys Gly Asn
                            85                  90                  95

Val Pro His Cys Cys Lys Lys Thr Pro Thr Val Val Asp Leu Leu Pro
                        100                 105                 110

Gly Val Pro Tyr Asn Gln Gln Phe Ser Asn Cys Cys Lys Gly Gly Val
                    115                 120                 125

Ile Gly Ala Trp Gly Gln Asp Pro Ser Ala Ala Val Ser Gln Phe Gln
                130                 135                 140
```

```
Val Ser Ala Gly Leu Ala Gly Thr Thr Asn Lys Thr Val Lys Leu Pro
145                 150                 155                 160

Lys Asn Phe Thr Leu Leu Gly Pro Gly Pro Gly Tyr Thr Cys Gly Pro
                165                 170                 175

Ala Lys Ile Val Pro Ser Thr Val Phe Leu Thr Thr Asp Lys Arg Arg
            180                 185                 190

Lys Thr Gln Ala Leu Met Thr Trp Asn Val Thr Cys Thr Tyr Ser Gln
        195                 200                 205

Phe Leu Ala Arg Lys His Pro Ser Cys Cys Val Ser Phe Ser Ser Phe
    210                 215                 220

Tyr Asn Asp Thr Ile Thr Pro Cys Pro Ser Cys Ala Cys Gly Cys Glu
225                 230                 235                 240

Asn Lys Lys Ser Cys Val Lys Ala Asp Ser Lys Ile Leu Thr Lys Lys
                245                 250                 255

Gly Leu Asn Thr Pro Lys Lys Asp Asn Thr Pro Leu Leu Gln Cys Thr
                260                 265                 270

His His Met Cys Pro Val Arg Val His Trp His Val Leu Thr Asn Tyr
            275                 280                 285

Lys Asp Tyr Trp Arg Val Lys Ile Ala Ile Thr Asn Phe Asn Tyr Arg
        290                 295                 300

Met Asn His Thr Leu Trp Thr Leu Ala Ile Gln His Pro Asn Leu Asn
305                 310                 315                 320

Asn Val Thr Gln Val Phe Ser Phe Asp Tyr Lys Pro Val Ser Pro Tyr
                325                 330                 335

Gly Ser Ile Asn Asp Thr Gly Met Phe Tyr Gly Thr Lys Phe Tyr Asn
                340                 345                 350

Asp Leu Leu Met Glu Ala Gly Pro Ser Gly Asn Val Gln Ser Glu Val
            355                 360                 365

Leu Leu Gln Lys Asp Gln Lys Thr Phe Thr Phe Lys Gln Gly Trp Ala
        370                 375                 380

Phe Pro Arg Lys Val Tyr Phe Asn Gly Asp Glu Cys Met Leu Pro Pro
385                 390                 395                 400

Pro Asp Ser Tyr Pro Phe Leu Pro Asn Ser Ala Gln Gly Asn Phe Ala
                405                 410                 415

Ser Phe Ser Leu Thr Ile Leu Leu Leu Phe Ile Ser Ile Trp
                420                 425                 430

<210> SEQ ID NO 45
<211> LENGTH: 5
<212> TYPE: PRT
<213> ORGANISM: Artificial
<220> FEATURE:
<223> OTHER INFORMATION: Poly-Arg tag sequence

<400> SEQUENCE: 45

Arg Arg Arg Arg Arg
1               5

<210> SEQ ID NO 46
<211> LENGTH: 6
<212> TYPE: PRT
<213> ORGANISM: Artificial
<220> FEATURE:
<223> OTHER INFORMATION: Poly-Arg tag sequence

<400> SEQUENCE: 46

Arg Arg Arg Arg Arg Arg
1               5
```

<210> SEQ ID NO 47
<211> LENGTH: 6
<212> TYPE: PRT
<213> ORGANISM: Artificial
<220> FEATURE:
<223> OTHER INFORMATION: Poly-His tag sequence

<400> SEQUENCE: 47

His His His His His His
1               5

<210> SEQ ID NO 48
<211> LENGTH: 8
<212> TYPE: PRT
<213> ORGANISM: Artificial
<220> FEATURE:
<223> OTHER INFORMATION: FLAG tag sequence

<400> SEQUENCE: 48

Asp Tyr Lys Asp Asp Asp Asp Lys
1               5

<210> SEQ ID NO 49
<211> LENGTH: 8
<212> TYPE: PRT
<213> ORGANISM: Artificial
<220> FEATURE:
<223> OTHER INFORMATION: Strep-tag II sequence

<400> SEQUENCE: 49

Trp Ser His Pro Gln Phe Glu Lys
1               5

<210> SEQ ID NO 50
<211> LENGTH: 10
<212> TYPE: PRT
<213> ORGANISM: Artificial
<220> FEATURE:
<223> OTHER INFORMATION: c-Myc tag sequence

<400> SEQUENCE: 50

Glu Gln Lys Leu Ile Ser Glu Glu Asp Leu
1               5                   10

<210> SEQ ID NO 51
<211> LENGTH: 22
<212> TYPE: DNA
<213> ORGANISM: Artificial
<220> FEATURE:
<223> OTHER INFORMATION: RT-PCR primer sequence

<400> SEQUENCE: 51
tgtgtttctc tctcgtcgtt cg                                              22

<210> SEQ ID NO 52
<211> LENGTH: 22
<212> TYPE: DNA
<213> ORGANISM: Artificial
<220> FEATURE:
<223> OTHER INFORMATION: RT-PCR primer sequence

<400> SEQUENCE: 52
tctttgagca tcaagtgcca gt                                              22

<210> SEQ ID NO 53

```
<211> LENGTH: 21
<212> TYPE: DNA
<213> ORGANISM: Artificial
<220> FEATURE:
<223> OTHER INFORMATION: RT-PCR primer sequence

<400> SEQUENCE: 53
atggcttgct tgattaccga a                                         21

<210> SEQ ID NO 54
<211> LENGTH: 21
<212> TYPE: DNA
<213> ORGANISM: Artificial
<220> FEATURE:
<223> OTHER INFORMATION: RT-PCR primer sequence

<400> SEQUENCE: 54
agaccccgta aaagtagccc a                                         21

<210> SEQ ID NO 55
<211> LENGTH: 21
<212> TYPE: DNA
<213> ORGANISM: Artificial
<220> FEATURE:
<223> OTHER INFORMATION: RT-PCR primer sequence

<400> SEQUENCE: 55
atttggcacc acacattcta c                                         21

<210> SEQ ID NO 56
<211> LENGTH: 22
<212> TYPE: DNA
<213> ORGANISM: Artificial
<220> FEATURE:
<223> OTHER INFORMATION: RT-PCR primer sequence

<400> SEQUENCE: 56
ataaccttcg tagattggga ct                                        22

<210> SEQ ID NO 57
<211> LENGTH: 30
<212> TYPE: DNA
<213> ORGANISM: Artificial
<220> FEATURE:
<223> OTHER INFORMATION: PCR primer sequence

<400> SEQUENCE: 57
ttggcgcgcc acacaccgag tcatcgctcg                                30

<210> SEQ ID NO 58
<211> LENGTH: 31
<212> TYPE: DNA
<213> ORGANISM: Artificial
<220> FEATURE:
<223> OTHER INFORMATION: PCR primer sequence

<400> SEQUENCE: 58
ccttaattaa cccctgccac gaatctgcta t                              31

<210> SEQ ID NO 59
<211> LENGTH: 29
<212> TYPE: DNA
<213> ORGANISM: Artificial
<220> FEATURE:
<223> OTHER INFORMATION: PCR primer sequence

<400> SEQUENCE: 59
```

```
cgggtacca aaggcattcg caacacaca                                              29

<210> SEQ ID NO 60
<211> LENGTH: 32
<212> TYPE: DNA
<213> ORGANISM: Artificial
<220> FEATURE:
<223> OTHER INFORMATION: PCR primer sequence

<400> SEQUENCE: 60
ccttaattaa ccaaaataca ttacgactgg ac                                         32

<210> SEQ ID NO 61
<211> LENGTH: 24
<212> TYPE: DNA
<213> ORGANISM: Artificial
<220> FEATURE:
<223> OTHER INFORMATION: PCR primer sequence

<400> SEQUENCE: 61
aaaagttcga cagcgtctcc gacc                                                  24

<210> SEQ ID NO 62
<211> LENGTH: 24
<212> TYPE: DNA
<213> ORGANISM: Artificial
<220> FEATURE:
<223> OTHER INFORMATION: PCR primer sequence

<400> SEQUENCE: 62
tctacacagc catcggtcca gacg                                                  24
```